(12) United States Patent
Minne et al.

(10) Patent No.: US 9,115,143 B2
(45) Date of Patent: Aug. 25, 2015

(54) SUBSTITUTED INDOLE DERIVATIVES AS GAMMA SECRETASE MODULATORS

(75) Inventors: Garrett Berlond Minne, Bissegem (BE); François Paul Bischoff, Vosselaar (BE); Henricus Jacobus Maria Gijsen, Breda (NL); Adriana Ingrid Velter, Antwerpen (BE); Serge Maria Aloysius Pieters, Hulst (NL); Didier Jean-Claude Berthelot, Edegem (BE)

(73) Assignees: Janssen Pharmaceuticals, Inc., Titusville, NJ (US); Cellzome Limited, Brentford, Middlesex (GB)

(*) Notice: Subject to any disclaimer, the term of this patent is extended or adjusted under 35 U.S.C. 154(b) by 0 days.

(21) Appl. No.: 14/233,078

(22) PCT Filed: Jul. 12, 2012

(86) PCT No.: PCT/EP2012/063667
§ 371 (c)(1),
(2), (4) Date: Jan. 15, 2014

(87) PCT Pub. No.: WO2013/010904
PCT Pub. Date: Jan. 24, 2013

(65) Prior Publication Data
US 2014/0148450 A1 May 29, 2014

(30) Foreign Application Priority Data
Jul. 15, 2011 (EP) .................................. 11174120

(51) Int. Cl.
*C07D 498/04* (2006.01)
*C07D 487/04* (2006.01)

(52) U.S. Cl.
CPC ............ *C07D 498/04* (2013.01); *C07D 487/04* (2013.01)

(58) Field of Classification Search
CPC ............................ C07D 487/04; C07D 498/04
USPC ....................................... 514/230.5; 544/105
See application file for complete search history.

(56) References Cited

U.S. PATENT DOCUMENTS

| | | | |
|---|---|---|---|
| 5,639,756 A * | 6/1997 | Anisimova et al. | 514/257 |
| 5,767,144 A | 6/1998 | Winn et al. | |
| 6,114,334 A | 9/2000 | Kerrigan et al. | |
| 7,923,563 B2 | 4/2011 | Kushida et al. | |
| 8,569,331 B2 * | 10/2013 | Ashwell et al. | 514/287 |
| 8,598,353 B2 | 12/2013 | Mjalli et al. | |
| 2002/0128319 A1 | 9/2002 | Koo et al. | |
| 2006/0004013 A1 | 1/2006 | Kimura et al. | |
| 2008/0280948 A1 | 11/2008 | Baumann et al. | |
| 2009/0062529 A1 | 3/2009 | Kimura et al. | |
| 2010/0137320 A1 | 6/2010 | Huang et al. | |

FOREIGN PATENT DOCUMENTS

| | | |
|---|---|---|
| CN | 101142194 (A) | 3/2008 |
| EP | 1757591 | 2/2007 |
| JP | 2003/502313 | 1/2003 |
| WO | WO 01/78721 | 10/2001 |
| WO | WO 01/87845 | 11/2001 |
| WO | WO 02/069946 | 9/2002 |
| WO | WO 2004/017963 | 3/2004 |
| WO | WO 2004/076448 | 9/2004 |
| WO | WO 2004/110350 | 12/2004 |
| WO | WO 2005/016892 | 5/2005 |
| WO | WO 2005/085245 | 9/2005 |
| WO | WO 2005/115990 | 12/2005 |
| WO | WO 2006/135667 | 12/2006 |
| WO | WO 2007/034252 | 3/2007 |
| WO | WO 2007/038314 | 4/2007 |
| WO | WO 2007/043786 | 4/2007 |
| WO | WO 2007/044895 | 4/2007 |

(Continued)

OTHER PUBLICATIONS

Citron et al. "Mutant Presenilins of Alzheimer's Disease Increase Production of 42-Residue Amyloid β-Protein in Both Transfected Cells and Transgenic Mice", Nature Medicine, Jan. 1997, 3(1), 67-72.
"Crystallization", Kirk-Othmer Encyclopedia of Chemical Technology, 2002, 8, 95-147.
Dorwald, "Side Reactions in Organic Synthesis", Wiley: VCH Weinheim Preface, Chapter 8, 2005, 45 pages.
Dyatkin et al., "Determination of the Absolute Configuration of a Key Tricyclic Component of a Novel Vasopressin Receptor Antagonist by Use of Vibrational Circular Dichroism", Chirality, 2002, 14, 215-219.
Eriksen et al., "NSAIDs and Enantiomers of Flurbiprofen Target Gamma-Secretase and Lower A-beta-42 In Vivo", J. Clin Invest, 2003, 112(3), 440-449.
Garofalo, "Patents Targeting Gamma-Secretase Inhibition and Modulation for the Treatment of Alzheimer's Disease: 2004-2008", Expert Opinion Ther. Patents, 2008, 18(7), 693-703.
Greene et al., "Protective Groups in Organic Synthesis", John Wiley & Sons, Inc., Third Edition, 1999, 3 pages.

(Continued)

*Primary Examiner* — Valerie Rodriguez-Garcia
(74) *Attorney, Agent, or Firm* — Baker & Hostetler LLP

(57) ABSTRACT

The present invention is concerned with novel substituted indole derivatives of Formula (I) wherein $R^1$, $R^2$, $R^3$, $A^1$, $A^2$, $A^3$, Y and X have the meaning defined in the claims. The compounds according to the present invention are useful as gamma secretase modulators. The invention further relates to processes for preparing such novel compounds, pharmaceutical compositions comprising said compounds as an active ingredient as well as the use of said compounds as a medicament.

(I)

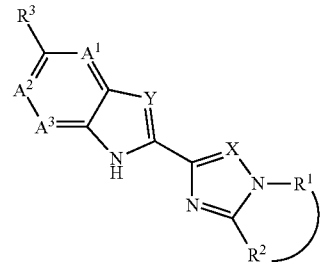

14 Claims, No Drawings

(56) References Cited

FOREIGN PATENT DOCUMENTS

| | | |
|---|---|---|
| WO | WO 2007/058942 | 5/2007 |
| WO | WO 2007/105053 | 9/2007 |
| WO | WO 2007/113276 | 10/2007 |
| WO | WO 2007/131991 | 11/2007 |
| WO | WO 2008/065199 | 6/2008 |
| WO | WO 2008/073370 | 6/2008 |
| WO | WO 2008/082490 | 7/2008 |
| WO | WO 2008/097538 | 8/2008 |
| WO | WO 2008/099210 | 8/2008 |
| WO | WO 2008/100412 | 8/2008 |
| WO | WO 2008/137139 | 11/2008 |
| WO | WO 2008/156580 | 12/2008 |
| WO | WO 2009/005729 | 1/2009 |
| WO | WO 2009/032277 | 3/2009 |
| WO | WO 2009/050227 | 4/2009 |
| WO | WO 2009/073777 | 6/2009 |
| WO | WO 2009/076352 | 6/2009 |
| WO | WO 2009/103652 | 8/2009 |
| WO | WO 2010/010188 | 1/2010 |
| WO | WO 2010/052199 | 5/2010 |
| WO | WO 2010/054067 | 5/2010 |
| WO | WO 2010/065310 | 6/2010 |
| WO | WO 2010/070008 | 6/2010 |
| WO | WO 2010/083141 | 7/2010 |
| WO | WO 2010/089292 | 8/2010 |
| WO | WO 2010/094647 | 8/2010 |
| WO | WO 2010/098487 | 9/2010 |
| WO | WO 2010/098488 | 9/2010 |
| WO | WO 2010/098495 | 9/2010 |
| WO | WO 2010/100606 | 9/2010 |
| WO | WO 2010/106745 | 9/2010 |
| WO | WO 2010/126745 | 11/2010 |
| WO | WO 2010/137320 | 12/2010 |
| WO | WO 2010/145883 | 12/2010 |
| WO | WO 2011/006903 | 1/2011 |
| WO | WO 2011/086098 | 7/2011 |
| WO | WO 2011/086099 | 7/2011 |
| WO | WO 2012/131539 | 4/2012 |
| WO | WO 2012/126984 | 9/2012 |
| WO | WO 2013/010904 | 1/2013 |

OTHER PUBLICATIONS

Guillory (Brittain Ed.). "Polymorphism in Pharmaceutical Solids" Marcel Dekker. Inc., NY, 1999, 50 pages.
International Patent Application No. PCT/EP2010/051843: International Search Report dated Jun. 1, 2010, 3 pages.
International Patent Application No. PCT/EP2011/050349: International Search Report dated Feb. 23, 2011, 3 pages.
International Patent Application No. PCT/EP2011/050350: International Search Report dated Feb. 23, 2011, 3 pages.
International Patent Application No. PCT/EP2012/063667: International Search Report dated Aug. 7, 2012, 4 pages.
International Patent Application No. PCT/IB2013/054014: International Search Report dated Aug. 20, 2013, 3 pages.
Jadhav et al. "Ammonium Metavanadate: A Novel Catalyst for Synthesis of 2-Substituted Benzimidazole Derivatives", Chinese Chemical Letters, 2009, 20, 292-295.
Jain et al., "Polymorphism in Pharmacy", Indian Drugs, 1986, 23(6), 315-329.
Larner, "Secretases as Therapeutic Targets in Alzheimer's Disease: Patents 2000-2004", Exp. Opinion Ther. Patents, 2004, 14, 1403-1420.
Marjaux et al., "γ-Secretase Inhibitors: Still in the running as Alzheimer's Therapeutics", Drug Discovery Today: Therapeutics Strategies, 2004, 1(1), 6 pages.
Matthews et al., "A Convenient Procedure for the Preparation of 4(5)-Cyanoimidazoles", J. Org. Chem., 1986 51, 3228-3231.
Moechars et al., "Early Phenotypic Changes in Transgenic Mice That Overexpress Different Mutants of Amyloid Precursor Protein in Brain", J. Biol. Chem., 1999, 274(10), 6483-6492.
Morihara et al., "Selective Inhibition of Aβ42 Production by NSAID R-Enantiomers", Journal of Neurochemistry, 2002, 83, 1009-1012.
Oumata et al., "Roscovitine-Derived, Dual-Specificity Inhibitors of Cyclin-Dependent Kinases and Casein Kinases 1", J. Med. Chem., 2008, 51, 5229-5242.
Peretto et al., "Synthesis and Biological Activity of Fluriprofen Analogues as Selective Inhibitors of β-Amyloid 1-42 Secretion", J Med Chem 2005, 48, 5705.
Schweisguth et al., "Regulation of Notch Signaling Activity", Current Biology, Feb. 3, 2004,14, R129-R138.
Sechi et al., "Design and Synthesis of Novel Indole β-Diketo Acid Derivatives as HIV-1 Integrase Inhibitors", J. Med. Chem., 2004, 47, 5298-5310.
Steiner, "Uncovering γ-Secretase", Current Alzheimer Research, 2004, 1(3), 175-181.
Taiwanese Patent Application No. 098125454: Search Report dated Aug. 27, 2013, 1 page (English Translation Only).
Taiwanese Patent Application No. 098143263: Office Action dated Dec. 6, 2013, 3 pages (English Translation Only).
Tanzi et al., "Twenty Years of the Alzheimer's Disease Amyloid Hypothesis: A Genetic Perspective", Cell, 2005, 120, 545-555.
Vippagunta et al., "Crystalline Solids", Advanced Drug Delivery Reviews, 2001, 48, 3-26.
Wang et al., "Preparation of a-Chloroketones by the Chloracetate Claisen Reaction", Synlett, 2000, 6, 902-904.
Weggen et al., "A Subset of NSAIDs Lower Amyloidegenic Aβ42 Independently of Cyclooxygenase Activity", Nature, Nov. 2001, 414, 212-216.
West, "Solid State Chemistry and its Applications", Wiley, New York, 1988, 16 pages (see pp. 358 & 365).
Yu et al. "Physical Characterization of Polymorphic Drugs: An Integrated Characterization Strategy", PSTT, 1998, 1(3), 118-127.
Zettl et al., "Exploring the Chemical Space of γ-Secretase Modulators" ,Trends in Pharmaceutical Sciences, 2010, 31(9), 402-410.

\* cited by examiner

SUBSTITUTED INDOLE DERIVATIVES AS GAMMA SECRETASE MODULATORS

CROSS REFERENCE TO RELATED APPLICATIONS

This application is the national stage of PCT Application No. PCT/EP2012/063667, filed Jul. 12, 2012, which claims priority from European Patent Application No. 11174120.3, filed Jul. 15, 2011, the entire disclosures of which are incorporated herein by reference.

FIELD OF THE INVENTION

The present invention is concerned with novel substituted indole derivatives useful as gamma secretase modulators. The invention further relates to processes for preparing such novel compounds, pharmaceutical compositions comprising said compounds as an active ingredient as well as the use of said compounds as a medicament.

BACKGROUND OF THE INVENTION

Alzheimer's disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major components of amyloid plaques are the amyloid beta (A-beta, Abeta or A$\beta$) peptides of various lengths. A variant thereof, which is the A$\beta$1-42-peptide (Abeta-42), is believed to be the major causative agent for amyloid formation. Another variant is the A$\beta$1-40-peptide (Abeta-40). AB is the proteolytic product of a precursor protein, beta amyloid precursor protein (beta-APP or APP).

Familial, early onset autosomal dominant forms of AD have been linked to missense mutations in the $\beta$-amyloid precursor protein ($\beta$-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations found to date, affect the quantitative or qualitative production of the amyloidogenic peptides known as Abeta-peptides (A$\beta$), specifically A$\beta$42, and have given strong support to the "amyloid cascade hypothesis" of AD (Tanzi and Bertram, 2005, Cell 120, 545). The likely link between A$\beta$ peptide generation and AD pathology emphasizes the need for a better understanding of the mechanisms of A$\beta$ production and strongly warrants a therapeutic approach at modulating A$\beta$ levels.

The release of A$\beta$ peptides is modulated by at least two proteolytic activities referred to as $\beta$- and $\gamma$-secretase cleavage at the N-terminus (Met-Asp bond) and the C-terminus (residues 37-42) of the A$\beta$ peptide, respectively. In the secretory pathway, there is evidence that $\beta$-secretase cleaves first, leading to the secretion of s-APP$\beta$ (s$\beta$) and the retention of a 11 kDa membrane-bound carboxy terminal fragment (CTF). The latter is believed to give rise to A$\beta$ peptides following cleavage by $\gamma$-secretase. The amount of the longer isoform, A$\beta$42, is selectively increased in patients carrying certain mutations in the region of a particular gene coding in a particular protein (presenilin), and these mutations have been correlated with early-onset familial AD. Therefore, A$\beta$42 is believed by many researchers to be the main culprit of the pathogenesis of AD.

It has now become clear that the $\gamma$-secretase activity cannot be ascribed to a single protein, but is in fact associated with an assembly of different proteins.

The gamma ($\gamma$)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until now, the $\gamma$-secretase-complex has become one of the prime targets in the search for compounds for the treatment of AD.

Various strategies have been proposed for targeting $\gamma$-secretase in AD, ranging from targeting the catalytic site directly, developing substrate-specific inhibitors and modulators of $\gamma$-secretase activity (Marjaux et al., 2004. Drug Discovery Today: Therapeutic Strategies, Volume 1, 1-6). Accordingly, a variety of compounds were described that have secretases as targets (Larner, 2004. Secretases as therapeutics targets in AD: patents 2000-2004. Expert Opin. Ther. Patents 14, 1403-1420).

Indeed, this finding was supported by biochemical studies in which an effect of certain Non-Steroidal Anti-Inflammatory Drugs (NSAIDs) on $\gamma$-secretase was shown (US 2002/0128319; Eriksen (2003) J. Clin. Invest. 112, 440). Potential limitations for the use of NSAIDs to prevent or treat AD are their inhibition activity of cyclooxygenase (COX) enzymes, which can lead to unwanted side effects, and their low CNS penetration (Peretto et al., 2005, J. Med. Chem. 48, 5705-5720). More recently the NSAID R-flurbiprofen, an enantiomer lacking Cox-inhibitory activity and related gastric toxicity, has failed in large phase III trial since the drug did not improve thinking ability or the ability of patients to carry out daily activities significantly more than those patients on placebo.

WO-2009/103652 relates to 1H-1,2,4-triazol-3-amine derivatives as modulators for A$\beta$;

WO-2010/010188 relates to [1,2,4]triazolo-[1,5-a]pyridine compounds, useful for the treatment of degenerative joint diseases and inflammatory diseases;

WO-2010/098495 relates to imidazolylpyrazine derivatives as therapeutic agents for AD;

US2010137320 relates to novel heterocyclic compounds that are modulators of $\gamma$-secretase;

WO-2010/070008 is concerned with novel substituted bicyclic imidazole derivatives useful as $\gamma$-secretase modulators WO-2010/094647 is concerned with novel substituted benzoxazole, benzimidazole, oxazolopyridine and imidazopyridine derivatives useful as γ-secretase modulators.

WO-2010/089292 is concerned with novel substituted bicyclic heterocyclic compounds useful as γ-secretase modulators.

WO-2010/145883 is concerned with novel substituted indazole and aza-indazole derivatives useful as γ-secretase modulators.

WO-2011/006903 is concerned with novel substituted triazole and imidazole derivatives useful as γ-secretase modulators.

There is a strong need for novel compounds which modulate γ-secretase activity thereby opening new avenues for the treatment of AD. It is an object of the present invention to overcome or ameliorate at least one of the disadvantages of the prior art, or to provide a useful alternative. The compounds of the present invention or part of the compounds of the present invention may have improved metabolic stability properties, improved central brain availability, improved solubilities, or reduced CYP (cytochrome P450) inhibition compared with the compounds disclosed in the prior art. It is accordingly an object of the present invention to provide such novel compounds.

SUMMARY OF THE INVENTION

It has been found that the compounds of the present invention are useful as γ-secretase modulators. The compounds according to the invention and the pharmaceutically acceptable compositions thereof, may be useful in the treatment or prevention of AD.

The present invention concerns novel compounds of Formula (I):

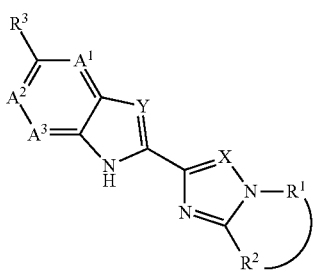

tautomers and stereoisomeric forms thereof, wherein
$R^3$ is selected from the group consisting of hydrogen, $C_{1-4}$alkyloxy, cyano and $Het^1$;
$A^1$ is $CR^{4a}$ or N; wherein $R^{4a}$ is hydrogen, halo or $C_{1-4}$alkyloxy optionally substituted with one or more substituents selected from the group consisting of $C_{1-4}$alkyloxy and halo;
$A^2$ is $CR^{4b}$ or N; wherein $R^{4b}$ is hydrogen, halo, $C_{1-4}$alkyloxy, cyano or $Het^2$;
$A^3$ is $CR^{4c}$ or N; wherein $R^{4c}$ is hydrogen, halo or $C_{1-4}$alkyloxy;
provided that maximum one of $A^1$, $A^2$ and $A^3$ is N;
$Het^1$ and $Het^2$ each independently represent a 5- or 6-membered heteroaryl selected from the group consisting of pyridinyl, imidazolyl, oxazolyl, 1,2,4-triazolyl and pyrazolyl; wherein said 5- or 6-membered heteroaryl may be substituted with one or more $C_{1-4}$alkyl substituents;

Y is N or $CR^a$; wherein $R^a$ is hydrogen, halo or $C_{1-4}$alkyl optionally substituted with one hydroxyl;
X is N or CH;
$R^1$ and $R^2$ are taken together to form a bivalent radical $-R^1-R^2-$ having formula (b-1) or (b-2)

$$—(CH_2)_m—Z—CH_2— \quad (b-1);$$

$$—CH_2—Z—(CH_2)_m— \quad (b-2);$$

m represents 2, 3 or 4;
Z represents a direct bond, $NR^5$ or O; wherein $R^5$ is hydrogen, $C_{1-4}$alkylcarbonyl, $Ar^1$, (C=O)—$Ar^1$ or $C_{1-4}$alkyl optionally substituted with one or more fluoro substituents;
wherein (b-1) or (b-2) is substituted on one or more $CH_2$ groups with one or two substituents each independently selected from the group consisting of $Ar^2$, (C=O)—$Ar^2$, O—$Ar^2$, $NR^6$—$Ar^2$, $C_{1-4}$alkylcarbonyl, fluoro, hydroxy, and $C_{1-4}$alkyl optionally substituted with one or more fluoro substituents;
each $Ar^1$ and $Ar^2$ independently represents phenyl, pyrazolyl or pyridinyl; wherein said phenyl, pyrazolyl or pyridinyl may be substituted with one or more substituents each independently selected from the group consisting of halo, cyano, $NR^7R^8$, morpholinyl, cyclo$C_{3-7}$alkyl,
$C_{1-4}$alkyl optionally substituted with one or more substituents each independently selected from the group consisting of $C_{1-4}$alkyloxy, fluoro and cyclo$C_{3-7}$alkyl, and
$C_{1-4}$alkyloxy optionally substituted with one or more substituents each independently selected from the group consisting of fluoro and cyclo$C_{3-7}$alkyl;
each $R^6$ independently is hydrogen, or $C_{1-4}$alkyl optionally substituted with one or more substituents each independently selected from the group consisting of fluoro and cyclo $C_{3-7}$alkyl;
each $R^7$ independently is hydrogen, $C_{1-4}$alkyl or $C_{1-4}$alkylcarbonyl;
each $R^8$ independently is hydrogen or $C_{1-4}$alkyl;
and the pharmaceutically acceptable addition salts, and the solvates thereof.

The present invention also concerns methods for the preparation of compounds of Formula (I) and pharmaceutical compositions comprising them.

The present compounds were found to modulate the γ-secretase activity in vitro and in vivo, and therefore may be useful in the treatment or prevention of AD, traumatic brain injury (TBI), dementia pugilistica, mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid; preferably AD and other disorders with Beta-amyloid pathology (e.g. glaucoma).

In view of the aforementioned pharmacology of the compounds of Formula (I), it follows that they may be suitable for use as a medicament.

More especially the compounds may be suitable in the treatment or prevention of AD, cerebral amyloid angiopathy, multi-infarct dementia, dementia pugilistica and Down syndrome.

The present invention also concerns the use of a compound according to the general Formula (I), the tautomers and the stereoisomeric forms thereof, and the pharmaceutically acceptable acid or base addition salts and the solvates thereof, for the manufacture of a medicament for the modulation of γ-secretase activity.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{1-4}$alkyloxy" as a group or part of a group refers to a radical having the Formula $OR^b$ wherein $R^b$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "cyclo$C_{3-7}$alkyl" alone or in combination, refers to a cyclic saturated hydrocarbon radical having from 3 to 7 carbon atoms. Non-limiting examples of suitable cyclo$C_{3-7}$alkyl include cyclopropyl, cyclobutyl, cyclopentyl, cyclohexyl and cycloheptyl.

The chemical names of the compounds of the present invention were generated according to the nomenclature rules agreed upon by the Chemical Abstracts Service, using Advanced Chemical Development, Inc., nomenclature software (ACD/Labs Release 12.00 Product version 12.01; Build 33104, 27 May 2009). In case of tautomeric forms, the name of the depicted tautomeric form was generated. It should be clear that the other non-depicted tautomeric form is also included within the scope of the present invention.

Hereinbefore and hereinafter, the term "compound of formula (I)" is meant to include the tautomers and stereoisomeric forms thereof, and the pharmaceutically acceptable addition salts, and the solvates thereof.

The terms "stereoisomers", "stereoisomeric forms" or "stereochemically isomeric forms" hereinbefore or hereinafter are used interchangeably.

The invention includes all stereoisomers of the compound of Formula (I) and tautomers thereof, either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms although not explicitly indicated in the above formula are intended to be included within the scope of the present invention.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as the salts thereof. Examples of such forms are e.g. hydrates, alcoholates and the like.

The compounds of Formula (I) as prepared in the processes described below may be synthesized in the form of racemic mixtures of enantiomers that can be separated from one another following art-known resolution procedures. An manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to Formula (I), comprises all isotopes and isotopic mixtures of this element. For example, when hydrogen is mentioned, it is understood to refer to $^1H$, $^2H$, $^3H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (I), or a pharmaceutically acceptable salt thereof, which contains at least one radioactive atom. For example, a compound can be labelled with positron or with gamma emitting radioactive isotopes. For radioligand-binding techniques, the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$ all of which are accelerator produced and have half-lives of 20, 100, 2 and 10 minutes (min) respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural referents unless the context clearly dictates otherwise. For example, "a compound" means 1 compound or more than 1 compound.

It should be understood that the term "compounds of Formula (I)" or "a compound of Formula (I)" as used in the specification, also covers the tautomers and stereoisomeric forms thereof, and the pharmaceutically acceptable addition salts, and the solvates thereof.

The terms described above and others used in the specification are well understood to those in the art.

Preferred features of the compounds of this invention are now set forth.

In an embodiment, the present invention concerns novel compounds of Formula (I), tautomers and stereoisomeric forms thereof, wherein $R^3$ is selected from the group consisting of $C_{1-4}$alkyloxy, cyano and Het$^1$;

$A^1$ is $CR^{4a}$ or N; wherein $R^{4a}$ is hydrogen, halo or $C_{1-4}$alkyloxy;

$A^2$ is $CR^{4b}$ or N; wherein $R^{4b}$ is hydrogen, halo, $C_{1-4}$alkyloxy, cyano or Het$^2$;

$A^3$ is $CR^{4c}$ or N; wherein $R^{4c}$ is hydrogen, halo or $C_{1-4}$alkyloxy;

provided that maximum one of $A^1$, $A^2$ and $A^3$ is N;

Het$^1$ and Het$^2$ each independently represent a 5- or 6-membered heteroaryl selected from the group consisting of pyridinyl, imidazolyl, oxazolyl, 1,2,4-triazolyl and pyrazolyl; wherein said 5- or 6-membered heteroaryl may be substituted with one or more $C_{1-4}$ alkyl substituents;

Y is N or CH;

X is N or CH;

$R^1$ and $R^2$ are taken together to form a bivalent radical -$R^1$-$R^2$- having formula (b-1) or (b-2)

$$—(CH_2)_m—Z—CH_2— \quad (b-1);$$

$$—CH_2—Z—(CH_2)_m— \quad (b-2);$$

m represents 2, 3 or 4;

Z represents a direct bond, $NR^5$ or O; wherein $R^5$ is hydrogen, $C_{1-4}$alkylcarbonyl, Ar$^1$, (C=O)—Ar$^1$ or $C_{1-4}$alkyl optionally substituted with one or more fluoro substituents;

wherein (b-1) or (b-2) is substituted on one or more $CH_2$ groups with one or two substituents each independently selected from the group consisting of Ar$^2$, (C=O)—Ar$^2$, O—Ar$^2$, NR$^6$—Ar$^2$, $C_{1-4}$alkylcarbonyl, fluoro, hydroxy, and $C_{1-4}$alkyl optionally substituted with one or more fluoro substituents;

each Ar$^1$ and Ar$^2$ independently represents phenyl or pyridinyl; wherein said phenyl or pyridinyl may be substituted with one or more substituents each independently selected from the group consisting of halo, cyano, $NR^7R^8$, morpholinyl, $C_{1-4}$alkyl optionally substituted with one or more substituents each independently selected from the group consisting of fluoro and cyclo$C_{3-7}$alkyl, and $C_{1-4}$alkyloxy optionally substituted with one or more substituents each independently selected from the group consisting of fluoro and cyclo$C_{3-7}$alkyl;

each $R^6$ independently is hydrogen, or $C_{1-4}$alkyl optionally substituted with one or more substituents each independently selected from the group consisting of fluoro and cyclo $C_{3-7}$alkyl;

each $R^7$ independently is hydrogen, $C_{1-4}$alkyl or $C_{1-4}$alkylcarbonyl;

each $R^8$ independently is hydrogen or $C_{1-4}$alkyl;

and the pharmaceutically acceptable addition salts, and the solvates thereof.

In an embodiment, the present invention concerns novel compounds of Formula (I), tautomers and stereoisomeric forms thereof, wherein $R^3$ is selected from the group consisting of $C_{1-4}$alkyloxy, cyano and Het$^1$;

$A^1$ is CH or N; $A^2$ is $CR^{4b}$ or N; wherein $R^{4b}$ is hydrogen, halo, $C_{1-4}$alkyloxy, cyano or Het$^2$;

$A^3$ is $CR^{4c}$ or N; wherein $R^{4c}$ is hydrogen, halo or $C_{1-4}$alkyloxy; provided that maximum one of $A^1$, $A^2$ and $A^3$ is N;

Het$^1$ and Het$^2$ each independently represent a 5- or 6-membered heteroaryl selected from the group consisting of pyridinyl, imidazolyl, oxazolyl, 1,2,4-triazolyl and pyrazolyl; wherein said 5- or 6-membered heteroaryl may be substituted with one or more $C_{1-4}$alkyl substituents;

Y is N or $CR^a$; wherein $R^a$ is hydrogen, halo or $C_{1-4}$alkyl optionally substituted with one hydroxyl;

X is N or CH;

$R^1$ and $R^2$ are taken together to form a bivalent radical -$R^1$-$R^2$- having formula (b-1) or (b-2)

—(CH$_2$)$_m$—Z—CH$_2$—    (b-1);

—CH$_2$—Z—(CH$_2$)$_m$—    (b-2);

m represents 2, 3 or 4;

Z represents a direct bond, NR$^5$ or O; wherein R$^5$ is hydrogen, $C_{1-4}$alkylcarbonyl, Ar$^1$, (C=O)—Ar$^1$ or $C_{1-4}$alkyl optionally substituted with one or more fluoro substituents;

wherein (b-1) or (b-2) is substituted on one or more CH$_2$ groups with one or two substituents each independently selected from the group consisting of Ar$^2$, (C=O)—Ar$^2$, O—Ar$^2$, NR$^6$—Ar$^2$, $C_{1-4}$alkylcarbonyl, fluoro, hydroxy, and $C_{1-4}$alkyl optionally substituted with one or more fluoro substituents;

each Ar$^1$ and Ar$^2$ independently represents phenyl, pyrazolyl or pyridinyl; wherein said phenyl, pyrazolyl or pyridinyl may be substituted with one or more substituents each independently selected from the group consisting of halo, cyano, NR$^7$R$^8$, morpholinyl, cycloC$_{3-7}$alkyl,
  $C_{1-4}$alkyl optionally substituted with one or more substituents each independently selected from the group consisting of $C_{1-4}$alkyloxy, fluoro and cycloC$_{3-7}$alkyl, and
  $C_{1-4}$alkyloxy optionally substituted with one or more substituents each independently selected from the group consisting of fluoro and cycloC$_{3-7}$alkyl;

each R$^6$ independently is hydrogen, or $C_{1-4}$alkyl optionally substituted with one or more substituents each independently selected from the group consisting of fluoro and cyclo C$_{3-7}$alkyl;

each R$^7$ independently is hydrogen, $C_{1-4}$alkyl or $C_{1-4}$alkylcarbonyl;

each R$^8$ independently is hydrogen or $C_{1-4}$alkyl;

and the pharmaceutically acceptable addition salts, and the solvates thereof.

In an embodiment, the present invention concerns novel compounds of Formula (I): tautomers and stereoisomeric forms thereof, wherein
tautomers and stereoisomeric forms thereof, wherein $R^3$ is selected from the group consisting of $C_{1-4}$alkyloxy, cyano and Het$^1$;

$A^1$ is $CR^{4a}$ or N; wherein $R^{4a}$ is hydrogen, halo or $C_{1-4}$alkyloxy optionally substituted with one or more substituents selected from the group consisting of $C_{1-4}$alkyloxy and halo;

$A^2$ is $CR^{4b}$ or N; wherein $R^{4b}$ is hydrogen, halo, $C_{1-4}$alkyloxy or cyano;

$A^3$ is $CR^{4c}$ or N; wherein $R^{4c}$ is hydrogen, halo or $C_{1-4}$alkyloxy;

provided that maximum one of $A^1$, $A^2$ and $A^3$ is N;

Het$^1$ and Het$^2$ each independently represent a 5- or 6-membered heteroaryl selected from the group consisting of pyridinyl, imidazolyl, oxazolyl, 1,2,4-triazolyl and pyrazolyl; wherein said 5- or 6-membered heteroaryl may be substituted with one or more $C_{1-4}$alkyl substituents;

Y is N or $CR^a$; wherein $R^a$ is hydrogen, halo or $C_{1-4}$alkyl optionally substituted with one hydroxyl;

X is N or CH;

$R^1$ and $R^2$ are taken together to form a bivalent radical -$R^1$-$R^2$- having formula (b-1) or (b-2)

—(CH$_2$)$_m$—Z—CH$_2$—    (b-1);

—CH$_2$—Z—(CH$_2$)$_m$—    (b-2);

m represents 2, 3 or 4;

Z represents a direct bond, NR$^5$ or O; wherein R$^5$ is hydrogen, $C_{1-4}$alkylcarbonyl, or $C_{1-4}$alkyl optionally substituted with one or more fluoro substituents;

wherein (b-1) or (b-2) is substituted on one or more CH$_2$ groups with one or two substituents each independently selected from the group consisting of Ar$^2$, $C_{1-4}$alkylcarbonyl, fluoro, hydroxy, and $C_{1-4}$alkyl optionally substituted with one or more fluoro substituents;

each Ar$^2$ independently represents phenyl, pyrazolyl or pyridinyl; wherein said phenyl, pyrazolyl or pyridinyl may be substituted with one or more substituents each independently selected from the group consisting of halo, cyano, NR$^7$R$^8$, morpholinyl, cycloC$_{3-7}$alkyl,
  $C_{1-4}$alkyl optionally substituted with one or more substituents each independently selected from the group consisting of $C_{1-4}$alkyloxy, fluoro and cycloC$_{3-7}$alkyl, and
  $C_{1-4}$alkyloxy optionally substituted with one or more substituents each independently selected from the group consisting of fluoro and cycloC$_{3-7}$alkyl;

each R$^7$ independently is hydrogen, $C_{1-4}$alkyl or $C_{1-4}$alkylcarbonyl;

each R$^8$ independently is hydrogen or $C_{1-4}$alkyl;

and the pharmaceutically acceptable addition salts, and the solvates thereof.

In an embodiment, the present invention concerns novel compounds of Formula (I): tautomers and stereoisomeric forms thereof, wherein $R^3$ is selected from the group consisting of $C_{1-4}$alkyloxy, cyano and Het$^1$;

$A^1$ is $CR^{4a}$ or N; wherein $R^{4a}$ is hydrogen, halo or $C_{1-4}$alkyloxy;

$A^2$ is $CR^{4b}$ or N; wherein $R^{4b}$ is hydrogen, halo, $C_{1-4}$alkyloxy, cyano or Het$^2$;

$A^3$ is $CR^{4c}$ or N; wherein $R^{4c}$ is hydrogen, halo or $C_{1-4}$alkyloxy;

provided that maximum one of $A^1$, $A^2$ and $A^3$ is N;

Het$^1$ and Het$^2$ each independently represent a 5- or 6-membered heteroaryl selected from the group consisting of pyridinyl, imidazolyl, oxazolyl, 1,2,4-triazolyl and pyrazolyl; wherein said 5- or 6-membered heteroaryl may be substituted with one or more $C_{1-4}$alkyl substituents;

Y is N or CH;

X is N or CH;

$R^1$ and $R^2$ are taken together to form a bivalent radical -$R^1$-$R^2$- having formula (b-1) or (b-2)

—(CH$_2$)$_m$—Z—CH$_2$—    (b-1);

—CH$_2$—Z—(CH$_2$)$_m$—    (b-2);

m represents 2, 3 or 4;

Z represents a direct bond, $NR^5$ or O; wherein $R^5$ is hydrogen, $C_{1-4}$alkylcarbonyl, $Ar^1$, (C=O)—$Ar^1$ or $C_{1-4}$alkyl optionally substituted with one or more fluoro substituents;

wherein (b-1) or (b-2) is substituted on one or more $CH_2$ groups with one or two $Ar^2$ substituents; in particular wherein (b-1) or (b-2) is substituted on one $CH_2$ group with one $Ar^2$ substituent;

each $Ar^1$ and $Ar^2$ independently represents phenyl or pyridinyl; wherein said phenyl or pyridinyl may be substituted with one or more substituents each independently selected from the group consisting of halo, cyano, $NR^7R^8$, morpholinyl, $C_{1-4}$alkyl optionally substituted with one or more substituents each independently selected from the group consisting of fluoro and cyclo$C_{3-7}$alkyl, and $C_{1-4}$alkyloxy optionally substituted with one or more substituents each independently selected from the group consisting of fluoro and cyclo$C_{3-7}$alkyl;

each $R^7$ independently is hydrogen, $C_{1-4}$alkyl or $C_{1-4}$alkylcarbonyl;

each $R^8$ independently is hydrogen or $C_{1-4}$alkyl;

and the pharmaceutically acceptable addition salts, and the solvates thereof.

In an embodiment, the present invention concerns novel compounds of Formula (I), tautomers and stereoisomeric forms thereof, wherein $R^3$ is selected from the group consisting of hydrogen, $C_{1-4}$alkyloxy, cyano and $Het^1$;

$A^1$ is $CR^{4a}$ or N; wherein $R^{4a}$ is hydrogen or $C_{1-4}$alkyloxy optionally substituted with one, two or three substituents selected from the group consisting of $C_{1-4}$alkyloxy and halo;

$A^2$ is $CR^{4b}$ or N; wherein $R^{4b}$ is hydrogen, $C_{1-4}$alkyloxy, cyano or $Het^2$; in particular wherein $R^{4b}$ is hydrogen, $C_{1-4}$alkyloxy or cyano;

$A^3$ is CH or N;

provided that maximum one of $A^1$, $A^2$ and $A^3$ is N;

$Het^1$ and $Het^2$ each independently represent a 5- or 6-membered heteroaryl selected from the group consisting of pyridinyl, imidazolyl, 1,2,4-triazolyl and pyrazolyl; wherein said 5- or 6-membered heteroaryl may be substituted with one $C_{1-4}$alkyl substituent;

Y is N or $CR^a$; wherein $R^a$ is hydrogen, halo or $C_{1-4}$alkyl optionally substituted with one hydroxyl;

X is N or CH;

$R^1$ and $R^2$ are taken together to form a bivalent radical -$R^1$-$R^2$- having formula (b-1)

  (b-1);

m represents 2 or 3;

Z represents a direct bond, $NR^5$ or O; wherein $R^5$ is $C_{1-4}$alkyl;

wherein (b-1) is substituted on one $CH_2$ group with one or two substituents each independently selected from the group consisting of $Ar^2$, hydroxy, and $C_{1-4}$alkyl;

each $Ar^2$ independently represents phenyl or pyrazolyl; wherein said phenyl or pyrazolyl may be substituted with one, two, three or four substituents each independently selected from the group consisting of halo, cyclo$C_{3-7}$alkyl, $C_{1-4}$alkyl optionally substituted with one, two or three substituents each independently selected from the group consisting of $C_{1-4}$alkyloxy and fluoro, and $C_{1-4}$alkyloxy optionally substituted with one, two or three fluoro substituents;

and the pharmaceutically acceptable addition salts, and the solvates thereof.

In an embodiment, the present invention concerns novel compounds of Formula (I), tautomers and stereoisomeric forms thereof, wherein $R^3$ is selected from the group consisting of $C_{1-4}$alkyloxy, cyano and $Het^1$; in particular $R^3$ is selected from the group consisting of cyano and $Het^1$;

$A^1$ is $CR^{4a}$ or N; wherein $R^{4a}$ is hydrogen or $C_{1-4}$alkyloxy;

$A^2$ is $CR^{4b}$ or N; wherein $R^{4b}$ is hydrogen, $C_{1-4}$alkyloxy, cyano or $Het^2$;

$A^3$ is CH or N;

provided that maximum one of $A^1$, $A^2$ and $A^3$ is N;

$Het^1$ and $Het^2$ each independently represent a 5- or 6-membered heteroaryl selected from the group consisting of pyridinyl, imidazolyl, oxazolyl, 1,2,4-triazolyl and pyrazolyl; wherein said 5- or 6-membered heteroaryl may be substituted with one or more $C_{1-4}$alkyl substituents;

Y is N or CH;

X is N or CH;

$R^1$ and $R^2$ are taken together to form a bivalent radical -$R^1$-$R^2$- having formula (b-1) or (b-2)

  (b-1);

  (b-2);

m represents 2, 3 or 4;

Z represents a direct bond, $NR^5$ or O; wherein $R^5$ is hydrogen, $C_{1-4}$alkylcarbonyl, $Ar^1$, (C=O)—$Ar^1$ or $C_{1-4}$alkyl optionally substituted with one or more fluoro substituents;

wherein (b-1) or (b-2) is substituted on one or more $CH_2$ groups with one or two substituents each independently selected from the group consisting of $Ar^2$, (C=O)—$Ar^2$, O—$Ar^2$, $NR^6$—$Ar^2$, $C_{1-4}$alkylcarbonyl, fluoro, hydroxy, and $C_{1-4}$alkyl optionally substituted with one or more fluoro substituents;

each $Ar^1$ and $Ar^2$ independently represents phenyl or pyridinyl; wherein said phenyl or pyridinyl may be substituted with one or more substituents each independently selected from the group consisting of halo, cyano, $NR^7R^8$, morpholinyl, $C_{1-4}$alkyl optionally substituted with one or more substituents each independently selected from the group consisting of fluoro and cyclo$C_{3-7}$alkyl, and $C_{1-4}$alkyloxy optionally substituted with one or more substituents each independently selected from the group consisting of fluoro and cyclo$C_{3-7}$alkyl;

each $R^6$ independently is hydrogen, or $C_{1-4}$alkyl optionally substituted with one or more substituents each independently selected from the group consisting of fluoro and cyclo $C_{3-7}$alkyl;

each $R^7$ independently is hydrogen, $C_{1-4}$alkyl or $C_{1-4}$alkylcarbonyl;

each $R^8$ independently is hydrogen or $C_{1-4}$alkyl;

and the pharmaceutically acceptable addition salts, and the solvates thereof.

In an embodiment, the present invention concerns novel compounds of Formula (I), tautomers and stereoisomeric forms thereof, wherein $R^3$ is selected from the group consisting of $C_{1-4}$alkyloxy, cyano and $Het^1$;

$A^1$ is $CR^{4a}$ or N; wherein $R^{4a}$ is hydrogen or $C_{1-4}$alkyloxy;

$A^2$ is $CR^{4b}$ or N; wherein $R^{4b}$ is hydrogen, $C_{1-4}$alkyloxy, cyano or $Het^2$;

$A^3$ is CH or N;

provided that maximum one of $A^1$, $A^2$ and $A^3$ is N;

$Het^1$ and $Het^2$ each independently represent a 5- or 6-membered heteroaryl selected from the group consisting of pyridinyl, imidazolyl, oxazolyl, 1,2,4-triazolyl and pyrazolyl; wherein said 5- or 6-membered heteroaryl may be substituted with one or more $C_{1-4}$alkyl substituents;
Y is N or CH;
X is N or CH;
$R^1$ and $R^2$ are taken together to form a bivalent radical -$R^1$-$R^2$- having formula (b-1) or (b-2)

$$-(CH_2)_m-Z-CH_2- \quad (b-1);$$

$$-CH_2-Z-(CH_2)_m- \quad (b-2);$$

m represents 2, 3 or 4;
Z represents a direct bond, $NR^5$ or O; wherein $R^5$ is hydrogen, $C_{1-4}$alkylcarbonyl, $Ar^1$, (C=O)—$Ar^1$ or $C_{1-4}$alkyl optionally substituted with one or more fluoro substituents;
wherein (b-1) or (b-2) is substituted on one or more $CH_2$ groups with one or two $Ar^2$ substituents; in particular wherein (b-1) or (b-2) is substituted on one $CH_2$ group with one $Ar^2$ substituent;
each $Ar^1$ and $Ar^2$ independently represents phenyl or pyridinyl; wherein said phenyl or pyridinyl may be substituted with one or more substituents each independently selected from the group consisting of halo, cyano, $NR^7R^8$, morpholinyl,
  $C_{1-4}$alkyl optionally substituted with one or more substituents each independently selected from the group consisting of fluoro and cyclo$C_{3-7}$alkyl, and
  $C_{1-4}$alkyloxy optionally substituted with one or more substituents each independently selected from the group consisting of fluoro and cyclo$C_{3-7}$alkyl;
each $R^7$ independently is hydrogen, $C_{1-4}$alkyl or $C_{1-4}$alkylcarbonyl;
each $R^8$ independently is hydrogen or $C_{1-4}$alkyl;
and the pharmaceutically acceptable addition salts, and the solvates thereof.

In an embodiment, the present invention concerns novel compounds of Formula (I), tautomers and stereoisomeric forms thereof, wherein
$R^3$ is selected from the group consisting of $C_{1-4}$alkyloxy, cyano and Het$^1$; in particular $R^3$ is selected from the group consisting of cyano and Het$^1$;
$A^1$ is $CR^{4a}$ or N; wherein $R^{4a}$ is hydrogen or $C_{1-4}$alkyloxy;
$A^2$ is $CR^{4b}$ or N; wherein $R^{4b}$ is hydrogen, $C_{1-4}$alkyloxy;
$A^3$ is CH or N;
provided that maximum one of $A^1$, $A^2$ and $A^3$ is N;
Het$^1$ represents a 5- or 6-membered heteroaryl selected from the group consisting of pyridinyl, imidazolyl, oxazolyl, 1,2,4-triazolyl and pyrazolyl; wherein said 5- or 6-membered heteroaryl may be substituted with one or more $C_{1-4}$alkyl substituents;
Y is N or CH;
X is N or CH;
$R^1$ and $R^2$ are taken together to form a bivalent radical -$R^1$-$R^2$- having formula (b-1) or (b-2)

$$-(CH_2)_m-Z-CH_2- \quad (b-1);$$

$$-CH_2-Z-(CH_2)_m- \quad (b-2);$$

m represents 2, 3 or 4;
Z represents a direct bond, $NR^5$ or O; wherein $R^5$ is hydrogen, $C_{1-4}$alkylcarbonyl, $Ar^1$, (C=O)—$Ar^1$ or $C_{1-4}$alkyl optionally substituted with one or more fluoro substituents;
wherein (b-1) or (b-2) is substituted on one $CH_2$ group with one substituent selected from the group consisting of $Ar^2$, (C=O)—$Ar^2$, O—$Ar^2$, $NR^6$—$Ar^2$, $C_{1-4}$alkylcarbonyl, hydroxy, and $C_{1-4}$alkyl optionally substituted with one or more fluoro substituents; in particular wherein (b-1) or (b-2) is substituted on one $CH_2$ group with one $Ar^2$ substituent;

$Ar^1$ and $Ar^2$ each independently represent phenyl or pyridinyl; wherein said phenyl or pyridinyl may be substituted with one or more substituents each independently selected from the group consisting of halo, cyano, $NR^7R^8$, morpholinyl,
  $C_{1-4}$alkyl optionally substituted with one or more substituents each independently selected from the group consisting of fluoro and cyclo$C_{3-7}$alkyl, and
  $C_{1-4}$alkyloxy optionally substituted with one or more substituents each independently selected from the group consisting of fluoro and cyclo$C_{3-7}$alkyl;
each $R^6$ independently is hydrogen, or $C_{1-4}$alkyl optionally substituted with one or more substituents each independently selected from the group consisting of fluoro and cyclo $C_{3-7}$alkyl;
each $R^7$ independently is hydrogen, $C_{1-4}$alkyl or $C_{1-4}$alkylcarbonyl;
each $R^8$ independently is hydrogen or $C_{1-4}$alkyl;
and the pharmaceutically acceptable addition salts, and the solvates thereof.

In an embodiment, the present invention concerns novel compounds of Formula (I), tautomers and stereoisomeric forms thereof, wherein
$R^3$ is selected from the group consisting of $C_{1-4}$alkyloxy, cyano and Het$^1$; in particular $R^3$ is selected from the group consisting of cyano and Het$^1$;
$A^1$ is $CR^{4a}$ or N; wherein $R^{4a}$ is hydrogen or $C_{1-4}$alkyloxy;
$A^2$ is $CR^{4b}$ or N; wherein $R^{4b}$ is hydrogen, $C_{1-4}$alkyloxy;
$A^3$ is CH or N;
provided that maximum one of $A^1$, $A^2$ and $A^3$ is N;
Het$^1$ represents a 5- or 6-membered heteroaryl selected from the group consisting of pyridinyl, imidazolyl, oxazolyl, 1,2,4-triazolyl and pyrazolyl; wherein said 5- or 6-membered heteroaryl may be substituted with one or more $C_{1-4}$alkyl substituents;
Y is N or CH; in particular CH;
X is N or CH;
$R^1$ and $R^2$ are taken together to form a bivalent radical -$R^1$-$R^2$- having formula (b-1)

$$-(CH_2)_m-Z-CH_2- \quad (b-1);$$

m represents 2, 3 or 4;
Z represents a direct bond or O;
wherein (b-1) is substituted on one $CH_2$ group with one $Ar^2$ substituent;
$Ar^2$ represents phenyl or pyridinyl; in particular phenyl; wherein said phenyl or pyridinyl may be substituted with one or more substituents each independently selected from the group consisting of halo, cyano, $NR^7R^8$, morpholinyl,
  $C_{1-4}$alkyl optionally substituted with one or more substituents each independently selected from the group consisting of fluoro and cyclo$C_{3-7}$alkyl, and
  $C_{1-4}$alkyloxy optionally substituted with one or more substituents each independently selected from the group consisting of fluoro and cyclo$C_{3-7}$alkyl;
each $R^7$ independently is hydrogen, $C_{1-4}$alkyl or $C_{1-4}$alkylcarbonyl;
each $R^8$ independently is hydrogen or $C_{1-4}$alkyl;
and the pharmaceutically acceptable addition salts, and the solvates thereof.

In an embodiment, the present invention concerns novel compounds of Formula (I), tautomers and stereoisomeric forms thereof, wherein
$R^3$ is selected from the group consisting of $C_{1-4}$alkyloxy, cyano and Het$^1$; in particular $R^3$ is selected from the group consisting of cyano and Het$^1$;
$A^1$ is $CR^{4a}$ or N; wherein $R^{4a}$ is hydrogen or $C_{1-4}$alkyloxy;

$A^2$ is $CR^{4b}$ or N; wherein $R^{4b}$ is hydrogen, $C_{1-4}$alkyloxy;
$A^3$ is CH or N;
provided that maximum one of $A^1$, $A^2$ and $A^3$ is N;
Het$^1$ represents a 5- or 6-membered heteroaryl selected from the group consisting of pyridinyl, imidazolyl, oxazolyl, 1,2,4-triazolyl and pyrazolyl; wherein said 5- or 6-membered heteroaryl may be substituted with one or more $C_{1-4}$alkyl substituents;
Y is N or CH;
X is N or CH;
$R^1$ and $R^2$ are taken together to form a bivalent radical -$R^1$-$R^2$- having formula (b-1)

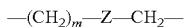   —(CH$_2$)$_m$—Z—CH$_2$—   (b-1);

m represents 2, 3 or 4;
Z represents a direct bond or O;
wherein (b-1) is substituted on one CH$_2$ group with one Ar$^2$ substituent;
Ar$^2$ represents phenyl or pyridinyl; in particular phenyl; wherein said phenyl or pyridinyl is substituted with one or more substituents each independently selected from the group consisting of halo, cyano, NR$^7$R$^8$, morpholinyl, $C_{1-4}$alkyl optionally substituted with one or more substituents each independently selected from the group consisting of fluoro and cycloC$_{3-7}$alkyl, and
$C_{1-4}$alkyloxy optionally substituted with one or more substituents each independently selected from the group consisting of fluoro and cycloC$_{3-7}$alkyl;
each R$^7$ independently is hydrogen, $C_{1-4}$alkyl or $C_{1-4}$alkylcarbonyl;
each R$^8$ independently is hydrogen or $C_{1-4}$alkyl;
and the pharmaceutically acceptable addition salts, and the solvates thereof.

In an embodiment, the present invention concerns novel compounds of Formula (I), tautomers and stereoisomeric forms thereof, wherein
$R^3$ is selected from the group consisting of $C_{1-4}$alkyloxy, cyano and Het$^1$; in particular R$^3$ is selected from the group consisting of cyano and Het$^1$;
$A^1$ is $CR^{4a}$ or N; wherein $R^{4a}$ is hydrogen or $C_{1-4}$alkyloxy;
$A^2$ is $CR^{4b}$ or N; wherein $R^{4b}$ is hydrogen or $C_{1-4}$alkyloxy;
$A^3$ is CH or N;
provided that maximum one of $A^1$, $A^2$ and $A^3$ is N;
Het$^1$ represents a 5- or 6-membered heteroaryl selected from the group consisting of pyridinyl, imidazolyl, and pyrazolyl; wherein said 5- or 6-membered heteroaryl is substituted with one $C_{1-4}$alkyl substituent;
Y is N or CH; in particular CH;
X is N or CH;
$R^1$ and $R^2$ are taken together to form a bivalent radical -$R^1$-$R^2$- having formula (b-1)

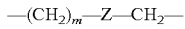   —(CH$_2$)$_m$—Z—CH$_2$—   (b-1);

m represents 2 or 3;
Z represents a direct bond or O;
wherein (b-1) is substituted on one CH$_2$ group with one Ar$^2$ substituent;
Ar$^2$ represents phenyl substituted with one or two substituents each independently selected from the group consisting of halo, $C_{1-4}$alkyl optionally substituted with one, two or three fluoro substituents, and
$C_{1-4}$alkyloxy optionally substituted with one, two or three fluoro substituents;
and the pharmaceutically acceptable addition salts, and the solvates thereof.

In an embodiment, the present invention concerns novel compounds of Formula (I), tautomers and stereoisomeric forms thereof, wherein
$R^3$ is selected from the group consisting of methoxy, cyano and Het$^1$; in particular R$^3$ is selected from the group consisting of cyano and Het$^1$;
$A^1$ is $CR^{4a}$ or N; wherein $R^{4a}$ is hydrogen or methoxy;
$A^2$ is $CR^{4b}$ or N; wherein $R^{4b}$ is hydrogen or methoxy;
$A^3$ is CH or N;
provided that maximum one of $A^1$, $A^2$ and $A^3$ is N;
Het$^1$ represents a 5- or 6-membered heteroaryl selected from the group consisting of 4-pyridinyl, 1-imidazolyl, and 4-pyrazolyl; wherein said 5- or 6-membered heteroaryl is substituted with one methyl substituent;
Y is N or CH; in particular CH;
X is N or CH;
$R^1$ and $R^2$ are taken together to form a bivalent radical -$R^1$-$R^2$- having formula (b-1)

—(CH$_2$)$_m$—Z—CH$_2$—   (b-1);

m represents 2 or 3;
Z represents a direct bond or O;
wherein (b-1) is substituted on one CH$_2$ group with one Ar$^2$ substituent;
Ar$^2$ represents phenyl substituted with one or two substituents each independently selected from the group consisting of chloro, fluoro, methyl optionally substituted with three fluoro substituents, and
methoxy optionally substituted with three fluoro substituents;
and the pharmaceutically acceptable addition salts, and the solvates thereof.

In an embodiment, the present invention concerns novel compounds of Formula (I), tautomers and stereoisomeric forms thereof, wherein
$R^3$ is cyano;
$A^1$ is $CR^{4a}$; wherein $R^{4a}$ is $C_{1-4}$alkyloxy; in particular wherein $R^{4a}$ is methoxy;
$A^2$ is CH;
$A^3$ is CH;
Y is CH;
X is CH;
$R^1$ and $R^2$ are taken together to form a bivalent radical
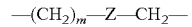   —(CH$_2$)$_2$—O—CH(Ar$^2$)—
Ar$^2$ represents phenyl; wherein said phenyl is substituted with one or two substituents each independently selected from the group consisting of halo, $C_{1-4}$alkyl and CF$_3$;
and the pharmaceutically acceptable addition salts, and the solvates thereof.

Another embodiment of the present invention relates to those compounds of formula (I) or any subgroup thereof as mentioned in any of the other embodiments wherein one or more, preferably all, of the following restriction applies:
(i) $R^3$ is cyano;
(ii) $A^1$ is $CR^{4a}$; wherein $R^{4a}$ is $C_{1-4}$alkyloxy; in particular wherein $R^{4a}$ is methoxy;
(iii) $A^2$ is CH;
(iv) $A^3$ is CH.

In an embodiment, the present invention relates to those compounds of formula (I), or any subgroup thereof as mentioned in any of the other embodiments, wherein $R^1$ and $R^2$ are taken together to form a bivalent radical -$R^1$-$R^2$- having formula (b-1); wherein (b-1) is substituted as defined in any of the other embodiments.

In an embodiment, the present invention relates to those compounds of formula (I), or any subgroup thereof as mentioned in any of the other embodiments, wherein $R^1$ and $R^2$ are taken together to form a bivalent radical -$R^1$-$R^2$- having formula (b-1); wherein (b-1) is substituted on one $CH_2$ group with one $Ar^2$ substituent.

In an embodiment, the present invention relates to those compounds of formula (I), or any subgroup thereof as mentioned in any of the other embodiments, wherein $R^1$ and $R^2$ are taken together to form a bivalent radical -$R^1$-$R^2$- having formula —$(CH_2)_4$— or —$(CH_2)_2$—O—$CH_2$—, wherein the bivalent radical is substituted with substituents as defined for any bivalent radical in any of the other embodiments.

In an embodiment, the present invention relates to those compounds of formula (I), or any subgroup thereof as mentioned in any of the other embodiments, wherein $R^1$ and $R^2$ are taken together to form a bivalent radical -$R^1$-$R^2$- having formula —$(CH_2)_4$—, —$(CH_2)_3$—O—$CH_2$—, —$(CH_2)_2$—$NR^5$—$CH_2$— or —$(CH_2)_2$—O—$CH_2$—, wherein the bivalent radical is substituted with substituents as defined for any bivalent radical in any of the other embodiments.

In an embodiment, the present invention relates to those compounds of formula (I), or any subgroup thereof as mentioned in any of the other embodiments, wherein $R^1$ and $R^2$ are taken together to form a bivalent radical -$R^1$-$R^2$- having formula —$(CH_2)_3$—CH($Ar^2$)— or —$(CH_2)_2$—O—CH($Ar^2$)—.

In an embodiment, the present invention relates to those compounds of formula (I), or any subgroup thereof as mentioned in any of the other embodiments, wherein $R^1$ and $R^2$ are taken together to form a bivalent radical -$R^1$-$R^2$- having formula —$(CH_2)_3$—CH($Ar^2$)—, —$(CH_2)_3$—O—CH($Ar^2$)—, —$(CH_2)_3$—C(OH)($Ar^2$)—, —C($CH_3$)($Ar^2$)—$CH_2$—O—$CH_2$—, —CH($Ar^2$)—$CH_2$—O—$CH_2$—, —$(CH_2)_2$—$NR^5$—CH($Ar^2$)— or —$(CH_2)_2$—O—CH($Ar^2$)—.

In an embodiment, the present invention relates to those compounds of formula (I), or any subgroup thereof as mentioned in any of the other embodiments, wherein $R^1$ and $R^2$ are taken together to form a bivalent radical -$R^1$-$R^2$- having formula —$(CH_2)_3$—CH($Ar^2$)— or —$(CH_2)_2$—O—CH($Ar^2$)—; wherein $Ar^2$ is phenyl substituted with one or two substituents selected from the group consisting of halo, $C_{1-4}$alkyl optionally substituted with one or more fluoro substituents, and $C_{1-4}$alkyloxy optionally substituted with one or more fluoro substituents.

In an embodiment, the present invention relates to those compounds of formula (I), or any subgroup thereof as mentioned in any of the other embodiments, wherein
$R^1$ and $R^2$ are taken together to form a bivalent radical -$R^1$-$R^2$- having formula (b-1) or (b-2), in particular (b-1); wherein the bivalent radical is substituted with substituents as defined in any of the other embodiments;
m represents 2, 3 or 4;
Z represents a direct bond or O.

In an embodiment, the present invention relates to those compounds of formula (I), or any subgroup thereof as mentioned in any of the other embodiments, wherein Z represents a direct bond or O; in particular a direct bond.

In an embodiment, the present invention relates to those compounds of formula (I), or any subgroup thereof as mentioned in any of the other embodiments, wherein Z represents O.

In an embodiment, the present invention relates to those compounds of formula (I), or any subgroup thereof as mentioned in any of the other embodiments, wherein $A^1$ is $CR^{4a}$; and wherein $R^{4a}$ is $C_{1-4}$alkyloxy; in particular wherein $R^{4a}$ is methoxy.

In an embodiment, the present invention relates to those compounds of formula (I), or any subgroup thereof as mentioned in any of the other embodiments, wherein (b-1) or (b-2) is substituted on one or more $CH_2$ groups with one or two substituents each independently selected from the group consisting of $Ar^2$,
(C=O)—$Ar^2$, $C_{1-4}$alkylcarbonyl, and $C_{1-4}$alkyl optionally substituted with one or more fluoro substituents;
in particular wherein (b-1) or (b-2) is substituted on one or more $CH_2$ groups with one or two $Ar^2$ substituents;
more in particular wherein (b-1) or (b-2) is substituted on one $CH_2$ group with one or two $Ar^2$ substituents;
even more in particular wherein (b-1) or (b-2) is substituted on one $CH_2$ group with one $Ar^2$ substituent.

In an embodiment, the present invention relates to those compounds of formula (I), or any subgroup thereof as mentioned in any of the other embodiments, wherein
(b-1) or (b-2) is substituted on one or more $CH_2$ groups with one or two substituents each independently selected from the group consisting of $Ar^2$,
(C=O)—$Ar^2$, $C_{1-4}$alkylcarbonyl, and $C_{1-4}$alkyl optionally substituted with one or more fluoro substituents;
in particular wherein (b-1) or (b-2) is substituted on one or more $CH_2$ groups with one or two $Ar^2$ substituents;
even more in particular wherein (b-1) or (b-2) is substituted on one $CH_2$ group with one $Ar^2$ substituent;
each $Ar^1$ and $Ar^2$ independently represents phenyl; wherein said phenyl may be substituted with one or more substituents each independently selected from the group consisting of halo, cyano, $NR^7R^8$, morpholinyl, $C_{1-4}$alkyl optionally substituted with one or more substituents each independently selected from the group consisting of fluoro and cyclo$C_{3-7}$alkyl, and
$C_{1-4}$alkyloxy optionally substituted with one or more substituents each independently selected from the group consisting of fluoro and cyclo$C_{3-7}$alkyl.

In an embodiment, the present invention relates to those compounds of formula (I), or any subgroup thereof as mentioned in any of the other embodiments, wherein
(b-1) or (b-2) is substituted on one or more $CH_2$ groups with one or two substituents each independently selected from the group consisting of $Ar^2$,
(C=O)—$Ar^2$, $C_{1-4}$alkylcarbonyl, and $C_{1-4}$alkyl optionally substituted with one or more fluoro substituents;
in particular wherein (b-1) or (b-2) is substituted on one or more $CH_2$ groups with one or two $Ar^2$ substituents;
even more in particular wherein (b-1) or (b-2) is substituted on one $CH_2$ group with one $Ar^2$ substituent;
each $Ar^1$ and $Ar^2$ independently represents phenyl substituted with one substituent in the ortho position and optionally one substituent in any of the other positions; the substituents on the phenyl group being selected from the group consisting of halo,
$C_{1-4}$alkyl optionally substituted with one or more fluoro substituents, and
$C_{1-4}$alkyloxy optionally substituted with one or more fluoro substituents.

In an embodiment, the present invention relates to those compounds of formula (I), or any subgroup thereof as mentioned in any of the other embodiments, wherein each $Ar^1$ and $Ar^2$, in particular $Ar^2$, independently represents phenyl substituted with one substituent in the ortho position and optionally one substituent in any of the other positions; the substituents on the phenyl group being selected from the group consisting of halo, $C_{1-4}$alkyl optionally substituted with one or more fluoro substituents, and $C_{1-4}$alkyloxy optionally substituted with one or more fluoro substituents.

In an embodiment, the present invention relates to those compounds of formula (I), or any subgroup thereof as mentioned in any of the other embodiments, wherein
R$^3$ is selected from the group consisting of C$_{1-4}$alkyloxy, cyano and Het$^1$;
A$^2$ is CH or N.

In an embodiment, the present invention relates to those compounds of formula (I), or any subgroup thereof as mentioned in any of the other embodiments, wherein each Ar$^1$ and Ar$^2$, in particular Ar$^2$, independently represents phenyl substituted with one methyl or trifluoromethyl substituent in the ortho position and optionally one substituent selected from the group consisting of halo, C$_{1-4}$alkyl optionally substituted with one or more fluoro substituents, and C$_{1-4}$alkyloxy optionally substituted with one or more fluoro substituents, in any of the other positions.

In an embodiment, the present invention relates to those compounds of formula (I), or any subgroup thereof as mentioned in any of the other embodiments, wherein each Ar$^1$ and Ar$^2$, in particular Ar$^2$, independently represents phenyl substituted with one trifluoromethyl substituent in the ortho position and optionally one substituent selected from the group consisting of halo, C$_{1-4}$alkyl optionally substituted with one or more fluoro substituents, and C$_{1-4}$alkyloxy optionally substituted with one or more fluoro substituents, in any of the other positions.

In an embodiment, the present invention relates to those compounds of formula (I), or any subgroup thereof as mentioned in any of the other embodiments, wherein each Ar$^1$ and Ar$^2$, in particular Ar$^2$, independently represents phenyl substituted with one or more substituents each independently selected from the group consisting of halo, cyano, NR$^7$R$^8$, morpholinyl, C$_{1-4}$alkyl, trifluoromethyl, C$_{1-4}$alkyloxy and trifluoromethyloxy.

In an embodiment, the present invention relates to those compounds of formula (I), or any subgroup thereof as mentioned in any of the other embodiments, wherein each Ar$^1$ and Ar$^2$, in particular Ar$^2$, independently represents phenyl or pyridinyl; wherein said phenyl or pyridinyl is substituted with one or more substituents each independently selected from the group consisting of halo, cyano, NR$^7$R$^8$, morpholinyl, C$_{1-4}$alkyl optionally substituted with one or more substituents each independently selected from the group consisting of fluoro and cycloC$_{3-7}$alkyl, and
C$_{1-4}$alkyloxy optionally substituted with one or more substituents each independently selected from the group consisting of fluoro and cycloC$_{3-7}$alkyl.

In an embodiment, the present invention relates to those compounds of formula (I), or any subgroup thereof as mentioned in any of the other embodiments, wherein each Ar$^1$ and Ar$^2$, in particular Ar$^2$, independently represents phenyl; wherein said phenyl is substituted with one or more substituents each independently selected from the group consisting of halo, cyano, NR$^7$R$^8$, morpholinyl, C$_{1-4}$alkyl optionally substituted with one or more substituents each independently selected from the group consisting of fluoro and cycloC$_{3-7}$alkyl, and
C$_{1-4}$alkyloxy optionally substituted with one or more substituents each independently selected from the group consisting of fluoro and cycloC$_{3-7}$alkyl.

In an embodiment, the present invention relates to those compounds of formula (I), or any subgroup thereof as mentioned in any of the other embodiments, wherein Ar$^2$ represents phenyl substituted with one or two substituents each independently selected from the group consisting of halo, methyl, trifluoromethyl, methoxy and trifluoromethyloxy.

In an embodiment, the present invention relates to those compounds of formula (I), or any subgroup thereof as mentioned in any of the other embodiments, wherein R$^{4a}$ and R$^{4b}$ are hydrogen.

In an embodiment, the present invention relates to those compounds of formula (I), or any subgroup thereof as mentioned in any of the other embodiments, wherein Het$^1$ and Het$^2$ each independently represent a 5- or 6-membered heteroaryl selected from the group consisting of pyridinyl, imidazolyl and pyrazolyl; in particular 4-pyridinyl, 1-imidazolyl and 4-pyrazolyl;
wherein said 5- or 6-membered heteroaryl may be, in particular is, substituted with one or more C$_{1-4}$alkyl substituents.

In an embodiment, the present invention relates to those compounds of formula (I), or any subgroup thereof as mentioned in any of the other embodiments, wherein Het$^1$ represents a 5- or 6-membered heteroaryl selected from the group consisting of pyridinyl, imidazolyl and pyrazolyl; in particular 4-pyridinyl, 1-imidazolyl and 4-pyrazolyl;
wherein said 5- or 6-membered heteroaryl is substituted with one or more C$_{1-4}$alkyl substituents.

In an embodiment, the present invention relates to those compounds of formula (I), or any subgroup thereof as mentioned in any of the other embodiments, wherein R$^3$ is selected from the group consisting of cyano and Het$^1$.

In an embodiment, the present invention relates to those compounds of formula (I), or any subgroup thereof as mentioned in any of the other embodiments, wherein Y is CH.

In an embodiment, the present invention relates to those compounds of formula (I), or any subgroup thereof as mentioned in any of the other embodiments, wherein X is CH.

In an embodiment, the present invention relates to those compounds of formula (I), or any subgroup thereof as mentioned in any of the other embodiments, wherein X is N.

Another embodiment of the present invention relates to those compounds of formula (I), or any subgroup thereof as mentioned in any of the other embodiments, wherein the expression "on one or more CH$_2$ groups" is restricted to "on one or two CH$_2$ groups"; in particular is restricted to "on one CH$_2$ group".

In an embodiment the compound of Formula (I) is selected from the group consisting of:
2-[5,6,7,8-tetrahydro-8-[2-(trifluoromethyl)phenyl][1,2,4]triazolo[1,5-a]pyridin-2-yl]-1H-indole-5-carbonitrile,
5,6,7,8-tetrahydro-2-[5-(4-methyl-1H-imidazol-1-yl)-1H-indol-2-yl]-8-[2-(trifluoromethyl)phenyl]-[1,2,4]triazolo[1,5-a]pyridine,
5,6,7,8-tetrahydro-2-[5-(2-methyl-4-pyridinyl)-1H-indol-2-yl]-8-[2-(trifluoromethyl)phenyl]-[1,2,4]triazolo[1,5-a]pyridine 0.2 HCl,
5,6,7,8-tetrahydro-2-[5-(2-methyl-4-pyridinyl)-1H-indol-2-yl]-8-[2-(trifluoromethyl)phenyl]-[1,2,4]triazolo[1,5-a]pyridine,
4-methoxy-2-[5,6,7,8-tetrahydro-8-[2-(trifluoromethyl)phenyl][1,2,4]triazolo[1,5-a]pyridin-2-yl]-1H-indole-5-carbonitrile,
6-methoxy-2-[5,6,7,8-tetrahydro-8-[2-(trifluoromethyl)phenyl][1,2,4]triazolo[1,5-a]pyridin-2-yl]-1H-indole-5-carbonitrile,
2-[5,6-dihydro-8-[2-(trifluoromethyl)phenyl]-8H-[1,2,4]triazolo[5,1-c][1,4]oxazin-2-yl]-1H-indole-5-carbonitrile,
5,6-dihydro-2-[5-(4-methyl-1H-imidazol-1-yl)-1H-indol-2-yl]-8-[2-(trifluoromethyl)phenyl]-8H-[1,2,4]triazolo[5,1-c][1,4]oxazine, 2-[5,6,7,8-tetrahydro-8-[2-(trifluoromethyl)phenyl][1,2,4]
triazolo[1,5-a]pyridin-2-yl]-1H-benzimidazole-5-carbonitrile,
5,6,7,8-tetrahydro-2-(5-methoxy-1H-indol-2-yl)-8-[2-(trifluoromethyl)phenyl]-[1,2,4]triazolo[1,5-a]pyridine,
2-[5,6,7,8-tetrahydro-8-[2-(trifluoromethoxy)phenyl][1,2,4]
triazolo[1,5-a]pyridin-2-yl]-1H-indole-5-carbonitrile,
2-[5,6,7,8-tetrahydro-8-[2-(trifluoromethyl)phenyl][1,2,4]
triazolo[1,5-a]pyridin-2-yl]-1H-pyrrolo[3,2-b]pyridine-5-carbonitrile,
2-[8-[2-fluoro-5-(trifluoromethyl)phenyl]-5,6,7,8-tetrahydro[1,2,4]triazolo[1,5-a]pyridin-2-yl]-1H-indole-5-carbonitrile,
2-[5,6,7,8-tetrahydro-8-[3-(trifluoromethoxy)phenyl][1,2,4]
triazolo[1,5-a]pyridin-2-yl]-1H-indole-5-carbonitrile,
2-[8-[4-fluoro-2-(trifluoromethyl)phenyl]-5,6,7,8-tetrahydro[1,2,4]triazolo[1,5-a]pyridin-2-yl]-1H-indole-5-carbonitrile,
2-[8-(4-fluoro-2-methylphenyl)-5,6,7,8-tetrahydro[1,2,4]
triazolo[1,5-a]pyridin-2-yl]-1H-indole-5-carbonitrile,
2-[5,6,7,8-tetrahydro-8-[2-(trifluoromethyl)phenyl]imidazo
[1,2-a]pyridin-2-yl]-1H-indole-5-carbonitrile,
2-[5,6,7,8-tetrahydro-8-(2-methylphenyl)[1,2,4]triazolo[1,
5-a]pyridin-2-yl]-1H-indole-5-carbonitrile,
5,6,7,8-tetrahydro-8-(2-methylphenyl)-2-[5-(1-methyl-1H-pyrazol-4-yl)-1H-indol-2-yl]-[1,2,4]triazolo[1,5-a]pyridine,
2-[8-(3-fluoro-2-methylphenyl)-5,6-dihydro-8H-[1,2,4]triazolo[5,1-c][1,4]oxazin-2-yl]-1H-indole-5-carbonitrile,
2-[5,6-dihydro-8-[2-methyl-5-(trifluoromethyl)phenyl]-8H-[1,2,4]triazolo[5,1-c][1,4]oxazin-2-yl]-1H-indole-5-carbonitrile,
2-[5,6,7,8-tetrahydro-8-[2-methyl-5-(trifluoromethyl)phenyl][1,2,4]triazolo[1,5-a]pyridin-2-yl]-1H-pyrrolo[2,3-b]
pyridine-5-carbonitrile,
2-[5,6,7,8-tetrahydro-8-(2-methylphenyl)[1,2,4]triazolo[1,
5-a]pyridin-2-yl]-1H-pyrrolo[3,2-b]pyridine-5-carbonitrile,
2-[5,6,7,8-tetrahydro-8-(2-methylphenyl)imidazo[1,2-a]pyridin-2-yl]-1H-indole-5-carbonitrile,
5,6,7,8-tetrahydro-8-(2-methylphenyl)-2-[5-(2-methyl-4-pyridinyl)-1H-pyrrolo[3,2-b]pyridin-2-yl]-[1,2,4]triazolo
[1,5-a]pyridine,
2-[5,6,7,8-tetrahydro-8-(2-methylphenyl)[1,2,4]triazolo[1,
5-a]pyridin-2-yl]-1H-indole-5-carbonitrile (R or S),
2-[5,6,7,8-tetrahydro-8-(2-methylphenyl)[1,2,4]triazolo[1,
5-a]pyridin-2-yl]-1H-indole-5-carbonitrile (S or R),
8-(3-fluoro-2-methylphenyl)-5,6-dihydro-2-[5-(4-methyl-1H-imidazol-1-yl)-1H-indol-2-yl]-8H-[1,2,4]triazolo[5,1-c][1,4]oxazine,
5,6,7,8-tetrahydro-2-[5-(4-methyl-1H-imidazol-1-yl)-1H-pyrrolo[3,2-b]pyridin-2-yl]-8-(2-methylphenyl)-[1,2,4]
triazolo[1,5-a]pyridine .HCl,
5,6,7,8-tetrahydro-2-[5-(4-methyl-1H-imidazol-1-yl)-1H-pyrrolo[3,2-b]pyridin-2-yl]-8-(2-methylphenyl)-[1,2,4]
triazolo[1,5-a]pyridine,
2-[8-(4-fluoro-2-methylphenyl)-5,6,7,8-tetrahydroimidazo
[1,2-a]pyridin-2-yl]-1H-indole-5-carbonitrile,
2-[8-(4-fluoro-2-methylphenyl)-5,6,7,8-tetrahydro[1,2,4]
triazolo[1,5-a]pyridin-2-yl]-1H-pyrrolo[2,3-b]pyridine-5-carbonitrile,
2-[5,6,7,8-tetrahydro-8-(2-methylphenyl)[1,2,4]triazolo[1,
5-a]pyridin-2-yl]-1H-pyrrolo[2,3-c]pyridine-5-carbonitrile,
2-[8-(4-fluoro-2-methylphenyl)-5,6,7,8-tetrahydro[1,2,4]
triazolo[1,5-a]pyridin-2-yl]-1H-indole-5-carbonitrile (R or S), 2-[8-(4-fluoro-2-methylphenyl)-5,6,7,8-tetrahydro[1,2,4]
triazolo[1,5-a]pyridin-2-yl]-1H-indole-5-carbonitrile (S or R),
2-[8-(2-chlorophenyl)-5,6,7,8-tetrahydroimidazo[1,2-a]pyridin-2-yl]-1H-indole-5-carbonitrile .HCl,
2-[8-(2-chlorophenyl)-5,6,7,8-tetrahydroimidazo[1,2-a]pyridin-2-yl]-1H-indole-5-carbonitrile,
5,6,7,8-tetrahydro-2-[5-(4-methyl-1H-imidazol-1-yl)-1H-pyrrolo[2,3-c]pyridin-2-yl]-8-(2-methylphenyl)-[1,2,4]
triazolo[1,5-a]pyridine,
8-(4-fluoro-2-methylphenyl)-5,6,7,8-tetrahydro-2-[5-(1-methyl-1H-pyrazol-4-yl)-1H-pyrrolo[3,2-b]pyridin-2-yl]-[1,
2,4]triazolo[1,5-a]pyridine,
8-(4-fluoro-2-methylphenyl)-5,6,7,8-tetrahydro-2-[5-(2-methyl-4-pyridinyl)-1H-pyrrolo[3,2-b]pyridin-2-yl]-[1,2,4]
triazolo[1,5-a]pyridine,
2-[5,6,7,8-tetrahydro-8-(2-methoxyphenyl)[1,2,4]triazolo
[1,5-a]pyridin-2-yl]-1H-indole-5-carbonitrile,
8-(4-fluoro-2-methylphenyl)-5,6-dihydro-2-[5-(4-methyl-1H-imidazol-1-yl)-1H-indo-2-yl]-8H-[1,2,4]triazolo[5,1-c][1,4]oxazine,
2-[5,6,7,8-tetrahydro-8-[2-(trifluoromethyl)phenyl][1,2,4]
triazolo[1,5-a]pyridin-2-yl]-1H-indole-6-carbonitrile,
2-[8-(2-chlorophenyl)-5,6,7,8-tetrahydro[1,2,4]triazolo[1,5-a]pyridin-2-yl]-1H-indole-5-carbonitrile,
2-[8-(4-fluoro-2-methylphenyl)-5,6,7,8-tetrahydroimidazo
[1,2-a]pyridin-2-yl]-1H-indole-5-carbonitrile (R or S),
2-[8-(4-fluoro-2-methylphenyl)-5,6,7,8-tetrahydroimidazo
[1,2-a]pyridin-2-yl]-1H-indole-5-carbonitrile (S or R),
8-(4-fluoro-2-methylphenyl)-5,6,7,8-tetrahydro-2-[5-(4-methyl-1H-imidazol-1-yl)-1H-pyrrolo[3,2-b]pyridin-2-yl]-
[1,2,4]triazolo[1,5-a]pyridine (R or S),
8-(4-fluoro-2-methylphenyl)-5,6,7,8-tetrahydro-2-[5-(4-methyl-1H-imidazol-1-yl)-1H-pyrrolo[3,2-b]pyridin-2-yl]-
[1,2,4]triazolo[1,5-a]pyridine (S or R),
2-[5,6,7,8-tetrahydro-8-(2-methoxyphenyl)imidazo[1,2-a]
pyridin-2-yl]-1H-indole-5-carbonitrile,
2-[8-(4-fluoro-2-methylphenyl)-5,6,7,8-tetrahydro[1,2,4]
triazolo[1,5-a]pyridin-2-yl]-5-(4-methyl-1H-imidazol-1-yl)-1H-pyrrolo[3,2-b]pyridine-3-methanol,
2-[8-(4-fluoro-2-methylphenyl)-5,6,7,8-tetrahydro[1,2,4]
triazolo[1,5-a]pyridin-2-yl]-1H-pyrrolo[2,3-c]pyridine-5-carbonitrile,
8-(4-fluoro-2-methylphenyl)-5,6-dihydro-2-[5-(4-methyl-1H-imidazol-1-yl)-1H-pyrrolo[3,2-b]pyridin-2-yl]-8H-
[1,2,4]triazolo[5,1-c][1,4]oxazine,
8-(4-fluoro-2-methylphenyl)-5,6,7,8-tetrahydro-2-[5-(1-methyl-1H-pyrazol-4-yl)-1H-pyrrolo[3,2-b]pyridin-2-yl]-[1,
2,4]triazolo[1,5-a]pyridine (R or S),
8-(4-fluoro-2-methylphenyl)-5,6,7,8-tetrahydro-2-[5-(1-methyl-1H-pyrazol-4-yl)-1H-pyrrolo[3,2-b]pyridin-2-yl]-[1,
2,4]triazolo[1,5-a]pyridine (S or R),
3-fluoro-2-[8-(4-fluoro-2-methylphenyl)-5,6,7,8-tetrahydro
[1,2,4]triazolo[1,5-a]pyridin-2-yl]-1H-indole-5-carbonitrile,
8-(4-fluoro-2-methylphenyl)-5,6,7,8-tetrahydro-2-[5-(4-methyl-1H-imidazol-1-yl)-1H-pyrrolo[2,3-c]pyridin-2-yl]-
[1,2,4]triazolo[1,5-a]pyridine,
2-[8-(4-fluoro-2-methylphenyl)-5,6,7,8-tetrahydroimidazo
[1,2-a]pyridin-2-yl]-1H-pyrrolo[2,3-c]pyridine-5-carbonitrile,
8-(4-fluoro-2-methylphenyl)-5,6,7,8-tetrahydro-2-[5-(4-methyl-1H-imidazol-1-yl)-1H-indol-2-yl]-[1,2,4]triazolo[1,
5-a]pyridine,
2-[8-(4-fluoro-2-methylphenyl)-5,6,7,8-tetrahydroimidazo
[1,2-a]pyridin-2-yl]-4-methoxy-1H-indole-5-carbonitrile, 2-[8-(2-ethyl-4-fluorophenyl)-5,6-dihydro-8H-[1,2,4]triazolo[5,1-c][1,4]oxazin-2-yl]-1H-indole-5-carbonitrile, 8-(4-fluoro-2-methylphenyl)-5,6,7,8-tetrahydro-2-[6-(4-methyl-1H-imidazol-1-yl)-1H-indol-2-yl]-[1,2,4]triazolo[1,5-a]pyridine, 2-[8-(4-fluoro-2-methylphenyl)-5,6,7,8-tetrahydroimidazo[1,2-a]pyridin-2-yl]-1H-pyrrolo[3,2-b]pyridine-5-carbonitrile, 8-(4-fluoro-2-methylphenyl)-5,6-dihydro-2-[4-methoxy-5-(1-methyl-1H-pyrazol-4-yl)-1H-indol-2-yl]-8H-imidazo[2,1-c][1,4]oxazine, 2-[8-(4-fluoro-2-methylphenyl)-5,6-dihydro-8H-imidazo[2,1-c][1,4]oxazin-2-yl]-4-methoxy-1H-indole-5-carbonitrile, 8-(4-fluoro-2-methylphenyl)-5,6,7,8-tetrahydro-2-[5-(4-methyl-1H-imidazol-1-yl)-1H-indol-2-yl]-[1,2,4]triazolo[1,5-a]pyridine (R or S), 8-(4-fluoro-2-methylphenyl)-5,6,7,8-tetrahydro-2-[5-(4-methyl-1H-imidazol-1-yl)-1H-indol-2-yl]-[1,2,4]triazolo[1,5-a]pyridine (S or R), 8-(4-fluoro-2-methylphenyl)-5,6,7,8-tetrahydro-2-[4-methoxy-5-(4-methyl-1H-imidazol-1-yl)-1H-indol-2-yl]-imidazo[1,2-a]pyridine (R or S), 8-(4-fluoro-2-methylphenyl)-5,6,7,8-tetrahydro-2-[4-methoxy-5-(4-methyl-1H-imidazol-1-yl)-1H-indol-2-yl]-imidazo[1,2-a]pyridine (S or R), 5,6,7,8-tetrahydro-8-(2-methoxyphenyl)-2-[5-(4-methyl-1H-imidazol-1-yl)-1H-indol-2-yl]-[1,2,4]triazolo[1,5-a]pyridine (R or S), 5,6,7,8-tetrahydro-8-(2-methoxyphenyl)-2-[5-(4-methyl-1H-imidazol-1-yl)-1H-indol-2-yl]-[1,2,4]triazolo[1,5-a]pyridine (S or R), 3-fluoro-2-[8-(4-fluoro-2-methylphenyl)-5,6,7,8-tetrahydro[1,2,4]triazolo[1,5-a]pyridin-2-yl]-1H-indole-5-carbonitrile (R or S), 3-fluoro-2-[8-(4-fluoro-2-methylphenyl)-5,6,7,8-tetrahydro[1,2,4]triazolo[1,5-a]pyridin-2-yl]-1H-indole-5-carbonitrile (S or R), 2-[8-(4-fluoro-2-methylphenyl)-5,6-dihydro-8H-[1,2,4]triazolo[5,1-c][1,4]oxazin-2-yl]-1H-indole-5-carbonitrile (R or S), 2-[8-(4-fluoro-2-methylphenyl)-5,6-dihydro-8H-[1,2,4]triazolo[5,1-c][1,4]oxazin-2-yl]-1H-indole-5-carbonitrile (S or R), 2-[8-(4-fluoro-2-methylphenyl)-5,6,7,8-tetrahydro[1,2,4]triazolo[1,5-a]pyridin-2-yl]-4-methoxy-1H-indole-5-carbonitrile, 8-(4-fluoro-2-methylphenyl)-5,6,7,8-tetrahydro-2-[5-(5-methyl-1H-1,2,4-triazol-1-yl)-1H-indol-2-yl]-[1,2,4]triazolo[1,5-a]pyridine, 8-(4-fluoro-2-methylphenyl)-5,6,7,8-tetrahydro-2-[5-(3-methyl-1H-1,2,4-triazol-1-yl)-1H-indol-2-yl]-[1,2,4]triazolo[1,5-a]pyridine, 8-(4-fluoro-2-methylphenyl)-5,6-dihydro-2-[5-(1-methyl-1H-pyrazol-4-yl)-1H-indol-2-yl]-8H-imidazo[2,1-c][1,4]oxazine, 8-(4-fluoro-2-methylphenyl)-5,6,7,8-tetrahydro-2-[4-methoxy-5-(4-methyl-1H-imidazol-1-yl)-1H-indol-2-yl]-[1,2,4]triazolo[1,5-a]pyridine (R or S), 8-(4-fluoro-2-methylphenyl)-5,6,7,8-tetrahydro-2-[4-methoxy-5-(4-methyl-1H-imidazol-1-yl)-1H-indol-2-yl]-[1,2,4]triazolo[1,5-a]pyridine (S or R), 8-[4-fluoro-2-(1-methylethyl)phenyl]-5,6-dihydro-2-[5-(4-methyl-1H-imidazol-1-yl)-1H-indol-2-yl]-8H-[1,2,4]triazolo[5,1-c][1,4]oxazine, 8-(4-fluoro-2-methylphenyl)-5,6-dihydro-2-[5-(1-methyl-1H-pyrazol-4-yl)-1H-pyrrolo[3,2-b]pyridin-2-yl]-8H-imidazo[2,1-c][1,4]oxazine (R or S), 8-(4-fluoro-2-methylphenyl)-5,6-dihydro-2-[5-(1-methyl-1H-pyrazol-4-yl)-1H-pyrrolo[3,2-b]pyridin-2-yl]-8H-imidazo[2,1-c][1,4]oxazine (S or R), 2-[8-(4-fluoro-2-methylphenyl)-5,6,7,8-tetrahydroimidazo[1,2-a]pyridin-2-yl]-5-(1-methyl-1H-pyrazol-4-yl)-1H-pyrrolo[3,2-b]pyridine (R or S), 2-[8-(4-fluoro-2-methylphenyl)-5,6,7,8-tetrahydroimidazo[1,2-a]pyridin-2-yl]-5-(1-methyl-1H-pyrazol-4-yl)-1H-pyrrolo[3,2-b]pyridine (S or R), 8-(4-fluoro-2-methylphenyl)-5,6-dihydro-2-[5-(2-methyl-4-pyridinyl)-1H-indol-2-yl]-8H-imidazo[2,1-c][1,4]oxazine, 8-(3,4-difluoro-2-methylphenyl)-5,6-dihydro-2-[5-(4-methyl-1H-imidazol-1-yl)-1H-indol-2-yl]-8H-[1,2,4]triazolo[5,1-c][1,4]oxazine, 8-(2-ethyl-4-fluorophenyl)-5,6-dihydro-2-[5-(4-methyl-1H-imidazol-1-yl)-1H-indol-2-yl]-8H-[1,2,4]triazolo[5,1-c][1,4]oxazine, 8-(4-fluoro-2-methylphenyl)-5,6-dihydro-2-[5-(1-methyl-1H-pyrazol-4-yl)-1H-pyrrolo[3,2-b]pyridin-2-yl]-8H-[1,2,4]triazolo[5,1-c][1,4]oxazine, 8-(4-fluoro-2-methylphenyl)-5,6-dihydro-2-[5-(1-methyl-1H-pyrazol-4-yl)-1H-indol-2-yl]-8H-[1,2,4]triazolo[5,1-c][1,4]oxazine, 8-(4-fluoro-2-methylphenyl)-5,6-dihydro-2-[5-(2-methyl-4-pyridinyl)-1H-indol-2-yl]-8H-[1,2,4]triazolo[5,1-c][1,4]oxazine, 2-[8-(4-fluoro-2-methylphenyl)-5,6-dihydro-8H-imidazo[2,1-c][1,4]oxazin-2-yl]-4-methoxy-1H-indole-5-carbonitrile (R or S), 2-[8-(4-fluoro-2-methylphenyl)-5,6-dihydro-8H-imidazo[2,1-c][1,4]oxazin-2-yl]-4-methoxy-1H-indole-5-carbonitrile (S or R), 8-(4-fluoro-2-methylphenyl)-5,6-dihydro-2-[5-(4-methyl-1H-imidazol-1-yl)-1H-indol-2-yl]-8H-[1,2,4]triazolo[5,1-c][1,4]oxazine (R or S), 8-(4-fluoro-2-methylphenyl)-5,6-dihydro-2-[5-(4-methyl-1H-imidazol-1-yl)-1H-indol-2-yl]-8H-[1,2,4]triazolo[5,1-c][1,4]oxazine (S or R), 8-(4-fluoro-2-methylphenyl)-5,6,7,8-tetrahydro-2-[5-(4-methyl-1H-imidazol-1-yl)-1H-pyrrolo[2,3-b]pyridin-2-yl]-[1,2,4]triazolo[1,5-a]pyridine (R or S), 8-(4-fluoro-2-methylphenyl)-5,6,7,8-tetrahydro-2-[5-(4-methyl-1H-imidazol-1-yl)-1H-pyrrolo[2,3-b]pyridin-2-yl]-[1,2,4]triazolo[1,5-a]pyridine (S or R), 2-[8-(4-fluoro-2-methylphenyl)-5,6-dihydro-8H-[1,2,4]triazolo[5,1-c][1,4]oxazin-2-yl]-4-methoxy-1H-indole-5-carbonitrile, 8-(4-fluoro-2-methylphenyl)-5,6-dihydro-2-[4-methoxy-5-(4-methyl-1H-imidazol-1-yl)-1H-indol-2-yl]-8H-imidazo[2,1-c][1,4]oxazine (R or S), 8-(4-fluoro-2-methylphenyl)-5,6-dihydro-2-[4-methoxy-5-(4-methyl-1H-imidazol-1-yl)-1H-indol-2-yl]-8H-imidazo[2,1-c][1,4]oxazine (S or R), 8-(4-fluoro-2-methylphenyl)-5,6,7,8-tetrahydro-2-[5-(2-methyl-4-pyridinyl)-1H-benzimidazol-2-yl]-[1,2,4]triazolo[1,5-a]pyridine (R or S), 8-(4-fluoro-2-methylphenyl)-5,6,7,8-tetrahydro-2-[5-(2-methyl-4-pyridinyl)-1H-benzimidazol-2-yl]-[1,2,4]triazolo[1,5-a]pyridine (S or R), 2-[8-(4-fluoro-2-methylphenyl)-5,6-dihydro-8H-[1,2,4]triazolo[5,1-c][1,4]oxazin-2-yl]-4-methoxy-1H-indole-5-carbonitrile (R or S), 2-[8-(4-fluoro-2-methylphenyl)-5,6-dihydro-8H-[1,2,4]triazolo[5,1-c][1,4]oxazin-2-yl]-4-methoxy-1H-indole-5-carbonitrile (S or R), 2-[5,6-dihydro-8-[2-(trifluoromethyl)phenyl]-8H-[1,2,4]triazolo[5,1-c][1,4]oxazin-2-yl]-4-methoxy-1H-indole-5-carbonitrile, 8-(4-fluoro-2-methylphenyl)-5,6,7,8-tetrahydro-2-[5-(4-methyl-1H-imidazol-1-yl)-1H-benzimidazol-2-yl]-[1,2,4]triazolo[1,5-a]pyridine (R or S), 8-(4-fluoro-2-methylphenyl)-5,6,7,8-tetrahydro-2-[5-(4-methyl-1H-imidazol-1-yl)-1H-benzimidazol-2-yl]-[1,2,4]triazolo[1,5-a]pyridine (S or R), 8-(4-fluoro-2-methylphenyl)-5,6,7,8-tetrahydro-2-[5-(5-methyl-1H-imidazol-1-yl)-1H-benzimidazol-2-yl]-[1,2,4]triazolo[1,5-a]pyridine, 8-(4,5-difluoro-2,3-dimethylphenyl)-5,6-dihydro-2-[5-(4-methyl-1H-imidazol-1-yl)-1H-indol-2-yl]-8H-[1,2,4]triazolo[5,1-c][1,4]oxazine, 2-[5,6-dihydro-8-[2-(trifluoromethyl)phenyl]-8H-[1,2,4]triazolo[5,1-c][1,4]oxazin-2-yl]-4-methoxy-1H-indole-5-carbonitrile (R or S), 2-[5,6-dihydro-8-[2-(trifluoromethyl)phenyl]-8H-[1,2,4]triazolo[5,1-c][1,4]oxazin-2-yl]-4-methoxy-1H-indole-5-carbonitrile (S or R), 2-[8-(2-chloro-6-fluorophenyl)-5,6-dihydro-8H-[1,2,4]triazolo[5,1-c][1,4]oxazin-2-yl]-4-methoxy-1H-indole-5-carbonitrile (R or S), 2-[8-(2-chloro-6-fluorophenyl)-5,6-dihydro-8H-[1,2,4]triazolo[5,1-c][1,4]oxazin-2-yl]-4-methoxy-1H-indole-5-carbonitrile (S or R), 2-[5-[2-fluoro-5-(trifluoromethyl)phenyl]-5,6-dihydro-5-methyl-8H-imidazo[2,1-c][1,4]oxazin-2-yl]-4-methoxy-1H-indole-5-carbonitrile, 2-[8-(2-chloro-6-fluorophenyl)-5,6-dihydro-8H-imidazo[2,1-c][1,4]oxazin-2-yl]-4-methoxy-1H-indole-5-carbonitrile, 2-(5,6-dihydro-5-phenyl-8H-imidazo[2,1-c][1,4]oxazin-2-yl)-4-methoxy-1H-indole-5-carbonitrile, 2-[5,6-dihydro-8-[2-(methoxymethyl)phenyl]-8H-imidazo[2,1-c][1,4]oxazin-2-yl]-4-methoxy-1H-indole-5-carbonitrile, 4-methoxy-2-[5,6,7,8-tetrahydro-8-[2-(methoxymethyl)phenyl][1,2,4]triazolo[1,5-a]pyridin-2-yl]-1H-indole-5-carbonitrile, 2-[8-(3-fluoro-2-methylphenyl)-5,6-dihydro-8H-imidazo[2,1-c][1,4]oxazin-2-yl]-4-methoxy-1H-indole-5-carbonitrile, 2-[8-[2-fluoro-5-(trifluoromethyl)phenyl]-5,6-dihydro-8H-[1,2,4]triazolo[5,1-c][1,4]oxazin-2-yl]-4-methoxy-1H-indole-5-carbonitrile, 2-[8-(2-chloro-6-fluorophenyl)-5,6-dihydro-8H-imidazo[2,1-c][1,4]oxazin-2-yl]-4-methoxy-1H-indole-5-carbonitrile (R or S), 2-[8-(2-chloro-6-fluorophenyl)-5,6-dihydro-8H-imidazo[2,1-c][1,4]oxazin-2-yl]-4-methoxy-1H-indole-5-carbonitrile (S or R), 2-[8-(2-fluoro-6-methylphenyl)-5,6-dihydro-8H-imidazo[2,1-c][1,4]oxazin-2-yl]-4-methoxy-1H-indole-5-carbonitrile, 2-[8-(2-chlorophenyl)-5,6-dihydro-8H-imidazo[2,1-c][1,4]oxazin-2-yl]-4-methoxy-1H-indole-5-carbonitrile, 2-[8-[2-fluoro-6-(trifluoromethyl)phenyl]-5,6-dihydro-8H-[1,2,4]triazolo[5,1-c][1,4]oxazin-2-yl]-4-methoxy-1H-indole-5-carbonitrile, 2-[9-(4-fluoro-2-methylphenyl)-6,7-dihydro-5H,9H-[1,2,4]triazolo[5,1-c][1,4]oxazepin-2-yl]-4-methoxy-1H-indole-5-carbonitrile, 2-[8-[2-fluoro-6-(trifluoromethyl)phenyl]-5,6-dihydro-8H-imidazo[2,1-c][1,4]oxazin-2-yl]-4-methoxy-1H-indole-5-carbonitrile, 2-[8-(3-fluoro-2-methylphenyl)-5,6-dihydro-8H-[1,2,4]triazolo[5,1-c][1,4]oxazin-2-yl]-4-methoxy-1H-indole-5-carbonitrile, 2-[8-[2-fluoro-5-(trifluoromethyl)phenyl]-5,6-dihydro-8H-imidazo[2,1-c][1,4]oxazin-2-yl]-4-methoxy-1H-indole-5-carbonitrile, 2-[8-(2-fluoro-6-methylphenyl)-5,6-dihydro-8H-[1,2,4]triazolo[5,1-c][1,4]oxazin-2-yl]-4-methoxy-1H-indole-5-carbonitrile, 2-[8-(2-chlorophenyl)-5,6-dihydro-8H-[1,2,4]triazolo[5,1-c][1,4]oxazin-2-yl]-4-methoxy-1H-indole-5-carbonitrile, 2-[8-[3-fluoro-2-(trifluoromethyl)phenyl]-5,6-dihydro-8H-imidazo[2,1-c][1,4]oxazin-2-yl]-4-methoxy-1H-indole-5-carbonitrile (R or S), 2-[8-[3-fluoro-2-(trifluoromethyl)phenyl]-5,6-dihydro-8H-imidazo[2,1-c][1,4]oxazin-2-yl]-4-methoxy-1H-indole-5-carbonitrile (S or R), 2-[8-(2-chlorophenyl)-5,6-dihydro-8H-imidazo[2,1-c][1,4]oxazin-2-yl]-4-methoxy-1H-indole-5-carbonitrile (R or S), 2-[8-(2-chlorophenyl)-5,6-dihydro-8H-imidazo[2,1-c][1,4]oxazin-2-yl]-4-methoxy-1H-indole-5-carbonitrile (S or R), 2-[8-[3-fluoro-2-(trifluoromethyl)phenyl]-5,6-dihydro-8H-[1,2,4]triazolo[5,1-c][1,4]oxazin-2-yl]-4-methoxy-1H-indole-5-carbonitrile (R or S), 2-[8-[3-fluoro-2-(trifluoromethyl)phenyl]-5,6-dihydro-8H-[1,2,4]triazolo[5,1-c][1,4]oxazin-2-yl]-4-methoxy-1H-indole-5-carbonitrile (S or R), 2-[8-(2-fluoro-3-methylphenyl)-5,6-dihydro-8H-imidazo[2,1-c][1,4]oxazin-2-yl]-4-methoxy-1H-indole-5-carbonitrile (R or S), 2-[8-(2-fluoro-3-methylphenyl)-5,6-dihydro-8H-imidazo[2,1-c][1,4]oxazin-2-yl]-4-methoxy-1H-indole-5-carbonitrile (S or R), 2-[8-(3-fluoro-2-methylphenyl)-5,6-dihydro-8H-imidazo[2,1-c][1,4]oxazin-2-yl]-4-methoxy-1H-indole-5-carbonitrile (R or S), 2-[8-(3-fluoro-2-methylphenyl)-5,6-dihydro-8H-imidazo[2,1-c][1,4]oxazin-2-yl]-4-methoxy-1H-indole-5-carbonitrile (S or R), 2-[8-(2-chlorophenyl)-5,6-dihydro-8H-[1,2,4]triazolo[5,1-c][1,4]oxazin-2-yl]-4-methoxy-1H-indole-5-carbonitrile (R or S), 2-[8-(2-fluoro-6-methylphenyl)-5,6-dihydro-8H-imidazo[2,1-c][1,4]oxazin-2-yl]-4-methoxy-1H-indole-5-carbonitrile (R or S), 2-[8-(2-fluoro-6-methylphenyl)-5,6-dihydro-8H-imidazo[2,1-c][1,4]oxazin-2-yl]-4-methoxy-1H-indole-5-carbonitrile (S or R), 2-[8-(2-chlorophenyl)-5,6-dihydro-8H-[1,2,4]triazolo[5,1-c][1,4]oxazin-2-yl]-4-methoxy-1H-indole-5-carbonitrile (S or R), 2-[8-(2-fluoro-6-methylphenyl)-5,6-dihydro-8H-[1,2,4]triazolo[5,1-c][1,4]oxazin-2-yl]-4-methoxy-1H-indole-5-carbonitrile (R or S), 2-[8-(2-fluoro-6-methylphenyl)-5,6-dihydro-8H-[1,2,4]triazolo[5,1-c][1,4]oxazin-2-yl]-4-methoxy-1H-indole-5-carbonitrile (S or R), 2-[8-(3-chloro-4-fluorophenyl)-5,6-dihydro-8H-imidazo[2,1-c][1,4]oxazin-2-yl]-4-methoxy-1H-indole-5-carbonitrile, 2-[8-(3-chloro-4-fluorophenyl)-5,6-dihydro-8H-[1,2,4]triazolo[5,1-c][1,4]oxazin-2-yl]-4-methoxy-1H-indole-5-carbonitrile, 2-[5,6-dihydro-8-[2-(methoxymethyl)phenyl]-8H-imidazo[2,1-c][1,4]oxazin-2-yl]-4-methoxy-1H-indole-5-carbonitrile (R or S), 2-[5,6-dihydro-8-[2-(methoxymethyl)phenyl]-8H-imidazo[2,1-c][1,4]oxazin-2-yl]-4-methoxy-1H-indole-5-carbonitrile (S or R), 4-methoxy-2-[5,6,7,8-tetrahydro-8-[2-(methoxymethyl)phenyl][1,2,4]triazolo[1,5-a]pyridin-2-yl]-1H-indole-5-carbonitrile (R or S), 4-methoxy-2-[5,6,7,8-tetrahydro-8-[2-(methoxymethyl)phenyl][1,2,4]triazolo[1,5-a]pyridin-2-yl]-1H-indole-5-carbonitrile (S or R), 2-[8-(3-fluoro-2-methylphenyl)-5,6-dihydro-8H-[1,2,4]triazolo[5,1-c][1,4]oxazin-2-yl]-4-methoxy-1H-indole-5-carbonitrile (R or S), 2-[8-(2-fluoro-3-methylphenyl)-5,6-dihydro-8H-[1,2,4]triazolo[5,1-c][1,4]oxazin-2-yl]-4-methoxy-1H-indole-5-carbonitrile (R or S), 2-[8-(2-fluoro-3-methylphenyl)-5,6-dihydro-8H-[1,2,4]triazolo[5,1-c][1,4]oxazin-2-yl]-4-methoxy-1H-indole-5-carbonitrile (S or R), 2-[8-(3-fluoro-2-methylphenyl)-5,6-dihydro-8H-[1,2,4]triazolo[5,1-c][1,4]oxazin-2-yl]-4-methoxy-1H-indole-5-carbonitrile (S or R), 2-[8-(5-fluoro-2-methylphenyl)-5,6-dihydro-8H-imidazo[2,1-c][1,4]oxazin-2-yl]-4-methoxy-1H-indole-5-carbonitrile, 2-[8-[2-fluoro-6-(trifluoromethyl)phenyl]-5,6-dihydro-8H-imidazo[2,1-c][1,4]oxazin-2-yl]-4-methoxy-1H-indole-5-carbonitrile (R or S), 2-[8-[2-fluoro-6-(trifluoromethyl)phenyl]-5,6-dihydro-8H-imidazo[2,1-c][1,4]oxazin-2-yl]-4-methoxy-1H-indole-5-carbonitrile (S or R), 2-[8-(3-chloro-4-fluorophenyl)-5,6-dihydro-8H-imidazo[2,1-c][1,4]oxazin-2-yl]-4-methoxy-1H-indole-5-carbonitrile (R or S), 2-[8-(3-chloro-4-fluorophenyl)-5,6-dihydro-8H-imidazo[2,1-c][1,4]oxazin-2-yl]-4-methoxy-1H-indole-5-carbonitrile (S or R), 2-[8-(3-chloro-4-fluorophenyl)-5,6-dihydro-8H-[1,2,4]triazolo[5,1-c][1,4]oxazin-2-yl]-4-methoxy-1H-indole-5-carbonitrile (R or S), 2-[8-(3-chloro-4-fluorophenyl)-5,6-dihydro-8H-[1,2,4]triazolo[5,1-c][1,4]oxazin-2-yl]-4-methoxy-1H-indole-5-carbonitrile (S or R), 2-[8-(5-fluoro-2-methylphenyl)-5,6-dihydro-8H-imidazo[2,1-c][1,4]oxazin-2-yl]-4-methoxy-1H-indole-5-carbonitrile (R or S), 2-[8-(5-fluoro-2-methylphenyl)-5,6-dihydro-8H-imidazo[2,1-c][1,4]oxazin-2-yl]-4-methoxy-1H-indole-5-carbonitrile (S or R), 2-[8-[2-fluoro-5-(trifluoromethyl)phenyl]-5,6-dihydro-8H-[1,2,4]triazolo[5,1-c][1,4]oxazin-2-yl]-4-methoxy-1H-indole-5-carbonitrile (R or S), 2-[8-[2-fluoro-5-(trifluoromethyl)phenyl]-5,6-dihydro-8H-[1,2,4]triazolo[5,1-c][1,4]oxazin-2-yl]-4-methoxy-1H-indole-5-carbonitrile (S or R), 2-[8-[2-fluoro-6-(trifluoromethyl)phenyl]-5,6-dihydro-8H-[1,2,4]triazolo[5,1-c][1,4]oxazin-2-yl]-4-methoxy-1H-indole-5-carbonitrile (R or S), 2-[8-[2-fluoro-6-(trifluoromethyl)phenyl]-5,6-dihydro-8H-[1,2,4]triazolo[5,1-c][1,4]oxazin-2-yl]-4-methoxy-1H-indole-5-carbonitrile (S or R), 2-[8-[2-fluoro-5-(trifluoromethyl)phenyl]-5,6-dihydro-8H-imidazo[2,1-c][1,4]oxazin-2-yl]-4-methoxy-1H-indole-5-carbonitrile (R or S), 2-[8-[2-fluoro-5-(trifluoromethyl)phenyl]-5,6-dihydro-8H-imidazo[2,1-c][1,4]oxazin-2-yl]-4-methoxy-1H-indole-5-carbonitrile (S or R), 2-[5,6-dihydro-8-[2-(trifluoromethyl)phenyl]-8H-imidazo[2,1-c][1,4]oxazin-2-yl]-4-methoxy-1H-indole-5-carbonitrile (S or R), 2-[5,6-dihydro-8-[2-(trifluoromethyl)phenyl]-8H-imidazo[2,1-c][1,4]oxazin-2-yl]-4-methoxy-1H-indole-5-carbonitrile (R or S), 2-[8-(4-fluoro-2-methylphenyl)-5,6,7,8-tetrahydro-7-methyl[1,2,4]triazolo[1,5-a]pyrazin-2-yl]-4-methoxy-1H-indole-5-carbonitrile, 2-[9-(4-fluoro-2-methylphenyl)-6,7-dihydro-5H,9H-[1,2,4]triazolo[5,1-c][1,4]oxazepin-2-yl]-4-methoxy-1H-indole-5-carbonitrile (R or S), 2-[9-(4-fluoro-2-methylphenyl)-6,7-dihydro-5H,9H-[1,2,4]triazolo[5,1-c][1,4]oxazepin-2-yl]-4-methoxy-1H-indole-5-carbonitrile (S or R), 2-[8-(4-fluoro-2-methylphenyl)-5,6-dihydro-8H-[1,2,4]triazolo[5,1-c][1,4]oxazin-2-yl]-4-(1-methylethoxy)-1H-indole-5-carbonitrile, 2-[8-(4-fluoro-2-methylphenyl)-5,6-dihydro-8H-imidazo[2,1-c][1,4]oxazin-2-yl]-4-(2-methoxyethoxy)-1H-indole-5-carbonitrile, 4-(2,2-difluoroethoxy)-2-[8-(4-fluoro-2-methylphenyl)-5,6-dihydro-8H-[1,2,4]triazolo[5,1-c][1,4]oxazin-2-yl]-1H-indole-5-carbonitrile, 2-[9-(4-fluoro-2-methylphenyl)-6,7-dihydro-5H,9H-imidazo[2,1-c][1,4]oxazepin-2-yl]-4-methoxy-1H-indole-5-carbonitrile, 4-methoxy-2-[5,6,7,8-tetrahydro-8-[3-methyl-1-(2,2,2-trifluoroethyl)-1H-pyrazol-5-yl]imidazo[1,2-a]pyridin-2-yl]-1H-indole-5-carbonitrile, 1H-indole-5-carbonitrile, 4-methoxy-2-[5,6,7,8-tetrahydro-8-[5-methyl-1-(2,2,2-trifluoroethyl)-1H-pyrazol-3-yl]imidazo[1,2-a]pyridin-2-yl]-2-[8-(4-fluoro-2-methylphenyl)-5,6-dihydro-8H-[1,2,4]triazolo[5,1-c][1,4]oxazin-2-yl]-4-(1-methylethoxy)-1H-indole-5-carbonitrile (R or S), 2-[8-(4-fluoro-2-methylphenyl)-5,6-dihydro-8H-[1,2,4]triazolo[5,1-c][1,4]oxazin-2-yl]-4-(1-methylethoxy)-1H-indole-5-carbonitrile (S or R), 4-methoxy-2-[5,6,7,8-tetrahydro-8-[3-methyl-1-(2,2,2-trifluoroethyl)-1H-pyrazol-5-yl]imidazo[1,2-a]pyridin-2-yl]-1H-indole-5-carbonitrile (R or S), 4-methoxy-2-[5,6,7,8-tetrahydro-8-[3-methyl-1-(2,2,2-trifluoroethyl)-1H-pyrazol-5-yl]imidazo[1,2-a]pyridin-2-yl]-1H-indole-5-carbonitrile (S or R), 4-ethoxy-2-[8-(4-fluoro-2-methylphenyl)-5,6-dihydro-8H-[1,2,4]triazolo[5,1-c][1,4]oxazin-2-yl]-1H-indole-5-carbonitrile, 2-[8-(4-fluoro-2-methylphenyl)-5,6,7,8-tetrahydro-8-hydroxy[1,2,4]triazolo[1,5-a]pyridin-2-yl]-4-methoxy-1H-indole-5-carbonitrile, 2-[8-(2-cyclopropylphenyl)-5,6-dihydro-8H-imidazo[2,1-c][1,4]oxazin-2-yl]-4-methoxy-1H-indole-5-carbonitrile (R or S), 2-[8-(2-cyclopropylphenyl)-5,6-dihydro-8H-imidazo[2,1-c][1,4]oxazin-2-yl]-4-methoxy-1H-indole-5-carbonitrile (S or R), 2-[5,6-dihydro-8-[2-(trifluoromethyl)phenyl]-8H-imidazo[2,1-c][1,4]oxazin-2-yl]-4-methoxy-1H-indole-5-carbonitrile, tautomers and stereoisomeric forms thereof,
and the pharmaceutically acceptable addition salts and the solvates thereof.

In an embodiment the compound of Formula (I) is selected from the group consisting of:
5,6,7,8-tetrahydro-2-[5-(4-methyl-1H-imidazol-1-yl)-1H-indol-2-yl]-8-[2-(trifluoromethyl)phenyl]-[1,2,4]triazolo[1,5-a]pyridine, and
5,6-dihydro-2-[5-(4-methyl-1H-imidazol-1-yl)-1H-indol-2-yl]-8-[2-(trifluoromethyl)phenyl]-8H-[1,2,4]triazolo[5,1-c][1,4]oxazine,
tautomers and stereoisomeric forms thereof,
and the pharmaceutically acceptable addition salts and the solvates thereof.

Preferred compounds are compounds 8 and 37, tautomers and stereoisomeric forms thereof, and pharmaceutically acceptable addition salts and solvates thereof.

Preferred compounds are compounds 41, 44 and 50, tautomers thereof, and pharmaceutically acceptable addition salts and solvates thereof.

Preferred compounds are compounds 41, 44 and 50.

All possible combinations of the above-indicated interesting embodiments are considered to be embraced within the scope of this invention.

Preparation of the Compounds

The present invention also encompasses processes for the preparation of compounds of Formula (I) and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999. The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry. The general preparation of some typical examples is shown below. The skilled person will realize that where the general preparation in the experimental procedures described below is exemplified for -$R^1$-$R^2$- having formula (b-1), analogous reaction protocols can be used to prepare the corresponding compounds having formula (b-2) for -$R^1$-$R^2$-; the same is valid for most of the reactions described for unprotected compounds: analogous reaction protocols can be used on the corresponding protected compounds.

Experimental Procedure 1a

A compound of formula (I) wherein X is N, hereby named a compound of formula (I-a), can be prepared, starting from a Suzuki reaction between an intermediate of formula (II-a) with an intermediate of formula (III-a1) wherein PG is a protecting group and B(OR$^9$)(OR$^{10}$) refers to the boronic acid B(OH)$_2$ or its corresponding boronate ester, such as a pinacol ester. After this first step, an intermediate of formula (IV-a1) is obtained. In a second step, a deprotection reaction of (IV-a1) is performed to obtain a compound of formula (I-a). In Scheme 1a, halo is defined as Cl, Br or I and all other variables are defined as mentioned hereabove.

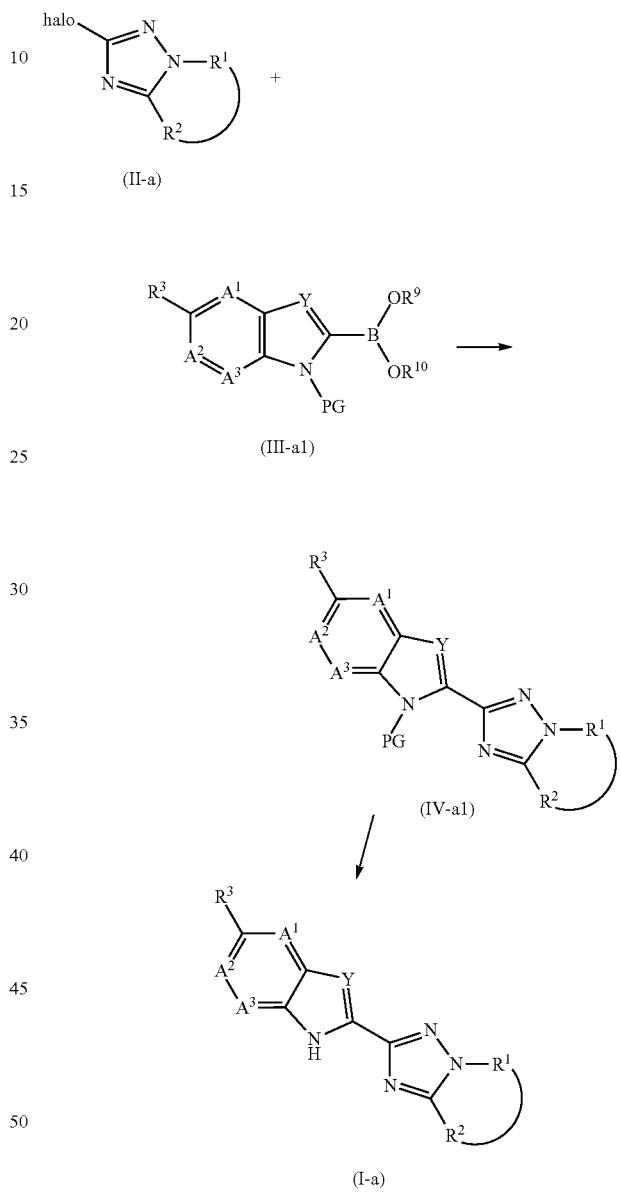

Scheme 1a

Experimental Procedure 1b

A compound of formula (I-a) wherein R$^3$ is restricted to R$^{3a}$ being cyano or Het$^1$, hereby named a compound of formula (I-a1), can also be prepared, starting from a Suzuki reaction between an intermediate of formula (II-a) with an intermediate of formula (III-a2) wherein PG is a protecting group and B(OR$^9$)(OR$^{10}$) refers to the boronic acid B(OH)$_2$ or its corresponding boronate ester, such as a pinacol ester. This reaction gives an intermediate of formula (IV-a2). An intermediate of formula (IV-a2) can be converted to an intermediate of formula (I-a1) with a deprotection reaction followed by a coupling reaction to introduce R$^{3a}$ via Suzuki reaction with aryl- or alkyl-boronates, or via palladium or copper catalysed reactions known to the person skilled in the art, such as for example the Rosenmund-von Braun reaction, the palladium catalyzed cyanation in the presence of zinc cyanide and the Buchwald-Hartwig coupling. In Scheme 1b, halo is defined as Cl, Br or I, and $R^{3a}$ is defined as cyano or $Het^1$. All other variables are defined as mentioned hereabove.

Scheme 1b

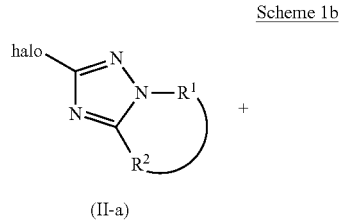

(II-a)

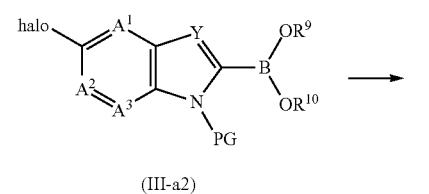

(III-a2)

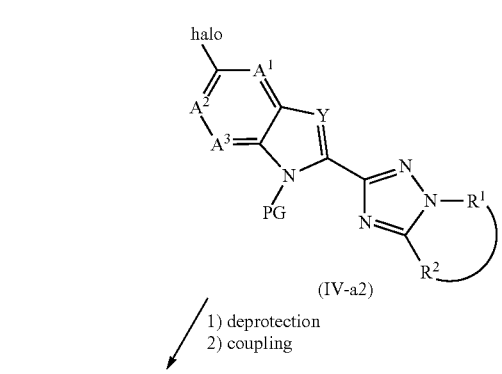

(IV-a2)

1) deprotection
2) coupling

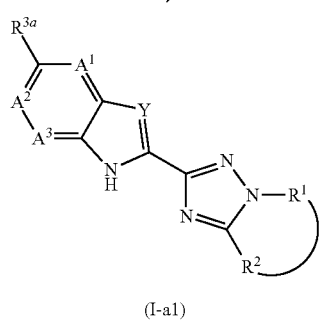

(I-a1)

The Suzuki reaction used in Scheme 1b, can also be used to prepare compounds of formula (I-a1) wherein $R^{3a}$ is $C_{1-4}$alkyloxy. To obtain these compounds, one should use (III-a3) as starting material instead of (III-a2):

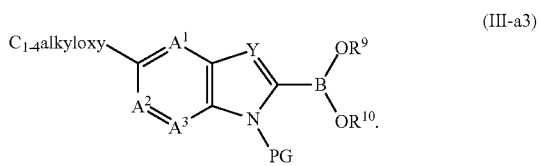

(III-a3)

Experimental Procedure 2

A compound of formula (I), wherein

Y is CH, CF or N;

X is N;

$R^1$ and $R^2$ are taken together to form a bivalent radical -$R^1$-$R^2$- having formula (b-1)

$$-(CH_2)_m-Z-(CH_2)-\qquad(b\text{-}1);$$

wherein Z is a direct bond, $NR^5$ or O; and $R^{16a}$ is hydrogen, $Ar^2$, (C=O)—$Ar^2$, $C_{1-4}$alkylcarbonyl, or $C_{1-4}$alkyl optionally substituted with one or more fluoro substituents;

or $R^{16a}$ additionally represents hydroxy, $OAr^2$ or $NR^6Ar^2$ provided that Z is a direct bond;

hereby named (I-b1), can be prepared, starting from a reaction between an intermediate of formula (V-b) with an appropriate intermediate of formula (VI) to give an intermediate of formula (VII-b). The reaction may be performed under protecting atmosphere such as, for example, $N_2$ atmosphere. The reaction typically is performed in an organic solvent such as, for example, methanol. Optionally, the reaction is performed in the presence of a base such as, for example, imidazole. The obtained intermediate (VII-b) can be converted into an intermediate of formula (I-b1) via Suzuki reaction with aryl- or alkyl-boronates, or via palladium or copper catalysed reactions known to the person skilled in the art, such as for example the Rosenmund-von Braun reaction, the palladium catalyzed cyanation in the presence of zinc cyanide and the Buchwald-Hartwig coupling. Alternatively, a compound of formula (I-b1) can be prepared in a single step by cyclizing an intermediate of formula (V-c), having already the desired residual $R^3$ in place, with an appropriate intermediate of formula (VI), under similar conditions to the ones described above. In Scheme 2, halo is defined as Cl, Br or I.

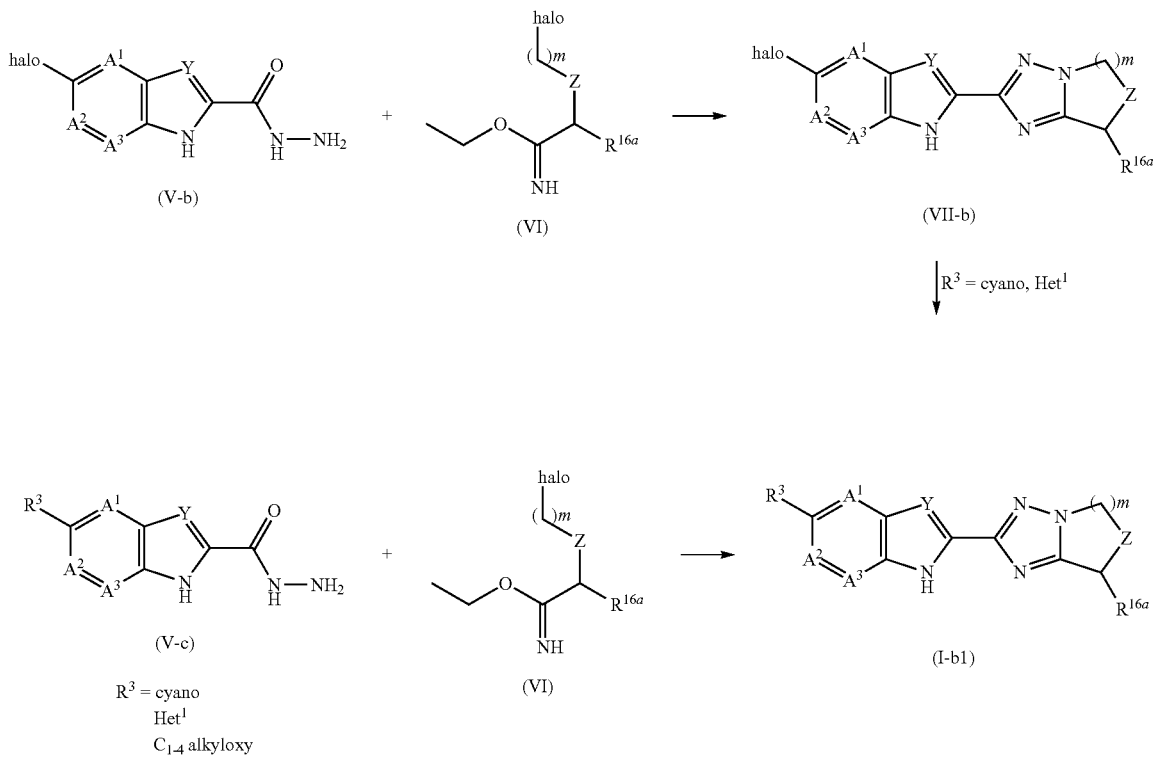

Experimental Procedure 3

A compound of formula (I) wherein Y is CH and X is N, hereby named a compound of formula (I-b2), can be prepared by an intramolecular hydroamination reaction of an intermediate of formula (II-b) in the presence of water and a salt such as, for example, potassium chloride in a suitable inert solvent, such as DMF. Stirring and microwave irradiation may enhance the rate of the reaction.

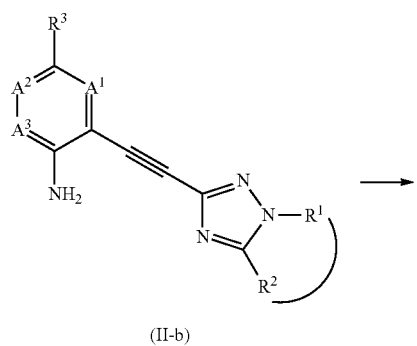

-continued

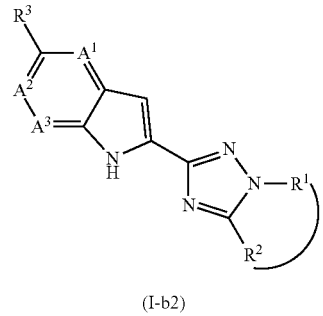

Experimental Procedure 4

A compound of formula (I) wherein X is CH, hereby named a compound of formula (I-c), can be prepared, starting from a condensation reaction between an intermediate of formula (VIII) wherein PG is a protecting group with an intermediate of formula (IX) to give an intermediate of formula (X), followed by a deprotection reaction of intermediate of formula (X) to a compound of formula (I-c). The condensation typically can be performed in an organic solvent such as, for example, ethanol. Optionally, the reaction is performed in the presence of a base such as, for example, $Na_2CO_3$. Alternatively, the analogous synthetic sequence can be applied to an intermediate of structure (VIII-a): the so-obtained intermediate (X-a) can subsequently be converted into intermediate (X) via either copper catalysed reaction with the desired heterocycle or palladium catalysed reaction with zinc cyanide or via Suzuki reaction with the suitable boron derivative.

In some cases the reaction sequence can be performed as well on the unprotected intermediates: in this case intermediate (X) is then not synthesized. When halo=Cl, an in situ Filkenstein reaction, using sodium iodide and acetone, may improve the reaction outcome. In Scheme 4, halo is defined as Cl, Br or I.
Scheme 4
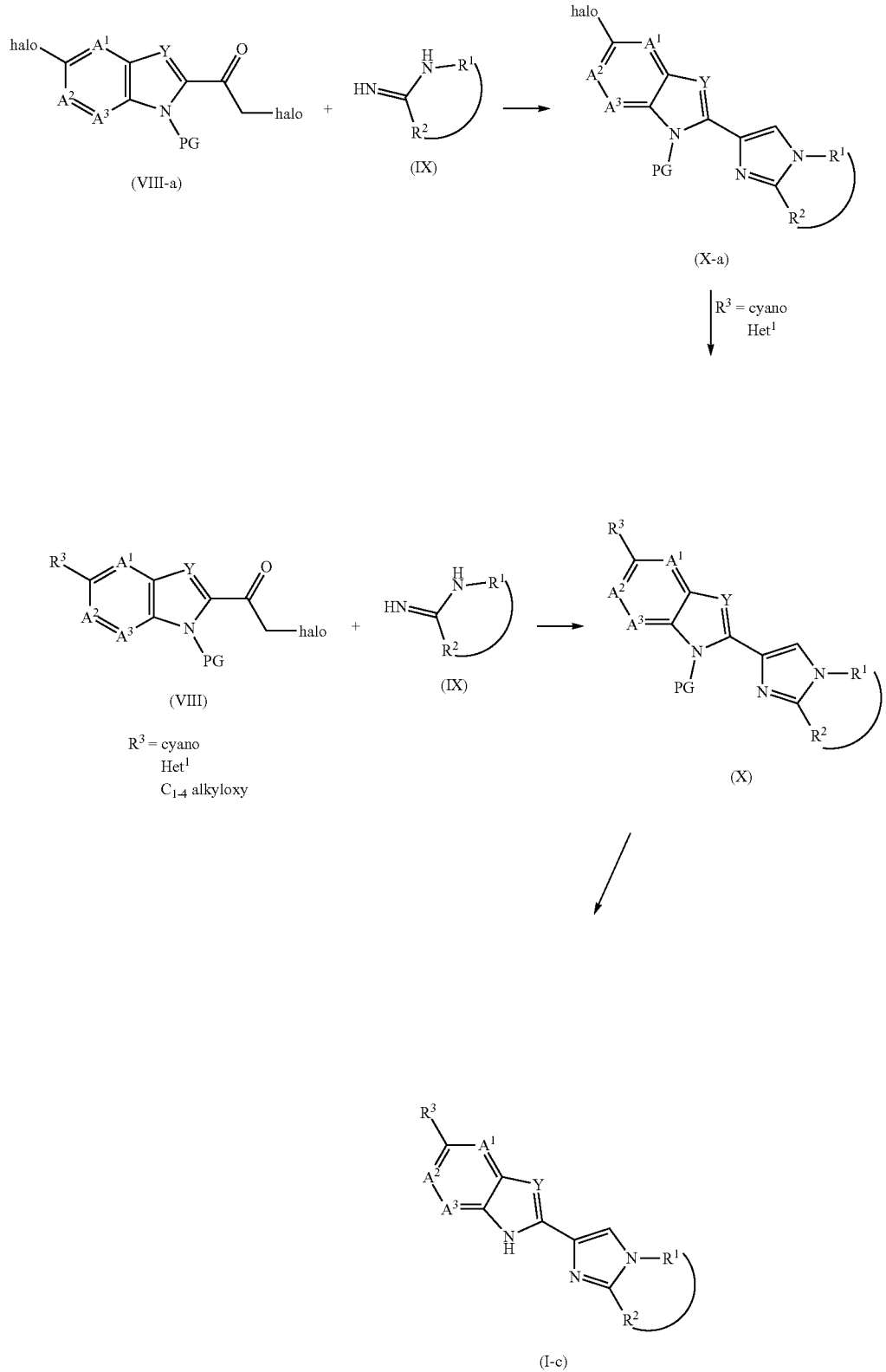

Experimental Procedure 5

An intermediate of formula (II-a), wherein

R¹ and R² are taken together to form a bivalent radical -R¹-R²- having formula (b-1)

—(CH$_2$)$_m$—Z—(CH$_2$)—        (b-1);

Z is O; and wherein a substituent $R^{16c}$ is present being hydrogen, $Ar^2$, (C=O)—$Ar^2$, $C_{1-4}$alkylcarbonyl, or $C_{1-4}$alkyl optionally substituted with one or more fluoro substituents; hereby named an intermediate of formula (II-a1);

can be prepared as set below in Scheme 5. Reaction of an intermediate of formula (XI) with an alkylating agent of formula (XII), wherein PG is a protecting group, leads to an intermediate of formula (XIII). Lithium-halogen exchange of (XIII), for example via treatment of (XIII) with n-BuLi at a temperature below −50° C., followed by quenching with an intermediate of formula (XIV-a) gives an intermediate of formula (XV). Deprotection of the intermediate of formula (XV) leads to intermediate of formula (XVI). This intermediate can be cyclised (dehydration) intramolecularly in acidic media such as, for example, para-toluene sulfonic acid, in a suitable solvent such as toluene or xylene at refluxing temperatures (Dean-Stark conditions) to give the required intermediate of formula (II-a1). The protecting group PG should be selected according to the known art to survive the reaction conditions of the steps leading to intermediate (XV), for example a tetrahydropyranyl group. Deprotection conditions to give intermediate (XVI) can be carried out according to procedures known in the art.

It will be appreciated by those skilled in the art that when $R^{16c}$ is (C=O)—$Ar^2$ or $C_{1-4}$alkylcarbonyl, the carbonyl group needs to be blocked by protecting groups. After the reaction, the protected carbonyl groups can be deprotected.

In Scheme 5, halo is defined as Cl, Br or I and all other variables are defined as mentioned hereabove.

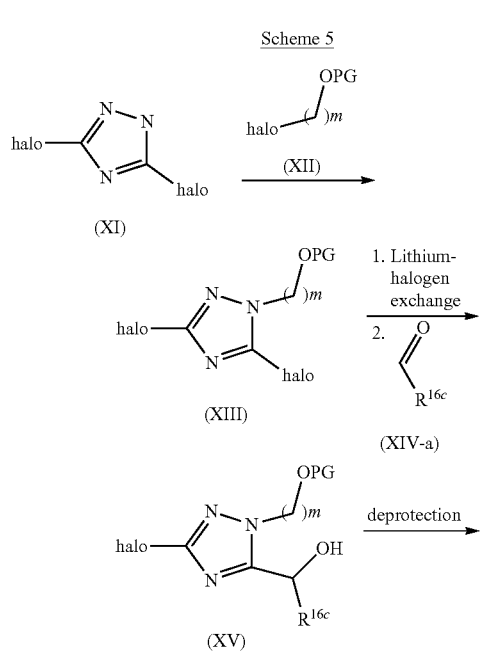

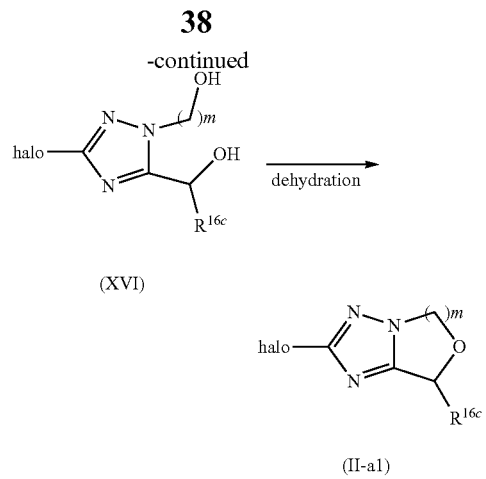

Experimental Procedure 6

An intermediate of formula (II-a), wherein

Z is a direct bond;

m=3; and wherein a substituent $R^{16d}$ is present being $Ar^2$ or $C_{1-4}$alkyl;

can be prepared according to Scheme 6. Reaction of an intermediate of formula (XVII) with an alkoxycarbonyl isothiocyanate intermediate such as, for example, alkoxycarbonyl isothiocyanate leads to an intermediate of formula (XVIII). Treatment of an intermediate of formula (XVIII) with hydroxylamine gives an intermediate of formula (XIX). An intermediate of formula (XIX) can be converted to an intermediate of formula (XXI) via Suzuki reactions. Reduction of an intermediate of formula (XXI) via reductive hydrogenation leads to intermediate of formula (XXII). This intermediate of formula (XXII) can be converted to the required intermediate of formula (II-a2) using typical conditions known to those skilled in the art. In Scheme 7, halo is defined as Cl, Br or I, $R^{11}$ is $C_{1-4}$alkyl, and $B(OR^{12})(OR^{13})$ refers to the boronic acid $B(OH)_2$ or its corresponding boronate ester, such as a pinacol ester. All other variables are defined as mentioned hereabove.

Scheme 6

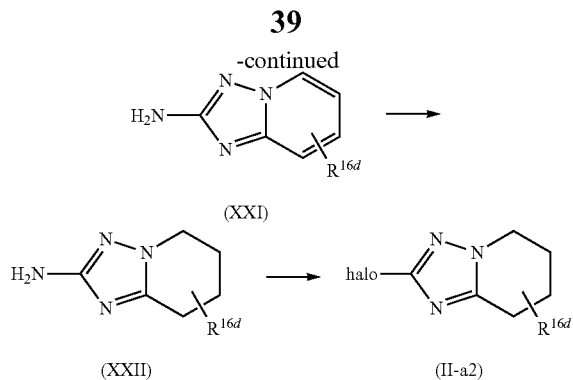

An intermediate of formula (II-a2) wherein $R^{16d}$ is $NR^6$—$Ar^2$ can be prepared by an analogous reaction protocol as described in Scheme 7 wherein the intermediate of formula (XX) is replaced by an intermediate of formula (XX-a) and will react under Buchwald conditions.

Similar, an intermediate of formula (II-a2) wherein $R^{16d}$ is $OAr^2$ can be prepared via a palladium-based reaction.

An analogous reaction protocol as described in scheme 6 can also be used to prepare compounds of formula (II-a2) wherein $R^{16d}$ is hydrogen. In this case 2-aminopyridine is used as the starting material.

Experimental Procedure 7

An intermediate of formula (V-b), wherein halo is defined as Cl, Br or I, can be prepared as set below in Scheme 7.

Intermediates of formula (XXVII) can be prepared following the teachings described in WO 2005/085245 and the Reissert indole synthesis (Reissert, Chemische Berichte 1897, 30, 1030) starting from an intermediate of formula (XOH). Alternatively an intermediate of formula (XXVII) can also be prepared in two steps starting from an intermediate of formula (XXV) following J. Med. Chem. 2004, 5298-5310 and WO 2010/065310. Reaction of an intermediate of formula (XXVII) with hydrazine gives the required intermediate of formula (V-b). Alternatively, intermediate (V-b) can be also be obtained in a single step by reaction of an acid such as (XLII) with hydrazine in the presence of a peptide coupling reagent, such as for example CDI (carbonyldiimidazole). In Scheme 7, halo is defined as Cl, Br or I, $R^{14}$ is $C_{1-4}$alkyl and all other variables are defined as before.

Scheme 7

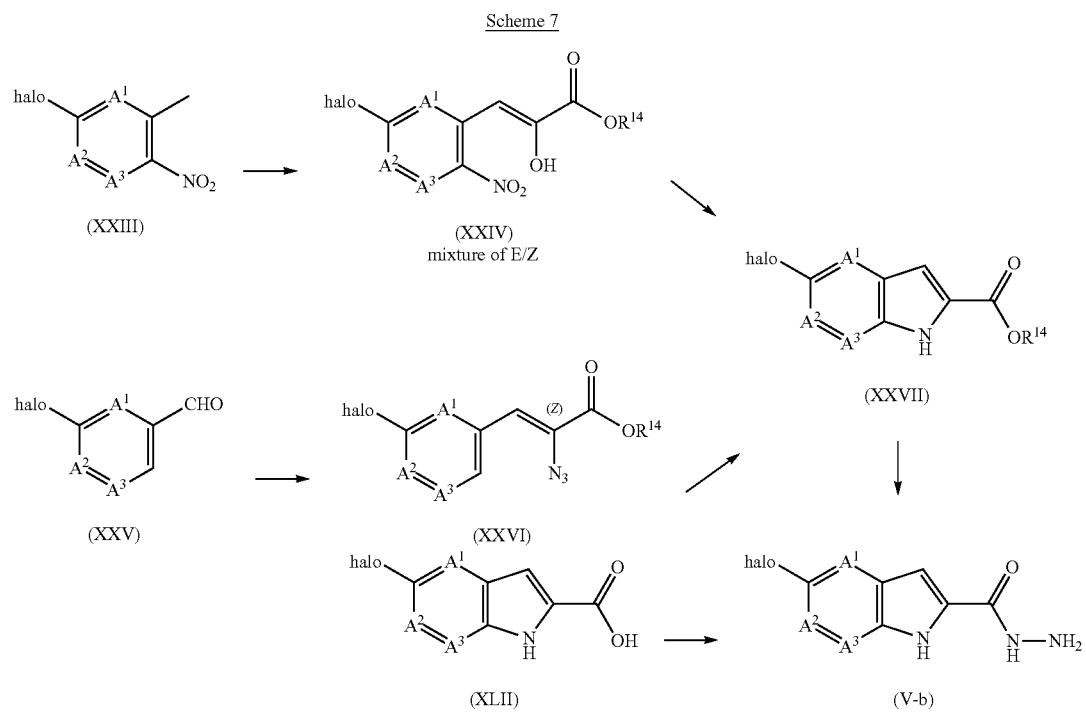

Alternatively, an intermediate of formula (V-c), wherein the residual $R^{3a}$=cyano or $Het^1$ is already in place, can be prepared as set below in Scheme 7a. For $R^{3a}$=$Het^1$, intermediate (XOH) can be converted into intermediate (XXIII-a) by methods known to the person skilled in the art, such as for example substitution of the halogen with the desired heterocycle. Intermediate (XXIII-a) can then undergo a synthetic sequence similar to the one reported in Scheme 7, to yield intermediate (V-c).

Intermediate (V-c) can also be obtained by exchanging the halo group for $R^{3a}$=cyano in intermediate (XXVII). This can be achieved for example by catalytic cyanation in the presence of zinc cyanide and a palladium catalyst. Intermediate (XXVII-a) can then be converted into intermediate (V-c) by mean of a synthetic sequence similar to the one reported in Scheme 7. The skilled in the art will notice that protection of the indole nitrogen can be necessary. In Scheme 7a halo is F, Cl, Br or I.

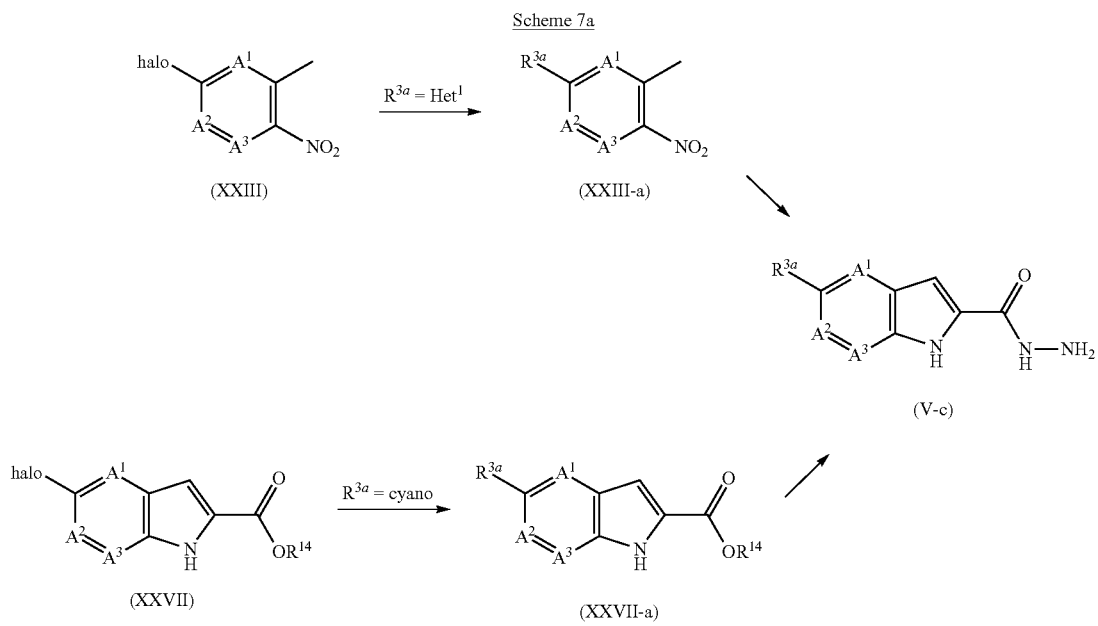

Experimental Procedure 8

An intermediate of formula (VI), wherein Z is a direct bond, hereby named (VI-a) can be prepared as set below in Scheme 8. Reaction of an intermediate with formula (XXVIII) with an alkylating agent of formula (XXIX) leads to intermediate of formula (XXX). This intermediate can be converted to an intermediate of formula (VI-a) using typical reaction conditions known to those skilled in the art. In Scheme 8, halo is defined as Cl, Br or I and all other variable are as defined before.

intermediate of formula (XXX-b). This intermediate can be converted to an intermediate of formula (VI-b) using typical reaction conditions known to those skilled in the art. In Scheme 9, halo is defined as Cl, Br or I and all other variable are defined as before. $R^{16b}$ is hydrogen, $Ar^2$, (C=O)—$Ar^2$, $C_{1-4}$alkylcarbonyl, or $C_{1-4}$alkyl optionally substituted with one or more fluoro substituents.

The skilled person will realize that carbonyl groups may need to be blocked by protecting groups. They can be deprotected after reaction.

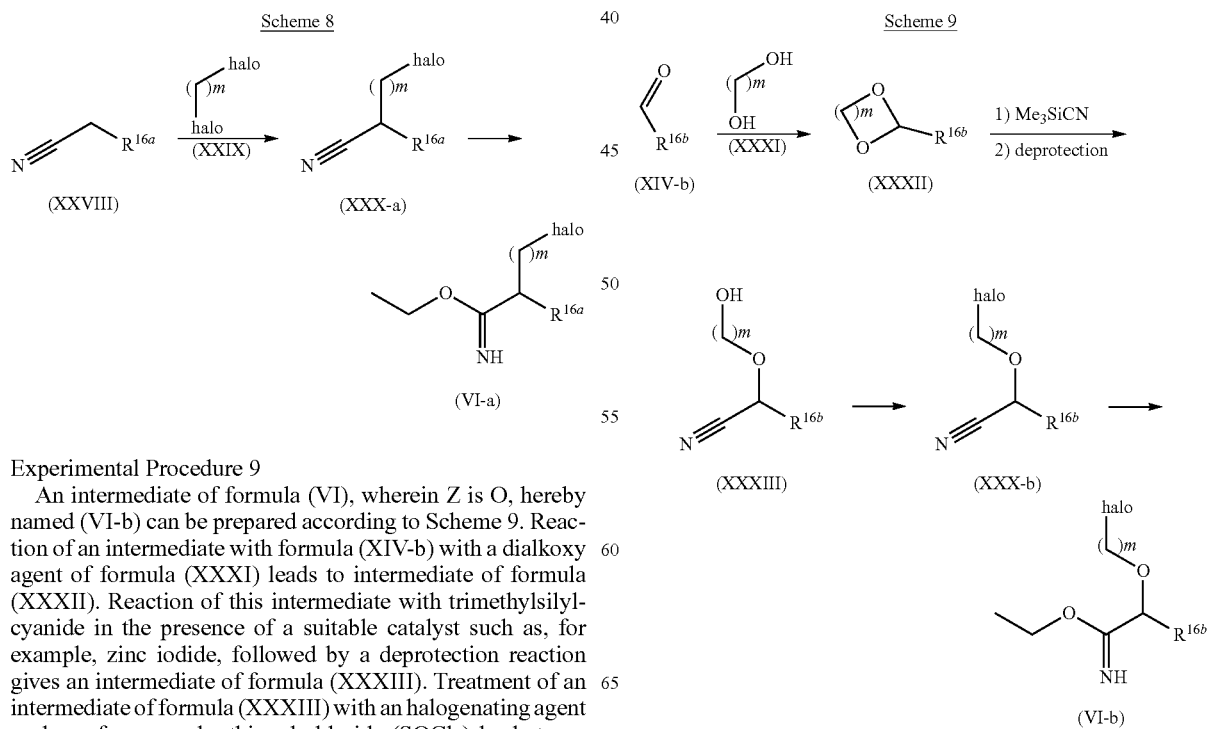

Experimental Procedure 9

An intermediate of formula (VI), wherein Z is O, hereby named (VI-b) can be prepared according to Scheme 9. Reaction of an intermediate with formula (XIV-b) with a dialkoxy agent of formula (XXXI) leads to intermediate of formula (XXXII). Reaction of this intermediate with trimethylsilyl-cyanide in the presence of a suitable catalyst such as, for example, zinc iodide, followed by a deprotection reaction gives an intermediate of formula (XXXIII). Treatment of an intermediate of formula (XXXIII) with an halogenating agent such as, for example, thionyl chloride (SOCl$_2$) leads to an Experimental Procedure 10

An intermediate of formula (II-b) can be prepared starting from an intermediate of formula (II-a) as set below in Scheme 10. Intermediate of formula (XXXIV) can be prepared via Sonogashira reaction from an intermediate of formula (II-a) using typical reaction conditions known by those skilled in the art, followed by a deprotection reaction. The intermediate of formula (XXXIV) can be converted to an intermediate of formula (II-b) via another Sonogashira reaction with an intermediate of formula (XXXV). In Scheme 10, halo is defined as Cl, Br or I and all other variable are defined as before.

Experimental Procedure 11

An intermediate of formula (VIII) wherein PG is a protecting group can be prepared as set below in Scheme 11. Protection of an intermediate of formula (XXXVI) followed by Stille reaction leads to intermediate of formula (XXXVII) using typical reaction conditions known by those skilled in the art. This intermediate can be converted to an intermediate of formula (VIII) using an halogenating agent such as, for example, N-bromosuccinimide. In Scheme 11, halo is defined as Cl, Br or I, $R^{15}$ is alkyl and all other variable are defined as before.

Scheme 10

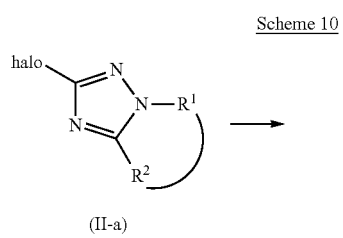

(II-a)

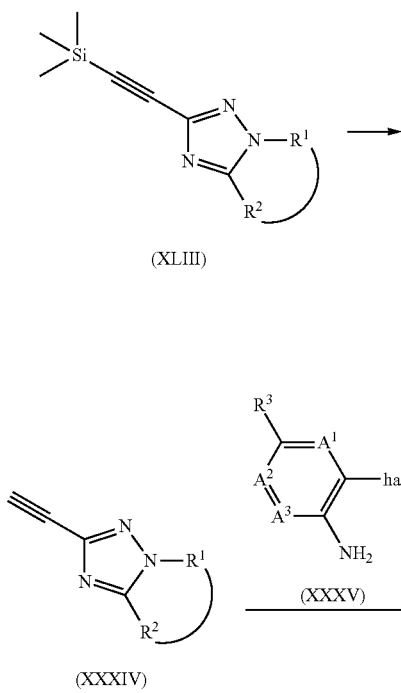

(XLIII)

(XXXIV)

(II-b)

Scheme 11

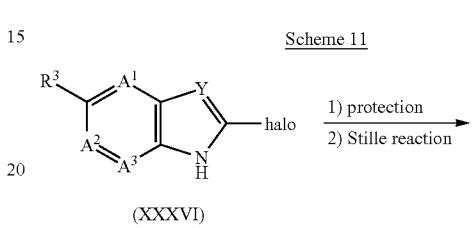

(XXXVI)

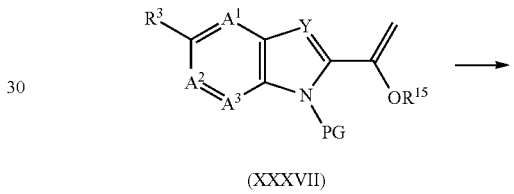

(XXXVII)

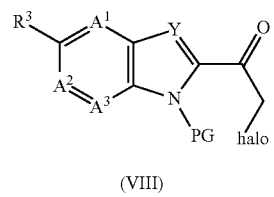

(VIII)

Alternatively, an intermediate of formula (VIII), where $R^{3b}$ is $C_{1-4}$alkyloxy, cyano and $Het^1$ or an halogen such as Cl, Br or I, hereby called intermediate (VIII-b), can be prepared by mean of a 4-step synthesis, starting from ester (XXXVIII). In the first step, the ester can undergo hydrolysis under standard conditions, such as for example by treating the intermediate in the presence of an hydroxide such as lithium hydroxide (LiOH). In the second step the ester should be converted into the corresponding acyl chloride using a suitable reagent, such as for example oxalyl chloride. The so-obtained intermediate (XL) can be sequentially treated with trimethylsilyldiazomethane, followed by hydrobromic acid, to afford intermediate (VIII), where halo is Br. Intermediate ester (XXXVIII) can also undergo a chloroacetate Claisen reaction (Wang et al. Synlett 2000, 6, 902) to afford in one step intermediate (VIII) where halo is Cl. Scheme 11a summarizes the synthetic route; PG is a suitable protecting group for indoles and $R^{3b}$ is cyano, $Het^1$, Br, Cl or I.

Scheme 11a

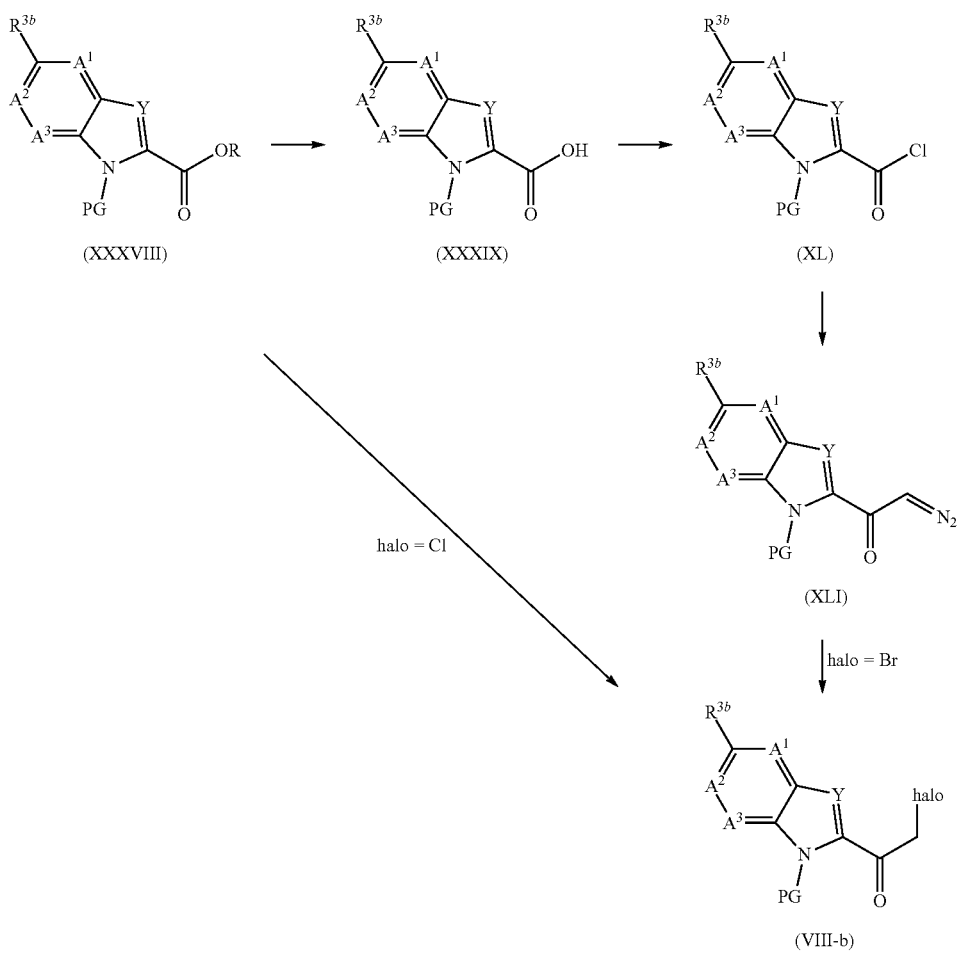

Experimental Procedure 12

An intermediate of formula (IX) wherein $R^1$ and $R^2$ are taken together to form a bivalent radical $-R^1-R^2-$ having formula (b-1)

$$-(CH_2)_m-Z-(CH_2)- \qquad (b-1);$$

Z is a direct bond or O; and wherein a substituent $R^{16e}$ is present being hydrogen, $Ar^2$, $(C=O)-Ar^2$, $C_{1-4}$alkylcarbonyl, or $C_{1-4}$alkyl optionally substituted with one or more fluoro substituents;

or $R^{16e}$ additionally represents hydroxy, $OAr^2$ or $NR^6Ar^2$ provided that Z is a direct bond;

hereby named an intermediate of formula (IX-a), can be prepared by a condensation reaction of an intermediate of formula (VI) with an ammonia source such as, for example, ammonia ($NH_3$). In Scheme 12, halo is defined as Cl, Br or I and all other variables are defined as before.

Scheme 12

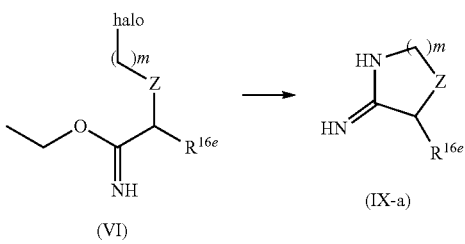

Experimental Procedure 13

An intermediate of formula (V-d) can be prepared according to Scheme 13. Condensation of an intermediate of formula (XLIV) with a trichloroacetimidate intermediate such as, for example, ethyl 2,2,2-trichloroacetimidate leads to an intermediate of formula (XLV). This intermediate can be activated by coupling reagents such as, for example, 1,1'-carbonyldiimidazole (CDI) or 1-[bis-(dimethylamino)methylene]-1H-benzotriazol-1-ium 3-oxide hexafluorophosphate (HBTU), and condensated with a protected hydrazine intermediate such as, for example, tert-butyl carbazate, followed by a deprotection reaction to give the required intermediate of formula (V-d). In Scheme 13, all variables are defined as before.

Scheme 13

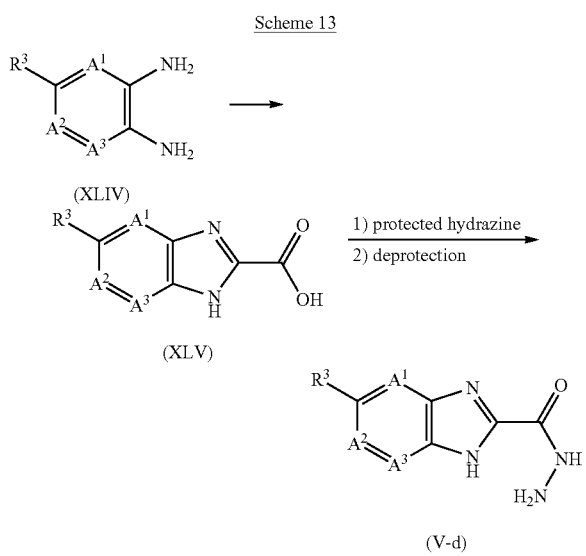

Experimental Procedure 14

An intermediate of formula (XLVIII), wherein Y is CF, can be prepared starting from intermediate ester (XLVI) via known indole fluorination methods, such as for example the conditions described in WO 2010/045188. Intermediate (XLVII) can then be converted into intermediate (XLVIII) for example by reaction with hydrazine. In Scheme 14, Y is CF and $R^{14}$ is an appropriate alkyl chain.

Scheme 14

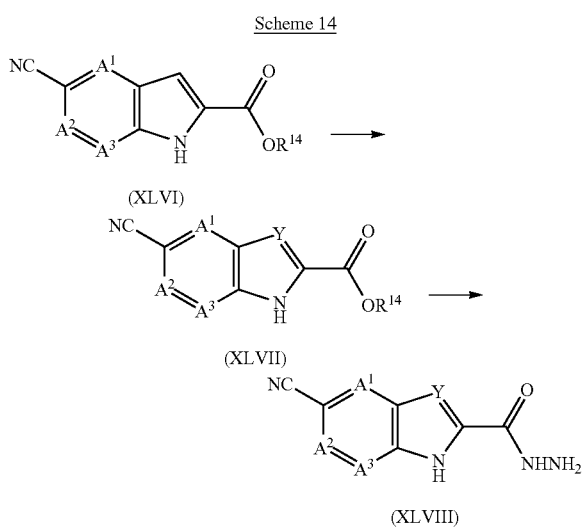

All starting materials can be obtained commercially or can be prepared by those skilled in the art.

In order to obtain the HCl salt forms of the compounds, several procedures known to those skilled in the art can be used. In a typical procedure, for example, the free base can be dissolved in DIPE or $Et_2O$ and subsequently, a 6 N HCl solution in 2-propanol or a 1 N HCl solution in $Et_2O$ can be added dropwise. The mixture typically is stirred for 10 minutes after which the product can be filtered off. The HCl salt usually is dried in vacuo.

Where necessary or desired, any one or more of the following further steps in any order may be performed:

Compounds of Formula (I), any subgroup thereof, addition salts, solvates, and stereochemical isomeric forms thereof can be converted into further compounds according to the invention using procedures known in the art.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak® AD (amylose 3,5 dimethylphenyl carbamate) or Chiralpak® AS, both purchased from Daicel Chemical Industries, Ltd, in Japan, or by Supercritical Fluid Chromatography (SFC).

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention modulate the γ-secretase activity. The compounds according to the invention and the pharmaceutically acceptable compositions thereof therefore may be useful in the treatment or prevention of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid; preferably AD.

The compounds according to the present invention and the pharmaceutically acceptable compositions thereof may be useful in the treatment or prevention of a disease or condition selected from the group consisting of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of γ-secretase modulators in therapy, it seems particularly advantageous not to interfere with the Notch-processing activity of the γ-secretase activity in order to avoid putative undesired side-effects.

While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42, without decreasing the production of smaller, less aggregatable forms of Aβ, i.e. Aβ38 and without concomitant inhibition of Notch processing. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, but does not necessarily indicate a total elimination of all symptoms.

The invention relates to a compound according to the general Formula (I), the tautomers and the stereoisomeric forms thereof, and the pharmaceutically acceptable acid or base addition salts and the solvates thereof, for use as a medicament.

The invention also relates to a compound according to the general Formula (I), the tautomers and the stereoisomeric forms thereof and the pharmaceutically acceptable acid or base addition salts and the solvates thereof, for use in the modulation of γ-secretase activity.

The invention also relates to a compound according to the general Formula (I), the tautomers and the stereoisomeric forms thereof, and the pharmaceutically acceptable acid or base addition salts and the solvates thereof, for use in the treatment or prevention of diseases or conditions selected from the group consisting of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid.

In an embodiment, said disease or condition is preferably AD.

The invention also relates to a compound according to the general Formula (I), the tautomers and the stereoisomeric forms thereof, and the pharmaceutically acceptable acid or base addition salts and the solvates thereof, for use in the treatment of said diseases.

The invention also relates to a compound according to the general Formula (I), the tautomers and the stereoisomeric forms thereof, and the pharmaceutically acceptable acid or base addition salts and the solvates thereof, for the treatment or prevention of said diseases.

The invention also relates to a compound according to the general formula (I), the tautomers and the stereoisomeric forms thereof, and the pharmaceutically acceptable acid or base addition salts and the solvates thereof, for the treatment or prevention, in particular treatment, of γ-secretase mediated diseases or conditions.

The invention also relates to the use of a compound according to the general Formula (I), the tautomers and the stereoisomeric forms thereof, and the pharmaceutically acceptable acid or base addition salts and the solvates thereof, for the manufacture of a medicament.

The invention also relates to the use of a compound according to the general Formula (I), the tautomers and the stereoisomeric forms thereof and the pharmaceutically acceptable acid or base addition salts and the solvates thereof, for the manufacture of a medicament for the modulation of γ-secretase activity.

The invention also relates to the use of a compound according to the general Formula (I), the tautomers and the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the tautomers and the stereoisomeric forms thereof and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), or any subgroup thereof with a $IC_{50}$ value for the inhibition of the production of Aβ42-peptide of less than 1000 nM, preferably less than 100 nM, more preferably less than 50 nM, even more preferably less than 20 nM as determined by a suitable assay, such as the assay used in the Examples below.

The compounds of the present invention can be administered to mammals, preferably humans for the treatment or prevention of any one of the diseases mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a tautomer or a stereoisomeric form thereof, or a pharmaceutically acceptable addition salt or a solvate thereof, to warm-blooded animals, including humans.

The present invention also concerns to the use of a compound of Formula (I) for the modulation of γ-secretase activity resulting in a decrease in the relative amount of Aβ42-peptides produced.

An advantage of the compounds or a part of the compounds of the present invention may be their enhanced CNS-penetration.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I).

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXAMPLES

Hereinafter, the term "DCM" means dichloromethane; "MeOH" means methanol;

"LCMS" means Liquid Chromatography/Mass spectrometry; "HPLC" means high-performance liquid chromatography; "sol." means solution(s); "o.l." means organic layer(s); "sat." means saturated; "aq." means aqueous; "r.t." means room temperature; "AcOH" means acetic acid; "m.p." means melting point; "$N_2$" means nitrogen, "RP" means reversed phase; "min" means minute(s); "h" means hour(s); "EtOAc" means ethyl acetate; "$Et_3N$" means triethylamine; "EtOH" means ethanol; "eq." means equivalent; "r.m." means reaction mixture(s); "DIPE" means diisopropyl ether; "MTBE" means tert-butyl methyl ether, "q.s." quantum sufficit; "TFA" means trifluoroacetic acid; "THF" means tetrahydrofuran; "DMF" means N,N-dimethyl formamide; "$Pd(PPh_3)_4$" means tetrakis(triphenylphosphine)palladium; "BuLi" means n-butyllithium; "iPrOH" means 2-propanol; "DME" means 1,2-dimethoxyethane; "SFC" means Supercritical Fluid Chromatography; "$MgSO_4$" means magnesium sulphate; "TBAF" means tetrabutylammonium fluoride; "OR"

means optical rotation; "DIPEA" means diisopropylethylamine; "KOAc" means potassium acetate; "w/w" means weight/weight %; "Et$_2$O" means diethyl ether; and "Pd(OAc)$_2$" means palladium(II) acetate; "PdCl$_2$(dppf)" means [1,1'-bis(diphenylphosphino)ferrocene]dichloropalladium; "PdCl$_2$(PPh$_3$)$_2$" means dichlorobis(triphenylphosphine)palladium; "NH$_4$Cl" means ammonium chloride; "d" means day(s); "PTSA" means p-toluensulphonic acid; "NaHCO$_3$" means sodium hydrogencarbonate; "TMSCN" means trimethylsilylcyanide; "DCE" means dichloroethane; "HCl" means hydrochloric acid; "NH$_3$" means ammonia; "NaOH" means sodium hydroxide; "Na$_2$SO$_4$" means sodium sulphate; "CH$_3$CN" means acetonitrile; "wt" means weight; "LiOH" means lithium hydroxide; "CHCl$_3$" means chloroform; "HBTU" means 0-benzotriazole-N,N,N',N'-tetramethyl-uronium-hexafluoro-phosphate; "Na$_2$CO$_3$" means sodium carbonate; "BBr$_3$" means boron tribromide; "PPh$_3$" means triphenylphosphine; "DIAD" means diisopropyl azodicarboxylate; "DAST" means diethylaminosulfur trifluoride; "K$_2$CO$_3$" means potassium carbonate; "CH$_3$I" means methyl iodide; "I$_2$" means iodine; "NaIO$_4$" means sodium periodate; "H$_2$SO$_4$" means sulphuric acid; "Na$_2$S$_2$O$_3$" means sodium thiosulphate; "NaH" means sodium hydride; "DMA" means dimethylacetamide; "dppf" means 1,1'-bis(diphenylphosphino)ferrocene; "HBr" means hydrobromic acid; "Pd$_2$dba$_3$" means tris-dibenzilideneacetone dipalladium; "DIPA" means diisopropylamine; "SEMCl" means 2-(trimethylsilyl)ethoxymethyl chloride; "NaCNBH$_3$" means sodium cyanoborohydride; "DIBAL-H" means diisobutylaluminium hydride; "MsCl" means methanesulphonyl chloride; "KCN" means potassium cyanide; "Pd/C" means palladium on carbon; "NH$_4$HCO$_3$" means ammonium hydrogencarbonate; "NaNO$_2$" means sodium nitrite; "conc." means concentrated; "CuBr" means copper bromide; "CuI" means copper iodide; "Na$_2$CO$_3$" means sodium carbonate; "K$_3$PO$_4$" means potassium carbonate; "NaI" means sodium iodide; "Zn(CN)$_2$" means zinc cyanide; "NaCN" means sodium cyanide; "ph." Means phase; "CO$_2$" means carbon dioxide; "O$_2$" means oxygen.

Microwave assisted reactions were performed in a single-mode reactor: Initiator™ Sixty EXP microwave reactor (Biotage AB), or in a multimode reactor: Personal Chemistry Emrys™ Optimizer Robotic Microwave Synthesizer (Biotage).

A. Preparation of the Intermediates

Example A1 a) Preparation of Intermediate 1

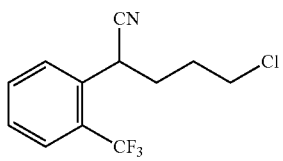

Potassium tert-butoxide (6.36 g, 56.7 mmol) was added at −10° C. under N$_2$ atmosphere to a sol. of 2-(trifluoromethyl-phenyl)acetonitrile (10 g, 76.23 mmol) in THF (70 mL). The r.m. was stirred at −10° C. for 10 min. Then, 1-bromo-3-chloro-propane (5.6 mL, 56.7 mmol) was slowly added dropwise to the r.m. and the mixture was stirred at 0-5° C. for 2 h. The mixture was quenched with a 10%. aq. NH$_4$Cl sol. The separated o.l. was dried (MgSO$_4$), filtered and the solvent evaporated in vacuo. The crude product was used in the following step without further purification. Yield: 14.13 g of intermediate 1 (quantitative yield).

b) Preparation of Intermediate 2

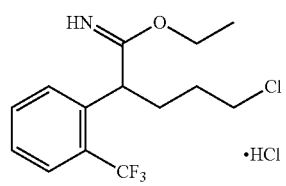 [SMILES: CCOC(=N)C(CCCCl)c1ccccc1C(F)(F)F ; Cl]

Acetyl chloride (30.7 mL, 432 mmol) was added dropwise at 0° C. under N$_2$ atmosphere to a sol. of intermediate 1 (14.1 g, 54 mmol) in EtOH (37.8 mL). The r.m. was stirred at r.t. for 3 d. The r.m. was cooled to 10° C. MTBE was added and the resulting suspension was stirred at r.t. for 2 h. The precipitated was filtered off, washed with MTBE and dried in vacuo. Yield: 7.72 g of intermediate 2 (46% yield; .HCl).

c) Preparation of Intermediate 3

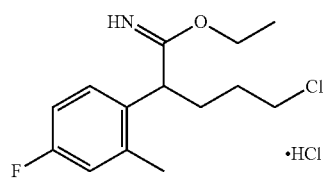 [SMILES: CCOC(=N)C(CCCCl)c1ccc(F)cc1C ; Cl]

Starting from (4-fluoro-2-methyl-phenyl)acetonitrile, intermediate 3 (.HCl) was prepared by using a procedure similar to the one described in example A1.

d) Preparation of Intermediate 4

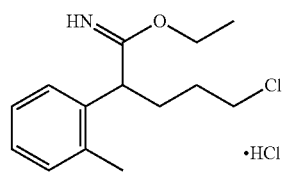 [SMILES: CCOC(=N)C(CCCCl)c1ccccc1C ; Cl]

Starting from o-tolylacetonitrile, intermediate 4 (.HCl) was prepared by using a procedure similar to the one described in example A1.

e) Preparation of Intermediate 5

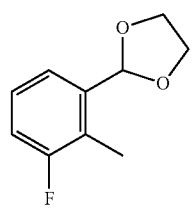

A mixture of 3-fluoro-2-methylbenzaldehyde (50 g, 3.62 mmol), ethylene glycol (101 mL, 1810 mmol) and PTSA (6.23 g, 36.2 mmol) in toluene (308 mL) was refluxed overnight using a Dean Stark apparatus. The reaction mixture was washed with a sat. sol. of NaHCO₃. The o.l. was dried (MgSO₄), filtered and evaporated. The residue was purified by flash column chromatography (silica; eluent: heptane/EtOAc from 100/0 to 80/20). The product fractions were collected and the solvent was evaporated in vacuo. Yield: 60 g of intermediate 5 (91% yield).

f) Preparation of Intermediate 6

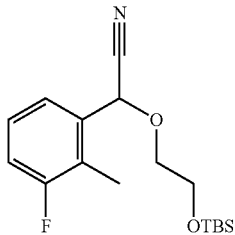 [SMILES: Cc1c(F)cccc1C(C#N)OCCO[Si](C)(C)C(C)(C)C]

Zinc iodide (3.5 g, 0.011 mol) was added in one portion to a stirred and cooled (−20° C.) sol. of intermediate 5 (40 g, 0.22 mol) and TMSCN (29 mL, 0.231 mol) in DCM (151 mL). The r.m. was allowed to reach r.t. and stirred for 90 min, then it was treated with a sat. sol. of NaHCO₃. The biphasic layer was separated and the o.l. washed with brine, then dried (MgSO₄), filtered and the filtrate concentrated in vacuo to give an oil, which was used as such in the next step. Yield: 55 g as a mixture of intermediate 6 and the corresponding deprotected alcohol.

g) Preparation of Intermediate 7

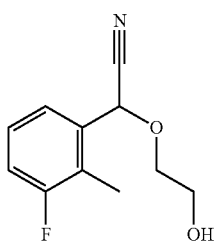

TBAF (1 M in THF, 58.6 mL, 0.0586 mol) was added to a sol. of intermediate 6 (mixture of the desired compound and the unprotected alcohol, 33 g) in THF (66 mL). After 1 h at r.t. the r.m. was concentrated in vacuo. Water (100 mL) and DCM (500 mL) were added to the residue and the layers were separated. The o.l. was washed with water (100 mL), dried (MgSO₄), filtered and concentrated in vacuo to give an oil, which was purified by filtration through a silica plug (eluent: DCM/(10% MeOH in DCM) 98/2). Yield: 22.3 g of intermediate 7 (91% yield).

h) Preparation of Intermediate 8

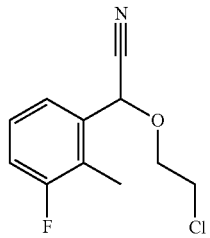

Thionyl chloride (6 mL, 82.8 mmol) was added dropwise to a hot (60° C.) sol. of intermediate 7 (13.7 g, 65.5 mmol) and pyridine (52.4 mL, 649 mmol) in DCE (172 mL). After 2 h of stirring at 60° C. the r.m. was allowed to cool down and then poured onto ice water. The layers were separated and the o.l. was treated twice with 1 M HCl, dried (MgSO₄), filtered and concentrated in vacuo to give an oil, which was pure enough to be used in the next step. Yield: 13 g of intermediate 8 (87% yield).

i) Preparation of Intermediate 9

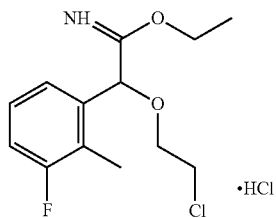 [SMILES: CCOC(=N)C(OCCCl)c1cccc(F)c1C ; Cl]

Intermediate 8 (9 g, 39.5 mmol) was dissolved in EtOH (28 mL) at r.t. under N₂ atmosphere. The sol. was cooled to a temperature between −15 and −10° C., then acetyl chloride (22.5 mL, 316 mmol) was added dropwise to the sol. The reaction mixture was stirred for 18 h at r.t., then it was cooled to 0° C. DIPE was added dropwise. The resulting white precipitate was filtered and dried in vacuo. Yield: 12 g of intermediate 9 (98% yield; HCl).

j) Preparation of Intermediate 10

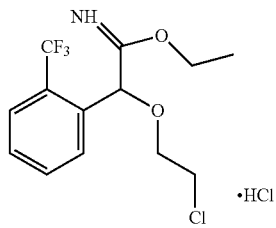 [SMILES: CCOC(=N)C(OCCCl)c1ccccc1C(F)(F)F ; Cl]

Starting from 2-trifluoromethylbenzaldehyde, intermediate 10 (.HCl) was prepared by using a procedure similar to the one described for the synthesis of intermediate 9.

k) Preparation of Intermediate 11

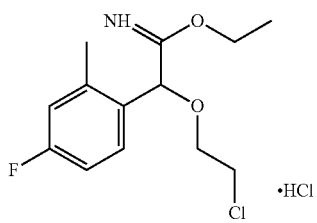 [SMILES: CCOC(=N)C(OCCCl)c1ccc(F)cc1C ; Cl]

Starting from 4-fluoro-2-methylbenzaldehyde, intermediate 11 (.HCl) was prepared by using a procedure similar to the one described for the synthesis of intermediate 9.

l) Preparation of Intermediate 12

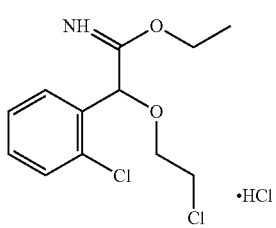 [SMILES: CCOC(=N)C(OCCCl)c1ccccc1Cl ; Cl]

Starting from 2-chlorobenzaldehyde, intermediate 12 (.HCl) was prepared by using a procedure similar to the one described for the synthesis of intermediate 9.

n) Preparation of Intermediate 14

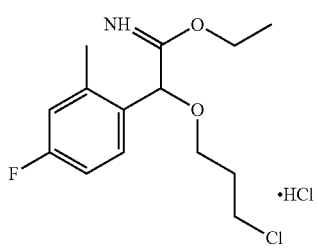 [SMILES: CCOC(=N)C(OCCCCl)c1ccc(F)cc1C ; Cl]

Starting from 4-fluoro-2-methylbenzaldehyde and 1,3-propanediol, intermediate 14 (.HCl) was prepared by using a procedure similar to the one described for the synthesis of intermediate 9.

Example A2 a) Preparation of Intermediate 15

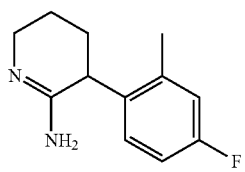

A mixture of intermediate 3 (2.5 g, 8.1 mmol) in a 7 M sol. of $NH_3$ in MeOH (4 mL) was stirred in a closed vial at r.t. for 5 days. The solid was filtered off and the filtrate was evaporated in vacuo. The residue was taken up in DCM and washed with an aq. 1 N NaOH sol. The o.l. was separated, dried ($Na_2SO_4$) and evaporated in vacuo. Yield: 1.4 g of intermediate 15 (84% yield) used as such in the next reaction step.

b) Preparation of Intermediate 16

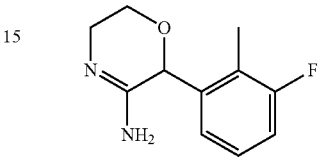

Intermediate 9 (12 g, 38.685 mmol) in $NH_3$ (7 M in MeOH, 32 mL) was stirred in closed vial over the weekend at 50° C. The r.m. was then allowed to reach r.t., then it was concentrated. DCM was added and the white precipitate obtained was filtered off. The residue was suspended in $CH_3CN$/DIPE, the solid filtered off and dried in vacuo. Yield: 6.6 g of intermediate 16 (82% yield).

c) Preparation of Intermediate 17

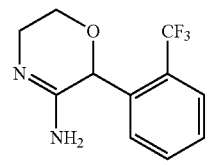 [SMILES: NC1=NCCOC1c1ccccc1C(F)(F)F]

Starting from intermediate 10, intermediate 17 was prepared by using a procedure similar to the one described for the synthesis of intermediate 16 (70% yield).

d) Preparation of Intermediate 18

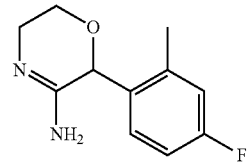

Starting from intermediate 11, intermediate 18 was prepared by using a procedure similar to the one described for the synthesis of intermediate 16 (46% yield).

e) Preparation of Intermediate 19

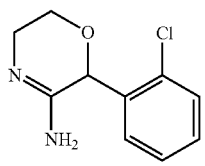

Starting from intermediate 12, intermediate 19 was prepared by using a procedure similar to the one described for the synthesis of intermediate 16 (89% yield).

Example A3 a) Preparation of Intermediate 20

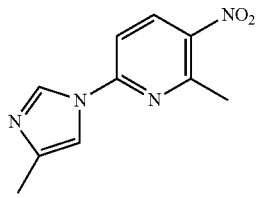 [SMILES: Cc1cn(-c2ccc([N+](=O)[O-])c(C)n2)cn1]

4-Methylimidazole (6.14 g, 73.3 mmol) was added to a sol. of 2-chloro-5-nitro-6-picoline (4.3 g, 24.42 mmol) in CH₃CN (64.5 mL). The r.m. was stirred at 100° C. in a pressure tube for 16 h. The r.m. was cooled to r.t. and the solvents evaporated in vacuo. The residue was washed with water and extracted with DCM. The o.l. was separated, dried (MgSO₄), filtered and the solvents evaporated in vacuo. The crude product was purified by flash column chromatography (silica; eluent: DCM/MeOH from 100/0 to 95/5). The product fractions were collected and the solvent evaporated in vacuo. The product was precipitated from DIPE, filtered off and dried in vacuo. Yield: 4.4 g of intermediate 20 (82% yield) as a pale yellow solid.

b) Preparation of Intermediate 21

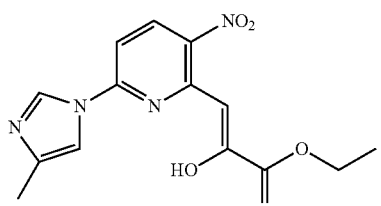

E/Z mixture

Diethyl oxalate (19 mL, 141.1 mmol) was added to an ice-bath cooled 24% wt ethanolic sol. of potassium ethoxide (9.5 mL, 24.2 mmol) under N₂ atmosphere. The r.m. was stirred at that temperature for 30 min. Subsequently, a sol. of intermediate 20 (4.4 g, 20.16 mmol) in THF (53 mL) was added dropwise. The r.m. was stirred at r.t. for 2 h, then a sat. aq. NH₄Cl sol. (150 mL) was added to the r.m. cooled with an ice-bath. The r.m. was stirred at r.t. for 30 min. The solid precipitated and was filtered off and washed with EtOH/water, then with DIPE and CH₃CN, and dried in vacuo. Yield: 3.5 g of intermediate 21 as an E/Z mixture as a yellow solid (54% yield).

c) Preparation of Intermediate 22

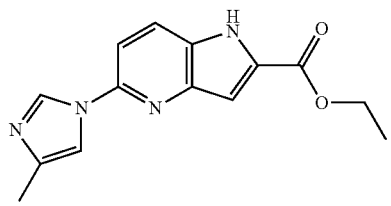 [SMILES: CCOC(=O)c1cc2nc(-n3cnc(C)c3)ccc2[nH]1]

To a sol. of intermediate 21 (3.5 g, 11 mmol) in THF (88 mL) and EtOH (33 mL) was added a sat. aq. NH₄Cl sol. (50 mL) under vigorous stirring. Iron (3 g, 54.1 mmol) was added portionwise to the mixture at r.t. and then the r.m. was heated at reflux for 2 h. The r.m. was cooled and filtered over diatomaceous earth and washed with warm THF/EtOH (1/1). The filtrate was evaporated in vacuo and the residue was stirred and refluxed in water (100 mL). The solid was filtered off, washed with warm water and dried in vacuo. Yield: 2.1 g of intermediate 22 (70% yield).

d) Preparation of Intermediate 23

Hydrazine hydrate (1.8 mL, 37 mmol) was added to a sol. of intermediate 22 (1 g, 3.7 mmol) in EtOH (10 mL) and the r.m. was stirred at reflux. The precipitate was filtered off, washed with EtOH, followed by DIPE and dried in vacuo. Yield: 729 mg of intermediate 23 (77% yield).

Example A4

Preparation of Intermediate 24

Starting from 6-chloro-2-methyl-3-nitro-pyridine, intermediate 24 was prepared according to the procedures as described in example A3.

Example A5 a) Preparation of Intermediate 25

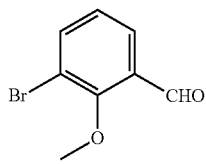

$K_2CO_3$ (13.51 g, 97.75 mmol) and $CH_3I$ (2.43 mL, 39.1 mmol) were added to a sol. of 3-bromo-2-hydroxybenzaldehyde (6.55 g, 32.58 mmol) in DMF (164 mL). The r.m. was stirred at r.t. for 18 h. The mixture was poured into a 1 N HCl sol. and the aq. layer was extracted with EtOAc. The o.l. was separated, dried ($MgSO_4$), filtered and concentrated in vacuo. Yield: 7 g of intermediate 25 (99% yield) as a brown-orange oil.

b) Preparation of Intermediate 26

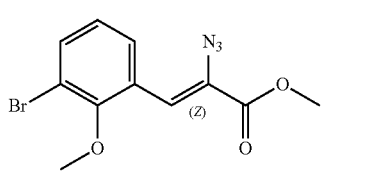 [SMILES: COC(=O)/C(=C/c1cccc(Br)c1OC)N=[N+]=[N-]]

Sodium methoxide (7.61 mL, 33.28 mmol, 25% w/w sol. in MeOH) was added to a cold sol. of intermediate 25 (2.39 g, 11.09 mmol) and methyl azidoacetate (3.83 g, 33.28 mmol) [prepared as described in J. Med. Chem., 2004, 21, 5298] in MeOH (10 mL). The r.m. was stirred at −15° C. for 2 h. Water was added and the white precipitate was filtered off and washed with water. The precipitate was dried in vacuo. Yield: 1.8 g of intermediate 26 (52% yield; Z-enantiomer).

c) Preparation of Intermediate 27

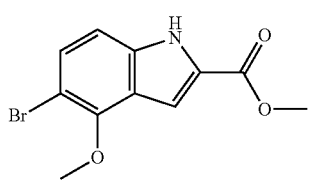 [SMILES: COC(=O)c1cc2c(OC)c(Br)ccc2[nH]1]

A sol. of intermediate 26 (1.6 g, 5.13 mmol) and rhodium (II)heptafluorobutyrate dimer (544 mg, 0.51 mmol) in toluene (4 mL) was stirred at 60° C. for 24 h. EtOAc was added after cooling to r.t., and the separated o.l. was washed with water and brine, dried ($MgSO_4$), filtered and evaporated in vacuo. The crude product was purified by flash column chromatography (silica; eluent: heptane/EtOAc from 98/2 to 60/40). The product fractions were collected and the solvent evaporated in vacuo. Yield: 210 mg of intermediate 27 (14% yield).

d) Preparation of Intermediate 28

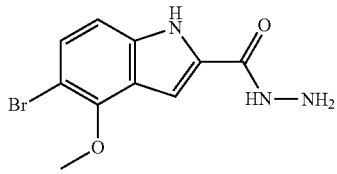 [SMILES: COc1c(Br)ccc2[nH]c(C(=O)NN)cc12]

A suspension of intermediate 27 (210 mg, 0.74 mmol) in hydrazine hydrate (4 mL) was stirred at 100° C. for 3 h. The r.m. was cooled down to r.t. and the precipitate was filtered off. Yield: 160 mg of intermediate 28 (76% yield) as a white solid.

Example A6 a) Preparation of Intermediate 29

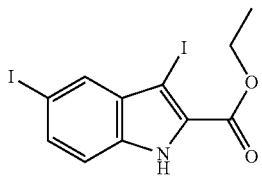 [SMILES: CCOC(=O)c1[nH]c2ccc(I)cc2c1I]

To a sol. of ethyl indole-2-carboxylate (10 g, 52.85 mmol) in EtOH (100 mL) were added $I_2$ (13.41 g, 52.85 mmol), $NaIO_4$ (5.65 g, 26.43 mmol) and $H_2SO_4$ (5.63 mL, 105.7 mmol). The r.m. was stirred at reflux for 2 h. After cooling to r.t. the mixture was poured into a sat. aq. $Na_2S_2O_3$ sol. The aq. layer was extracted three times with EtOAc and the combined o.l. were washed with brine, dried ($MgSO_4$), filtered and evaporated in vacuo. Yield: 24 g of intermediate 29 (79% yield).

b) Preparation of Intermediate 30

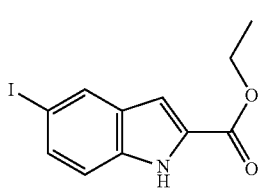

Concentrated HCl (45.45 mL, 544.21 mmol) was added to a suspension of intermediate 29 (24 g, 54.42 mmol) in EtOH (240 mL). Then, zinc dust (55 g, 843 mmol) was added portionwise over 90 min. The r.m. was stirred at r.t. for 24 h and then filtered over diatomaceous earth and washed with DCM. Water was added and the aq. layer was extracted with DCM. The o.l. was treated with a sat. aq. $NaHCO_3$ sol. The bilayer was filtered over diatomaceous earth and the separated o.l. was washed with brine, dried ($MgSO_4$), filtered and evaporated in vacuo. The yellow solid so obtained was recrystallised from CH$_3$CN. The crystals were filtered off to yield a first batch of intermediate 30. The filtrate was evaporated in vacuo and the crude product was purified by flash column chromatography (silica; eluent: heptane/EtOAc from 100/0 to 80/20). The product fractions were collected and the solvent evaporated in vacuo. The residue was recrystallised from CH$_3$CN to yield a second batch of intermediate 30, which was combined with the first fraction previously obtained. Yield: 8.3 g of intermediate 30 (48% yield).

c) Preparation of Intermediate 31

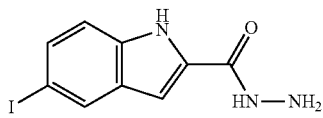 [SMILES: NNC(=O)c1cc2cc(I)ccc2[nH]1]

A suspension of intermediate 30 (8 g, 25.39 mmol) in hydrazine hydrate (150 mL) was stirred at 90° C. for 4 h. The r.m. was cooled down to r.t. and the precipitate was filtered off. Yield: 6.55 g of intermediate 31 (86%% yield) as a white solid.

Example A7 a) Preparation of Intermediate 32

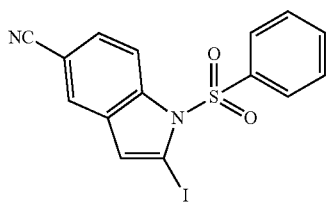 [SMILES: N#Cc1ccc2c(c1)cc(I)n2S(=O)(=O)c1ccccc1]

A sol. of 2-iodo-1H-indole-5-carbonitrile (0.59 g, 2.20 mmol) in THF (15 mL) was added to a suspension of NaH (60% as a dispersion in mineral oil; 0.13 g, 3.30 mmol) in THF (10 mL) under N$_2$ atmosphere at 0° C. The r.m. was stirred at r.t. for 30 min. and then cooled to 0° C. Benzenesulfonyl chloride (0.31 mL, 2.42 mmol) was added slowly. The mixture was stirred at r.t. until the starting material had been completely consumed. The mixture was poured into water (50 mL) and extracted with EtOAc (3×50 mL). The combined o.l. were washed with brine (50 mL), dried (MgSO$_4$) and the solvent evaporated in vacuo. The residue was triturated with DIPE to provide a solid. Yield: 668 mg of intermediate 32 (74% yield) used in the next step without further purification.

b) Preparation of Intermediate 33

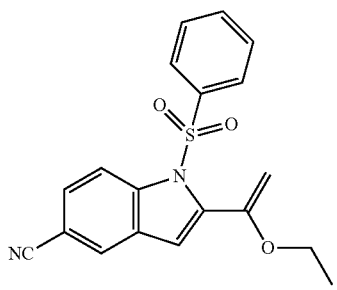 [SMILES: C=C(OCC)c1cc2cc(C#N)ccc2n1S(=O)(=O)c1ccccc1]

A mixture of intermediate 32 (668 mg, 1.64 mmol), tributyl (1-ethoxyvinyl)tin (0.61 mL, 1.8 mmol) and Pd(PPh$_3$)$_4$ (94.55 mg, 0.08 mmol) in toluene (16 mL) was stirred overnight at 120° C. The solvent was evaporated in vacuo and the crude product was purified by flash column chromatography (silica; eluent: DCM). The product fractions were collected and the solvent evaporated in vacuo. Yield: 590 mg of intermediate 33 (85% yield).

c) Preparation of Intermediate 34

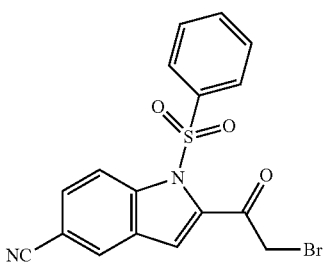 [SMILES: N#Cc1ccc2c(c1)cc(C(=O)CBr)n2S(=O)(=O)c1ccccc1]

N-bromosuccinimide (50 mg, 0.28 mmol) was added to a mixture of intermediate 33 (100 mg, 0.28 mmol) in THF (2 mL) and water (0.2 mL). The r.m. was stirred at r.t. for 15 min. The solvent was evaporated in vacuo and the residue was partitioned between DCM and brine. The o.l. was separated, dried (MgSO$_4$), filtered and the solvent evaporated in vacuo. The crude product was purified by flash column chromatography (silica; eluent: heptane/DCM from 100/0 to 0/100). The product fractions were collected and the solvent evaporated in vacuo. Yield: 25 mg of intermediate 34 (22%% yield).

Example A8 a) Preparation of Intermediate 35

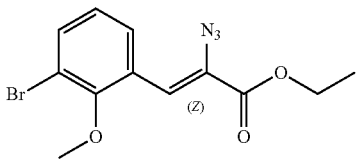 [SMILES: CCOC(=O)/C(=C/c1cccc(Br)c1OC)N=[N+]=[N-]]

Intermediate 35 was prepared via a procedure similar to the one reported for the preparation of intermediate 26, using sodium ethoxide instead of sodium methoxide. The crude material was purified via flash column chromatography (eluent: heptane/DCM from 90/10 to 50/50) to give a solid (58% yield).

b) Preparation of Intermediate 36

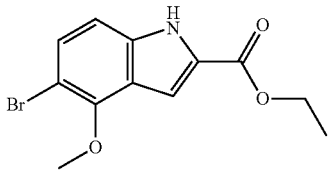 [SMILES: CCOC(=O)c1cc2c(OC)c(Br)ccc2[nH]1]

A suspension of intermediate 35 (25 g, 76.652 mmol) in xylene (0.5 L) was heated at reflux for 1 h. The reaction mixture was evaporated in vacuo. The product was partially precipitated by stirring the residue in a small amount of DIPE (40 mL). The solid was filtered off and washed with DIPE (10 mL), to give a first batch of intermediate. The filtrate was concentrated and its residue was purified by flash column chromatography (silica; eluent: heptane/DCM from 90/10 to 30/70). The product fractions were collected and evaporated to give a second batch of intermediate, that was joined to the first one. Yield: 18 g of intermediate 36 (79% yield).

Example A9 a) Preparation of Intermediate 37

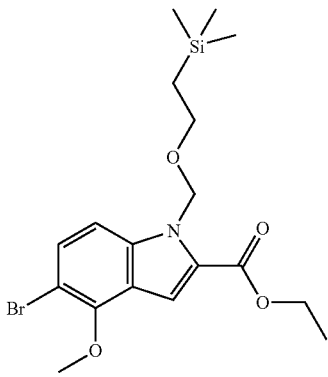 [SMILES: CCOC(=O)c1cc2c(OC)c(Br)ccc2n1COCC[Si](C)(C)C]

NaH (60% dispersion in mineral oil, 3.018 g, 75.469 mmol) was added portionwise to intermediate 36 (18 g, 60.375 mmol) in THF (147 mL) at 0° C. and under $N_2$. After the addition, the reaction was allowed to reach r.t., then stirred at r.t. for 1 h, prior to being cooled again to 0° C. SEMCl was then added dropwise, at 0° C., and the reaction mixture allowed to warm up to r.t. and then stirred for 2 h. The reaction was quenched by the addition of water, then the biphasic layer was separated and the aq. layer was extracted with EtOAc (×2). The combined o.l. were dried ($MgSO_4$), filtered and concentrated. The residue was purified via flash column chromatography (silica; eluent: heptane/DCM from 90:10 to 50:50). The product fractions were collected and concentrated in vacuo to afford the desired intermediate. Yield: 25 g of intermediate 37 (97% yield) as a yellowish oil.

b) Preparation of Intermediate 38

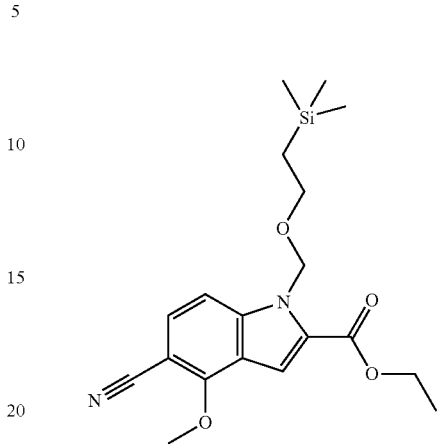

Intermediate 37 (22 g, 51.354 mmol), dppf (1.707 g, 3.081 mmol), zinc (0.504 g, 7.703 mmol), $Zn(CN)_2$ (9.045 g, 77.031 mmol) and DMA (150 mL) were added in a round bottom flask. The sol. was then degassed and $Pd_2dba_3$ (1.411 g, 1.541 mmol) was added. The reaction mixture was stirred at 160° C. for 75 min under $N_2$, then it was diluted with water and the product was extracted with EtOAc. Before separation, the layers were filtered over diatomaceous earth to remove the undesired solids. The o.l. was dried ($MgSO_4$), filtered and evaporated. The residue was purified by flash column chromatography (silica; eluent: DCM). The product fractions were collected and concentrated to afford the desired intermediate. Yield: 19.2 g of intermediate 38 (quantitative) as a yellowish solid.

c) Preparation of Intermediate 39

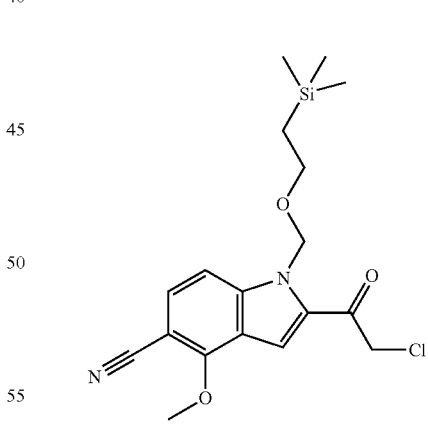

To a sol. of DIPA (22.87 mL, 162.74 mmol) in THF (25 mL), BuLi (1.6 M in hexanes, 99.8 mL, 159.67 mmol)) was added dropwise over 20 min at −78° C., and the resulting mixture was stirred 1 h at this temperature. A white precipitate was formed. Chloroacetic acid (7.254 g, 76.767 mmol) in THF (30 mL) was then added over 30 min and the resulting mixture stirred 30 min at −78° C. Intermediate 38 (11.5 g, 30.707 mmol) in THF (80 mL) was then added over 45 min and the r.m. stirred for 90 min. The r.m. was then quenched by addition of AcOH (18.6 mL) in THF (25 mL) at −78° C., stirred at this temperature for 15 min, then warmed up to 5-10° C. in an ice-water bath. EtOAc (200 mL) and water (200 mL) were then added and the phases separated. The o.l. was washed with a sat. sol. of NaHCO₃, then with brine, dried (MgSO₄), filtered and concentrated. The residue solidified spontaneously. Yield: 11.1 g of intermediate 39 (95% yield).

Example A10 a) Preparation of Intermediate 40

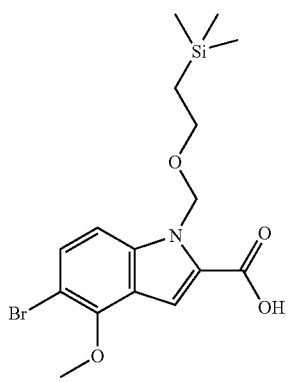 [SMILES: COc1c(Br)ccc2c1cc(C(=O)O)n2COCC[Si](C)(C)C]

LiOH (900 mg, 37.58 mmol) was added to intermediate 37 (4 g, 9.34 mmol) in EtOH (34 mL) and water (4.3 mL), and the r.m. stirred at r.t. for 1 h. The volatiles were evaporated in vacuo, then the aq. residue treated with HCl 1 M (37.6 mL). The resulting slurry was extracted with CHCl₃ (×3). The combined org. layers were dried (MgSO₄), filtered and evaporated to give the product as a white solid, that was dried in vacuo overnight. The intermediate was pure enough to be used as such in the next step. Yield: 3.7 g of intermediate 40 (99% yield).

b) Preparation of Intermediate 41

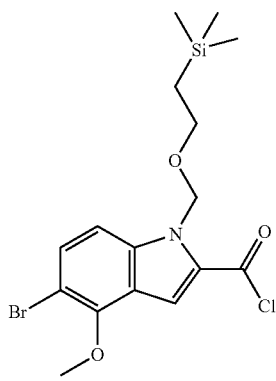 [SMILES: COc1c(Br)ccc2c1cc(C(=O)Cl)n2COCC[Si](C)(C)C]

Intermediate 40 (3.13 g, 7.818 mmol) was suspended in DCM (30 mL). DMF (30 μL) was added, followed by oxalyl chloride (3.969 mL, 46.91 mmol). This resulting mixture was stirred at r.t. for 1 h under N₂. The solvent and excess of reagent were evaporated and co-evaporated with toluene, providing the crude compound, which was used as such for the next reaction step. Yield: 3.25 g of intermediate 41 as a yellow oil (99% yield).

c) Preparation of Intermediate 42

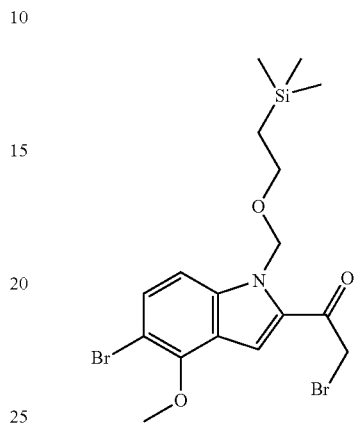

Intermediate 41 (2.46 g, 5.874 mmol) in CH₃CN (20 mL) was cooled to a temperature between −5 to 0° C., then (trimethylsilyl)diazomethane (2 M in hexanes, 6.46 mL, 12.923 mmol) was added. The reaction was allowed to warm to r.t. and it was stirred for 2.5 h, then it was cooled in an ice-bath and HBr (48% in water, 1.462 mL, 12.923 mmol) was added slowly to the mixture. After 20 min the mixture was diluted with DCM, poured into a sat. sol. of NaHCO₃ and stirred for 10 min. The o.l. was separated and the aq. phase was extracted with DCM. The combined o.l. were dried, filtered and concentrated, to give a crude pure enough to be used as such in the subsequent step. Yield: 2.47 g of intermediate 42 (88% yield).

Example A11 a) Preparation of Intermediate 43

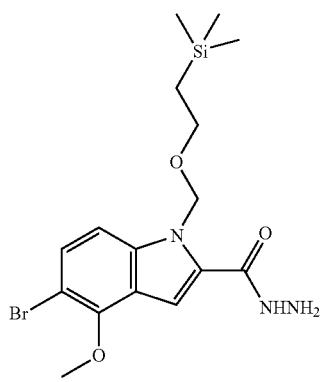 [SMILES: COc1c(Br)ccc2c1cc(C(=O)NN)n2COCC[Si](C)(C)C]

Starting from intermediate 37, intermediate 43 was prepared using a procedure similar to the one described for the synthesis of intermediate 23 (99% yield).

Example A12 a) Preparation of Intermediate 44

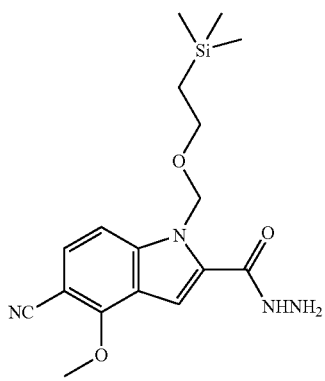 [SMILES: COc1c(C#N)ccc2c1cc(C(=O)NN)n2COCC[Si](C)(C)C]

Starting from intermediate 37, intermediate 44 was prepared using a procedure similar to the one described for the synthesis of intermediate 23. An additional batch of intermediate was collected from column chromatography of the filtrate (silica; eluent: heptane/EtOAc from 80/20 to 0/100). Total yield: 15 g of intermediate 44 (87% yield).

Example A13 a) Preparation of Intermediate 45

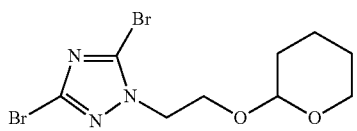 [SMILES: Brc1nc(Br)n(CCOC2CCCCO2)n1]

To a sol. of 3,5-dibromo-1H-1,2,4-triazole (60 g, 264.48 mmol) in $CH_3CN$ (600 mL) were added 2-(2-bromoethoxy)tetrahydro-2H-pyran (48.01 mL, 317.38 mmol) and DIPEA (48.08 mL, 290.93 mmol). The r.m. was stirred at 90° C. for 3 h. The mixture was then diluted with EtOAc and washed with a sat. aq. $NaHCO_3$ sol. and brine. The separated o.l. was dried ($MgSO_4$), filtered and the solvent evaporated in vacuo. The crude product was purified by flash column chromatography (silica; eluent: DCM/(7 N $NH_3$ in MeOH) from 100/0 to 97/3). The product fractions were collected and the solvent evaporated in vacuo. Yield: 72 g of intermediate 45 (77% yield).

b) Preparation of Intermediate 46

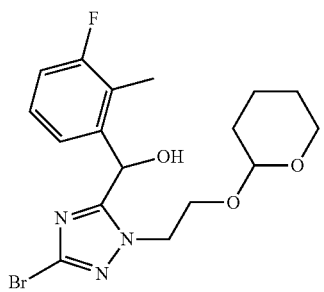 [SMILES: Cc1c(F)cccc1C(O)c1nc(Br)nn1CCOC1CCCCO1]

To a sol. of intermediate 45 (5 g, 14.08 mmol) in THF (250 mL) was added 2.5 M BuLi (5.6 mL, 14.08 mmol) at −78° C. The r.m. was stirred at −78° C. for 20 min. Then, a sol. of 3-fluoro-2-methylbenzaldehyde (2.3 g, 16.9 mmol) in THF (50 mL) was added. The r.m. was stirred at −78° C. for 20 min. and then quenched by the addition of a sat. aq. $NH_4Cl$ sol. The mixture was then allowed to warm to r.t., diluted with water and extracted with EtOAc. The separated o.l. was dried ($MgSO_4$), filtered and the solvent evaporated in vacuo. The crude product was purified by flash column chromatography (silica; eluent: DCM/(7 N $NH_3$ in MeOH) from 100/0 to 99/1). The product fractions were collected and the solvent evaporated in vacuo. Yield: 5.5 g of intermediate 46 (94% yield).

c) Preparation of Intermediate 47

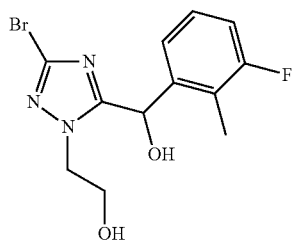 [SMILES: Cc1c(F)cccc1C(O)c1nc(Br)nn1CCO]

To a sol. of intermediate 46 (5.5 g, 13.3 mmol) in MeOH (300 mL) was added p-toluenesulfonic acid monohydrate (457 mg, 2.65 mmol). The r.m. was stirred at r.t. for 2 h. Subsequently, the r.m. was concentrated in vacuo and the residue was dissolved in DCM and washed with a sat. aq. $NaHCO_3$ sol. The separated o.l. was dried ($MgSO_4$), filtered and the solvent evaporated in vacuo. Yield: 4.35 g of intermediate 47 (99%% yield).

d) Preparation of Intermediate 48

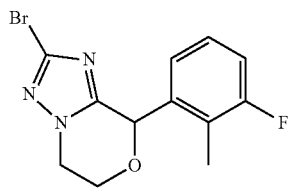 [SMILES: Cc1c(F)cccc1C1OCCn2nc(Br)nc21]

A sol. of intermediate 47 (4.36 g, 13.2 mmol) and p-toluenesulfonic acid monohydrate (2.51 g, 13.2 mmol) in xylene (644 mL) was stirred at reflux for 25 h using a Dean Stark apparatus. After cooling to r.t. the mixture was washed with a 1 M NaOH sol. (×2) and with brine (×1). The separated o.l. was dried ($Na_2SO_4$), filtered and the solvent evaporated in vacuo. The crude product was purified by flash column chromatography (silica; eluent: DCM/(7 N $NH_3$ in MeOH) from 100/0 to 90/10). The product fractions were collected and the solvent evaporated in vacuo. The brownish oil so obtained was treated with DIPE to provide a solid. Yield: 2.5 g of intermediate 48 (60% yield).

Example A14

Preparation of Intermediate 49

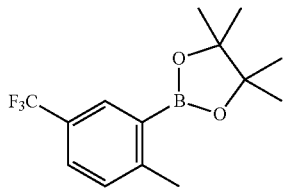 [SMILES: Cc1ccc(C(F)(F)F)cc1B1OC(C)(C)C(C)(C)O1]

A suspension of 2-methyl-5-(trifluoromethyl)bromobenzene (20 g, 83.67 mmol), bis(pinacolato)diboron (42.49 g, 167.34 mmol), KOAc (24.63 g, 251.01 mmol) and PdCl$_2$ (dppf) (1.84 g, 2.51 mmol) in DMF (600 mL) was stirred at 150° C. for 10 min. under microwave irradiation. The mixture was filtered through diatomaceous earth and washed with EtOAc. The separated o.l. was washed with brine, dried (MgSO$_4$), filtered and the solvent evaporated in vacuo. The residue was dissolved in Et$_2$O and washed with brine followed by a sat. aq. NaHCO$_3$ sol. The separated o.l. was dried (MgSO$_4$), filtered and the solvent evaporated in vacuo. The crude product was purified by flash column chromatography (silica; eluent: heptane/DCM from 100/0 to 0/100). The product fractions were collected and the solvent evaporated in vacuo. Yield: 16 g of intermediate 49 (67% yield).

Example A15 a) Preparation of Intermediate 50

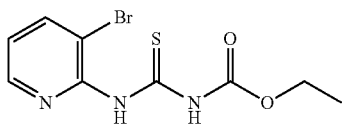 [SMILES: CCOC(=O)NC(=S)Nc1ncccc1Br]

Ethoxycarbonyl isothiocyanate (25 g, 191 mmol) was added to a sol. of 2-amino-3-bromopyridine (28.68 g, 166 mmol) in 1,4-dioxane (500 mL). The r.m. was stirred at r.t. overnight. The solvent was evaporated in vacuo and the residue was suspended in DIPE. The precipitate was filtered off and dried in vacuo at 60° C. Yield: 50 g of intermediate 50 (99% yield).

b) Preparation of Intermediate 51

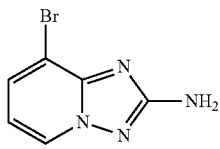 [SMILES: Nc1nc2c(Br)cccn2n1]

To a sol. of intermediate 50 (55 g, 181 mmol) in EtOH (300 mL) were added MeOH (300 mL), hydroxylamine hydrochloride (62.83 g, 904 mmol) and DIPEA (694 mL, 543 mmol). The r.m. was stirred at r.t. for 6 h. The mixture was concentrated in vacuo and the residue was suspended in DIPE. The precipitate was filtered off. Yield: 37 g of intermediate 51 (96% yield).

c) Preparation of Intermediate 52

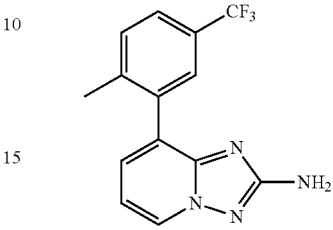

Intermediate 49 (16 g, 55.92 mmol) and water (75 mL) were added to a sol. of intermediate 51 (7.94 g, 37.28 mmol) in DME (200 mL). Then, Pd(PPh$_3$)$_4$ (4.31 g, 3.73 mmol) was added and the r.m. was stirred at 150° C. for 10 min. under microwave irradiation. The mixture was filtered through diatomaceous earth and concentrated in vacuo. The crude product was purified by flash column chromatography (silica; eluent: DCM/(7 N NH$_3$ in MeOH) from 100/0 to 97/3). The product fractions were collected and the solvent evaporated in vacuo to yield 7 g of a first fraction of intermediate 52. The impure fractions were also collected, evaporated in vacuo and the crude product was purified by RP preparative HPLC [RP Vydac Denali C18 (10 mm, 250 g, 5 cm); mobile phase: 0.25% NH$_4$HCO$_3$ sol. in water/CH$_3$CN]. The product fractions were collected and the solvent evaporated in vacuo. The crude product was further purified by RP preparative SFC [Diol; mobile phase: CO$_2$, MeOH (with 0.2% isopropylamine)]. The product fractions were collected and the solvent evaporated in vacuo to yield 4 g of a second fraction of intermediate 52. Yield: 11 g of intermediate 52 (quantitative yield).

d) Preparation of Intermediate 53

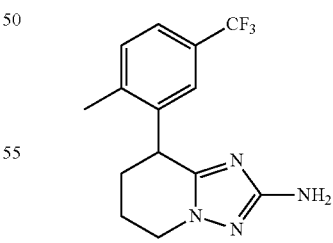

To a suspension of Pd/C 10% (1 g) in MeOH (100 mL) was added intermediate 52 (7.1 g, 24.29 mmol) and 6 N in isopropanol HCl sol. (4.05 mL) under N$_2$ atmosphere. The r.m. was stirred at 50° C. under H$_2$ atmosphere until 2 eq. of H$_2$ were absorbed. The catalyst was filtered off over diatomaceous earth and the filtrate evaporated in vacuo. The residue was partitioned between DCM and water. The separated o.l.

was dried (MgSO$_4$), filtered and the solvent evaporated in vacuo. Yield: 1.05 g of intermediate 53 (15% yield).

e) Preparation of Intermediate 54

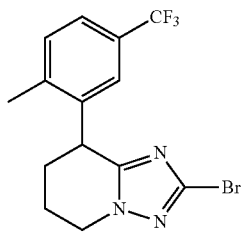 [SMILES: Cc1ccc(C(F)(F)F)cc1C1CCCn2nc(Br)nc21]

A sol. of NaNO$_2$ (1.05 g, 15.19 mmol) in water (60 mL) was added dropwise over 45 min. to a sol. of intermediate 53 (2.25 g, 7.59 mmol) in a conc. aq. HBr sol. (60 mL) at 0° C. The mixture was warmed to r.t. and further stirred for 15 min. The r.m. was cooled to 0° C. and CuBr (2.19 g, 15.19 mmol) was added portionwise. The mixture was stirred at r.t. for 1 h. and then diluted with EtOAc and washed with aq. NH$_3$ sol. The separated o.l. was dried (MgSO$_4$), filtered and the solvent evaporated in vacuo. The crude product was purified by flash column chromatography (silica; eluent: heptane/EtOAc from 100/0 to 90/10). The product fractions were collected and the solvent evaporated in vacuo. Yield: 2 g of intermediate 54 (73% yield).

Example A16

Preparation of Intermediate 55

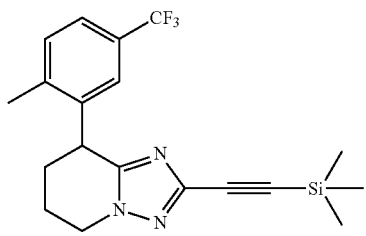

A mixture of intermediate 54 (500 mg, 1.39 mmol) in DMF (9 mL) was degassed with N$_2$ for 15 min. Then, trimethylsilylacetylene (0.96 mL, 6.94 mmol), Et$_3$N (0.39 mL, 2.78 mmol), CuI (11 mg, 0.06 mmol) and Pd(PPh$_3$)$_4$ (347 mg, 0.14 mmol) were added. The mixture was purged with N$_2$ for 10 min. and then stirred at 100° C. overnight. The solvent was evaporated and the residue taken up in EtOAc. The mixture was filtered off over diatomaceous earth. The filtrate was washed with brine. The separated o.l. was dried (MgSO$_4$), filtered and the solvent evaporated in vacuo. The crude product was purified by flash column chromatography (silica;

eluent: heptane/DCM from 50/50 to 0/100). The product fractions were collected and the solvent evaporated in vacuo. Yield: 348 mg of intermediate 55 (66% yield).

Example A17

Preparation of Intermediate 56

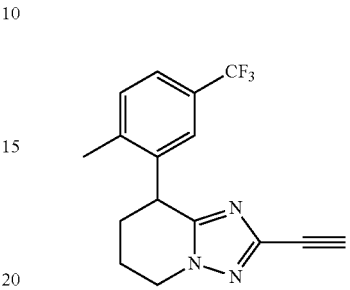

A mixture of intermediate 55 (205 mg, 0.54 mmol) in THF (1 mL) was added slowly to a mixture of TBAF 1 M in THF (0.54 mL, 0.54 mmol) and AcOH (0.04 mL, 0.71 mmol) in THF (1 mL). The r.m. was stirred at r.t. for 1 h. The solvent was evaporated and the residue taken up in DCM and washed with a sat. aq. Na$_2$CO$_3$ sol. The separated o.l. was dried (MgSO$_4$), filtered and the solvent evaporated in vacuo. The crude product was purified by flash column chromatography (silica; eluent: heptane/DCM from 50/50 to 0/100). The product fractions were collected and the solvent evaporated in vacuo. Yield: 85 mg of intermediate 56 (51% yield).

Example A18

Preparation of Intermediate 57

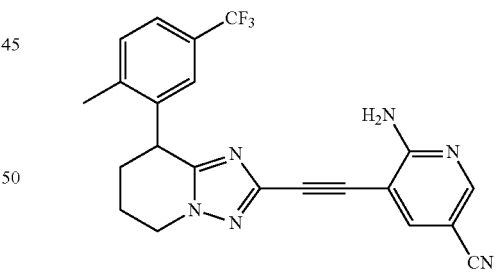

A mixture of intermediate 56 (85 mg, 0.28 mmol) in DMF (2 mL) was degassed with N$_2$ for 15 min. Then, 2-amino-3-bromo-5-cyanopyridine (55 mg, 0.28 mmol), Et$_3$N (0.08 mL, 0.56 mmol), CuI (2 mg, 0.01 mmol) and Pd(PPh$_3$)$_4$ (70 mg, 0.03 mmol) were added. The mixture was purged with N$_2$ for 10 min. and then stirred at 100° C. overnight. The solvent was evaporated and the residue taken up in EtOAc. The mixture was filtered off over diatomaceous earth. The filtrate was washed with brine. The separated o.l. was dried (MgSO$_4$), filtered and the solvent evaporated in vacuo. The crude product was purified by flash column chromatography (silica;

eluent: heptane/DCM from 50/50 to 0/100). The product fractions were collected and the solvent evaporated in vacuo. Yield: 91 mg of intermediate 57 (77%% yield).

Example A19

Preparation of Intermediate 58

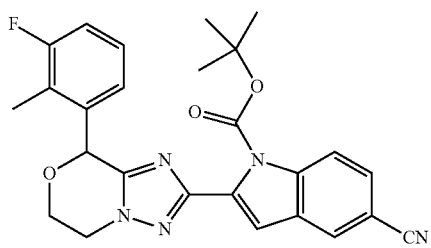 [SMILES: Cc1c(F)cccc1C1OCCn2nc(-c3cc4cc(C#N)ccc4n3C(=O)OC(C)(C)C)nc21]

K₃PO₄ (408 mg, 1.92 mmol) and water (1.33 mL) were added to a sol. of intermediate 48 (200 mg, 0.64 mmol) and N-tert-butoxycarbonyl-5-cyano-1H-indole-2-boronic acid (220 mg, 0.77 mmol) in THF (13.3 mL). The solvent was degassed with N₂ and 2-dicyclohexylphosphino-2',6'-dimethoxy-1,1'-biphenyl (26.8 mg, 0.064 mmol) and Pd(OAc)₂ (14.7 mg, 0.064 mmol) were added. The r.m. was degassed again and stirred in a sealed tube at 40° C. for 16 h. The solvent was evaporated in vacuo and the residue was partioned between water and DCM. The o.l. was separated, dried over MgSO₄, filtered and the solvent evaporated in vacuo. The crude product was purified by flash column chromatography (silica; eluent: heptane/EtOAc from 100/0 to 50/50). The product fractions were collected and the solvent evaporated in vacuo to provide an off-white solid. Yield: 245 mg of intermediate 58 (81% yield).

Example A20 a) Preparation of Intermediate 59

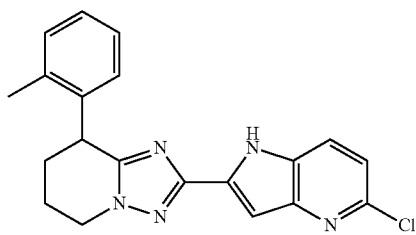 [SMILES: Cc1ccccc1C1CCCn2nc(-c3cc4nc(Cl)ccc4[nH]3)nc21]

Imidazole (1.94 g, 28.5 mmol) and intermediate 4 (1.38 g, 4.75 mmol) were added to a sol. of intermediate 24 (500 mg, 2.27 mmol) in MeOH (4.5 mL). The r.m. was stirred at 35° C. for 16 h and at 60° C. then for 16 h. The solvent was evaporated in vacuo. The residue was partioned between a sat. aq. NaHCO₃ sol. and DCM. The o.l. was separated, dried over MgSO₄, filtered and the solvent evaporated in vacuo. The crude product was purified twice by flash column chromatography (silica; eluent: heptane in EtOAc from 100/0 to 50/50). The product fractions were collected and the solvent evaporated in vacuo. The product was crystallized from DIPE, filtered off and dried in vacuo. Yield: 279 mg of intermediate 59 (32% yield) as white solid.

b) Preparation of Intermediate 60

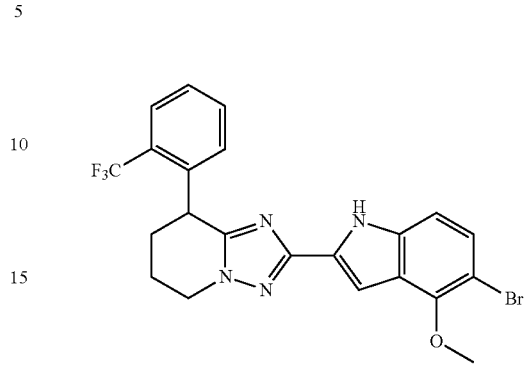

Starting from intermediate 28 and intermediate 2, intermediate 60 was prepared by using a procedure similar to the one described for the synthesis of intermediate 59.

c) Preparation of Intermediate 61

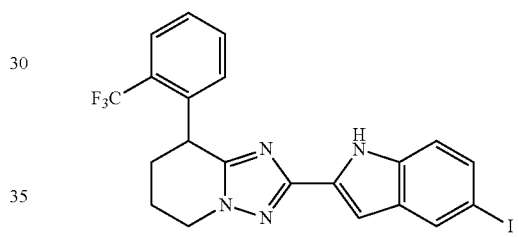

Starting from intermediate 31 and intermediate 2, intermediate 61 was prepared by using a procedure similar to the one described for the synthesis of intermediate 59.

Example A21

Preparation of Intermediate 62

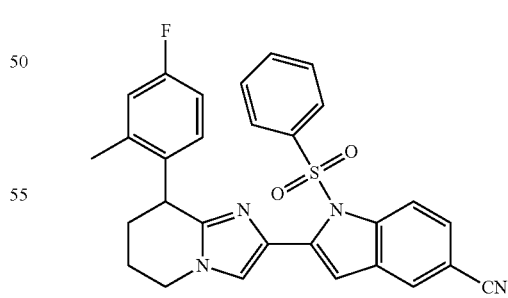

A suspension of intermediate 34 (180 mg, 0.45 mmol), intermediate 15 (276 mg, 1.34 mmol) and Na₂CO₃ (59 mg, 0.56 mmol) in EtOH (5 mL) was stirred at r.t. for 2 h. Then the r.m. was stirred at 80° C. for 4 h. The r.m. was cooled to r.t., filtered and the solvent evaporated in vacuo. The residue was pardoned between brine and DCM. The o.l. was separated, dried over MgSO₄, filtered and the solvent evaporated in vacuo. The crude product was used in the next step without further purification. Yield: 292 mg of intermediate 62.

Example A22 a) Preparation of Intermediate 63

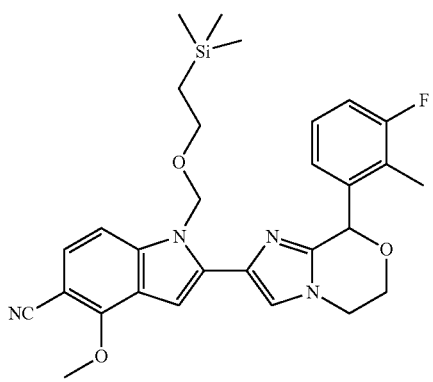 [SMILES: COc1c(C#N)ccc2c1cc(-c1cn3c(n1)C(c1cccc(F)c1C)OCC3)n2COCC[Si](C)(C)C]

NaI (297 mg, 1.979 mmol) was added to a mixture of intermediate 39 (600 mg, 1.583 mmol), intermediate 16 (659 mg, 3.167 mmol) and Na₂CO₃ (210 mg, 1.979 mmol) in acetone (11.8 mL). The r.m. was stirred at r.t. over the weekend, then warmed to 50° C. overnight, and then the solvent was evaporated. The residue was dissolved in DCM, and the o.l. was washed with water, sat. NaHCO₃ and brine, dried (MgSO₄), filtered and evaporated to give a crude, which was passed through a short column (silica; eluent: heptane/EtOAc, from 100/0 to 50/50). All product fractions were collected and the solvent evaporated, to give the desired intermediate, pure enough to be used as such in the next step. Yield: 708 mg of intermediate 63 (84% yield).

b) Preparation of Intermediate 64

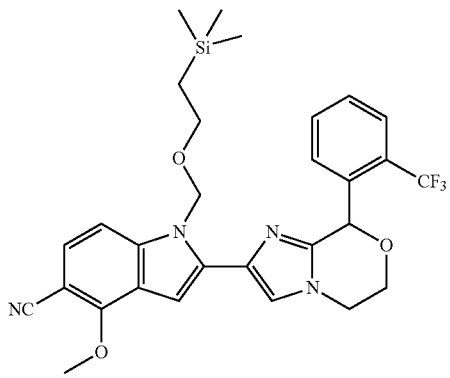

Starting from intermediate 39 and intermediate 17, intermediate 64 was prepared by using a procedure similar to the one described for the synthesis of intermediate 63 (87% yield).

c) Preparation of Intermediate 65

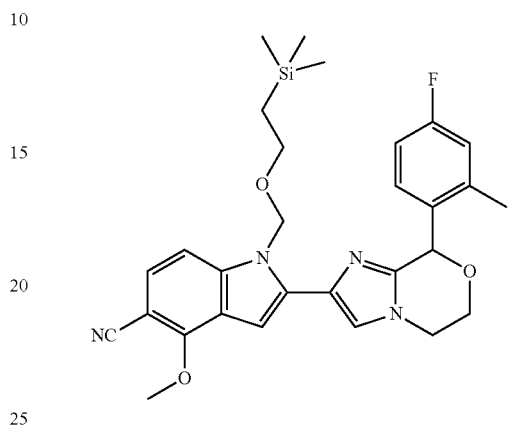

Starting from intermediate 39 and intermediate 18, intermediate 65 was prepared by using a procedure similar to the one described for the synthesis of intermediate 63 (74% yield).

Alternative Preparation of Intermediate 65 a1) Preparation of Intermediate 66

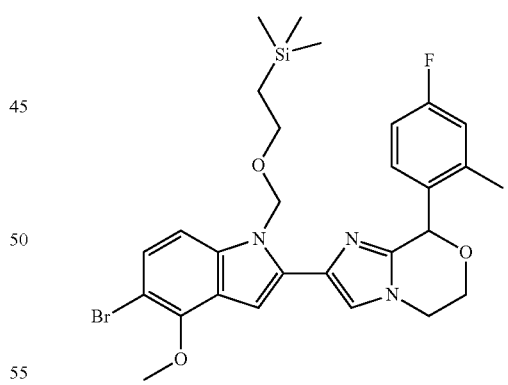

Na₂CO₃ (686 mg, 6.469 mmol) was added to intermediate 42 (2.47 g, 5.175 mmol) and intermediate 18 (2.155 g, 10.351 mmol), and the r.m. was stirred at r.t. overnight. The mixture was concentrated in vacuo, and the resulting residue was dissolved in DCM, washed with water and dried (MgSO₄), to give a crude that was purified via flash column chromatography (silica; eluent: heptane/EtOAc from 100/0 to 0/100). The product fractions were collected and the solvent evaporated. Yield: 2.3 g of intermediate 66 (76% yield).

b1) Preparation of Intermediate 65

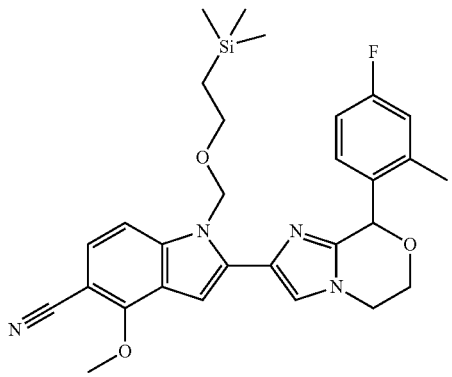 [SMILES: COc1c(C#N)ccc2c1cc(-c1cn3c(n1)C(c1ccc(F)cc1C)OCC3)n2COCC[Si](C)(C)C]

Intermediate 66 (2.7 g, 4.603 mmol) was dissolved in DMF (17.5 mL). Zn(CN)$_2$ (414 mg, 3.452 mmol) was added and the mixture was degassed with N$_2$. Pd(PPh$_3$)$_4$ (319 mg, 0.276 mmol) was then added and the mixture was stirred (×4) for 1.5 h at 160° C. under microwave irradiation. The DMF was removed in vacuo, the residue was dissolved in DCM and washed with water. The o.l. was dried (MgSO$_4$), filtered and evaporated, to give the desired intermediate, used as such in the subsequent step. Yield: 2.91 g of intermediate 65 (80% purity, 95% yield).

d) Preparation of Intermediate 67

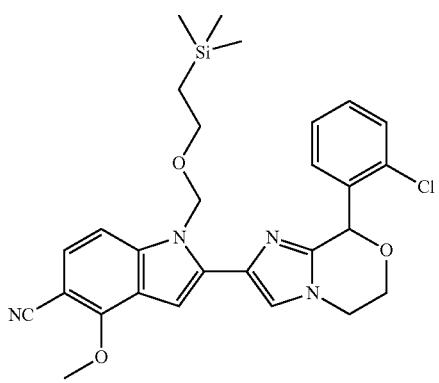 [SMILES: COc1c(C#N)ccc2c1cc(-c1cn3c(n1)C(c1ccccc1Cl)OCC3)n2COCC[Si](C)(C)C]

Starting from intermediate 39 and intermediate 19, intermediate 67 was prepared by using a procedure similar to the one described for the synthesis of intermediate 63 (89% yield).

Example A23 a) Preparation of Intermediate 68

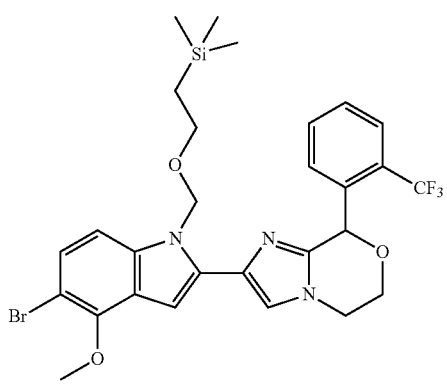 [SMILES: COc1c(Br)ccc2c1cc(-c1cn3c(n1)C(c1ccccc1C(F)(F)F)OCC3)n2COCC[Si](C)(C)C]

To a sol. of intermediate 43 (1.93 g, 1.658 mmol) and imidazole (3.805 g, 55.891 mmol) in MeOH (8.8 mL) was added intermediate 10 (2.885 g, 8.334 mmol) and the reaction mixture was stirred at r.t. for 16 h, then heated at 120° C. for 40 min under microwave irradiation. The mixture was concentrated, the residue dissolved in DCM and the o.l. was washed with a sat. NaHCO$_3$ sol. The o.l. was dried (MgSO$_4$), filtered and the solvent evaporated in vacuo. The resulting oil was purified via flash column chromatography (silica; heptane/EtOAc, from 100/0 to 70/30) to give two batches of the desired intermediate, both pure enough to be used in the subsequent step. Combined yields: 1.513 g of intermediate 68 (52% yield).

b) Preparation of Intermediate 69

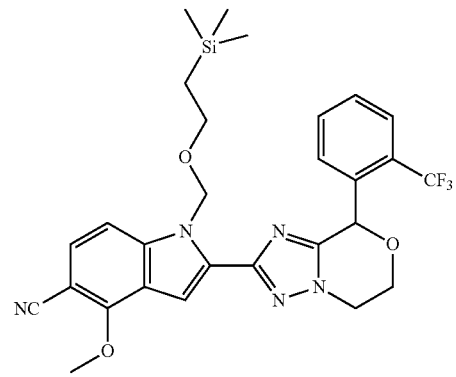 [SMILES: COc1c(C#N)ccc2c1cc(-c1nc3n(n1)CCOC3c1ccccc1C(F)(F)F)n2COCC[Si](C)(C)C]

Intermediate 68 (1.5 g, 2.406 mmol) was dissolved in DMF (9 mL), Zn(CN)$_2$ (217 mg, 1.8 mmol) was added and the mixture was degassed under N$_2$. Pd(PPh$_3$)$_4$ (167 mg, 0.144 mmol) was then added and the mixture was stirred for 1.5 h at 160° C. under microwave irradiation. The solvent was then evaporated in vacuo and the residue was dissolved in EtOAc and washed with water. The o.l. was dried (MgSO$_4$), filtered and concentrated, and the residual purified via flash column chromatography (silica; heptane/EtOAc from 100/0 to 70/30). Yield: 433 mg of intermediate 69 (32% yield).

Example A24 a) Preparation of Intermediate 70

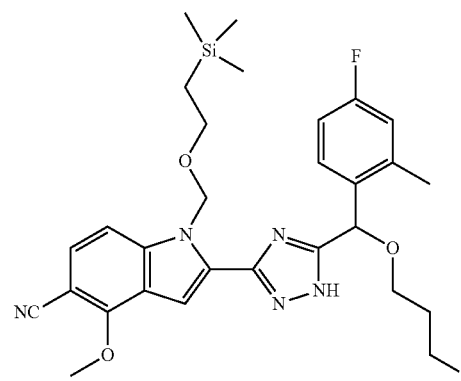

To a sol. of intermediate 44 (600 mg, 1.664 mmol) and imidazole (1.360 g, 19.973 mmol) in MeOH (3.37 mL) was added intermediate 14 (958 mg, 3.329 mmol) and the reaction mixture was stirred at r.t. for 4 h, then overnight at 60° C. in an oil bath, then at 120° C. for 40 min under microwave irradiation. The mixture was concentrated and dissolved in EtOAc, washed with a sat. NaHCO$_3$ sol. and brine. The o.l. was dried (Na$_2$SO$_4$), filtered and the solvent evaporated in vacuo to give a crude product that was purified by flash column chromatography (silica; eluent: heptane/EtOAc from 100/0 to 50/50). Yield: 541 mg of intermediate 70 (56% yield); 44 mg of 75% pure intermediate 71 were also collected.

b) Preparation of Intermediate 71

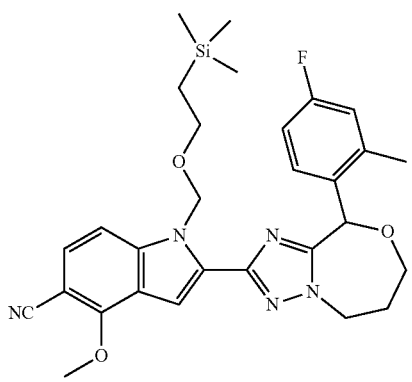 [SMILES: COc1c(C#N)ccc2c1cc(-c1nc3n(n1)CCCOC3c1ccc(F)cc1C)n2COCC[Si](C)(C)C]

Intermediate 70 (163 mg, 0.279 mmol) was dissolved in THF (2 mL) and NaH (60% dispersion in mineral oil, 12 mg, 0.307 mmol) was added. The r.m. was stirred under $N_2$ at reflux for 4 h and then at reflux overnight. After cooling to r.t. water and EtOAc were added and the phases separated. The o.l. was washed with brine. The combined water layers were extracted again with EtOAc. The combined o.l. were dried ($Na_2SO_4$) and evaporated until dryness to give a crude which was purified by flash column chromatography (silica: eluent: heptane/EtOAc from 100/0 to 0/100). Desired intermediate was collected and evaporated until dryness. Yield: 79 mg of intermediate 71 (35% yield, 68% purity).

Example A25 a) Preparation of Intermediate 72

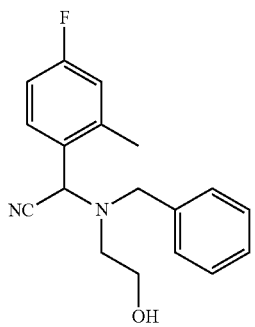 [SMILES: Cc1cc(F)ccc1C(C#N)N(CCO)Cc1ccccc1]

4-Fluoro-2-methylbenzaldehyde (15 g, 108.58 mmol) and MeOH (7.5 mL) were added to a sol. of sodium bisulfite (12.429 g, 119.44 mmol) in water (225 mL) at r.t., and the mixture was stirred at r.t. for 10 min. NaCN (12.491 g, 249.744 mmol) was added and the reaction mixture was stirred at r.t. for 40 min. N-Benzylethanolamine (17.24 g, 114.014 mmol) and MeOH (22.5 mL) were added and the mixture was further stirred at r.t. for 16 h. The reaction mixture was diluted with EtOAc and the o.l. was separated, washed with water, then with brine, dried ($MgSO_4$) and filtered. The solvent was removed in vacuo and the residue was triturated and suspended in DIPE and then filtered to afford a first batch of the desired intermediate. The filtrate was evaporated and again the residue was triturated in DIPE. The suspension was stirred overnight at r.t. and filtered to afford a second batch of the desired intermediate. Combined yields: 21.87 g of intermediate 72 (67% yield).

b) Preparation of Intermediate 73

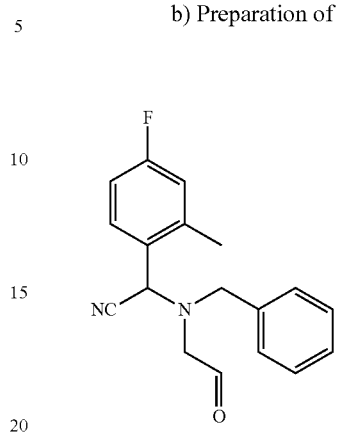

To a sol. of intermediate 72 (3.5 g, 11.731 mmol) and $Et_3N$ (9.783 mL, 7.0385 mmol) in DMSO (56 mL) was added dropwise sulfur trioxide pyridine complex (5.6 g, 35.192 mmol) in DMSO (56 mL). The resulting mixture was stirred at r.t. for 1 h and diluted with $Et_2O$ and aq. $NH_4Cl$. The mixture was further diluted with $H_2O$ and the aq. ph. was extracted with $Et_2O$, dried ($MgSO_4$) and concentrated in vacuo to afford a crude oil. Purification was done via flash column chromatography (silica; eluent: heptane/EtOAc from 100/0 to 70/30). Yield: 3 g of intermediate 73 (86% yield).

c) Preparation of Intermediate 74

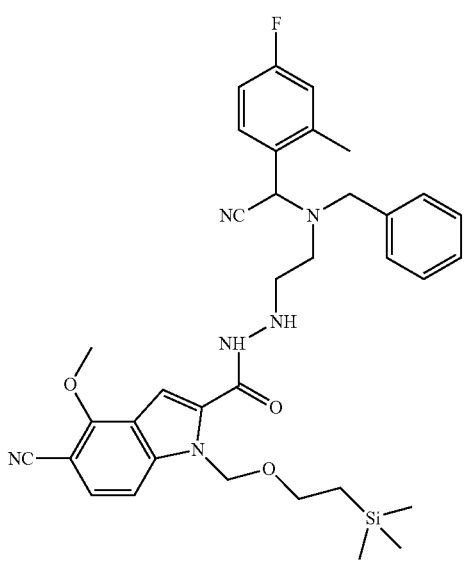 [SMILES: COc1c(C#N)ccc2c1cc(C(=O)NNCCN(Cc1ccccc1)C(C#N)c1ccc(F)cc1C)n2COCC[Si](C)(C)C]

To a sol. of intermediate 73 (2.25 g, 7.593 mmol) in DCM (118 mL) was added intermediate 44 (2.027 g, 5.624 mmol), AcOH (2.4 mL) and MeOH (24 mL), The reaction was stirred for 5 min, then $NaCNBH_3$ (848 mg, 13.498 mmol) was added and the reaction mixture was then stirred for 16 h. The mixture was diluted with EtOAc and washed with sat. aq. $NaHCO_3$, dried ($MgSO_4$) and concentrated in vacuo. Purification was done using flash column chromatography (silica; eluent: DCM/EtOAc from 100/0 to 70/30). Yield: 3 g of intermediate 74 (83% yield).

d) Preparation of Intermediate 75

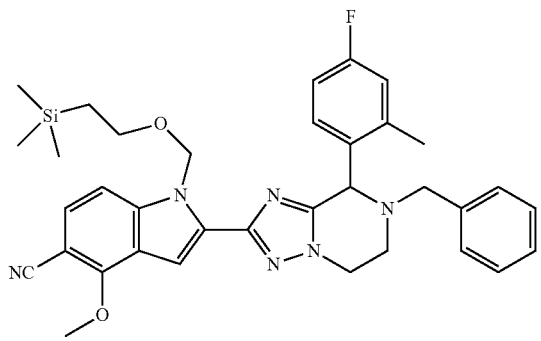 [SMILES: COc1c(C#N)ccc2c1cc(-c1nc3n(n1)CCN(Cc1ccccc1)C3c1ccc(F)cc1C)n2COCC[Si](C)(C)C]

AcOH (4.3 mL) was added to intermediate 74 (3.65 g, 5.696 mmol) in toluene (49 mL). The reaction mixture was stirred at 80° C. for 20 h, then concentrated and partitioned between sat. NaHCO$_3$ sol. and EtOAc. The o.l. was dried (MgSO$_4$), allowed to pass through a silica pad and then concentrated in vacuo. Purification was done using flash column chromatography (silica; eluent: DCM/EtOAc from 100/o to 70/30). The product fractions were collected and evaporated. Yield: 1.75 g of intermediate 75 (49% yield).

e) Preparation of Intermediate 76

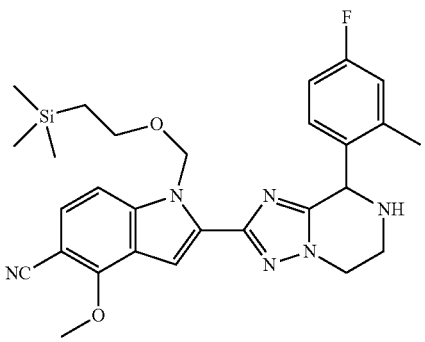

Intermediate 75 (500 mg, 0.803 mmol) in MeOH (67 mL) was hydrogenated in the presence of 10% Pd/C (73 mg, 0.069 mmol) at 50° C. The reaction mixture was filtered over diatocemateous earth. The filtrate was concentrated and the residue was purified by flash column chromatography (silica; eluent: DCM/(7 N NH$_3$ in MeOH) from 100/0 to 95/5 as eluent. The product fractions were collected and evaporated. Yield: 380 mg of intermediate 76 (89% yield).

f) Preparation of Intermediate 77

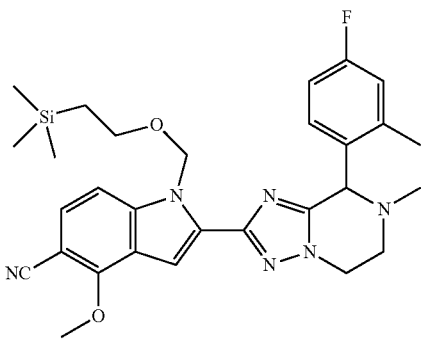

Intermediate 76 (120 mg, 0.225 mmol), paraformaldehyde (180 mg, 2.218 mmol) and AcOH (0.5 mL) were stirred in DCM (5 mL) at r.t. for 5 min, then NaCNBH$_3$ (60 mg, 0.955 mmol) was added and the reaction mixture was then stirred for 20 h. The mixture was taken up in EtOAc and neutralized with sat. Na$_2$CO$_3$, the o.l. was dried (MgSO$_4$), filtered and evaporated. The residue was purified via flash column chromatography (silica; eluent: DCM/(7 N NH$_3$ in MeOH) from 100/0 to 99/1). The product fractions were collected and evaporated. Yield: 60 mg of intermediate 77 (49% yield).

Example A26 a) Preparation of Intermediate 78

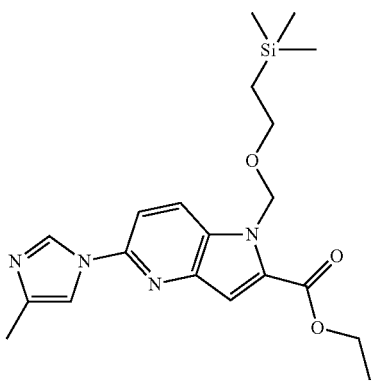 [SMILES: CCOC(=O)c1cc2nc(-n3cnc(C)c3)ccc2n1COCC[Si](C)(C)C]

Starting from intermediate 22, intermediate 78 was prepared by using a procedure similar to the one described for the synthesis of intermediate 37 (65% yield).

b) Preparation of Intermediate 79

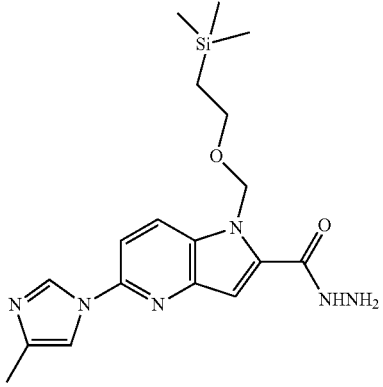 [SMILES: Cc1cn(-c2ccc3c(cc(C(=O)NN)n3COCC[Si](C)(C)C)n2)cn1]

Starting from intermediate 78, intermediate 79 was prepared by using a procedure similar to the one described for the synthesis of intermediate 23 (67% yield).

c) Preparation of Intermediate 80

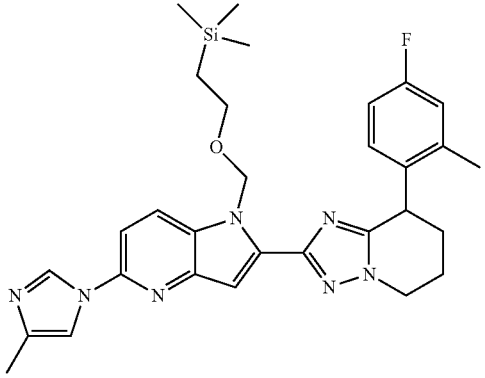

Starting from intermediate 79 and intermediate 3, intermediate 80 was prepared by using a procedure similar to the one described for the synthesis of intermediate 59 (quantitative yield).

Example A27 a) Preparation of Intermediate 81

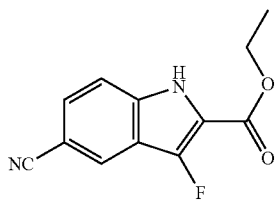 [SMILES: CCOC(=O)c1[nH]c2ccc(C#N)cc2c1F]

A mixture of N-fluoro-2,4,6-trimethylpyridinium triflate (4 g, 13.829 mmol) and ethyl 5-cyano-1H-indole-2-carboxylate (911 mg, 4251 mmol) in 1,1,2,2-tetrachloroethane (28 mL) was heated at 100° C. for 8 h, then stirred at r.t. overnight. The reaction was then heated up again at 100° C. for 8 h and stirred at r.t. overnight. After this time heating the reaction again to 100° C. did not push the reaction forward. The mixture was allowed to cool down, diluted with EtOAc, then extracted with water (×2) and brine. The o.l. was collected, dried and the solvent evaporated to give a yellow mixture, that was joined to a second batch of crude material obtained following a similar reaction procedure starting from 270 mg (1.26 mmol) of ethyl 5-cyano-1H-indole-2-carboxylate. The crude was azeotroped with toluene (×2) to remove residual 1,1,2,2-tetrachloroethane, then purified by Prep HPLC [RP Vydac Denali C18-10 µm, 200 g, 5 cm; mobile phase: 0.25% NH$_4$HCO$_3$ sol. in water/CH$_3$CN]. The desired fractions were collected, evaporated, dissolved again in MeOH and evaporated, yielding a fraction which was further purified by Prep SFC [Chiralpak Diacel AD 30×250 mm; mobile phase: CO$_2$, iPrOH with 0.2% iPrNH$_2$] to give the desired intermediate. Combined yield: 223 mg of intermediate 81 (17% yield).

Example A28 a) Preparation of Intermediate 82

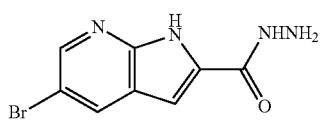 [SMILES: NNC(=O)c1cc2cc(Br)cnc2[nH]1]

5-Bromo-7-azaindole-2-carboxylic acid (500 mg, 2.074 mmol) and carbodiimidazole (420 mg, 2.593 mmol) were dissolved in CH$_3$CN (7.6 mL) and the mixture was stirred at 60° C. for 75 min, then it was cooled to r.t. and hydrazine hydrate (1.514 mL, 31.115 mmol) was added. The mixture was stirred at 60° C. for 75 min, the formed precipitate was filtered and washed with DIPE. The crude was used without further purification for the subsequent reaction. The yield was assumed to be quantitative.

Example A29 a) Preparation of Intermediate 83

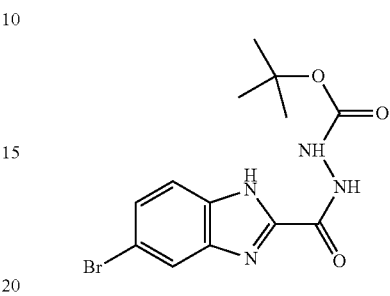

5-Bromo-1H-benzoimidazole-2-carboxylic acid (5 g, 20.743 mmol) was stirred in DCM (200 mL) and DIPEA (10.7 mL, 62.229 mmol) and HBTU (9.44 g, 24.892 mmol) were added. The r.m. was stirred at r.t. for 1 h, then tert-butylcarbazate (3.016 mmol, 22.817 mmol) dissolved in 20 mL of DCM was added dropwise and the r.m. was stirred at r.t. for 20 h. The r.m. was then washed with a sol. of Na$_2$CO$_3$. The o.l. was dried (MgSO$_4$), filtered and evaporated. The residue was purified by flash column chromatography (silica; eluent: DCM/MeOH from 98/2 to 97/3). The fractions containing the product were collected, concentrated, the residue stirred in Et$_2$O, the precipitate filtered off and dried in vacuo at 60° C. Yield: 7 g of intermediate 83 (95% yield).

b) Preparation of Intermediate 84

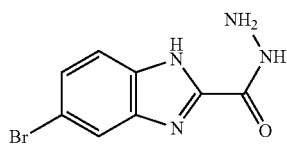 [SMILES: NNC(=O)c1nc2cc(Br)ccc2[nH]1]

Intermediate 83 (7.7 g, 21.678 mmol) was stirred in MeOH (40 mL), HCl 5-6 N in iPrOH was added and the r.m. was stirred at r.t. for 24 h. A precipitate was formed, that was filtered off and dried in vacuo at 60° C. Yield: 5.7 g of intermediate 84 (90% yield).

Example A30 a) Preparation of Intermediate 85

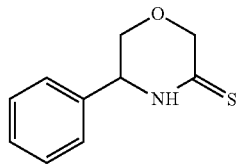 [SMILES: S=C1COCC(c2ccccc2)N1]

Phosphorus pentasulfide (3.312 g, 14.898 mmol) was added to a sol. of 5-phenylmorpholin-3-one (3.3 g, 18.623 mmol) and THF (90 mL) at r.t. The r.m. was heated at reflux temperature for 30 min, then cooled to r.t., filtered over diatomaceous earth and washed several times with DCM. The o.l. was evaporated in vacuo until dryness to give a crude material, which was dissolved in DCM (q.s.)/MeOH (q.s.). The DCM was then evaporated, and the desired product precipitated out of the solution. The mixture was allowed to reach r.t., filtered and washed with heptanes/EtOAc 1/1. The residue was dissolved again in DCM/MeOH and the solvent evaporated until dryness to give a first batch of desired intermediate 85 (1.77 g, 49% yield). The filtrate was evaporated in vacuo until dryness to give a second batch of impure material (2.1 g).

b) Preparation of Intermediate 86

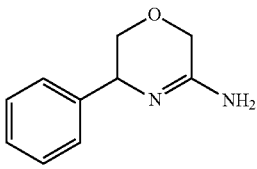 [SMILES: NC1=NC(c2ccccc2)COC1]

Intermediate 85 (375 mg, 1.94 mmol) and NH$_3$ (7 M in MeOH, 20 mL) was stirred at 60° C. in a closed pressure tube overnight, then the solvent evaporated and the residue dissolved in fresh NH$_3$ (7 M in MeOH, 20 mL). The r.m. was stirred at 60° C. for 2 d. The solvent was then evaporated until dryness and the residue dissolved in DCM/MeOH 8/2 and washed with water. The water layer was extracted with DCM/MeOH 8/2 (×2), then the water layer was evaporated until dryness, the residue stirred with DCM/MeOH 8/2 and the suspension filtered. The filtrate was evaporated until dryness to afford the desired intermediate. Yield: 269 mg of intermediate 86 (77% yield).

Example A31 a) Preparation of Intermediate 87

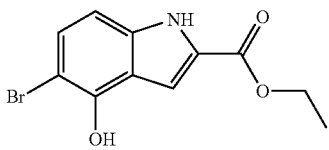 [SMILES: CCOC(=O)c1cc2c(O)c(Br)ccc2[nH]1]

BBr$_3$ (1 M in DCM, 45 mL, 45 mmol) was added dropwise to intermediate 36 (4.5 g, 15.094 mmol) in DCM (45 mL) at −70° C. under N$_2$. After addition the reaction mixture was allowed to reach 0° C., and it became an orange-brown sol. after 1 h at 0° C. The reaction was then added dropwise to 300 mL of EtOH and stirred at r.t. for 1 h, then it was concentrated to 50 mL and taken up in EtOAc (500 mL) and water (200 mL). Brine (100 mL) was then added, the o.l. separated, dried (MgSO$_4$), filtered and concentrated. The product was suspended in DIPE and the solid filtered off, washed and dried. Yield: 3 g of intermediate 87 (70% yield).

b) Preparation of Intermediate 88

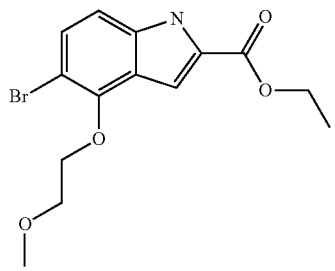 [SMILES: CCOC(=O)c1cc2c(OCCOC)c(Br)ccc2[nH]1]

Intermediate 87 (2.841 g, 10 mmol), 2-methoxyethanol (951 mg, 12.5 mmol) and PPh$_3$ 3.67 g, 14 mmol) were stirred in THF (25 mL) in a cold water bath. DIAD (2.83 g, 14 mmol) was added dropwise over 10 min, then the reaction mixture was stirred at r.t. for 1 h. The solvent was evaporated and the residue was purified via flash column chromatography (silica; eluent: heptane/EtOAc from 90/10 to 50/50). The product fractions were collected and evaporated, to afford a solid after evaporation. Yield: 2.6 g, of intermediate 88 (76% yield).

c) Preparation of Intermediate 89

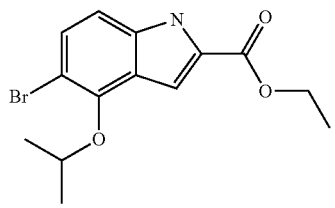 [SMILES: CCOC(=O)c1cc2c(OC(C)C)c(Br)ccc2[nH]1]

Starting from intermediate 87, intermediate 89 was prepared by using a procedure similar to the one described for the synthesis of intermediate 88 (70% yield).

c1) Preparation of Intermediate 90

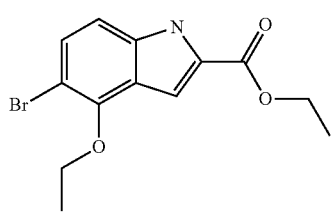 [SMILES: CCOC(=O)c1cc2c(OCC)c(Br)ccc2[nH]1]

Starting from intermediate 87, intermediate 90 was prepared by using a procedure similar to the one described for the synthesis of intermediate 88 (39% yield).

D) Preparation of Intermediate 91

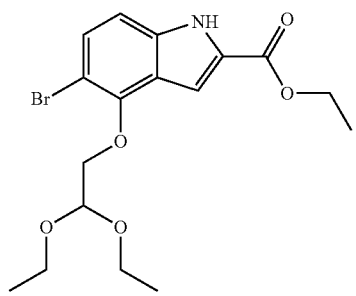 [SMILES: CCOC(=O)c1cc2c(OCC(OCC)OCC)c(Br)ccc2[nH]1]

Starting from intermediate 87, intermediate 91 was prepared by using a procedure similar to the one described for the synthesis of intermediate 88 (56% yield).

e) Preparation of Intermediate 92

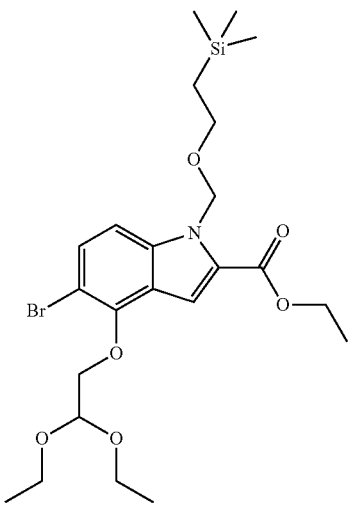 [SMILES: CCOC(=O)c1cc2c(OCC(OCC)OCC)c(Br)ccc2n1COCC[Si](C)(C)C]

Starting from intermediate 91, intermediate 92 was prepared by using a procedure similar to the one described for the synthesis of intermediate 37 (quantitative yield).

f) Preparation of Intermediate 93

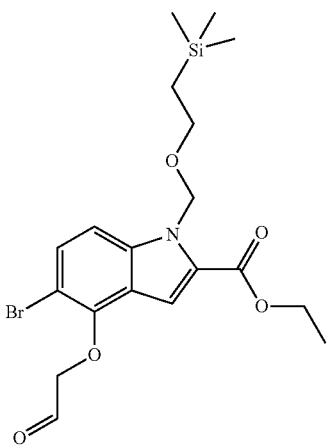 [SMILES: CCOC(=O)c1cc2c(OCC=O)c(Br)ccc2n1COCC[Si](C)(C)C]

Intermediate 92 (500 mg, 0.942 mmol) and PTSA (81 mg, 0.471 mmol) were stirred in acetone (24 mL) and water (0.54 mL) at 45° C. for 4 d, then the reaction mixture was taken up in DCM and washed with water. The o.l. was dried (MgSO$_4$), filtered and evaporated. The residue was purified by flash column chromatography (silica; eluent: heptane/EtOAc from 90/10 to 30/70). The product fractions were collected and evaporated. Yield: 300 mg of intermediate 93 (70% yield).

g) Preparation of Intermediate 94

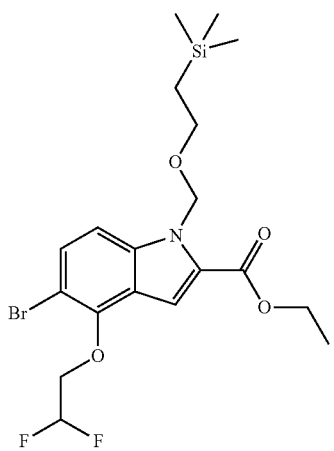 [SMILES: CCOC(=O)c1cc2c(OCC(F)F)c(Br)ccc2n1COCC[Si](C)(C)C]

DAST (159 mg, 0.986 mmol) was added dropwise to intermediate 93 (300 mg, 0.657 mmol) in DCM (4 mL) under N$_2$ at 0° C. The reaction mixture was stirred at r.t. for 2 hours. DCM and water were added, the o.l. was dried (MgSO$_4$), filtered and evaporated. The residue was purified by flash column chromatography (silica; eluent: heptane/EtOAc from 90/10 to 30/70. The product fractions were collected and evaporated. Yield: 220 mg of intermediate 94 (87% LC-MS purity, 61% yield).

Example A32 a) Preparation of Intermediates 95 and 96

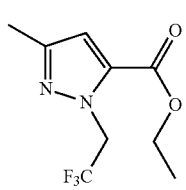

95

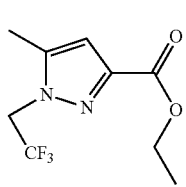

96

NaH (60% as a dispersion in mineral oil, 3.867 g, 96.68 mmol) was dissolved in DMF (300 mL) under N$_2$ at 0° C. To this sol. was added ethyl 3-methylpyrazole-5-carboxylate in DMF (80 mL) over 10 min at 0° C. After the addition, the reaction mixture was stirred for 10 min at 0° C. and at r.t. for 40 min. To the mixture was added 2,2,2-trifluoroethyl trifluoromethanesulfonate (13.9 mL, 96.68 mmol) and the mixture was stirred at r.t. for 3 h. EtOH was added at 0° C. to quench the reaction. Water was added to the mixture and the water layer was extracted with EtOAc. The o.l. were then washed with brine and the solvent was removed in vacuo to give a crude which was purified via flash column chromatography (silica; eluent: heptane/EtOAc from 100/0 to 60/40), to afford the desired intermediates. Yields: 7.46 g of intermediate 95 (36% yield) and 8.04 g of intermediate 96 (38% yield).

b) Preparation of Intermediate 97

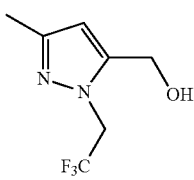

DIBAL-H (1.5 M in toluene, 63 mL, 94.753 mmol) was added slowly to intermediate 95 (7.46 g, 31.58 mmol) in DCM (149 mL) at −78° C. under $N_2$. The reaction was then quenched with MeOH and allowed to warm to r.t., then it was diluted with DCM and treated with an aq. sol. of Rochelle's salt (10%) and the suspension left to stir vigorously for 20 min. The two layers were separated, and the o.l. dried ($MgSO_4$), filtered and evaporated, to give a crude material, used as such in the subsequent step. Yield: 4.9 g of intermediate 97 (80% yield).

c) Preparation of Intermediate 98

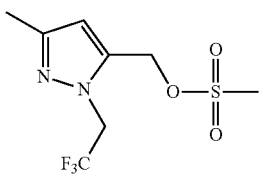

Intermediate 97 (4.9 g, 25.237 mmol) was dissolved in DCM (192 mL). The sol. was cooled to 0° C. MsCl (2.156 mL, 27.761 mmol) and $Et_3N$ (3.859 mL, 27.761 mmol) were added and the reaction mixture was stirred for 1 h at r.t. Water was added and the o.l. was washed with a saturated sol. of $Na_2CO_3$, dried with $Na_2SO_4$, filtered and concentrated in vacuo to give the desired intermediate. Yield: 6.608 g of intermediate 98 (96% yield).

d) Preparation of Intermediate 99

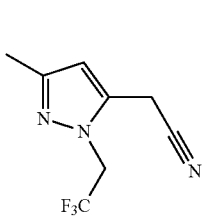

Intermediate 98 (6.6 g, 24.243 mmol) and KCN (5.525 g, 84.849 mmol) were dissolved in $CH_3CN$ (122 mL) under $N_2$. The reaction mixture was stirred overnight at r.t. $Na_2CO_3$ was added to the reaction mixture and the pH was checked (>8). EtOAc was added and the aq. ph. extracted (×2). The o.l. were combined and dried with $Na_2CO_3$, filtered and concentrated in vacuo to give a crude which was used as such in the subsequent step. Yield: 5.12 g of intermediate 99 (92% GC-MS purity, 96% yield).

e) Preparation of Intermediate 100

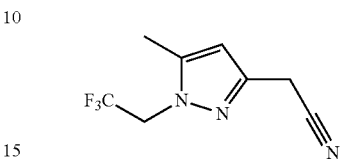

Starting from intermediate 96, intermediate 100 was prepared by using a procedure similar to the ones described for the synthesis of intermediate 99.

B. Preparation of the Compounds

Example B1

Preparation of Compound 1

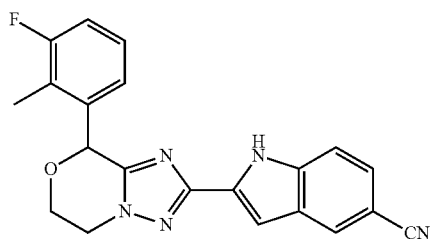 [SMILES: Cc1c(F)cccc1C1OCCn2nc(-c3cc4cc(C#N)ccc4[nH]3)nc21]

TFA (0.78 mL, 10.21 mmol) was added to a sol. of intermediate 58 (245 mg, 0.517 mmol) in DCM (7.8 mL). The r.m. was stirred at r.t. for 16 h. Then the r.m. was neutralized with a sat. aq. $NaHCO_3$ sol. The o.l. was separated, dried ($MgSO_4$), filtered and the solvent evaporated in vacuo. The product was crystallized from $CH_3CN$, filtered off and dried in the oven to give a white solid. Yield: 105 mg of compound 1 (54%).

Example B2

Preparation of Compound 2

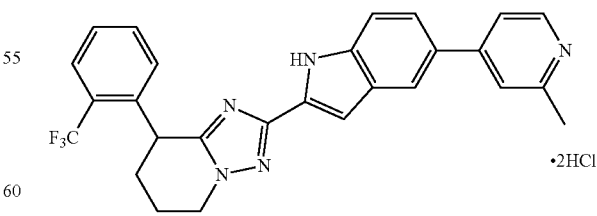

2-Picoline-4-boronic acid (188 mg, 1.377 mmol), $PPh_3$ (18 mg, 0.0689 mmol), a 1.5 M aq. sol. of $K_2CO_3$ (1.7 mL, 2.582 mmol) and $Pd(OAc)_2$ (11 mg, 0.0482 mmol) were added to a degassed sol. of intermediate 61 (350 mg, 0.689 mmol) in dioxane (5 mL). The r. m. was stirred at 120° C. for 24 h. The r.m. was poured into water and the aq. layer was extracted with DCM. The separated o.l. was dried (MgSO$_4$), filtered and the solvent evaporated in vacuo. The crude product was purified by flash column chromatography (silica; eluent: DCM/(7 N NH$_3$ in MeOH) from 100/0 to 97/3). The product fractions were collected and the solvent evaporated in vacuo. The product was dissolved in DIPE and 2 drops of a 6 N HCl sol. in iPrOH was added. The solvent was evaporated in vacuo and the product was crystallized from CH$_3$CN, filtered off and dried. Yield: 32 mg of compound 2 (8%% yield; 0.2 HCl).

Example B3

Preparation of Compound 3

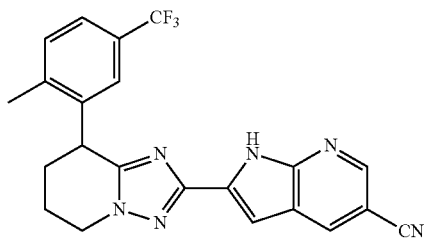 [SMILES: Cc1ccc(C(F)(F)F)cc1C1CCCn2nc(-c3cc4cc(C#N)cnc4[nH]3)nc21]

A sol. of intermediate 57 (90 mg, 0.213 mmol) and potassium chloride (9 mg, 0.121 mmol) in water (1 mL) and DMF (0.5 mL) was stirred at 200° C. for 45 min under microwave irradiation. The r.m. was stirred (×2) at 200° C. for 30 min under microwave irradiation. The mixture was extracted with EtOAc (×2). The o.l. was separated, dried over MgSO$_4$, filtered and the solvent evaporated in vacuo. The crude product was purified by RP HPLC [RP SunFire Prep C18 OBD-5 μm, 19×100 mm; mobile phase: 0.25% NH$_4$HCO$_3$ sol. in water/CH$_3$CN]. Yield: 9 mg of compound 3 (10% yield).

Example B4

Preparation of Compound 4

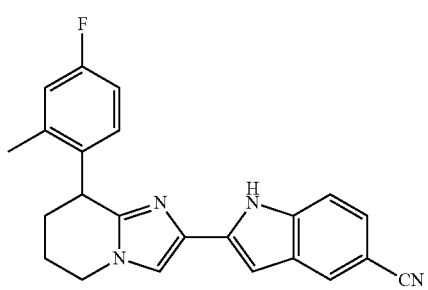 [SMILES: Cc1cc(F)ccc1C1CCCn2cc(-c3cc4cc(C#N)ccc4[nH]3)nc21]

A sol. of intermediate 62 (292 mg, 0.45 mmol, 78% pure) in MeOH (2.3 mL) and a 1 M aq. sol. of NaOH (5.0 mL, 5.0 mmol) was stirred at r.t. for 20 h. Then a 1 M aq. sol. of NaOH (0.67 mLr, 0.67 mmol) was added and the r.m. was stirred at r.t. for 20 h. The r.m. was acidified to pH 5 with a 1 M aq. sol. of HCl. The aq. layer was extracted with DCM. The separated o.l. was dried (MgSO$_4$), filtered and the solvent evaporated in vacuo. The crude product was purified twice by flash column chromatography (silica; eluent: heptane/DCM from 20/80 to 0/100). The product fractions were collected and the solvent evaporated in vacuo. As the crude product still contained intermediate 38, it was dissolved in MeOH (1 mL) and stirred again with a 1 M aq. sol. of NaOH (2 mL, 2 mmol) for 20 h. The r.m. was acidified to pH 6 with a 1 M aq. sol. of HCl. The aq. layer was extracted with DCM. The separated o.l. was dried (MgSO$_4$), filtered and the solvent evaporated in vacuo. The product was precipitated from DIPE, filtered off and dried in vacuo. Yield: 68 mg of compound 4 (41%% yield).

Example B5

Preparation of Compound 5

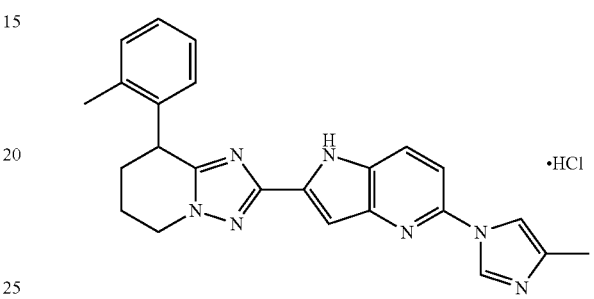

Imidazole (2.32 g, 34.1 mmol) and intermediate 4 (1.65 g, 5.69 mmol) were added to a sol. of intermediate 23 (729 mg, 2.84 mmol) in MeOH (5.4 mL) at 0° C. under N$_2$ atmosphere. The r.m. was stirred at 35° C. for 16 h and at 60° C. then for 16 h. The solvent was evaporated in vacuo. The residue was stirred in water/DCM (1/1). The precipitate was filtered off. The product was converted in HCl salt using a 6 N HCl sol. in iPrOH. The product was recrystallized from iPrOH, filtered off and dried in vacuo. Yield: 284 mg of compound 5 (19% yield; .HCl) as pale yellow solid.

Example B6

Preparation of Compound 6

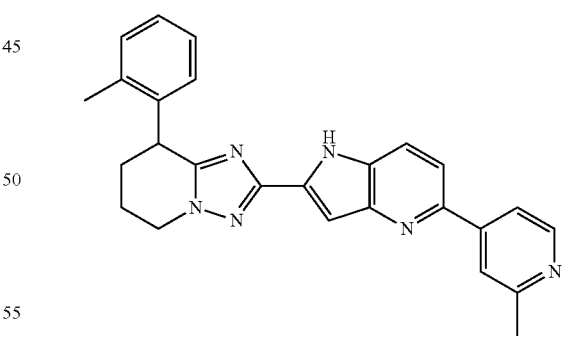

2-Picoline-4-boronic acid (115 mg, 0.84 mmol), Pd(PPh$_3$)$_4$ (88 mg, 0.077 mmol), a 2 M aq. sol. of K$_2$CO$_3$ (1.15 mL, 2.3 mmol) were added to a degassed sol. of intermediate 59 (279 mg, 0.77 mmol) in DME (4 mL). The r.m. was stirred at 160° C. for 2 h under microwave irradiation. The r.m. was poured into water and the aq. layer was extracted with DCM. The separated o.l. was dried (MgSO$_4$), filtered and the solvent evaporated in vacuo. The crude product was purified by flash column chromatography (silica; eluent: DCM/(7 N NH$_3$ in MeOH) from 100/0 to 95/5). The product fractions were collected and the solvent evaporated in vacuo. The crude product was purified by RP HPLC [RP SunFire Prep C18 OBD-10 μm, 30×150 mm; mobile phase: 0.25% NH$_4$HCO$_3$ sol. in water/CH$_3$CN]. The product fractions were collected and the solvent evaporated in vacuo. Yield: 48 mg of compound 6 (15% yield).

Example B7

Preparation of Compound 7

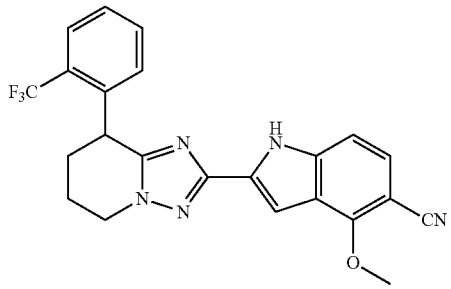 [SMILES: COc1c(C#N)ccc2[nH]c(-c3nc4n(n3)CCCC4c3ccccc3C(F)(F)F)cc12]

A mixture of intermediate 60 (300 mg, 0.61 mmol), Pd(PPh$_3$)$_4$ (42 mg, 0.037 mmol) and Zn(CN)$_2$ (54 mg, 0.46 mmol) in DMF (1.35 mL) was stirred at 80° C. for 24 h. Additional Pd(PPh$_3$)$_4$ (42 mg, 0.037 mmol) and Zn(CN)$_2$ (54 mg, 0.46 mmol) were added and the r.m. was stirred at 135° C. for 150 min under microwave irradiation. The r.m. was diluted with EtOAc and the mixture was washed with water. The separated o.l. was dried (MgSO$_4$), filtered and the solvent evaporated in vacuo. The crude product was purified by flash column chromatography (silica; eluent: DCM/(7 N NH$_3$ in MeOH) from 100/0 to 99/1). The product fractions were collected and the solvent evaporated in vacuo. The product was crystallized from DIPE, filtered off and dried in vacuo. Yield: 40 mg of compound 7 (15% yield).

Example B8

Preparation of Compound 8

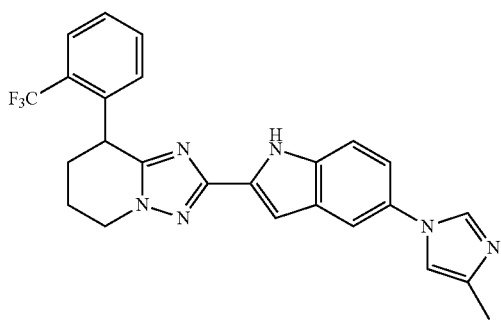 [SMILES: Cc1cn(-c2ccc3[nH]c(-c4nc5n(n4)CCCC5c4ccccc4C(F)(F)F)cc3c2)cn1]

CuI (94 mg, 0.49 mmol), cesium carbonate (961 mg, 2.95 mmol) and N,N'-dimethylethylenediamine (0.052 mL, 0.49 mmol) were added to a sol. of intermediate 61 (500 mg, 0.98 mmol) and 4-methylimidazole (323 mg, 3.93 mmol) in DMF (3 mL). The r.m. was stirred for 48 h at 120° C. The r.m. was poured into water. The aq. layer was extracted with EtOAc (×2). The separated o.l. was dried (MgSO$_4$), filtered and the solvent evaporated in vacuo. The crude product was purified by flash column chromatography (silica; eluent: DCM/(7 N NH$_3$ in MeOH) from 100/0 to 97/3). The product fractions were collected and the solvent evaporated in vacuo. The product was crystallized from CH$_3$CN, filtered off and dried in vacuo. Yield: 57 mg of compound 8 (12% yield).

Example B9

Preparation of Compounds 10 and 11

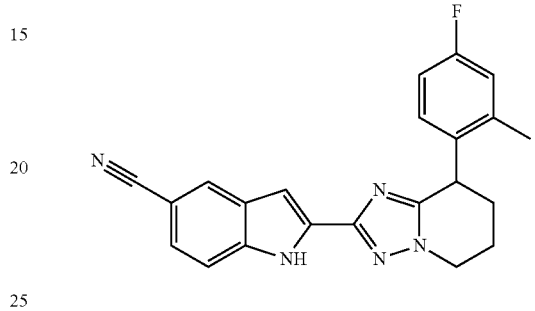

Compound 9: mixture of R and S enantiomers
Compound 10: R or S (OR: −87.92° (589 nm; 20° C.; 0.72 w/v %; MeOH))
Compound 11: S or R (OR: +72.53° (589 nm; 20° C.; 0.95 w/v %; MeOH))

Compound 9 (mixture of R and S enantiomers) was prepared by following an analogous reaction protocol as described in Example B5. An amount of compound 9 (337 mg) was separated into its enantiomers by preparative SFC [Chiralcel Diacel OJ 20×250 mm; mobile phase: CO$_2$, MeOH with 0.2% 2-propylamine]. The respective product fractions were collected and evaporated. Both residues were re-dissolved in MeOH and the two sol. were evaporated again yielding 2 different products:

Product 1: 120 mg of compound 10 (36% yield; R or S; OR: −87.92° (589 nm; 20° C.; 0.72 w/v %; MeOH)).

Product 2: Compound 11 was stirred in heptane (q.s.), filtered, and dried in the vacuum oven (3 days). Yield: 130 mg of compound 11 (39% yield; S or R; OR: +72.53° (589 nm; 20° C.; 0.95 w/v %; MeOH)).

Example B10

Preparation of Compounds 13 and 14

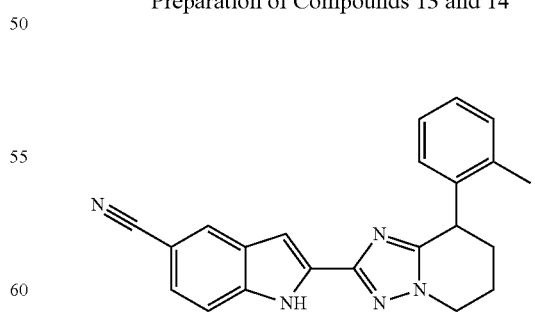

Compound 12: mixture of R and S enantiomers
Compound 13: R or S (OR: −96.61° (589 nm; 20° C.; 0.3985 w/v %; MeOH))
Compound 14: S or R (OR: +97.42° (589 nm; 20° C.; 0.4465 w/v %; MeOH))

Compound 12 (mixture of R and S enantiomers) was prepared by following an analogous reaction protocol as described in Example B7. An amount of compound 12 (150 mg) was separated into its enantiomers by preparative SFC [Chiralcel Diacel OJ 20×250 mm; mobile phase: CO$_2$, MeOH with 0.2% 2-propylamine]. The respective product fractions were collected and evaporated. Both residues were re-dissolved in MeOH and the two sol. were evaporated again. The two different residues were co-evaporated with MeOH, triturated with DIPE, filtered and dried, yielding 2 different products:

Product 1: 56 mg of compound 13 (37% yield; R or S; OR: −96.61° (589 nm; 20° C.; 0.3985 w/v %; MeOH)).

Product 2: 55 mg of compound 14 (37% yield; S or R; OR: +97.42° (589 nm; 20° C.; 0.4465 w/v %; MeOH)).

Example B11

Preparation of Compounds 41 and 42

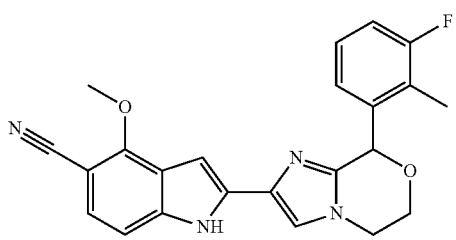 [SMILES: COc1c(C#N)ccc2[nH]c(-c3cn4c(n3)C(c3cccc(F)c3C)OCC4)cc12]

Compound 40: mixture of R and S enantiomers

Compound 41: R or S (OR: −84.34° (589 nm; 20° C.; 0.415 w/v %, DMF))

Compound 42: S or R (OR: +69.05° (589 nm; 20° C.; 0.475 w/v %, DMF))

Intermediate 63 (3.3 g, 80% purity, 4.956 mmol) was cooled at 0° C., then TFA (7 mL, 94.472 mmol) was added carefully. After the addition was finished, the water bath was removed and the r.m. was stirred at r.t. for 6 h, then cooled using an ice-bath. NaOH (1 M, 109 mL, 109 mmol) and THF (121 mL) were added and the pH of the reaction checked (>7). The r.m. was stirred for 30 min, then quenched with NH$_4$Cl. DCM was added, the o.l. was separated and dried (MgSO$_4$), filtered and the solvent was evaporated in vacuo. The residue was purified by flash column chromatography (silica; eluent: heptane/EtOAc from 100/0 to 30/70). The product fractions were collected and the solvent was evaporated. The residue was suspended in CH$_3$CN and the precipitate filtered off and dried to give the desired compound (1.3 g, 65%). An amount of compound 40 (114 mg) was separated into its enantiomers by preparative SFC [Chiralcel Diacel OD 20×250 mm; mobile phase: CO$_2$, MeOH with 0.2% 2-propylamine]. The respective product fractions were collected and evaporated. Both residues were re-dissolved in MeOH and the two sol. were evaporated again, to yield compounds 41 and 42.

Product 1: 43 mg of compound 41 (38% yield; R or S; OR: −84.34° (589 nm; 20° C.; 0.415 w/v %; DMF)).

Product 2: 44 mg of compound 42 (39% yield; S or R; OR: +69.05° (589 nm; 20° C.; 0.475 w/v %; DMF)).

Example B12

Preparation of Compounds 44 and 45

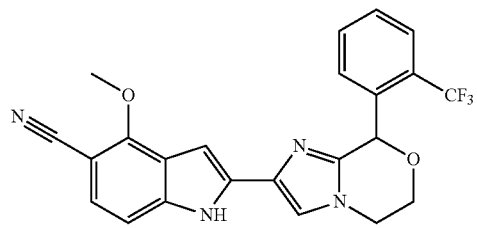 [SMILES: COc1c(C#N)ccc2[nH]c(-c3cn4c(n3)C(c3ccccc3C(F)(F)F)OCC4)cc12]

Compound 43: mixture of R and S enantiomers

Compound 44: S or R (OR: −115.13° (589 nm; 20° C.; 0.357 w/v %; DMF); enantiomer A (SFC-MS))

Compound 45: R or S (enantiomer B (SFC-MS))

Compound 43 (mixture of R and S enantiomers) was prepared by following an analogous reaction protocol as described in Example B11. An amount of compound 43 (5.47 g) was separated into its enantiomers by preparative SFC [Chiralcel Diacel OD 20×250 mm; mobile phase: CO$_2$, MeOH with 0.2% 2-propylamine]. The respective product fractions were collected and evaporated. Both residues were re-dissolved in MeOH and the two sol. were evaporated again. The two different residues were recrystallized from CH$_3$CN, yielding compounds 44 and 45.

Product 1: 2.04 g of compound 44 (37% yield; S or R; OR: −115.13° (589 nm; 20° C.; 0.357 w/v %; DMF); enantiomer A (SFC-MS)).

Product 2: 1.9 g of compound 45 (35% yield; R or S; enantiomer B (SFC-MS)).

Example B13

Preparation of Compounds 47 and 48

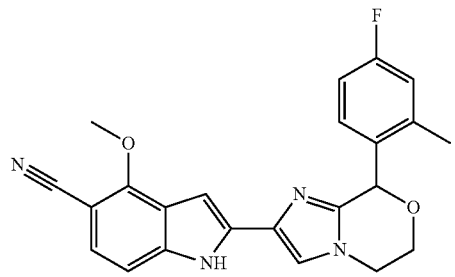 [SMILES: COc1c(C#N)ccc2[nH]c(-c3cn4c(n3)C(c3ccc(F)cc3C)OCC4)cc12]

Compound 46: mixture of R and S enantiomers

Compound 47: R or S (OR: −73.46° (589 nm; 20° C.; 0.3825 w/v %, DMF))

Compound 48: S or R (OR: +71.78° (589 nm; 20° C.; 0.9 w/v %, DMF))

Compound 46 (mixture of R and S enantiomers) was prepared by following an analogous reaction protocol as described in Example B11. An amount of compound 46 (547 mg) was separated into its enantiomers by preparative SFC [Chiralcel Diacel OD 20×250 mm; mobile phase: CO$_2$, MeOH with 0.2% 2-propylamine]. The respective product fractions were collected and evaporated. Both residues were re-dissolved in MeOH and the two sol. were evaporated again, to yield compounds 47 and 48.

Product 1: 178 mg of compound 47 (33% yield; R or S; OR: −73.46° (589 nm; 20° C.; 0.3825 w/v %; DMF)).

Product 2: 175 mg of compound 48 (32% yield; S or R; OR: +71.78° (589 nm; 20° C.; 0.9 w/v %; DMF)).

Example B14

Preparation of Compounds 50 and 51

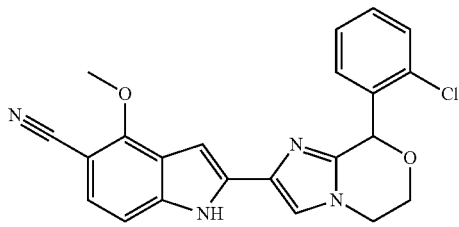 [SMILES: COc1c(C#N)ccc2[nH]c(-c3cn4c(n3)C(c3ccccc3Cl)OCC4)cc12]

Compound 49: mixture of R and S enantiomers
Compound 50: R or S (OR: −45.64° (589 nm; 20° C.; 0.298 w/v %, DMF))
Compound 51: S or R (OR: +49.05° (589 nm; 20° C.; 0.685 w/v %, DMF))

Compound 49 (mixture of R and S enantiomers) was prepared by following an analogous reaction protocol as described in Example B11. An amount of compound 49 (120 mg) was separated into its enantiomers by preparative SFC [Chiralcel Diacel OD 20×250 mm; mobile phase: $CO_2$, MeOH with 0.2% 2-propylamine]. The respective product fractions were collected and evaporated, to yield compounds 50 and 51.

Product 1: 47 mg of compound 50 (39% yield; R or S; OR: −45.64° (589 nm; 20° C.; 0.298 w/v %; DMF)).

Product 2: 47 mg of compound 51 (39% yield; S or R; OR: +49.05° (589 nm; 20° C.; 0.685 w/v %; DMF)).

Example B15

Preparation of Compounds 53 and 54

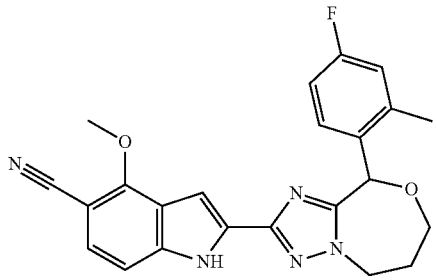 [SMILES: COc1c(C#N)ccc2[nH]c(-c3nc4n(n3)CCCOC4c3ccc(F)cc3C)cc12]

Compound 52: mixture of R and S enantiomers
Compound 53: R or S (OR: +20.53° (589 nm; 20° C.; 0.38 w/v %, DMF))
Compound 54: S or R (OR: −23.71° (589 nm; 20° C.; 0.35 w/v %, DMF))

Compound 52 (mixture of R and S enantiomers) was prepared by following an analogous reaction protocol as described in Example B11. An amount of compound 52 (105 mg) was separated into its enantiomers by preparative SFC [Chiralcel Diacel OJ 20×250 mm; mobile phase: $CO_2$, MeOH with 0.2% 2-propylamine]. The respective product fractions were collected and evaporated. Both residues were re-dissolved in MeOH and the two sol. were evaporated again, to yield compounds 53 and 54.

Product 1: 55 mg of compound 53 (29% yield; R or S; OR: +20.53° (589 nm; 20° C.; 0.38 w/v %; DMF)). Product 2: 53 mg of compound 54 (28% yield; S or R; OR: −23.71° (589 nm; 20° C.; 0.35 w/v %; DMF)).

Example B16

Preparation of Compounds 56 and 57

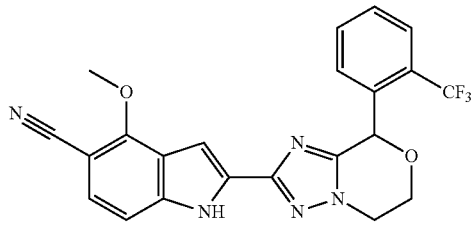 [SMILES: COc1c(C#N)ccc2[nH]c(-c3nc4n(n3)CCOC4c3ccccc3C(F)(F)F)cc12]

Compound 55: mixture of R and S enantiomers
Compound 56: R or S (enantiomer A (SFC-MS))
Compound 57: S or R (enantiomer B (SFC-MS))

Compound 55 (mixture of R and S enantiomers) was prepared by following an analogous reaction protocol as described in Example B11. An amount of compound 55 (148 mg) was separated into its enantiomers by preparative SFC [Chiralcel Diacel OD 20×250 mm; mobile phase: $CO_2$, MeOH with 0.2% 2-propylamine]. The respective product fractions were collected and evaporated. Both residues were re-dissolved in MeOH and the two sol. were evaporated again, to yield compounds 56 and 57.

Product 1: 63 mg of compound 56 (43% yield; R or S; enantiomer A (SFC-MS)).

Product 2: 60 mg of compound 57 (41% yield; S or R; enantiomer B (SFC-MS)).

Example B17

Preparation of Compound 58

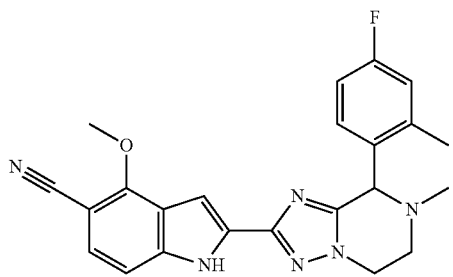 [SMILES: COc1c(C#N)ccc2[nH]c(-c3nc4n(n3)CCN(C)C4c3ccc(F)cc3C)cc12]

TFA (2 mL, 26.168 mmol) was added to intermediate 77 (75 mg, 0.137 mmol) in DCM (4.39 mL, 68.591 mmol) at 0° C., then the r.m. was stirred at r.t. for 5 h. After this time the r.m. was diluted with DCM and added to a cold sol. of sat. $NaHCO_3$ at 0° C. and stirred for 10 min. The pH was checked (>7). DCM was added and the reaction extracted. The o.l. was dried ($MgSO_4$), filtered and evaporated until dryness to give a crude which was dissolved in THF (3.29 mL). NaOH (1 M in water, 0.412 mL, 0.412 mmol) was added at r.t. and the r.m. stirred for 30 min, then neutralized by addition of sat. aq. $NH_4Cl$ and extracted with EtOAc. The o.l. was washed with brine, dried ($Na_2SO_4$), filtered and evaporated until dryness. The residue was purified via flash column chromatography (silica; DCM/(7 N $NH_3$ in MeOH) from 100/0 to 99/1). The product fractions were collected and evaporated to give compound 58 as a solid. Yield: 30 mg of compound 58 (53% yield).

Example B18

Preparation of Compound 59

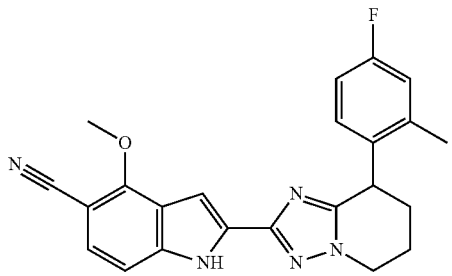 [SMILES: COc1c(C#N)ccc2[nH]c(-c3nc4n(n3)CCCC4c3ccc(F)cc3C)cc12]

Compound 59 (mixture of R and S enantiomers) was prepared by following an analogous reaction protocol as described in Example B11 (88% yield).

Example B19

Preparation of Compound 60

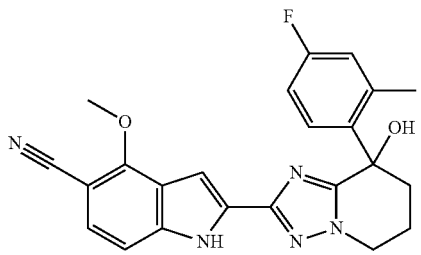 [SMILES: COc1c(C#N)ccc2[nH]c(-c3nc4n(n3)CCCC4(O)c3ccc(F)cc3C)cc12]

To a sol. of compound 59 (290 mg, 0.722 mmol) in DMF (12 mL) was added NaH (60% dispersion in mineral oil, 87 mg, 2.167 mmol) and then $O_2$ was bubbled through the stirred sol. for 2 d. The r.m was diluted with EtOAc and washed with brine. The o.l. was dried ($MgSO_4$), filtered and concentrated in vacuo. Purification was done via flash column chromatography (silica; eluent: heptane/EtOAc from 100/0 to 0/100), to give a fraction which was further purified by Prep HPLC [RP Vydac Denali C18—10 μm, 200 g, 5 cm; mobile phase: 0.25% $NH_4HCO_3$ sol. in water/$CH_3CN$]. The desired fractions were collected, evaporated, dissolved in MeOH and evaporated again, yielding the desired compound. Yield: 52 mg of compound 60 (17% yield).

By using analogous reaction protocols as described in the foregoing examples, the compounds listed in Tables 1a, 1b, 1c, 1d, 1e, 1f, 1g, 1h and 1i have been prepared.

'Co. No.' means compound number.

'Pr.' refers to the Example number in analogy to which protocol the compound was synthesized.

B1* refers to [2-(trimethylsilyl)ethoxy]methyl (SEM) deprotection instead of tert-butoxycarbonyl (tBOC) deprotection (conditions very similar: acidic deprotection by TFA or HCl followed by NaOH treatment).

† indicates that the reaction was performed on a protected substrate, and a deprotection following standard methods known to the person skilled in the art was performed as the last step.

In case no specific stereochemistry is indicated for a stereocenter of a compound, or in case no optical rotation (OR) or SFCMS is reported, this means that the compound was obtained as a mixture of the R and the S enantiomers.

In case no salt form is indicated, the compound was obtained as a free base.

TABLE 1a (I-1)

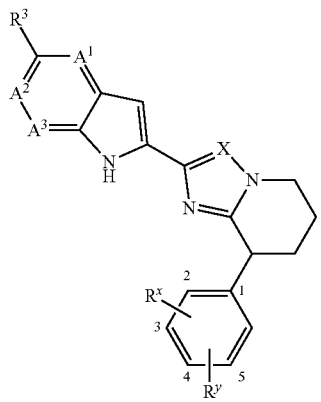

| Co. No. | Pr. | $R^3$ | $A^1$ | $A^2$ | $A^3$ | X | $R^x$ | $R^y$ | Salt forms/ Stereochemistry/ Optical Rotation (OR) |
|---|---|---|---|---|---|---|---|---|---|
| 15 | B4 | CN | CH | CH | CH | CH | 2-$CH_3$ | H | |
| 4 | B4 | CN | CH | CH | CH | CH | 2-$CH_3$ | 4-F | |
| 16 | B1* | CN | CH | CH | CH | CH | 2-Cl | H | •HCl |
| 17 | B4 | CN | CH | CH | CH | CH | 2-$CF_3$ | H | |
| 18 | B7 | CN | CH | CH | CH | N | 2-$CF_3$ | H | |
| 12 | B7 | CN | CH | CH | CH | N | 2-$CH_3$ | H | |
| 19 | B1* | CN | CH | CH | CH | N | 2-$OCH_3$ | H | |
| 20 | B7 | CN | CH | CH | CH | N | 3-$OCF_3$ | H | |

TABLE 1a-continued

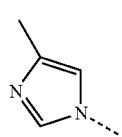

(I-1)

| Co. No. | Pr. | R³ | A¹ | A² | A³ | X | R$^x$ | R$^y$ | Salt forms/ Stereochemistry/ Optical Rotation (OR) |
|---|---|---|---|---|---|---|---|---|---|
| 13 | B10 | CN | CH | CH | CH | N | 2-CH₃ | H | OR: −96.61° (589 nm; 20° C.; 0.3985 w/v %; MeOH) |
| 14 | B10 | CN | CH | CH | CH | N | 2-CH₃ | H | OR: +97.42° (589 nm; 20° C.; 0.4465 w/v %; MeOH) |
| 21 | B7 | CN | CH | CH | CH | N | 2-F | 5-CF₃ | |
| 22 | B7 | CN | CH | CH | CH | N | 2-CF₃ | 4-F | |
| 9 | B5 | CN | CH | CH | CH | N | 2-CH₃ | 4-F | |
| 10 | B9 | CN | CH | CH | CH | N | 2-CH₃ | 4-F | OR: −87.92° (589 nm; 20° C.; 0.72 w/v %; MeOH) |
| 11 | B9 | CN | CH | CH | CH | N | 2-CH₃ | 4-F | OR: +72.83° (589 nm; 20° C.; 0.95 w/v %; MeOH) |
| 23 | B5 | CN | CH | CH | N | N | 2-CH₃ | 4-F | |
| 3 | B3 | CN | CH | CH | N | N | 2-CH₃ | 5-CF₃ | |
| 24 | B7 | CN | CH | N | CH | N | 2-CH₃ | H | |
| 25 | B7 | CN | N | CH | CH | N | 2-CH₃ | H | |
| 26 | B7 | CN | N | CH | CH | N | 2-CF₃ | H | |
| 27 | B7 | CN | N | CH | CH | N | 2-OCF₃ | H | |
| 7 | B7 | CN | COCH₃ | CH | CH | N | 2-CF₃ | H | |
| 28 | B7 | CN | CH | COCH₃ | CH | N | 2-CF₃ | H | |
| 29 | B7 | OCH₃ | CH | CH | CH | N | 2-CF₃ | H | |
| 8 | B8 | 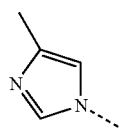 | CH | CH | CH | N | 2-CF₃ | H | |
| 30 | B5 | 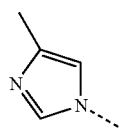 | CH | N | CH | N | 2-CH₃ | H | |
| 5 | B5 | 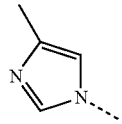 | N | CH | CH | N | 2-CH₃ | H | •HCl |

TABLE 1a-continued

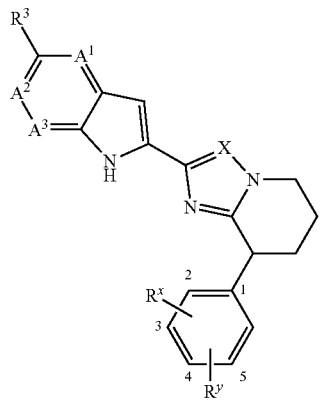

(I-1)

| Co. No. | Pr. | R³ | A¹ | A² | A³ | X | Rˣ | Rʸ | Salt forms/ Stereochemistry/ Optical Rotation (OR) |
|---|---|---|---|---|---|---|---|---|---|
| 31 | B2 | 1-methyl-pyrazol-4-yl | CH | CH | CH | N | 2-CH₃ | H | |
| 32 | B1* | 1-methyl-pyrazol-4-yl | N | CH | CH | N | 2-CH₃ | 4-F | |
| 2 | B2 | 2-methyl-pyridin-4-yl | CH | CH | CH | N | 2-CF₃ | H | •2HCl |
| 6 | B6 | 2-methyl-pyridin-4-yl | N | CH | CH | N | 2-CH₃ | H | |
| 33 | B1* | 2-methyl-pyridin-4-yl | N | CH | CH | N | 2-CH₃ | 4-F | |
| 61 | B7 | H | CH | C—CN | CH | N | 2-CF₃ | H | |
| 62 | B7† | CN | CH | CH | CH | N | 2-Cl | H | |
| 63 | B11 | CN | CH | CH | CH | CH | 2-CH₃ | 4-F | OR: +75.64° (589 nm; 20° C.; 0.5645 w/v %; DMF) |
| 64 | B11 | CN | CH | CH | CH | CH | 2-CH₃ | 4-F | OR: −77.41° (589 nm; 20° C.; 0.704 w/v %; DMF) |
| 65 | B5† | 4-methyl-imidazol-1-yl | N | CH | CH | N | 2-CH₃ | 4-F | OR: −45.52° (589 nm; 20° C.; 0.3515 w/v %; DMF) |

TABLE 1a-continued (I-1)

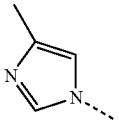

| Co. No. | Pr. | R³ | A¹ | A² | A³ | X | Rˣ | Rʸ | Salt forms/ Stereochemistry/ Optical Rotation (OR) |
|---|---|---|---|---|---|---|---|---|---|
| 66 | B5† | 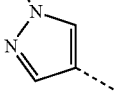 | N | CH | CH | N | 2-CH₃ | 4-F | OR: +48.58° (589 nm; 20° C.; 0.2635 w/v %; DMF) |
| 67 | B11 | CN | CH | CH | CH | CH | 2-OCH₃ | H | |
| 68 | B7† | CN | CH | N | CH | N | 2-CH₃ | 4-F | |
| 69 | B6† | 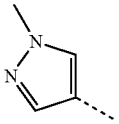 | N | CH | CH | N | 2-CH₃ | 4-F | R or S |
| 70 | B6† | 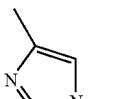 | N | CH | CH | N | 2-CH₃ | 4-F | S or R |
| 71 | B5 | 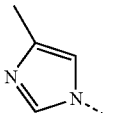 | CH | N | CH | N | 2-CH₃ | 4-F | |
| 72 | B7† | CN | CH | N | CH | CH | 2-CH₃ | 4-F | |
| 73 | B5 | 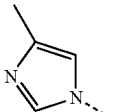 | CH | CH | CH | N | 2-CH₃ | 4-F | |
| 74 | B7† | CN | COCH₃ | CH | CH | CH | 2-CH₃ | 4-F | |
| 75 | B7† | CN | N | CH | CH | CH | 2-CH₃ | 4-F | |
| 76 | B5 | 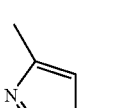 | CH | CH | CH | N | 2-CH₃ | 4-F | R or S; enantiomer A (SFC-MS) |
| 77 | B5 | 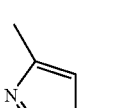 | CH | CH | CH | N | 2-CH₃ | 4-F | S or R; enantiomer B (SFC-MS) |

TABLE 1a-continued

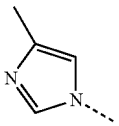

(I-1)

| Co. No. | Pr. | R³ | A¹ | A² | A³ | X | Rˣ | Rʸ | Salt forms/ Stereochemistry/ Optical Rotation (OR) |
|---|---|---|---|---|---|---|---|---|---|
| 78 | B8† | 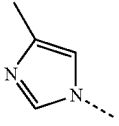 | COCH₃ | CH | CH | CH | 2-CH₃ | 4-F | R or S; enantiomer A (SFC-MS) |
| 79 | B8† | 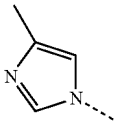 | COCH₃ | CH | CH | CH | 2-CH₃ | 4-F | S or R; enantiomer B (SFC-MS) |
| 80 | B8† | 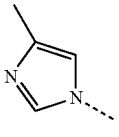 | CH | CH | CH | N | 2-OCH₃ | H | R or S; enantiomer A (SFC-MS) |
| 81 | B8† | 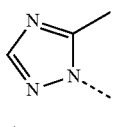 | CH | CH | CH | N | 2-OCH₃ | H | S or R; enantiomer B (SFC-MS) |
| 59 | B18 | CN | COCH₃ | CH | CH | N | 2-CH₃ | 4-F | |
| 82 | B8† | 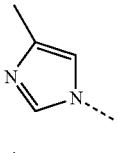 | CH | CH | CH | N | 2-CH₃ | 4-F | |
| 83 | B8† | 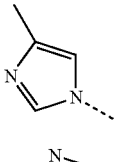 | COCH₃ | CH | CH | N | 2-CH₃ | 4-F | R or S; enantiomer A (SFC-MS) |
| 84 | B8† | 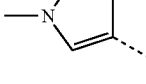 | COCH₃ | CH | CH | N | 2-CH₃ | 4-F | S or R; enantiomer B (SFC-MS) |
| 85 | B6† |  | N | CH | CH | CH | 2-CH₃ | 4-F | OR: +29.49° (589 nm; 20° C.; 0.59 w/v %; DMF) |

TABLE 1a-continued
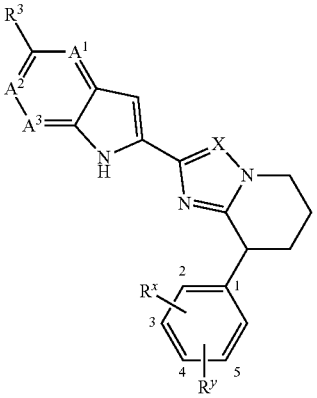
(I-1)
| Co. No. | Pr. | R³ | A¹ | A² | A³ | X | Rˣ | Rʸ | Salt forms/ Stereochemistry/ Optical Rotation (OR) |
|---|---|---|---|---|---|---|---|---|---|
| 86 | B6† | 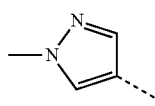 | N | CH | CH | CH | 2-CH₃ | 4-F | OR: −45.94° (589 nm; 20° C.; 0.505 w/v %; DMF) |
| 87 | B8† | 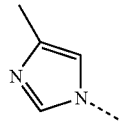 | CH | CH | N | N | 2-CH₃ | 4-F | R or S; enantiomer A (SFC-MS) |
| 88 | B8† | 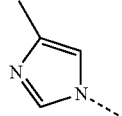 | CH | CH | N | N | 2-CH₃ | 4-F | S or R; enantiomer B (SFC-MS) |
| 89 | B5† | CN | COCH₃ | CH | CH | N | 2-CH₂OCH₃ | H | |
| 90 | B5† | CN | COCH₃ | CH | CH | N | 2-CH₂OCH₃ | H | OR: −26.46° (589 nm; 20° C.; 0.48 w/v %; DMF) |
| 91 | B5† | CN | COCH₃ | CH | CH | N | 2-CH₂OCH₃ | H | OR: +24.35° (589 nm; 20° C.; 0.46 w/v %; DMF) |
| 92 | B8† | 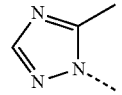 | CH | CH | CH | N | 2-CH₃ | 4-F | |

TABLE 1b (cPr means cyclopropyl)

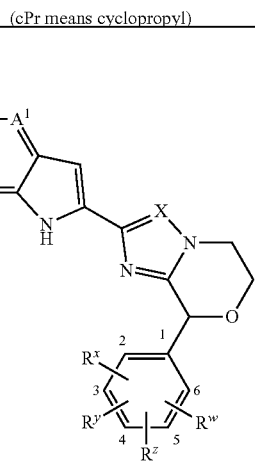

(I-2)

| Co. No. | Pr. | R³ | A¹ | X | Rˣ | Rʸ | Rᶻ | Rʷ | Salt forms/ Stereochemistry/ Optical Rotation (OR) |
|---|---|---|---|---|---|---|---|---|---|
| 1 | B1 | CN | CH | N | 2-CH₃ | 3-F | H | H | |
| 34 | B1 | CN | CH | N | 2-CH₃ | 5-CF₃ | H | H | |
| 35 | B7 | CN | CH | N | 2-CF₃ | H | H | H | |
| 36 | B8 | 4-methylimidazol-1-yl | CH | N | 2-CH₃ | 3-F | H | H | |
| 37 | B8 | 4-methylimidazol-1-yl | CH | N | 2-CF₃ | H | H | H | |
| 39 | B5 | 4-methylimidazol-1-yl | CH | N | 2-CH₃ | 4-F | H | H | |
| 94 | B5 | 4-methylimidazol-1-yl | N | N | 2-CH₃ | 4-F | H | H | |
| 95 | B5 | CN | CH | N | 2-CH₂CH₃ | 4-F | H | H | |
| 96 | B6† | 1-methylpyrazol-4-yl | COCH₃ | CH | 2-CH₃ | 4-F | H | H | |
| 46 | B11 | CN | COCH₃ | CH | 2-CH₃ | 4-F | H | H | |
| 97 | B5 | CN | CH | N | 2-CH₃ | 4-F | H | H | R or S; enantiomer A (SFC-MS) |
| 98 | B5 | CN | CH | N | 2-CH₃ | 4-F | H | H | S or R; enantiomer B (SFC-MS) |
| 99 | B6† | 1-methylpyrazol-4-yl | CH | CH | 2-CH₃ | 4-F | H | H | |

TABLE 1b-continued (cPr means cyclopropyl)

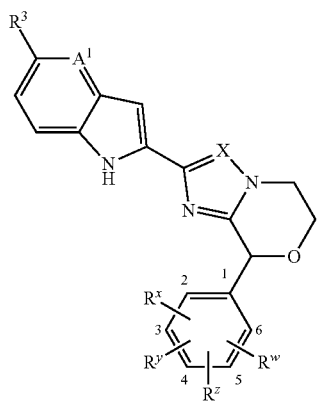

(I-2)

| Co. No. | Pr. | R³ | A¹ | X | Rˣ | Rʸ | Rᶻ | Rʷ | Salt forms/ Stereochemistry/ Optical Rotation (OR) |
|---|---|---|---|---|---|---|---|---|---|
| 100 | B5 | 4-methylimidazolyl | CH | N | 2-CH(CH₃)₂ | 4-F | H | H | |
| 101 | B6† | 1-methylpyrazol-4-yl | N | CH | 2-CH₃ | 4-F | H | H | R or S; enantiomer A (SFC-MS) |
| 102 | B6† | 1-methylpyrazol-4-yl | N | CH | 2-CH₃ | 4-F | H | H | S or R; enantiomer B (SFC-MS) |
| 103 | B6† | 2-methylpyridin-4-yl | CH | CH | 2-CH₃ | 4-F | H | H | |
| 104 | B5 | 4-methylimidazolyl | CH | N | 2-CH₃ | 3-F | 4-F | H | |
| 105 | B5 | 4-methylimidazolyl | CH | N | 2-CH₂CH₃ | 4-F | H | H | |
| 106 | B6 | 1-methylpyrazol-4-yl | N | N | 2-CH₃ | 4-F | H | H | |
| 107 | B6 | 1-methylpyrazol-4-yl | CH | N | 2-CH₃ | 4-F | H | H | |

TABLE 1b-continued (cPr means cyclopropyl)

(I-2)

| Co. No. | Pr. | R³ | A¹ | X | Rˣ | Rʸ | Rᶻ | Rʷ | Salt forms/ Stereochemistry/ Optical Rotation (OR) |
|---|---|---|---|---|---|---|---|---|---|
| 108 | B6 | 2-methylpyridin-4-yl | CH | N | 2-CH₃ | 4-F | H | H | |
| 47 | B13 | CN | COCH₃ | CH | 2-CH₃ | 4-F | H | H | OR: −73.46° (589 nm; 20° C.; 0.3825 w/v %; DMF) |
| 48 | B13 | CN | COCH₃ | CH | 2-CH₃ | 4-F | H | H | OR: +71.78° (589 nm; 20° C.; 0.9 w/v %; DMF) |
| 109 | B5 | 4-methylimidazol-1-yl | CH | N | 2-CH₃ | 4-F | H | H | R or S; enantiomer A (SFC-MS) |
| 110 | B5 | 4-methylimidazol-1-yl | CH | N | 2-CH₃ | 4-F | H | H | S or R; enantiomer B (SFC-MS) |
| 111 | B7† | CN | COCH₃ | N | 2-CH₃ | 4-F | H | H | |
| 112 | B8† | 4-methylimidazol-1-yl | COCH₃ | CH | 2-CH₃ | 4-F | H | H | R or S; enantiomer A (SFC-MS) |
| 113 | B8† | 4-methylimidazol-1-yl | COCH₃ | CH | 2-CH₃ | 4-F | H | H | S or R; enantiomer B (SFC-MS) |
| 114 | B7† | CN | COCH₃ | CH | 2-CH₃ | 4-F | H | H | OR: −66.33° (589 nm; 20° C.; 0.199 w/v %; DMF) |
| 115 | B7† | CN | COCH₃ | CH | 2-CH₃ | 4-F | H | H | OR: +60.45° (589 nm; 20° C.; 0.177 w/v %; DMF) |
| 55 | B11 | CN | COCH₃ | N | 2-CF₃ | H | H | H | |

TABLE 1b-continued (cPr means cyclopropyl)

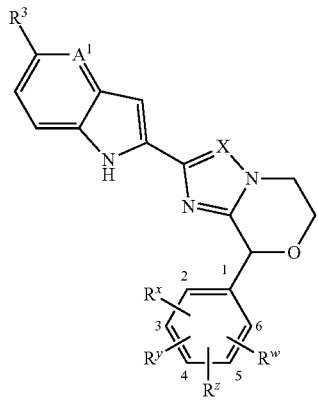

(I-2)

| Co. No. | Pr. | R³ | A¹ | X | Rˣ | Rʸ | Rᶻ | Rʷ | Salt forms/ Stereochemistry/ Optical Rotation (OR) |
|---|---|---|---|---|---|---|---|---|---|
| 116 | B5 | (4-methylimidazolyl) | CH | N | 2-CH₃ | 3-CH₃ | 4-F | 5-F | |
| 56 | B16 | CN | COCH₃ | CH | 2-CF₃ | H | H | H | R or S; enantiomer A (SFC-MS) |
| 57 | B16 | CN | COCH₃ | CH | 2-CF₃ | H | H | H | S or R; enantiomer B (SFC-MS) |
| 117 | B5† | CN | COCH₃ | CH | 2-Cl | 6-F | H | H | R or S; enantiomer A (SFC-MS) |
| 118 | B5† | CN | COCH₃ | CH | 2-Cl | 6-F | H | H | S or R; enantiomer B (SFC-MS) |
| 119 | B7† | CN | COCH₃ | CH | 2-Cl | 6-F | H | H | |
| 120 | B11 | CN | COCH₃ | CH | 2-CH₂OCH₃ | H | H | H | |
| 121 | B5† | CN | COCH₃ | N | 2-F | 5-CF₃ | H | H | |
| 40 | B11 | CN | COCH₃ | CH | 2-CH₃ | 3-F | H | H | |
| 122 | B7† | CN | COCH₃ | CH | 2-Cl | 6-F | H | H | R or S; enantiomer A (SFC-MS) |
| 123 | B7† | CN | COCH₃ | CH | 2-Cl | 6-F | H | H | S or R; enantiomer B (SFC-MS) |
| 124 | B11 | CN | COCH₃ | CH | 2-F | 6-CH₃ | H | H | |
| 49 | B11 | CN | COCH₃ | CH | 2-Cl | H | H | H | |
| 125 | B5† | CN | COCH₃ | N | 2-F | 6-CF₃ | H | H | |
| 126 | B11 | CN | COCH₃ | CH | 2-F | 6-CF₃ | H | H | |
| 127 | B5† | CN | COCH₃ | N | 2-CH₃ | 3-F | H | H | |
| 128 | B11 | CN | COCH₃ | N | 2-F | 5-CF₃ | H | H | |
| 129 | B5† | CN | COCH₃ | N | 2-F | 6-CH₃ | H | H | |
| 130 | B5† | CN | COCH₃ | N | 2-Cl | H | H | H | |
| 131 | B11 | CN | COCH₃ | CH | 2-CF₃ | 3-F | H | H | R or S; enantiomer A (SFC-MS) |
| 132 | B11 | CN | COCH₃ | CH | 2-CF₃ | 3-F | H | H | S or R; enantiomer B (SFC-MS) |
| 50 | B14 | CN | COCH₃ | CH | 2-Cl | H | H | H | OR: −45.64° (589 nm; 20° C.; 0.298 w/v %; DMF) |
| 51 | B14 | CN | COCH₃ | CH | 2-Cl | H | H | H | OR: +49.05° (589 nm; 20° C.; 0.685 w/v %; DMF) |
| 133 | B5† | CN | COCH₃ | N | 2-CF₃ | 3-F | H | H | R or S; enantiomer A (SFC-MS) |

TABLE 1b-continued (cPr means cyclopropyl)

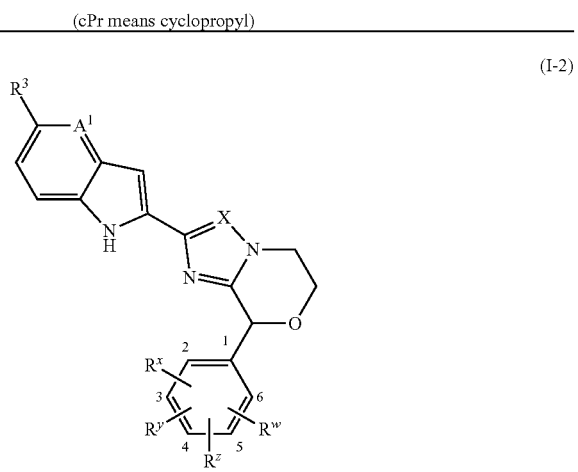
(I-2)

| Co. No. | Pr. | R³ | A¹ | X | Rˣ | Rʸ | Rᶻ | Rʷ | Salt forms/ Stereochemistry/ Optical Rotation (OR) |
|---|---|---|---|---|---|---|---|---|---|
| 134 | B5† | CN | COCH₃ | N | 2-CF₃ | 3-F | H | H | S or R; enantiomer B (SFC-MS) |
| 135 | B11 | CN | COCH₃ | CH | 2-F | 3-CH₃ | H | H | R or S; enantiomer A (SFC-MS) |
| 136 | B11 | CN | COCH₃ | CH | 2-F | 3-CH₃ | H | H | S or R; enantiomer B (SFC-MS) |
| 41 | B11 | CN | COCH₃ | CH | 2-CH₃ | 3-F | H | H | OR: −84.34° (589 nm; 20° C.; 0.415 w/v %; DMF) |
| 42 | B11 | CN | COCH₃ | CH | 2-CH₃ | 3-F | H | H | OR: +69.05° (589 nm; 20° C.; 0.475 w/v %; DMF) |
| 137 | B5† | CN | COCH₃ | N | 2-Cl | H | H | H | OR: −29.34° (589 nm; 20° C.; 0.91 w/v %; DMF) |
| 138 | B11 | CN | COCH₃ | CH | 2-F | 6-CH₃ | H | H | OR: −69.74° (589 nm; 20° C.; 0.575 w/v %; DMF) |
| 139 | B11 | CN | COCH₃ | CH | 2-F | 6-CH₃ | H | H | OR: +69.08° (589 nm; 20° C.; 0.705 w/v %; DMF) |
| 140 | B5† | CN | COCH₃ | N | 2-Cl | H | H | H | OR: +30.67° (589 nm; 20° C.; 0.75 w/v %; DMF) |
| 141 | B5† | CN | COCH₃ | N | 2-F | 6-CH₃ | H | H | OR: −56.17° (589 nm; 20° C.; 0.81 w/v %; DMF) |
| 142 | B5† | CN | COCH₃ | N | 2-F | 6-CH₃ | H | H | OR: +60.75° (589 nm; 20° C.; 0.80 w/v %; DMF) |
| 143 | B11 | CN | COCH₃ | CH | 3-Cl | 4-F | H | H | |
| 144 | B5† | CN | COCH₃ | N | 3-Cl | 4-F | H | H | |
| 145 | B11 | CN | COCH₃ | CH | 2-CH₂OCH₃ | H | H | H | OR: −67.86° (589 nm; 20° C.; 0.42 w/v %; DMF) |
| 146 | B11 | CN | COCH₃ | CH | 2-CH₂OCH₃ | H | H | H | OR: +63.24° (589 nm; 20° C.; 0.37 w/v %; DMF) |
| 147 | B5† | CN | COCH₃ | N | 2-CH₃ | 3-F | H | H | OR: −56.91° (589 nm; 20° C.; 0.55 w/v %; DMF) |
| 148 | B5† | CN | COCH₃ | N | 2-F | 3-CH₃ | H | H | R or S; enantiomer A (SFC-MS) |
| 149 | B5† | CN | COCH₃ | N | 2-F | 3-CH₃ | H | H | S or R; enantiomer B (SFC-MS) |
| 150 | B5† | CN | COCH₃ | N | 2-CH₃ | 3-F | H | H | OR: +66.15° (589 nm; 20° C.; 0.585 w/v %; DMF) |

TABLE 1b-continued (cPr means cyclopropyl)

(I-2)

| Co. No. | Pr. | R³ | A¹ | X | Rˣ | Rʸ | Rᶻ | Rʷ | Salt forms/ Stereochemistry/ Optical Rotation (OR) |
|---|---|---|---|---|---|---|---|---|---|
| 151 | B11 | CN | COCH₃ | CH | 2-CH₃ | 5-F | H | H | |
| 152 | B11 | CN | COCH₃ | CH | 2-F | 6-CF₃ | H | H | OR: +102.44° (589 nm; 20° C.; 0.45 w/v %; DMF) |
| 153 | B11 | CN | COCH₃ | CH | 2-F | 6-CF₃ | H | H | OR: −94.89° (589 nm; 20° C.; 0.45 w/v %; DMF) |
| 154 | B11 | CN | COCH₃ | CH | 3-Cl | 4-F | H | H | OR: −188° (589 nm; 20° C.; 0.325 w/v %; DMF) |
| 155 | B11 | CN | COCH₃ | CH | 3-Cl | 4-F | H | H | OR: +182.9° (589 nm; 20° C.; 0.345 w/v %; DMF) |
| 156 | B5† | CN | COCH₃ | N | 3-Cl | 4-F | H | H | OR: −158.1° (589 nm; 20° C.; 0.315 w/v %; DMF) |
| 157 | B5† | CN | COCH₃ | N | 3-Cl | 4-F | H | H | OR: +150.15° (589 nm; 20° C.; 0.333 w/v %; DMF) |
| 158 | B11 | CN | COCH₃ | CH | 2-CH₃ | 5-F | H | H | OR: −86.15° (589 nm; 20° C.; 0.325 w/v %; DMF) |
| 159 | B11 | CN | COCH₃ | CH | 2-CH₃ | 5-F | H | H | OR: +86.11° (589 nm; 20° C.; 0.36 w/v %; DMF) |
| 160 | B5† | CN | COCH₃ | N | 2-F | 5-CF₃ | H | H | R or S; enantiomer A (SFC-MS) |
| 161 | B5† | CN | COCH₃ | N | 2-F | 5-CF₃ | H | H | S or R; enantiomer B (SFC-MS) |
| 162 | B5† | CN | COCH₃ | N | 2-F | 6-CF₃ | H | H | OR: +84° (589 nm; 20° C.; 0.95 w/v %; DMF) |
| 163 | B5† | CN | COCH₃ | N | 2-F | 6-CF₃ | H | H | OR: −91.68° (589 nm; 20° C.; 0.95 w/v %; DMF) |
| 164 | B11 | CN | COCH₃ | CH | 2-F | 5-CF₃ | H | H | OR: −108.77° (589 nm; 20° C.; 0.73 w/v %; DMF) |
| 165 | B11 | CN | COCH₃ | CH | 2-F | 5-CF₃ | H | H | OR: +114.56° (589 nm; 20° C.; 0.57 w/v %; DMF) |
| 43 | B11 | CN | COCH₃ | CH | 2-CF₃ | H | H | H | |
| 44 | B12 | CN | COCH₃ | CH | 2-CF₃ | H | H | H | S or R; OR: −115.13° (589 nm; 20° C.; 0.357 w/v %; DMF) enantiomer A (SFC-MS) |

TABLE 1b-continued (cPr means cyclopropyl)

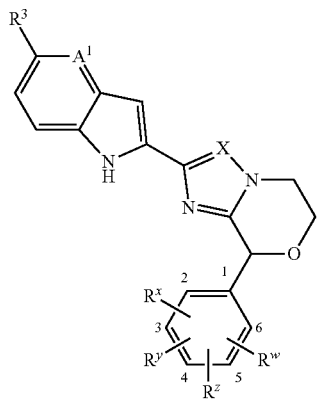

(I-2)

| Co. No. | Pr. | R³ | A¹ | X | Rˣ | Rʸ | Rᶻ | Rʷ | Salt forms/ Stereochemistry/ Optical Rotation (OR) |
|---|---|---|---|---|---|---|---|---|---|
| 45 | B12 | CN | | COCH₃ | CH | 2-CF₃ | H | H | H | R or S; enantiomer B (SFC-MS) |
| 166 | B5† | CN | | COCH(CH₃)₂ | N | 2-CH₃ | 4-F | H | H | |
| 167 | B11 | CN | | COC₂H₄OCH₃ | N | 2-CH₃ | 4-F | H | H | |
| 168 | B5† | CN | | COCH₂CHF₂ | N | 2-CH₃ | 4-F | H | H | |
| 169 | B11 | CN | | COCH₃ | CH | 2-cPr | H | H | H | OR: +39.19° (589 nm; 20° C.; 0.37 w/v %; DMF) |
| 170 | B11 | CN | | COCH₃ | CH | 2-cPr | H | H | H | OR: −40.27° (589 nm; 20° C.; 0.37 w/v %; DMF) |
| 171 | B5† | CN | | COCH₃ | N | 2-CH₃ | 4-F | H | H | |
| 172 | B5† | CN | | COCH(CH₃)₂ | N | 2-CH₃ | 4-F | H | H | S or R; enantiomer A (SFC-MS) |
| 173 | B5† | CN | | COCH(CH₃)₂ | N | 2-CH₃ | 4-F | H | H | R or S; enantiomer B (SFC-MS) |

TABLE 1c

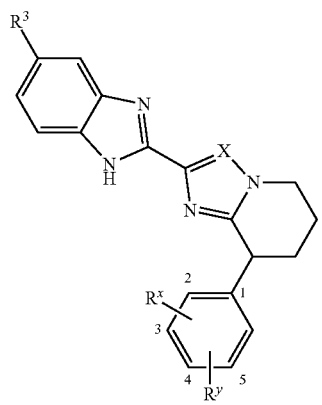

(I-3)

| Co. No. | Pr. | R³ | X | Rˣ | Rʸ | Salt forms/ Stereochemistry/ Optical Rotation (OR) |
|---|---|---|---|---|---|---|
| 38 | B5 | CN | N | 2-CF₃ | H | |
| 174 | B6 | 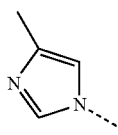 | N | 2-CH₃ | 4-F | R or S; enantiomer A (SFC-MS) |
| 175 | B6 | 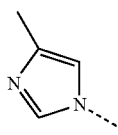 | N | 2-CH₃ | 4-F | S or R; enantiomer B (SFC-MS) |
| 176 | B8 | 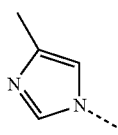 | N | 2-CH₃ | 4-F | OR: −46.13° (589 nm; 20° C.; 0.3165 w/v %; DMF) |
| 179 | B8 | 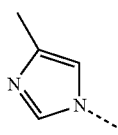 | N | 2-CH₃ | 4-F | OR: +50.49° (589 nm; 20° C.; 0.309 w/v %; DMF) |
| 177 | B8 | 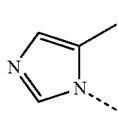 | N | 2-CH₃ | 4-F | |

TABLE 1d

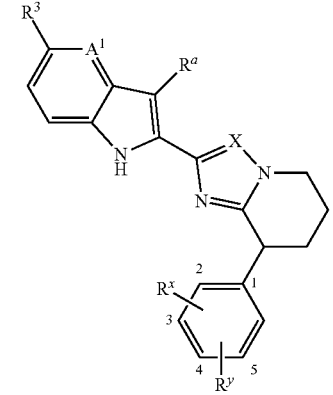

(I-4)

| Co. No. | Pr. | R³ | A¹ | Rᵃ | X | Rˣ | Rʸ | Salt forms/ Stereochemistry/ Optical Rotation (OR) |
|---|---|---|---|---|---|---|---|---|
| 178 | B11# | 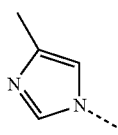 | | CH₂OH | N | 2-CH₃ | 4-F | |
| 180 | B5 | CN | CH | F | N | 2-CH₃ | 4-F | |
| 181 | B5 | CN | CH | F | N | 2-CH₃ | 4-F | R or S; enantiomer A (SFC-MS) |
| 182 | B5 | CN | CH | F | N | 2-CH₃ | 4-F | S or R; enantiomer B (SFC-MS) |

B11# means that the compound was obtained as a side product of a reaction using the method B11

TABLE 1e

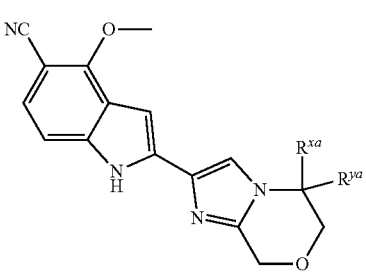

(I-5)

| Co. No. | Pr. | Rˣᵃ | Rʸᵃ | Salt forms/Stereochemistry/ Optical Rotation (OR) |
|---|---|---|---|---|
| 183 | B7† | CH₃ | 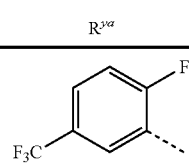 | |
| 184 | B11 | H | 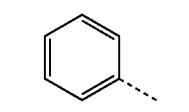 | |

TABLE 1f

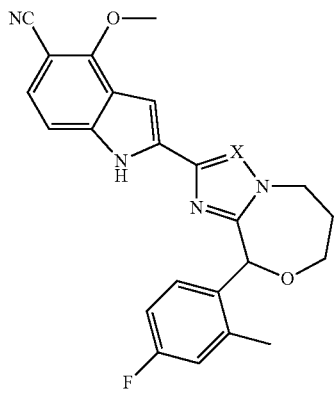
(I-6)

| Co. No. | Pr. | X | Salt forms/Stereochemistry/ Optical Rotation (OR) |
|---|---|---|---|
| 52 | B11 | N | |
| 53 | B15 | N | OR: +20.53° (589 nm; 20° C.; 0.38 w/v %; DMF) |
| 54 | B15 | N | OR: −23.71° (589 nm; 20° C.; 0.35 w/v %; DMF) |
| 185 | B11 | CH | |

TABLE 1g

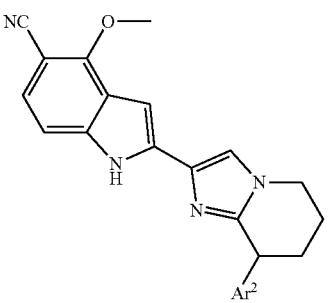
(I-7)

| Co. No | Pr. | Ar² | Salt forms/ Stereochemistry/ Optical Rotation (OR) |
|---|---|---|---|
| 186 | B11 | ![pyrazole-CH2CF3] | |
| 187 | B11 | ![pyrazole-CH2CF3] | |
| 188 | B11 | ![pyrazole-CH2CF3] | OR: −92.19° (589 nm; 20° C.; 0.32 w/v %; DMF) |

TABLE 1g-continued

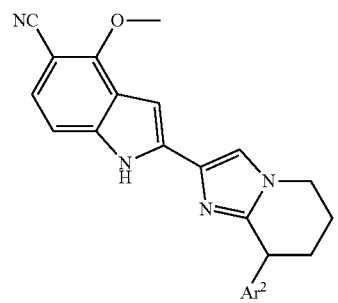
(I-7)

| Co. No | Pr. | Ar² | Salt forms/ Stereochemistry/ Optical Rotation (OR) |
|---|---|---|---|
| 189 | B11 | ![pyrazole-CH2CF3] | OR: +95.15° (589 nm; 20° C.; 0.33 w/v %; DMF) |

TABLE 1h

| Co. No. | Pr. | Compound | Salt forms/ Stereo- chemistry/ Optical Rotation (OR) |
|---|---|---|---|
| 60 | B19 |  | |

TABLE 1i

| Co. No. | Pr. | Compound | Salt forms/ Stereo- chem- istry/ Optical Rotation (OR) |
|---|---|---|---|
| 58 | B17 |  | |

TABLE 1i-continued

| Co. No. Pr. | Compound | Salt forms/ Stereo- chem- istry/ Optical Rotation (OR) |
|---|---|---|
| 93 B8 | (structure) | |

Analytical Part

All analytical results were obtained with experimental uncertainties that are commonly associated with the analytical method.

Optical Rotation

For optical rotations (OR), the values reported are $[\alpha]_D^{20}$ values which indicate the optical rotation measured with light at the wavelength of the D-line of sodium (589 nm) at a temperature of 20° C. The cell pathlength is 1 dm.

LCMS (Liquid Chromatography/Mass Spectrometry)

General Procedure A

The LC measurement was performed using an Acquity UPLC (Ultra Performance Liquid Chromatography) (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds (sec) using a dwell time of 0.02 sec. The capillary needle voltage was 3.5 kV and the source temperature was maintained at 140° C. $N_2$ was used as the nebulizer gas. Data acquisition was performed with a Waters-Micromass MassLynx-Openlynx data system.

General Procedure B

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure C

The HPLC measurement was performed using an Agilent G1956A LC/MSD quadrupole coupled to an Agilent 1100 series liquid chromatography system comprising a binary pump with degasser, an autosampler, a column oven (thermostated), a UV detector (diode array detector) and a column as specified in the respective methods below. Flow from the column was split to a MS spectrometer. The MS detector was configured with an electrospray ionization source (atmospheric pressure). The capillary voltage was 3 kV, the fragmentor voltage was set to 70 V, and the quadrupole temperature was maintained at 100° C. The drying gas flow and temperature values were 12.0 L/min and 300 or 350° C., respectively. Nitrogen was used as the nebulizer gas (at a pressure of 35 psig). Data acquisition was performed with an Agilent Chemstation data system.

LCMS Method 1

In addition to general procedure A: Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 mL/min. Two mobile phases (25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 mL was used. Cone voltage was 30 V for positive ionization mode and 30 V for negative ionization mode.

LCMS Method 2

In addition to general procedure A: Reversed phase UPLC was carried out on a bridged ethylsiloxane/silica hybrid (BEH) C18 column (1.7 μm, 2.1×50 mm; Waters Acquity) with a flow rate of 0.8 mL/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

LCMS Method 3

In addition to general procedure B: Reversed phase HPLC was carried out on an Xterra MS C18 column (3.5 μm, 4.6× 100 mm) with a flow rate of 1.6 mL/min. Three mobile phases (mobile phase A: 95% 25 mM ammoniumacetate in $H_2O$+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS Method 4

In addition to general procedure A: Reversed phase UPLC was carried out on a bridged ethylsiloxane/silica hybrid (BEH) C18 column (1.7 μm, 2.1×50 mm; Waters Acquity) with a flow rate of 0.8 mL/min. Two mobile phases (mobile phase A: 10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

LCMS Method 5

In addition to general procedure A: Reversed phase UPLC was carried out on a BEH C18 column (1.7 μm, 2.1×50 mm; Waters Acquity) with a flow rate of 0.8 mL/min. Two mobile phases (10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 30 V for positive ionization mode and 30 V for negative ionization mode.

LCMS Method 6

In addition to general procedure A: Reversed phase UPLC was carried out on a BEH C18 column (1.7 μm, 2.1×50 mm;

Waters Acquity) with a flow rate of 0.8 mL/min. Two mobile phases (10 mM ammonium acetate in H$_2$O/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used. Cone voltage was 10 V for positive ionization mode and 20 V for negative ionization mode.

LCMS Method 7

In addition to general procedure B: Column heater was set at 45° C. Reversed phase HPLC was carried out on an Atlantis C18 column (3.5 µm, 4.6×100 mm) with a flow rate of 1.6 mL/min. Two mobile phases (mobile phase A: 70% methanol+30% H$_2$O; mobile phase B: 0.1% formic acid in H$_2$O/methanol 95/5) were employed to run a gradient condition from 100% B to 5% B+95% A in 9 minutes and hold these conditions for 3 minutes. An injection volume of 10 µl was used. Cone voltage was 10 V for positive ionization mode and 20 V for negative ionization mode.

LCMS Method 8

In addition to general procedure C: Reversed phase HPLC was carried out on a YMC-Pack ODS-AQ C18 column (4.6×50 mm) with a flow rate of 2.6 mL/min. A gradient run was used from 95% (water+0.1% formic acid) and 5% acetonitrile to 95% acetonitrile in 4.80 minutes and was hold for 1.00 minute. Mass spectra were acquired by scanning from 100 to 1400 m/z. UV-PDA (photo diode array) acquisition range was set to 190-400 nm. Injection volume was typically between 2-10 µl. Column temperature was 35° C.

LCMS Method 9

In addition to general procedure C: Reversed phase HPLC was carried out on a Phenomenex Kinetex XB-C18 column (4.6×50 mm; 2.6 µm particles) at 35° C., with a flow rate of 3.0 mL/min. A gradient elution was performed from 95% (water+0.1% formic acid)/5% Acetonitrile to 5% (water+0.1% formic acid)/95% Acetonitrile in 4.20 minutes, then the final mobile phase composition was held for an additional 0.70 min. The injection volume was 2 µl. MS and UV-PDA (photo diode array) acquisition ranges were set to 100-1200 m/z and 190-400 nm respectively.

Melting Points

For compounds 9, 12, 20, 21, 22 and 27, m.p. were determined in open capillary tubes on a Mettler FP62 apparatus. Melting points (m.p.) were measured with a temperature ranging from 50° C. to 300° C., using a gradient of 10° C./minute. The m.p. value was read from a digital display.

The m.p. for the other compounds were determined with a DSC823e (Mettler-Toledo). Standard, m.p. were measured with a temperature gradient of 10° C./min. The m.p. of compounds 18 and 38 were measured with a temperature gradient of 30° C./min.

The results of the analytical measurements are shown in table 2a.

TABLE 2a

Retention time (R$_t$) in min., [M + H]$^+$ peak (protonated molecule), LCMS method and m.p. (melting point in ° C.). (n.d. means not determined)

| Co. No. | R$_t$ | [M + H]$^+$ | LCMS Method | m.p. (° C.) |
|---|---|---|---|---|
| 1 | 1.02 | 374 | 5 | 225.2 |
| 2 | 1.10 | 474 | 2 | n.d. |
| 3 | 1.12 | 423 | 4 | n.d. |
| 4 | 1.09 | 371 | 6 | n.d. |
| 5 | 5.65 | 410 | 3 | 189.4 |
| 6 | 0.95 | 421 | 6 | 266.5 |
| 7 | 1.14 | 438 | 1 | n.d. |
| 8 | 7.06 | 463 | 7 | n.d. |
| 9 | 3.01 | 372 | 9 | 244.9 |
| 10 | 1.09 | 372 | 4 | n.d. |
| 11 | 1.09 | 372 | 4 | n.d. |
| 12 | 3.49 | 354 | 8 | 142.1 |
| 13 | 1.04 | 354 | 4 | n.d. |
| 14 | 1.04 | 354 | 4 | n.d. |
| 15 | 6.11 | 353 | 3 | n.d. |
| 16 | 1.09 | 373 | 6 | n.d. |
| 17 | 1.19 | 407 | 4 | n.d. |
| 18 | 1.12 | 408 | 1 | 229.0 |
| 19 | 1.02 | 370 | 6 | 139.6 |
| 20 | 3.21 | 424 | 9 | 225.1 |
| 21 | 3.14 | 426 | 9 | 184.3 |
| 22 | 3.20 | 426 | 9 | 265.0 |
| 23 | 0.98 | 373 | 6 | n.d. |
| 24 | 0.96 | 355 | 6 | n.d. |
| 25 | 1.02 | 355 | 4 | 264.9 |
| 26 | 1.02 | 409 | 5 | 272.3 |
| 27 | 3.72 | 424 | 8 | 179.3 |
| 28 | 1.12 | 438 | 1 | n.d. |
| 29 | 1.13 | 413 | 5 | 183.0 |
| 30 | 0.92 | 410 | 6 | n.d. |
| 31 | 0.99 | 409 | 5 | 223.8 |
| 32 | 5.34 | 428 | 3 | 281.7 |
| 33 | 5.79 | 439 | 3 | 267.2 |
| 34 | 1.11 | 424 | 5 | n.d. |
| 35 | 1.05 | 410 | 1 | n.d. |
| 36 | 0.99 | 429 | 4 | 261.3 |
| 37 | 0.97 | 465 | 1 | n.d. |
| 38 | 0.97 | 409 | 1 | 252.2 |
| 39 | 0.98 | 429 | 4 | 278.8 |
| 40 | 1.03 | 403 | 6 | n.d. |
| 41 | 0.99 | 403 | 6 | n.d. |
| 42 | 0.99 | 403 | 6 | 246.0 |
| 43 | 1.09 | 439 | 4 | n.d. |
| 44 | 1.00 | 439 | 6 | n.d. |
| 45 | 1.01 | 439 | 6 | n.d. |
| 46 | 1.00 | 403 | 6 | 236.2 |
| 47 | 0.99 | 403 | 6 | 242.6 |
| 48 | 1.04 | 403 | 6 | 244.4 |
| 49 | 1.00 | 405 | 6 | n.d. |
| 50 | 0.96 | 405 | 6 | 254.3 |
| 51 | 0.96 | 405 | 6 | 255.6 |
| 52 | 1.10 | 419 | 6 | n.d. |
| 53 | 1.03 | 418 | 6 | n.d. |
| 54 | 1.03 | 418 | 6 | n.d. |
| 55 | 1.02 | 440 | 6 | n.d. |
| 56 | 1.02 | 440 | 6 | n.d. |
| 57 | 1.02 | 440 | 6 | n.d. |
| 58 | 1.10 | 417 | 6 | n.d. |
| 59 | 1.09 | 402 | 6 | n.d. |
| 60 | 0.98 | 418 | 6 | 287.1 |
| 61 | 6.27 | 408 | 3 | 175.7 |
| 62 | 1.07 | 374 | 6 | 208.6 |
| 63 | 1.09 | 371 | 6 | n.d. |
| 64 | 1.09 | 371 | 6 | n.d. |
| 65 | 0.92 | 428 | 6 | n.d. |
| 66 | 0.92 | 428 | 6 | n.d. |
| 67 | 1.08 | 369 | 4 | 251.0 |
| 68 | 0.97 | 373 | 6 | n.d. |
| 69 | n.d. | n.d. | — | 283.3 |
| 70 | n.d. | n.d. | — | 283.1 |
| 71 | 0.94 | 428 | 6 | n.d. |
| 72 | 0.99 | 372 | 6 | 255.5 |
| 73 | 1.01 | 427 | 6 | n.d. |
| 74 | 1.07 | 401 | 6 | n.d. |
| 75 | 0.96 | 372 | 6 | n.d. |
| 76 | 1.00 | 427 | 6 | n.d. |
| 77 | 1.00 | 427 | 6 | n.d. |
| 78 | 1.03 | 456 | 6 | n.d. |
| 79 | 1.03 | 456 | 6 | n.d. |
| 80 | 0.95 | 425 | 6 | n.d. |
| 81 | 0.95 | 425 | 6 | n.d. |
| 82 | 0.94 | 428 | 6 | n.d. |

TABLE 2a-continued

Retention time ($R_t$) in min., [M + H]$^+$ peak (protonated molecule), LCMS method and m.p. (melting point in ° C.). (n.d. means not determined)

| Co. No. | $R_t$ | [M + H]$^+$ | LCMS Method | m.p. (° C.) |
|---|---|---|---|---|
| 83 | 0.99 | 457 | 4 | n.d. |
| 84 | 0.99 | 457 | 4 | n.d. |
| 85 | 0.89 | 427 | 4 | n.d. |
| 86 | 0.89 | 427 | 4 | n.d. |
| 87 | 0.92 | 428 | 6 | n.d. |
| 88 | 0.92 | 428 | 6 | n.d. |
| 89 | n.d. | n.d. | — | n.d. |
| 90 | 0.98 | 414 | 6 | n.d. |
| 91 | 0.98 | 414 | 6 | n.d. |
| 92 | 0.95 | 428 | 6 | n.d. |
| 93 | 1.01 | 427 | 6 | n.d. |
| 94 | 0.86 | 430 | 4 | n.d. |
| 95 | 1.07 | 388 | 6 | n.d. |
| 96 | 0.97 | 458 | 6 | n.d. |
| 97 | 1.01 | 374 | 4 | 255.0 |
| 98 | n.d. | n.d. | n.d. | 253.5 |
| 99 | 5.54 | 428 | 3 | n.d. |
| 100 | 1.04 | 457 | 6 | 297.5 |
| 101 | 0.84 | 429 | 4 | n.d. |
| 102 | 0.84 | 429 | 4 | n.d. |
| 103 | 1.01 | 439 | 4 | 191.8 |
| 104 | 1.01 | 447 | 4 | n.d. |
| 105 | 1.02 | 443 | 4 | 285.7 |
| 106 | 0.87 | 430 | 6 | 263.8 |
| 107 | 0.99 | 429 | 6 | n.d. |
| 108 | 1.06 | 440 | 4 | n.d. |
| 109 | 0.96 | 429 | 6 | 278.9 |
| 110 | 0.95 | 429 | 6 | 278.0 |
| 111 | 1.00 | 404 | 6 | n.d. |
| 112 | 0.95 | 458 | 6 | n.d. |
| 113 | 0.95 | 458 | 6 | n.d. |
| 114 | n.d. | n.d. | — | 257.5 |
| 115 | 1.03 | 404 | 4 | 257.4 |
| 116 | 1.04 | 461 | 4 | 285.1 |
| 117 | 1.01 | 424 | 6 | n.d. |
| 118 | 1.01 | 424 | 6 | n.d. |
| 119 | n.d. | n.d. | — | n.d. |
| 120 | 0.92 | 415 | 6 | n.d. |
| 121 | 1.08 | 458 | 6 | n.d. |
| 122 | 1.00 | 423 | 6 | n.d. |
| 123 | 1.00 | 423 | 6 | n.d. |
| 124 | 1.03 | 403 | 4 | n.d. |
| 125 | 1.05 | 458 | 6 | n.d. |
| 126 | 1.04 | 457 | 6 | n.d. |
| 127 | 1.04 | 404 | 6 | n.d. |
| 128 | 1.07 | 457 | 6 | n.d. |
| 129 | 1.00 | 404 | 6 | n.d. |
| 130 | 1.01 | 406 | 6 | n.d. |
| 131 | 1.02 | 457 | 6 | n.d. |
| 132 | 1.02 | 457 | 6 | n.d. |
| 133 | 1.03 | 458 | 6 | n.d. |
| 134 | 1.02 | 458 | 6 | n.d. |
| 135 | 0.97 | 403 | 6 | n.d. |
| 136 | 0.97 | 403 | 6 | n.d. |
| 137 | 0.97 | 406 | 6 | 197.5 |
| 138 | 0.95 | 403 | 6 | 297.0 |
| 139 | 0.95 | 403 | 6 | 296.2 |
| 140 | 0.96 | 406 | 6 | n.d. |
| 141 | 0.96 | 404 | 6 | 244.4 |
| 142 | 0.96 | 404 | 6 | 244.8 |
| 143 | 1.01 | 423 | 6 | n.d. |
| 144 | 1.05 | 424 | 6 | n.d. |
| 145 | 0.92 | 415 | 6 | n.d. |
| 146 | 0.92 | 415 | 6 | n.d. |
| 147 | n.d. | n.d. | — | 240.4 |
| 148 | 0.98 | 404 | 6 | n.d. |
| 149 | 0.98 | 404 | 6 | n.d. |
| 150 | 1.02 | 404 | 6 | 238.2 |
| 151 | 0.98 | 403 | 6 | n.d. |
| 152 | 1.03 | 457 | 6 | n.d. |
| 153 | 1.03 | 457 | 6 | n.d. |
| 154 | 1.07 | 423 | 6 | n.d. |
| 155 | 1.11 | 423 | 6 | n.d. |
| 156 | n.d. | n.d. | — | 267.3 |
| 157 | 1.10 | 424 | 4 | 265.5 |
| 158 | 0.98 | 403 | 6 | 280.1 |
| 159 | 0.98 | 403 | 6 | 277.1 |
| 160 | 1.03 | 458 | 6 | n.d. |
| 161 | 1.03 | 458 | 6 | n.d. |
| 162 | 0.99 | 458 | 6 | n.d. |
| 163 | 0.99 | 458 | 6 | n.d. |
| 164 | 1.06 | 457 | 6 | n.d. |
| 165 | 1.05 | 457 | 6 | n.d. |
| 166 | 1.15 | 432 | 6 | n.d. |
| 167 | 1.04 | 447 | 6 | n.d. |
| 168 | 5.90 | 454 | 3 | n.d. |
| 169 | 1.06 | 411 | 6 | 270.8 |
| 170 | 1.06 | 411 | 6 | 269.8 |
| 171 | 1.10 | 418 | 6 | n.d. |
| 172 | 1.14 | 432 | 6 | n.d. |
| 173 | 1.13 | 432 | 6 | n.d. |
| 174 | 6.50 | 439 | 7 | n.d. |
| 175 | 6.50 | 439 | 7 | n.d. |
| 176 | 6.09 | 428 | 7 | n.d. |
| 177 | 5.95 | 428 | 7 | n.d. |
| 178 | 0.92 | 458 | 6 | 247.3 |
| 179 | 6.10 | 428 | 7 | n.d. |
| 180 | 1.09 | 390 | 4 | n.d. |
| 181 | 1.08 | 390 | 4 | n.d. |
| 182 | 1.08 | 390 | 4 | n.d. |
| 183 | n.d. | n.d. | — | n.d. |
| 184 | n.d. | n.d. | — | n.d. |
| 185 | 1.09 | 418 | 6 | n.d. |
| 186 | n.d. | n.d. | — | n.d. |
| 187 | 0.95 | 455 | 6 | n.d. |
| 188 | 1.02 | 455 | 6 | n.d. |
| 189 | 1.02 | 455 | 6 | n.d. |

SFC-MS

For SFC-MS, an analytical SFC system from Berger Instruments (Newark, Del., USA) was used comprising a dual pump control module (FCM-1200) for delivery of $CO_2$ and modifier, a thermal control module for column heating (TCM2100) with temperature control in the range 1-150° C. and column selection valves (Valco, VICI, Houston, Tex., USA) for 6 different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

In case e.g. 15% of mobile phase B was used, this means that 15% of mobile phase B and 85% of mobile phase A were used (total sum 100%).

One of the following columns was used for each SFC-MS measurement: Chiralpak® AS-H; Chiralcel® OD-H; and Chiralcel® OJ-H. All SFC-MS columns were obtained from Chiral Technologies Europe, which is a subsidiary of DAICEL CHEMICALS INDUSTRIES Ltd.

Co. No. 174-175: SFC-MS was carried out on a AS-H column (250×4.6 mm) with a flow rate of 3 ml/min. Two mobile phases (mobile phase A: $CO_2$; mobile phase B: MeOH containing 0.2% isopropylamine (iPrNH$_2$)) were employed. 15% B was hold for 15 min. Column temperature was set at 30° C. Under these conditions, Co. No. 174 ('enantiomer A')

had a shorter retention time ($R_t$) on the column than Co. No. 175 ('enantiomer B'). The measurement was compared against the racemic mixture.

Co. No. 181-182: SFC-MS was carried out on a AS-H column (500×4.6 mm) with a flow rate of 3 ml/min. Two mobile phases (mobile phase A: $CO_2$; mobile phase B: MeOH containing 0.2% $iPrNH_2$) were employed. 15% B was hold for 15 min. Column temperature was set at 30° C. Under these conditions, Co. No. 181 ('enantiomer A') had a shorter retention time ($R_t$) on the column than Co. No. 182 ('enantiomer B'). The measurement was compared against the racemic mixture.

Co. No. 76-77: SFC-MS was carried out on a AS-H column (500×4.6 mm) with a flow rate of 3 ml/min. Two mobile phases (mobile phase A: $CO_2$; mobile phase B: MeOH containing 0.2% $iPrNH_2$) were employed. 40% B was hold for 15 min. Column temperature was set at 30° C. Under these conditions, Co. No. 76 ('enantiomer A') had a shorter retention time ($R_t$) on the column than Co. No. 77 ('enantiomer B'). The measurement was compared against the racemic mixture.

Co. No. 80-81: SFC-MS was carried out on a AS-H column (250×4.6 mm) with a flow rate of 3 ml/min. Two mobile phases (mobile phase A: $CO_2$; mobile phase B: MeOH containing 0.2% $iPrNH_2$) were employed. 35% B was hold for 15 min. Then a gradient was applied from 35% B to 50% B in 1.5 min and hold for 4.1 min. Column temperature was set at 30° C. Under these conditions, Co. No. 80 ('enantiomer A') had a shorter retention time ($R_t$) on the column than Co. No. 81 ('enantiomer B').

Co. No. 109-110: SFC-MS was carried out on a AS-H column (250×4.6 mm) with a flow rate of 3 ml/min. Two mobile phases (mobile phase A: $CO_2$; mobile phase B: iPrOH containing 0.2% $iPrNH_2$) were employed. 35% B was hold for 15 min. Column temperature was set at 30° C. Under these conditions, Co. No. 109 ('enantiomer A') had a shorter retention time ($R_t$) on the column than Co. No. 110 ('enantiomer B').

Co. No. 160-161: SFC-MS was carried out on a AS-H column (250×4.6 mm) with a flow rate of 3 ml/min. Two mobile phases (mobile phase A: $CO_2$; mobile phase B: MeOH containing 0.2% $iPrNH_2$) were employed. 15% B was hold for 15 min. Column temperature was set at 30° C. Under these conditions, Co. No. 160 ('enantiomer A') had a shorter retention time ($R_t$) on the column than Co. No. 161 ('enantiomer B').

Co. No. 87-88: SFC-MS was carried out on a AS-H column (250×4.6 mm) with a flow rate of 3 ml/min. Two mobile phases (mobile phase A: $CO_2$; mobile phase B: MeOH containing 0.2% $iPrNH_2$) were employed. A gradient was applied from 10% B to 40% B at 1.6%/minute rate. Subsequenity, a gradient was applied from 40% B to 50% B in 2 min. 50% B was hold for 3.6 min. Column temperature was set at 30° C. Under these conditions, Co. No. 87 ('enantiomer A') had a shorter retention time ($R_t$) on the column than Co. No. 88 ('enantiomer B'). The measurement was compared against the racemic mixture.

Co. No. 83-84: SFC-MS was carried out on a OD-H column (250×4.6 mm) with a flow rate of 3 ml/min. Two mobile phases (mobile phase A: $CO_2$; mobile phase B: MeOH containing 0.2% $iPrNH_2$) were employed. First, 35% B was hold for 19 min. Subsequently, a gradient was applied from 35% B to 50% B in 1.5 min and hold for 4.1 min. Column temperature was set at 30° C. Under these conditions, Co. No. 83 ('enantiomer A') had a shorter $R_t$ on the column than Co. No. 84 ('enantiomer B'). The measurement was compared against the racemic mixture.

Co. No. 56-57: SFC-MS was carried out on a OD-H column (250×4.6 mm) with a flow rate of 3 ml/min. Two mobile phases (mobile phase A: $CO_2$; mobile phase B: MeOH containing 0.2% $iPrNH_2$) were employed. 20% B was hold for 15 min. Column temperature was set at 30° C. Under these conditions, Co. No. 56 ('enantiomer A') had a shorter $R_t$ on the column than Co. No. 57 ('enantiomer B'). The measurement was compared against the racemic mixture.

Co. No. 112-113: SFC-MS was carried out on a OD-H column (250×4.6 mm) with a flow rate of 3 ml/min. Two mobile phases (mobile phase A: $CO_2$; mobile phase B: MeOH containing 0.2% $iPrNH_2$) were employed. 35% B was hold for 15 min. Column temperature was set at 30° C. Under these conditions, Co. No. 112 ('enantiomer A') had a shorter $R_t$ on the column than Co. No. 113 ('enantiomer B'). The measurement was compared against the racemic mixture.

Co. No. 44-45: SFC-MS was carried out on a OD-H column (250×4.6 mm) with a flow rate of 3 ml/min. Two mobile phases (mobile phase A: $CO_2$; mobile phase B: iPrOH containing 0.2% $iPrNH_2$) were employed. 25% B was hold for 15 min. Column temperature was set at 23° C. Under these conditions, Co. No. 44 ('enantiomer A') had a shorter $R_t$ on the column than Co. No. 45 ('enantiomer B'). The measurement was compared against the racemic mixture.

Co. No. 78-79: SFC-MS was carried out on a OD-H column (500×4.6 mm) with a flow rate of 3 ml/min. Two mobile phases (mobile phase A: $CO_2$; mobile phase B: iPrOH containing 0.2% $iPrNH_2$) were employed. 35% B was hold for 15 min. Column temperature was set at 30° C. Under these conditions, Co. No. 78 ('enantiomer A') had a shorter $R_t$ on the column than Co. No. 79 ('enantiomer B'). The measurement was compared against the racemic mixture.

Co. No. 97-98: SFC-MS was carried out on a OD-H column (500×4.6 mm) with a flow rate of 3 ml/min. Two mobile phases (mobile phase A: $CO_2$; mobile phase B: MeOH containing 0.2% $iPrNH_2$) were employed. 25% B was hold for 15 min. Column temperature was set at 30° C. Under these conditions, Co. No. 97 ('enantiomer A') had a shorter $R_t$ on the column than Co. No. 98 ('enantiomer B'). The measurement was compared against the racemic mixture.

Co. No. 148-149: SFC-MS was carried out on a OD-H column (250×4.6 mm) with a flow rate of 3 ml/min. Two mobile phases (mobile phase A: $CO_2$; mobile phase B: MeOH containing 0.2% $iPrNH_2$) were employed. 25% B was hold for 15 min. Column temperature was set at 23° C. Under these conditions, Co. No. 148 ('enantiomer A') had a shorter $R_t$ on the column than Co. No. 149 ('enantiomer B'). The measurement was compared against the racemic mixture.

Co. No. 122-123: SFC-MS was carried out on a OD-H column (250×4.6 mm) with a flow rate of 3 ml/min. Two mobile phases (mobile phase A: $CO_2$; mobile phase B: MeOH containing 0.2% $iPrNH_2$) were employed. 40% B was hold for 15 min. Column temperature was set at 30° C. Under these conditions, Co. No. 122 ('enantiomer A') had a shorter $R_t$ on the column than Co. No. 123 ('enantiomer B'). The measurement was compared against the racemic mixture.

Co. No. 101-102: SFC-MS was carried out on a OD-H column (250×4.6 mm) with a flow rate of 3 ml/min. Two mobile phases (mobile phase A: $CO_2$; mobile phase B: EtOH containing 0.2% $iPrNH_2$) were employed. 30% B was hold for 15 min. Column temperature was set at 30° C. Under these conditions, Co. No. 101 ('enantiomer A') had a shorter $R_t$ on the column than Co. No. 102 ('enantiomer B'). The measurement was compared against the racemic mixture.

Co. No. 131-132: SFC-MS was carried out on a OD-H column (250×4.6 mm) with a flow rate of 3 ml/min. Two mobile phases (mobile phase A: $CO_2$; mobile phase B: MeOH containing 0.2% iPrNH$_2$) were employed. 20% B was hold for 15 min. Column temperature was set at 30° C. Under these conditions, Co. No. 131 ('enantiomer A') had a shorter R$_t$ on the column than Co. No. 132 ('enantiomer B'). The measurement was compared against the racemic mixture.

Co. No. 133-134: SFC-MS was carried out on a OD-H column (250×4.6 mm) with a flow rate of 3 ml/min. Two mobile phases (mobile phase A: CO$_2$; mobile phase B: MeOH containing 0.2% iPrNH$_2$) were employed. 20% B was hold for 15 min. Column temperature was set at 23° C. Under these conditions, Co. No. 133 ('enantiomer A') had a shorter R$_t$ on the column than Co. No. 134 ('enantiomer B'). The measurement was compared against the racemic mixture.

Co. No. 135-136: SFC-MS was carried out on a OD-H column (250×4.6 mm) with a flow rate of 3 ml/min. Two mobile phases (mobile phase A: CO$_2$; mobile phase B: MeOH containing 0.2% iPrNH$_2$) were employed. 30% B was hold for 15 min. Column temperature was set at 23° C. Under these conditions, Co. No. 135 ('enantiomer A') had a shorter R$_t$ on the column than Co. No. 136 ('enantiomer B'). The measurement was compared against the racemic mixture.

Co. No. 172-173: SFC-MS was carried out on a OD-H column (250×4.6 mm) with a flow rate of 3 ml/min. Two mobile phases (mobile phase A: CO$_2$; mobile phase B: MeOH containing 0.2% iPrNH$_2$) were employed. 30% B was hold for 15 min. Column temperature was set at 30° C. Under these conditions, Co. No. 173 ('enantiomer A') had a shorter R$_t$ on the column than Co. No. 172 ('enantiomer B'). The measurement was compared against the racemic mixture.

Co. No. 117-118: SFC-MS was carried out on a OJ-H column (250×4.6 mm) with a flow rate of 3 ml/min. Two mobile phases (mobile phase A: CO$_2$; mobile phase B: MeOH containing 0.2% iPrNH$_2$) were employed. 30% B was hold for 15 min. Column temperature was set at 30° C. Under these conditions, Co. No. 117 ('enantiomer A') had a shorter R$_t$ on the column than Co. No. 118 ('enantiomer B'). The measurement was compared against the racemic mixture.

NMR

For a number of compounds, $^1$H NMR spectra were recorded on a 300 MHz Ultrashield magnet, a Bruker DPX-360, a Bruker DPX-400 or on a Bruker Avance 600 spectrometer with standard pulse sequences, operating at 360 MHz, 400 MHz and 600 MHz respectively, using CHLOROFORM-d (deuterated chloroform, CDCl$_3$) or DMSO-d$_6$ (deuterated DMSO, dimethyl-d6 sulfoxide) as solvents. Chemical shifts (δ) are reported in parts per million (ppm) relative to tetramethylsilane (TMS), which was used as internal standard.

TABLE 2b $^1$H NMR results

| Co. No. | $^1$H NMR result* |
|---|---|
| 1 | (400 MHz, DMSO-d$_6$) δ ppm 2.21 (d, J = 2.1 Hz, 3 H), 4.25 (ddd, J = 12.3, 10.1, 4.0 Hz, 1 H), 4.36-4.44 (m, 2 H), 4.47-4.54 (m, 1 H), 6.26 (s, 1 H), 7.01 (dd, J = 2.0, 0.8 Hz, 1 H), 7.16 (dd, J = 7.3, 1.6 Hz, 1 H), 7.18-7.28 (m, 2 H), 7.44 (dd, J = 8.5, 1.6 Hz, 1 H), 7.53 (d, J = 8.5 Hz, 1 H), 8.07-8.08 (m, 1 H), 12.21 (s, 1 H) |
| 2 | (360 MHz, DMSO-d$_6$) δ ppm 1.89-2.06 (m, 1 H), 2.13-2.28 (m, 2 H), 2.28-2.44 (m, 1 H), 2.77 (s, 3 H), 4.27-4.50 (m, 2 H), 4.60 (dd, J = 9.0, 6.0 Hz, 1 H), 7.00 (d, J = 1.8 Hz, 1 H), 7.31 (d, J = 7.7 Hz, 1 H), 7.52 (t, J = 7.7 Hz, 1 H), 7.56 (d, J = 8.4 Hz, 1 H), 7.63 (t, J = 7.5 Hz, 1 H), 7.76-7.86 (m, 2 H), 8.20 (dd, J = 6.4, 1.6 Hz, 1 H), 8.25-8.39 (m, 2 H), 8.70 (d, J = 6.2 Hz, 1 H), 12.03 (s, 1 H) |
| 3 | (360 MHz, CHLOROFORM-d) δ ppm 2.00 (br. s., 1 H), 2.36 (s, 6 H), 4.43 (t, J = 6.0 Hz, 2 H), 4.60 (dd, J = 7.9, 6.0 Hz, 1 H), 6.96-7.14 (m, 2 H), 7.28 (br. s., 1 H), 7.41 (d, J = 7.3 Hz, 1 H), 8.21 (d, J = 1.8 Hz, 1 H), 8.62 (d, J = 1.5 Hz, 1 H), 11.74 (br. s., 1 H) |
| 4 | (360 MHz, DMSO-d$_6$) δ ppm 1.81 (br. s., 1 H), 1.98 (br. s., 2 H), 2.21 (br. s., 1 H), 2.32 (s, 3 H), 4.15 (br. s., 2 H), 4.43 (t, J = 6.8 Hz, 1 H), 6.65 (d, J = 1.8 Hz, 1 H), 6.79-6.87 (m, 1 H), 6.87-6.96 (m, 1 H), 7.05 (dd, J = 10.1, 2.7 Hz, 1 H), 7.31 (dd, J = 8.4, 1.8 Hz, 1 H), 7.44 (d, J = 8.4 Hz, 1 H), 7.67 (s, 1 H), 7.93 (s, 1 H), 11.75 (s, 1 H) |
| 5 | (400 MHz, DMSO-d$_6$) δ ppm 1.87-1.98 (m, 1 H), 2.07-2.21 (m, 2 H), 2.24-2.34 (m, 1 H), 2.35 (s, 3 H), 2.36 (d, J = 0.8 Hz, 3 H), 4.49-4.46 (m, 2 H), 4.59 (dd, J = 7.9, 6.3 Hz, 1 H), 6.89 (dd, J = 7.7, 1.6 Hz, 1 H), 6.99 (d, J = 2.0 Hz, 1 H), 7.12 (td, J = 7.5, 1.7 Hz, 1 H), 7.17 (td, J = 7.3, 1.5 Hz, 1 H), 7.23 (d, J = 7.3 Hz, 1 H), 7.68 (d, J = 8.5 Hz, 1 H), 7.99 (d, J = 8.9 Hz, 1 H), 8.21 (s, 1 H), 9.81 (s, 1 H), 12.37 (d, J = 2.0 Hz, 1 H), 15.05 (br. s, 1 H) |
| 6 | (360 MHz, DMSO-d$_6$) δ ppm 1.92 (br. s., 1 H), 2.14 (br. s., 2 H), 2.29 (br. s., 1 H), 2.36 (s, 3 H), 2.55 (s, 3 H), 4.38 (q, J = 5.7 Hz, 2 H), 4.59 (t, J = 7.0 Hz, 1 H), 6.90 (d, J = 7.3 Hz, 1 H), 7.00 (s, 1 H), 7.07-7.21 (m, 2 H), 7.21-7.29 (m, 1 H), 7.75-7.89 (m, 3 H), 7.95 (s, 1 H), 8.50 (d, J = 5.5 Hz, 1 H), 12.05 (s, 1 H) |
| 7 | (360 MHz, DMSO-d$_6$) δ ppm 1.87-2.04 (m, 1 H), 2.12-2.26 (m, 2 H), 2.27-2.40 (m, 1 H), 4.26 (s, 3 H), 4.29-4.45 (m, 2 H), 4.59 (dd, J = 9.1, 5.9 Hz, 1 H), 7.14 (d, J = 8.4 Hz, 1 H), 7.20 (d, J = 1.5 Hz, 1 H), 7.26 (d, J = 8.4 Hz, 1 H), 7.29 (d, J = 7.7 Hz, 1 H), 7.51 (t, J = 7.7 Hz, 1 H), 7.63 (t, J = 7.5 Hz, 1 H), 7.78 (d, J = 8.1 Hz, 1 H), 12.26 (s, 1 H) |
| 8 | (360 MHz, DMSO-d$_6$) δ ppm 1.89-2.06 (m, 1 H), 2.16 (s, 3 H), 2.17-2.22 (m, 2 H), 2.28-2.40 (m, 1 H), 4.27-4.45 (m, 2 H), 4.59 (dd, J = 9.1, 5.9 Hz, 1 H), 6.88 (d, J = 1.5 Hz, 1 H), 7.26 (dd, J = 8.8, 2.2 Hz, 1 H), 7.28-7.35 (m, 2 H), 7.44 (d, J = 8.8 Hz, 1 H), 7.51 (t, J = 7.7 Hz, 1 H), 7.62 (d, J = 7.3 Hz, 1 H), 7.66 (d, J = 2.2 Hz, 1 H), 7.79 (d, J = 7.3 Hz, 1 H), 7.96 (d, J = 1.1 Hz, 1 H), 11.75 (d, J = 1.1 Hz, 1 H) |
| 10 | (360 MHz, CHLOROFORM-d) δ ppm 1.87-2.00 (m, 1 H), 2.04-2.17 (m, 1 H), 2.19-2.35 (m, 5 H), 4.35 (t, J = 5.9 Hz, 2 H), 4.44 (t, J = 6.6 Hz, 1 H), 6.63-6.80 (m, 2 H), 6.85 (dd, J = 9.7, 2.4 Hz, 1 H), 7.09 (d, J = 1.5 Hz, 1 H), 7.31 (d, J = 8.4 Hz, 1 H), 7.38 (dd, J = 8.6, 1.3 Hz, 1 H), 7.98 (s, 1 H), 9.86 (br. s., 1 H) |
| 14 | (360 MHz, CDCl$_3$) δ ppm 1.95-2.17 (m, 2 H), 2.18-2.35 (m, 2 H), 2.37 (s, 3 H), 4.27-4.44 (m, 2 H), 4.54 (t, J = 6.2 Hz, 1 H), 6.74 (d, J = 7.3 Hz, 1 H), 7.06-7.13 (m, 2 |

TABLE 2b-continued

<sup>1</sup>H NMR results

| Co. No. | <sup>1</sup>H NMR result* |
|---|---|
| | H), 7.14-7.23 (m, 2 H), 7.35 (d, J = 8.8 Hz, 1 H), 7.40 (dd, J = 8.4, 1.5 Hz, 1 H), 7.99 (s, 1 H), 9.43 (br. s., 1 H) |
| 20 | (300 MHz, CDCl<sub>3</sub>) δ ppm 1.93-2.26 (m, 3 H), 2.26-2.48 (m, 1 H), 4.29 (m, J = 5.8, 5.8 Hz, 3 H), 6.88-6.98 (m, 2 H), 7.01-7.12 (m, 2 H), 7.20-7.27 (m, 1 H), 7.27-7.38 (m, 2 H), 7.92 (s, 1 H), 9.59 (br. s., 1 H) |
| 31 | (400 MHz, DMSO-d<sub>6</sub>) δ ppm 1.81-2.00 (m, 1 H), 2.00-2.21 (m, 2 H), 2.27 (m, J = 9.9, 4.2 Hz, 1 H), 2.35 (s, 3 H), 3.85 (s, 3 H), 4.27-4.39 (m, 2 H), 4.55 (t, J = 7.1 Hz, 1 H), 6.79 (d, J = 1.2 Hz, 1 H), 6.88 (d, J = 6.9 Hz, 1 H), 7.11 (td, J = 7.3, 1.6 Hz, 1 H), 7.16 (td, J = 7.4, 1.4 Hz, 1 H), 7.22 (d, J = 7.3 Hz, 1 H), 7.28 (dd, J = 8.3, 1.4 Hz, 1 H), 7.33 (d, J = 8.5 Hz, 1 H), 7.67 (s, 1 H), 7.77 (d, J = 0.8 Hz, 1 H), 8.01 (s, 1 H), 11.53 (s, 1 H) |
| 36 | (600 MHz, DMSO-d<sub>6</sub>) δ ppm 2.16 (d, J = 0.9 Hz, 3 H), 2.21 (d, J = 1.8 Hz, 3 H), 4.22-4.29 (m, 1 H), 4.36-4.43 (m, 2 H), 4.45-4.54 (m, 1 H), 6.26 (s, 1 H), 6.91 (dd, J = 2.1, 0.8 Hz, 1 H), 7.14-7.18 (m, 1 H), 7.20-7.24 (m, 1 H), 7.26 (dd, J = 7.3, 5.6 Hz, 1 H), 7.28 (dd, J = 8.7, 2.1 Hz, 1 H), 7.33 (s, 1 H), 7.46 (dt, J = 8.7, 0.7 Hz, 1 H), 7.68 (d, J = 2.2 Hz, 1 H), 7.96 (d, J = 1.0 Hz, 1 H), 11.80 (d, J = 1.6 Hz, 1 H) |
| 37 | (360 MHz, DMSO-d<sub>6</sub>) δ ppm 2.17 (s, 3 H), 4.27-4.47 (m, 3 H), 4.47-4.64 (m, 1 H), 6.27 (s, 1 H), 6.93 (d, J = 1.5 Hz, 1 H), 7.29 (dd, J = 8.6, 2.0 Hz, 1 H), 7.35 (s, 1 H), 7.47 (d, J = 8.4 Hz, 1 H), 7.52 (d, J = 7.3 Hz, 1 H), 7.61-7.78 (m, 3 H), 7.87 (d, J = 7.3 Hz, 1 H), 8.00 (s, 1 H), 11.80 (s, 1 H) |
| 38 | (400 MHz, DMSO-d<sub>6</sub>) δ ppm 1.94-2.10 (m, 1 H), 2.12-2.33 (m, 2 H), 2.33-2.40 (m, 1 H), 4.33-4.49 (m, 2 H), 4.68 (dd, J = 8.7, 6.3 Hz, 1 H), 7.21 (d, J = 7.7 Hz, 1 H), 7.41-7.51 (m, 2 H), 7.52-7.60 (m, 1 H), 7.66 (d, J = 8.5 Hz, 1 H), 7.73 (d, J = 7.7 Hz, 1 H), 7.93 (s, 1 H) |
| 41 | (360 MHz, CHLOROFORM-d) δ ppm 2.20 (d, J = 1.8 Hz, 3 H), 4.03-4.21 (m, 2 H), 4.23-4.34 (m, 5 H), 6.00 (s, 1 H), 6.76 (d, J = 1.8 Hz, 1 H), 6.84 (d, J = 7.3 Hz, 1 H), 6.91 (d, J = 8.4 Hz, 1 H), 6.95-7.08 (m, 2 H), 7.17 (d, J = 8.4 Hz, 1 H), 7.31 (s, 1 H), 9.75 (br. s., 1 H) |
| 44 | (360 MHz, DMSO-d<sub>6</sub>) δ ppm 4.08-4.39 (m, 7 H), 6.13 (s, 1 H), 6.93 (d, J = 1.5 Hz, 1 H), 7.11 (dd, J = 8.4, 0.7 Hz, 1 H), 7.17 (d, J = 8.4 Hz, 1 H), 7.39 (d, J = 7.7 Hz, 1 H), 7.58-7.72 (m, 2 H), 7.78 (s, 1 H), 7.83 (dd, J = 7.9, 1.3 Hz, 1 H), 11.78 (s, 1 H) |
| 48 | (360 MHz, CHLOROFORM-d) δ ppm 2.17 (s, 3 H), 4.03-4.21 (m, 2 H), 4.23-4.37 (m, 5 H), 5.91 (s, 1 H), 6.64 (td, J = 8.4, 2.6 Hz, 1 H), 6.73 (d, J = 1.8 Hz, 1 H), 6.76 (dd, J = 9.9, 2.6 Hz, 1 H), 6.87 (d, J = 8.4 Hz, 1 H), 6.92 (dd, J = 8.4, 5.9 Hz, 1 H), 7.15 (d, J = 8.4 Hz, 1 H), 7.29 (s, 1 H), 10.40 (br. s., 1 H) |
| 50 | (360 MHz, CHLOROFORM-d) δ ppm 4.08-4.21 (m, 2 H), 4.25-4.39 (m, 5 H), 6.22 (s, 1 H), 6.74-6.80 (m, 1 H), 6.90 (dd, J = 8.4, 0.7 Hz, 1 H), 7.13-7.20 (m, 3 H), 7.23-7.30 (m, 1 H), 7.32 (s, 1 H), 7.36-7.43 (m, 1 H), 9.77 (br. s., 1 H) |
| 53 | (360 MHz, DMSO-d<sub>6</sub>) δ ppm 2.15 (d, J = 12.4 Hz, 2 H), 2.28 (s, 3 H), 3.99-4.14 (m, 1 H), 4.17-4.23 (m, 1 H), 4.24 (s, 3 H), 4.52-4.73 (m, 2 H), 6.03 (s, 1 H), 7.00-7.09 (m, 1 H), 7.09-7.19 (m, 3 H), 7.24-7.30 (m, 1 H), 7.36 (dd, J = 8.6, 6.0 Hz, 1 H), 12.16 (br. s., 1 H) |
| 56 | (360 MHz, CHLOROFORM-d) δ ppm 4.18-4.29 (m, 1 H), 4.32 (s, 3 H), 4.34-4.42 (m, 1 H), 4.42-4.62 (m, 2 H), 6.25 (s, 1 H), 6.98 (dd, J = 8.4, 0.7 Hz, 1 H), 7.26 (d, J = 8.4 Hz, 1 H), 7.29-7.36 (m, 2 H), 7.46-7.64 (m, 2 H), 7.71-7.84 (m, 1 H), 9.23 (br. s., 1 H) |
| 58 | (360 MHz, CHLOROFORM-d) δ ppm 2.26 (s, 3 H), 2.32 (s, 3 H), 3.01 (ddd, J = 12.6, 10.8, 4.0 Hz, 1 H), 3.29-3.43 (m, 1 H), 4.32 (s, 3 H), 4.36 (br. s., 1 H), 4.39-4.51 (m, 1 H), 4.55 (s, 1 H), 6.78-6.91 (m, 2 H), 6.95 (d, J = 8.4 Hz, 1 H), 7.19 (dd, J = 8.4, 5.9 Hz, 1 H), 7.24 (d, J = 8.4 Hz, 1 H), 7.27 (d, J = 2.2 Hz, 1 H), 9.46 (br. s., 1 H) |
| 59 | (400 MHz, CHLOROFORM-d) δ ppm 1.92-1.99 (m, 1 H), 2.05-2.19 (m, 1 H), 2.19-2.36 (m, 2 H), 2.37 (s, 3 H), 4.31-4.38 (m, 5 H), 4.48 (t, J = 6.5 Hz, 1 H), 6.70-6.75 (m, 1 H), 6.76-6.84 (m, 1 H), 6.92 (dd, J = 9.7, 2.8 Hz, 1 H), 6.99 (dd, J = 8.5, 0.8 Hz, 1 H), 7.24-7.28 (m, 1 H), 7.31 (dd, J = 2.0, 0.8 Hz, 1 H), 9.43 (br. s., 1 H) |
| 60 | (600 MHz, DMSO-d<sub>6</sub>) δ ppm 1.75 (s, 3 H), 1.97 (dt, J = 13.8, 3.1 Hz, 1 H), 2.05 (d, J = 11.4 Hz, 1 H), 2.18-2.28 (m, 1 H), 2.35-2.47 (m, 1 H), 4.26 (s, 3 H), 4.26-4.32 (m, 1 H), 4.45 (dd, J = 12.5, 4.5 Hz, 1 H), 6.48 (br. s., 1 H), 6.97 (dd, J = 10.1, 2.6 Hz, 1 H), 7.08 (td, J = 8.5, 2.9 Hz, 1 H), 7.15 (d, J = 8.5 Hz, 1 H), 7.21 (d, J = 0.7 Hz, 1 H), 7.27 (d, J = 8.5 Hz, 1 H), 7.79 (dd, J = 8.8, 6.3 Hz, 1 H), 12.33 (br. s., 1 H) |

*in the case of enantiomers only one compound is reported

Pharmacology

A) Screening of the Compounds of the Invention for γ-Secretase-Modulating Activity Screening was carried out using SKNBE2 human neuroblastoma cells carrying the hAPP 695—wild type, grown in Dulbecco's Modified Eagle's Medium/Nutrient mixture F-12 (DMEM/NUT-mix F-12) (HAM) provided by Invitrogen (cat no. 10371-029) containing 5% Serum/Fe supplemented with 1% non-essential amino acids, 1-glutamine 2 mM, Hepes 15 mM, penicillin 50 U/mL (units/mL) en streptomycin 50 µg/mL. Cells were grown to near confluency.

The screening was performed using a modification of the assay as described in Citron et al (1997) Nature Medicine 3: 67. Briefly, cells were plated in a 384-well plate at 10$^4$ cells/well in Ultraculture (Lonza, BE12-725F) supplemented with 1% glutamine (Invitrogen, 25030-024), 1% non-essential amino acid (NEAA), penicillin 50 U/mL en streptomycin 50 µg/mL in the presence of test compound at different test concentrations. The cell/compound mixture was incubated overnight at 37° C., 5% $CO_2$. The next day the media were assayed by two sandwich immuno-assays, for Aβ42 and Aβtotal.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission. To quantify the amount of Aβ42 in the cell supernatant, monoclonal antibody specific to the C-terminus of Aβ42 (JRF/cAβ42/26) was coupled to the receptor beads and biotinylated antibody specific to the N-terminus of Aβ (JRF/AβN/25) was used to react with the donor beads. To quantify the amount of Aβ total in the cell supernatant, monoclonal antibody specific to the N-terminus of Aβ (JRF/AβN/25) was coupled to the receptor beads and biotinylated antibody specific to the mid region of Aβ (biotinylated 4G8) was used to react with the donor beads.

To obtain the values reported in Table 3, the data are calculated as percentage of the maximum amount of amyloid Beta 42 measured in the absence of the test compound. The sigmoidal dose response curves were analyzed using nonlinear regression analysis with percentage of the control plotted against the log concentration of the compound. A 4-parameter equation was used to determine the $IC_{50}$.

TABLE 3

("n.d." means not determined)

| Co. No. | IC50 Aβ42 (μM) | IC50 Aβtotal (μM) |
|---|---|---|
| 18 | 0.117 | >10 |
| 8 | 0.046 | >10 |
| 2 | 0.022 | 7.413 |
| 7 | 0.035 | >10 |
| 28 | 0.107 | >10 |
| 61 | 3.981 | >10 |
| 35 | 0.363 | >10 |
| 37 | 0.048 | 0.832 |
| 38 | 0.871 | >10 |
| 29 | 4.786 | >15.136 |
| 27 | 0.339 | >10 |
| 26 | 0.331 | >10 |
| 21 | 0.355 | >10 |
| 20 | 0.275 | >10 |
| 22 | 0.138 | >10 |
| 9 | 0.138 | >10 |
| 17 | 0.087 | >10 |
| 12 | 0.126 | >10 |
| 31 | 0.076 | >10 |
| 1 | 0.295 | >10 |
| 34 | 0.692 | >10 |
| 3 | 0.437 | >10 |
| 25 | 0.398 | >10 |
| 15 | 0.089 | >10 |
| 6 | 0.047 | >10 |
| 13 | 0.072 | >10 |
| 14 | 2.951 | >10 |
| 36 | 0.062 | >10 |
| 5 | 0.105 | >10 |
| 4 | 0.087 | >10 |
| 23 | 0.589 | >10 |
| 24 | 0.257 | >10 |
| 10 | 0.102 | >10 |
| 11 | 3.467 | >10 |
| 16 | 0.112 | >10 |
| 30 | 0.052 | >10 |
| 32 | 0.148 | >10 |
| 33 | 0.049 | >10 |

TABLE 3-continued ("n.d." means not determined)

| Co. No. | IC50 Aβ42 (μM) | IC50 Aβtotal (μM) |
|---|---|---|
| 19 | 0.661 | >10 |
| 62 | 0.245 | >10 |
| 63 | 4.467 | >10 |
| 64 | 0.068 | >10 |
| 65 | 0.046 | 7.244 |
| 66 | 0.447 | >10 |
| 67 | 0.501 | >10 |
| 39 | 0.038 | 0.214 |
| 178 | 0.058 | >10 |
| 68 | 0.316 | >10 |
| 94 | 0.170 | 1.820 |
| 69 | 0.117 | >10 |
| 70 | 1.000 | >10 |
| 180 | 0.178 | >10 |
| 71 | 0.065 | >10 |
| 72 | 0.126 | >10 |
| 73 | 0.043 | >10 |
| 74 | 0.112 | >10 |
| 95 | 0.355 | >10 |
| 93 | 1.479 | >10 |
| 75 | 0.174 | >10 |
| 96 | 0.074 | >10 |
| 46 | 0.054 | >10 |
| 76 | 0.141 | >10 |
| 77 | 0.024 | >10 |
| 78 | 0.030 | >10 |
| 79 | 0.186 | >10 |
| 80 | 0.468 | >10 |
| 81 | 0.074 | >10 |
| 181 | 5.888 | >10 |
| 182 | 0.117 | >10 |
| 97 | 0.219 | >10 |
| 98 | 5.495 | >10 |
| 59 | 0.025 | 3.715 |
| 82 | 0.066 | >10 |
| 92 | 0.170 | >10 |
| 99 | 0.078 | >10 |
| 83 | 0.014 | 2.344 |
| 84 | 0.048 | 5.370 |
| 100 | 0.048 | >10 |
| 101 | 2.188 | >10 |
| 102 | 0.089 | >10 |
| 85 | 9.120 | >10 |
| 86 | 0.112 | >10 |
| 103 | 0.026 | >10 |
| 104 | 0.044 | >10 |
| 105 | 0.034 | >10 |
| 106 | 0.447 | >10 |
| 107 | 0.148 | >10 |
| 108 | 0.040 | >10 |
| 47 | 0.023 | >10 |
| 48 | 1.023 | >10 |
| 109 | 0.537 | >10 |
| 110 | 0.036 | >10 |
| 87 | 0.447 | >10 |
| 88 | 0.065 | >10 |
| 111 | 0.093 | >10 |
| 112 | 0.021 | >10 |
| 113 | 0.151 | >10 |
| 174 | 0.110 | >10 |
| 175 | 0.028 | >10 |
| 114 | 0.032 | >10 |
| 115 | 1.479 | >10 |
| 55 | 0.072 | >10 |
| 179 | 0.407 | >10 |
| 176 | 0.089 | >10 |
| 177 | 2.512 | >10 |
| 116 | 0.033 | >10 |
| 56 | 0.045 | >10 |
| 57 | 0.603 | >10 |
| 117 | 0.037 | >10 |
| 118 | 3.802 | >10 |
| 183 | 2.884 | >10 |
| 119 | 0.055 | >10 |

TABLE 3-continued ("n.d." means not determined)

| Co. No. | IC50 Aβ42 (μM) | IC50 Aβtotal (μM) |
|---|---|---|
| 184 | 3.090 | 5.370 |
| 120 | 0.123 | >10 |
| 89 | 0.056 | >10 |
| 40 | 0.035 | >10 |
| 121 | 0.110 | >10 |
| 122 | 0.039 | >10 |
| 123 | 2.818 | >10 |
| 124 | 0.047 | >10 |
| 49 | 0.058 | >10 |
| 125 | 0.071 | >10 |
| 52 | 0.044 | >10 |
| 126 | 0.055 | >10 |
| 127 | 0.033 | >10 |
| 128 | 0.060 | >10 |
| 129 | 0.046 | >10 |
| 130 | 0.079 | >10 |
| 131 | 0.027 | 6.457 |
| 132 | 0.490 | >10 |
| 50 | 0.031 | >10 |
| 51 | 0.708 | >10 |
| 133 | 0.059 | >10 |
| 134 | 1.000 | >10 |
| 135 | 0.036 | >10 |
| 136 | 1.259 | >10 |
| 41 | 0.020 | >10 |
| 42 | 0.468 | >10 |
| 137 | 0.049 | >10 |
| 138 | 0.019 | >10 |
| 139 | 1.622 | >10 |
| 140 | 1.148 | >10 |
| 141 | 0.028 | >10 |
| 142 | 2.818 | >10 |
| 143 | 0.186 | >10 |
| 144 | 0.214 | >10 |
| 145 | 0.110 | >10 |
| 146 | 6.166 | >10 |
| 90 | 0.040 | >10 |
| 91 | 1.202 | >10 |
| 147 | 0.031 | >10 |
| 148 | 0.074 | >10 |
| 149 | 1.862 | >10 |
| 150 | 2.188 | >10 |
| 151 | 0.054 | >10 |
| 152 | 3.802 | >10 |
| 153 | 0.036 | >10 |
| 154 | 0.065 | >10 |
| 155 | 1.479 | >10 |
| 156 | 0.085 | >10 |
| 157 | 7.586 | >10 |
| 158 | 0.023 | >10 |
| 159 | 0.676 | >10 |
| 160 | 5.129 | >10 |
| 161 | 0.098 | >10 |
| 162 | 6.918 | >10 |
| 163 | 0.052 | >10 |
| 164 | 0.041 | >10 |
| 165 | 4.365 | >10 |
| 44 | 0.021 | >10 |
| 45 | 0.372 | >10 |
| 58 | 0.049 | >10 |
| 53 | 0.035 | >10 |
| 54 | 2.344 | >10 |
| 166 | 0.347 | >10 |
| 167 | 0.257 | >10 |
| 168 | 0.245 | >10 |
| 185 | 0.126 | >10 |
| 186 | 0.661 | >10 |
| 187 | 8.318 | >10 |
| 173 | 0.251 | >10 |
| 172 | >10 | >10 |
| 188 | 0.107 | >10 |
| 189 | 7.943 | >10 |
| 171 | 0.151 | >10 |
| 60 | 0.138 | >10 |
| 170 | 0.011 | >10 |
| 169 | 0.759 | >10 |
| 43 | n.d. | n.d. |

B) Demonstration of In Vivo Efficacy

B-1a) Aβ42

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Animals treated with the Aβ42 lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 mL of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ1-42, Bachem) were prepared in 1.5 mL Eppendorf tube in Ultraculture, with final concentrations ranging from 10000 to 0.3 pg/mL. The samples and standards were co-incubated with HRPO-labelled N-terminal antibody JRF/rAµ/2 for Aβ42 detection and with the biotinylated mid-domain antibody 4G8 for Aβtotal detection. 50 µl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of AB, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Ill.). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Ill.). A reading was performed after 10 to 15 min (excitation 320 nm/emission 420 nm).

In this model a Aβ42 lowering compared to untreated animals would be advantageous, in particular a Aβ42 lowering with at least 10%, more in particular a Aβ42 lowering with at least 20%.

B-2a) Aβ38

Aβ38 increasing agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ38 increasing agents can be administered in any standard form using any standard method. For example, but not limited to, Aβ38 increasing agents can be in the form of liquid, tablets or capsules that are taken orally or by injection. Aβ38 increasing agents can be administered at any dose that is sufficient to significantly increase levels of Aβ38 in the blood, plasma, serum, cerebrospinal fluid (CSF), or brain.

To determine whether acute administration of an Aβ38 increasing agents would increase Aβ38 levels in vivo, non-transgenic rodents, e.g. mice or rats were used. Animals treated with the Aβ38 increasing agents were examined and compared to those untreated or treated with vehicle and brain levels of soluble Aβ38 and total Aβ were quantitated by standard techniques, for example, using ELISA. Treatment periods varied from hours (h) to days and were adjusted based on the results of the Aβ38 increase once a time course of onset of effect could be established.

A typical protocol for measuring Aβ38 increase in vivo is shown but it is only one of many variations that could be used to optimize the levels of detectable Aβ. For example, Aβ38 increasing agents were formulated in 20% of Captisol® (a sulfobutyl ether of β-cyclodextrin) in water or 20% hydroxypropyl β cyclodextrin. The Aβ38 increasing agents were administered as a single oral dose or by any acceptable route of administration to overnight fasted animals. After 4 h, the animals were sacrificed and Aβ38 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 mL of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ38.

To quantify the amount of Aβtotal and Aβ38 in the soluble fraction of the brain homogenates, Enzyme-Linked-Immunosorbent-Assays were used. Briefly, the standards (a dilution of synthetic Aβ1-40 and Aβ1-38, ANASPEC) were prepared in 1.5 mL Eppendorf tube in Ultraculture, with final concentrations ranging from 10000 to 0.3 pg/mL. The samples and standards were co-incubated with HRPO-labelled N-terminal antibody for Aβ38 detection and with the biotinylated mid-domain antibody 4G8 for Aβtotal detection. 50 µl of conjugate/sample or conjugate/standards mixtures were then added to the antibody-coated plate (the capture antibodies selectively recognize the C-terminal end of Aβ38, antibody J&JPRD/Aβ38/5, for Aβ38 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ38 quantification was finished by addition of Quanta Blu fluorogenic peroxidase substrate according to the manufacturer's instructions (Pierce Corp., Rockford, Ill.). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Ill.). A reading was performed after 10 to 15 min (excitation 320 nm/emission 420 nm).

In this model a Aβ38 increase compared to untreated animals would be advantageous, in particular a Aβ38 increase with at least 10%, more in particular a Aβ38 increase with at least 20%.

B-3a) Results

The results are shown in Table 4 (dose 30 mg/kg oral dosing) (value for untreated animals as control (Ctrl) was set at 100):

| Co. No. | Aβ38 (% vs Ctrl)_Mean | Aβ42 (% vs Ctrl)_Mean | Aβtotal (% vs Ctrl)_Mean |
| --- | --- | --- | --- |
| 7 | 120 | 82 | 96 |
| 8 | 181 | 41 | 86 |
| 9 | 87 | 66 | 97 |
| 12 | 96 | 94 | 91 |
| 18 | 87 | 88 | 102 |
| 20 | 122 | 93 | 113 |
| 37 | 118 | 64 | 93 |
| 6 | 78 | 79 | 87 |
| 13 | 116 | 79 | 80 |
| 5 | 123 | 106 | 80 |
| 4 | 141 | 63 | 82 |
| 10 | 115 | 72 | 105 |
| 16 | 120 | 74 | 95 |
| 30 | 118 | 91 | 97 |
| 63 | 98 | 121 | 121 |
| 64 | 122 | 48 | 100 |
| 65 | 101 | 82 | 108 |
| 39 | 132 | 74 | 99 |
| 178 | 122 | 123 | 112 |
| 69 | 106 | 83 | 122 |
| 71 | 115 | 108 | 115 |
| 73 | 120 | 43 | 80 |
| 74 | 117 | 49 | 85 |
| 96 | 124 | 55 | 92 |
| 46 | 109 | 52 | 88 |
| 77 | 168 | 104 | 102 |
| 182 | 132 | 122 | 118 |
| 59 | 91 | 55 | 86 |
| 99 | 96 | 63 | 115 |
| 102 | 82 | 98 | 121 |
| 47 | 87 | 45 | 117 |
| 111 | 107 | 87 | 120 |
| 114 | 88 | 95 | n.d. |
| 55 | 130 | 55 | 111 |
| 176 | 93 | 93 | 101 |
| 117 | 106 | 63 | 103 |

B-1b) Aβ42

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Animals treated with the Aβ42 lowering agent were examined and compared to those untreated or treated with vehicle and brain levels of soluble Aβ42, Aβ40, Aβ38, and Aβ37 were quantitated by Meso Scale Discovery's (MSD) electrochemiluminescence detection technology. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβ.

To quantify the amount of Aβ42, Aβ40, Aβ38, and Aβ37 in the soluble fraction of the brain homogenates, simultaneous specific detection of Aβ42, Aβ40, Aβ38, and Aβ37 was performed using MSD's electro-chemiluminescence multiplex detection technology. In this assay purified monoclonal antibodies specific for Abeta37 (JRD/Aβ37/3), Abeta38 (J&JPRD/Aβ38/5), Abeta40 (JRF/cAβ40/28), and Abeta42 (JRF/cAβ42/26) were coated on MSD 4-plex plates. Briefly, the standards (a dilution of synthetic Aβ42, Aβ40, Aβ38, and Aβ37) were prepared in 1.5 ml Eppendorf tube in Ultraculture, with final concentrations ranging from 10000 to 0.3 pg/m. The samples and standards were co-incubated with Sulfo-tag labelled JRF/rAβ/2 antibody to the N-terminus of Aβ as detector antibody. 50 μl of conjugate/sample or conjugate/standards mixtures were then added to the antibody-coated plate. The plate was allowed to incubate overnight at 4° C. in order to allow formation of the antibody-amyloid complex. Following this incubation and subsequent wash steps the assay was finished by adding read buffer according to the manufacturer's instructions (Meso Scale Discovery, Gaithersburg, Md.).

The SULFO-TAG emits light upon electrochemical stimulation initiated at the electrode. MSD Sector instrument SI6000 was used for signal read-out.

In this model a Aβ42 lowering compared to untreated animals would be advantageous, in particular a Aβ42 lowering with at least 10%, more in particular a Aβ42 lowering with at least 20%.

B-2b) Aβ38

Aβ38 increasing agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ38 increasing agents can be administered in any standard form using any standard method. For example, but not limited to, Aβ38 increasing agents can be in the form of liquid, tablets or capsules that are taken orally or by injection.

Aβ38 increasing agents can be administered at any dose that is sufficient to significantly increase levels of Aβ38 in the blood, plasma, serum, cerebrospinal fluid (CSF), or brain.

To determine whether acute administration of an Aβ38 increasing agents would increase Aβ38 levels in vivo, non-transgenic rodents, e.g. mice or rats were used. Animals treated with the Aβ38 increasing agents were examined and compared to those untreated or treated with vehicle and brain levels of soluble Aβ42, Aβ40, Aβ38, and Aβ37 were quantitated by MSD electrochemiluminescence detection technology. Treatment periods varied from hours (h) to days and were adjusted based on the results of the Aβ38 increase once a time course of onset of effect could be established.

A typical protocol for measuring Aβ38 increase in vivo is shown but it is only one of many variations that could be used to optimize the levels of detectable Aβ. For example, Aβ38 increasing agents were formulated in 20% of Captisol® (a sulfobutyl ether of β-cyclodextrin) in water or 20% hydroxypropyl β cyclodextrin. The Aβ38 increasing agents were administered as a single oral dose or by any acceptable route of administration to overnight fasted animals. After 4 h, the animals were sacrificed and Aβ38 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβ.

To quantify the amount of Aβ42, Aβ40, Aβ38, and Aβ37 in the soluble fraction of the brain homogenates, simultaneous specific detection of Aβ42, Aβ40, Aβ38, and Aβ37 was performed using MSD's electro-chemiluminescence multiplex detection technology. In this assay purified monoclonal antibodies specific for Abeta37 (JRD/Aβ37/3), Abeta38 (J&JPRD/Aβ38/5), Abeta40 (JRF/cAβ40/28), and Abeta42 (JRF/cAβ42/26) were coated on MSD 4-plex plates. Briefly, the standards (a dilution of synthetic Aβ42, Aβ40, Aβ38, and Aβ37) were prepared in 1.5 ml Eppendorf tube in Ultraculture, with final concentrations ranging from 10000 to 0.3 pg/m. The samples and standards were co-incubated with Sulfo-tag labelled JRF/rAβ/2 antibody to the N-terminus of Aβ as detector antibody. 50 µl of conjugate/sample or conjugate/standards mixtures were then added to the antibody-coated plate. The plate was allowed to incubate overnight at 4° C. in order to allow formation of the antibody-amyloid complex. Following this incubation and subsequent wash steps the assay was finished by adding read buffer according to the manufacturer's instructions (Meso Scale Discovery, Gaitherburg, Md.).

The SULFO-TAG emits light upon electrochemical stimulation initiated at the electrode. MSD Sector instrument SI6000 was used for signal read-out.

In this model a Aβ38 increase compared to untreated animals would be advantageous, in particular a Aβ38 increase with at least 10%, more in particular a Aβ38 increase with at least 20%.

B-3b) Results

The results are shown in Table 5 (dose 30 mg/kg oral dosing) (value for untreated animals as control (Ctrl) was set at 100):

| Co. No. | Aβ40 (% vs Ctrl)_Mean | Aβ42 (% vs Ctrl)_Mean | Aβ38 (% vs Ctrl)_Mean |
|---|---|---|---|
| 47 | 56 | 55 | 222 |
| 55 | 94 | 68 | 148 |
| 176 | 111 | 103 | 126 |
| 56 | 91 | 54 | 139 |
| 117 | 112 | 79 | 147 |
| 122 | 90 | 74 | 145 |
| 131 | 72 | 62 | 144 |
| 50 | 46 | 43 | 141 |
| 133 | 107 | 98 | 119 |
| 41 | 35 | 34 | 140 |
| 138 | 90 | 75 | 117 |
| 147 | 79 | 67 | 160 |
| 148 | 118 | 110 | 132 |
| 153 | 76 | 60 | 236 |
| 154 | 101 | 90 | 170 |
| 158 | 87 | 66 | 140 |
| 164 | 81 | 65 | 141 |
| 44 | 31 | 27 | 110 |
| 53 | 79 | 74 | 78 |

Composition Examples

"Active ingredient" (a.i.) as used throughout these examples relates to a compound of Formula (I), including any tautomer or stereoisomeric form thereof, or a pharmaceutically acceptable addition salt or a solvate thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 mL.

3. Injectable

A parenteral composition is prepared by stirring 1.5% (weight/volume) of active ingredient in 0.9% NaCl solution or in 10% by volume propylene glycol in water.

4. Ointment

| | | |
|---|---|---|
| Active ingredient | 5 to 1000 | mg |
| Stearyl alcohol | 3 | g |
| Lanoline | 5 | g |
| White petroleum | 15 | g |
| Water | ad 100 | g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of Formula (I)

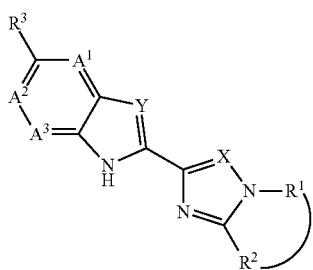

(I)

or a tautomer or a stereoisomeric form thereof, wherein
$R^3$ is selected from the group consisting of hydrogen, $C_{1-4}$-alkyloxy, cyano and $Het^1$;
$A^1$ is $CR^{4a}$ or N; wherein $R^{4a}$ is hydrogen, halo or $C_{1-4}$-alkyloxy optionally substituted with one or more substituents selected from the group consisting of $C_{1-4}$-alkyloxy and halo;
$A^2$ is $CR^{4b}$ or N; wherein $R^{4b}$ is hydrogen, halo, $C_{1-4}$-alkyloxy, cyano or $Het^2$;
$A^3$ is $CR^{4c}$ or N; wherein $R^{4c}$ is hydrogen, halo or $C_{1-4}$-alkyloxy;
provided that maximum one of $A^1$, $A^2$ and $A^3$ is N;
$Het^1$ and $Het^2$ each independently represent a 5- or 6-membered heteroaryl selected from the group consisting of pyridinyl, imidazolyl, oxazolyl, 1,2,4-triazolyl and pyrazolyl, wherein said 5- or 6-membered heteroaryl may be substituted with one or more $C_{1-4}$-alkyl substituents;
Y is N or $CR^a$; wherein $R^a$ is hydrogen, halo or $C_{1-4}$-alkyl optionally substituted with one hydroxyl;
X is N or CH;
$R^1$ and $R^2$ are taken together to form a bivalent radical $-R^1-R^2-$ having formula (b-1) or (b-2)

(b-1);

(b-2);

wherein:
m represents 2, 3 or 4;
Z represents a direct bond, $NR^5$ or O; wherein $R^5$ is hydrogen, $C_{1-4}$alkylcarbonyl, $Ar^1$, (C=O)—$Ar^1$ or $C_{1-4}$-alkyl optionally substituted with one or more fluoro substituents;

(b-1) or (b-2) is substituted on one or more $CH_2$ groups with one or two substituents each independently selected from the group consisting of $Ar^2$, (C=O)—$Ar^2$, O—$Ar^2$, $NR^6$—$Ar^2$, $C_{1-4}$-alkylcarbonyl, fluoro, hydroxy, and $C_{1-4}$-alkyl optionally substituted with one or more fluoro substituents;
each $Ar^1$ and $Ar^2$ independently represents phenyl, pyrazolyl or pyridinyl; wherein said phenyl, pyrazolyl or pyridinyl may be substituted with one or more substituents each independently selected from the group consisting of halo, cyano, $NR^7R^8$, morpholinyl, cyclo$C_{3-7}$alkyl, $C_{1-4}$-alkyl optionally substituted with one or more substituents each independently selected from the group consisting of $C_{1-4}$-alkyloxy, fluoro and cyclo$C_{3-7}$alkyl, and $C_{1-4}$-alkyloxy optionally substituted with one or more substituents each independently selected from the group consisting of fluoro and cyclo$C_{3-7}$alkyl;
each $R^6$ independently is hydrogen, or $C_{1-4}$-alkyl optionally substituted with one or more substituents each independently selected from the group consisting of fluoro and cyclo$C_{3-7}$alkyl;
each $R^7$ independently is hydrogen, $C_{1-4}$-alkyl or $C_{1-4}$-alkylcarbonyl; and,
each $R^8$ independently is hydrogen or $C_{1-4}$-alkyl;
or a pharmaceutically acceptable addition salt or a solvate thereof.

2. The compound according to claim 1, wherein
$R^3$ is selected from the group consisting of $C_{1-4}$-alkyloxy, cyano and $Het^1$;
$A^1$ is $CR^{4a}$ or N, wherein $R^{4a}$ is hydrogen, halo or $C_{1-4}$-alkyloxy;
provided that maximum one of $A^1$, $A^2$ and $A^3$ is N;
Y is N or CH;
each $Ar^1$ and $Ar^2$ independently represents phenyl or pyridinyl, wherein said phenyl or pyridinyl may be substituted with one or more substituents each independently selected from the group consisting of halo, cyano, $NR^7R^8$, morpholinyl, $C_{1-4}$-alkyl optionally substituted with one or more substituents each independently selected from the group consisting of fluoro and cyclo$C_{3-7}$alkyl, and $C_{1-4}$-alkyloxy optionally substituted with one or more substituents each independently selected from the group consisting of fluoro and cyclo$C_{3-7}$alkyl.

3. The compound according to claim 1, wherein
$R^3$ is $C_{1-4}$-alkyloxy, cyano or $Het^1$;
$A^1$ is $CR^{4a}$ or N, wherein $R^{4a}$ is hydrogen or $C_{1-4}$-alkyloxy;
$A^2$ is $CR^{4b}$ or N, wherein $R^{4b}$ is hydrogen, $C_{1-4}$-alkyloxy, cyano or $Het^2$;
$A^3$ is CH or N;
provided that maximum one of $A^1$, $A^2$ and $A^3$ is N; and,
Y is N or CH;
wherein (b-1) or (b-2) is substituted on one or more $CH_2$ groups with one or two $Ar^2$ substituents; and,
each $Ar^1$ and $Ar^2$ independently represents phenyl or pyridinyl, wherein said phenyl or pyridinyl may be substituted with one or more substituents each independently selected from the group consisting of halo, cyano, $NR^7R^8$, morpholinyl, $C_{1-4}$-alkyl optionally substituted with one or more substituents each independently selected from the group consisting of fluoro and cyclo$C_{3-7}$alkyl, and $C_{1-4}$-alkyloxy optionally substituted with one or more substituents each independently selected from the group consisting of fluoro and cyclo$C_{3-7}$alkyl.

4. The compound according to claim 1, wherein
$R^3$ is selected from the group consisting of $C_{1-4}$-alkyloxy, cyano and $Het^1$;
$A^1$ is $CR^{4a}$ or N, wherein $R^{4a}$ is hydrogen or $C_{1-4}$-alkyloxy;
$A^2$ is $CR^{4b}$ or N, wherein $R^{4b}$ is hydrogen, $C_{1-4}$-alkyloxy;
$A^3$ is CH or N;
provided that maximum one of $A^1$, $A^2$ and $A^3$ is N;
$Het^1$ represents a 5- or 6-membered heteroaryl selected from the group consisting of pyridinyl, imidazolyl, oxazolyl, 1,2,4-triazolyl and pyrazolyl, wherein said 5- or 6-membered heteroaryl may be substituted with one or more $C_{1-4}$-alkyl substituents;
Y is N or CH;
$R^1$ and $R^2$ are taken together to form a bivalent radical -$R^1$-$R^2$- having formula (b-1)

—(CH$_2$)$_m$—Z—CH$_2$—   (b-1);

wherein:
Z represents a direct bond or O;
(b-1) is substituted on one CH$_2$ group with one $Ar^2$ substituent; and,
$Ar^2$ represents phenyl or pyridinyl, wherein said phenyl or pyridinyl may be substituted with one or more substituents each independently selected from the group consisting of halo, cyano, $NR^7R^8$, morpholinyl, $C_{1-4}$-alkyl optionally substituted with one or more substituents each independently selected from the group consisting of fluoro and cyclo$C_{3-7}$alkyl, and $C_{1-4}$-alkyloxy optionally substituted with one or more substituents each independently selected from the group consisting of fluoro and cyclo$C_{3-7}$alkyl.

5. The compound according to claim 1, wherein
$A^1$ is $CR^{4a}$ or N; wherein $R^{4a}$ is hydrogen or $C_{1-4}$-alkyloxy optionally substituted with one, two or three substituents selected from the group consisting of $C_{1-4}$-alkyloxy and halo;
$A^2$ is $CR^{4b}$ or N, wherein $R^{4b}$ is hydrogen, $C_{1-4}$-alkyloxy, cyano or $Het^2$;
$A^3$ is CH or N;
provided that maximum one of $A^1$, $A^2$ and $A^3$ is N;
$Het^1$ and $Het^2$ each independently represent a 5- or 6-membered heteroaryl selected from the group consisting of pyridinyl, imidazolyl, 1,2,4-triazolyl and pyrazolyl, wherein said 5- or 6-membered heteroaryl may be substituted with one $C_{1-4}$-alkyl substituent;
$R^1$ and $R^2$ are taken together to form a bivalent radical -$R^1$-$R^2$- having formula (b-1)

—(CH$_2$)$_m$—Z—CH$_2$—   (b-1);

wherein:
m represents 2 or 3;
Z represents a direct bond, $NR^5$ or O, wherein $R^5$ is $C_{1-4}$-alkyl;
(b-1) is substituted on one CH$_2$ group with one or two substituents each independently selected from the group consisting of $Ar^2$, hydroxy, and $C_{1-4}$-alkyl; and,
each $Ar^2$ independently represents phenyl or pyrazolyl, wherein said phenyl or pyrazolyl may be substituted with one, two, three or four substituents each independently selected from the group consisting of halo, cyclo$C_{3-7}$alkyl, $C_{1-4}$-alkyl optionally substituted with one, two or three substituents each independently selected from the group consisting of $C_{1-4}$-alkyloxy and fluoro, and $C_{1-4}$-alkyloxy optionally substituted with one, two or three fluoro substituents.

6. The compound according to claim 1, wherein
$R^3$ is cyano;
$A^1$ is $CR^{4a}$; wherein $R^{4a}$ is $C_{1-4}$-alkyloxy;
$A^2$ is CH;
$A^3$ is CH;
Y is CH;
X is CH;
$R^1$ and $R^2$ are taken together to form a bivalent radical —(CH$_2$)$_2$—O—CH($Ar^2$)—; and
$Ar^2$ represents phenyl, wherein said phenyl is substituted with one or two substituents each independently selected from the group consisting of halo, $C_{1-4}$-alkyl and $CF_3$.

7. The compound according to claim 1, wherein $R^1$ and $R^2$ are taken together to form a bivalent radical -$R^1$-$R^2$- having formula (b-1) or (b-2), wherein the (b-1) or (b-2) is substituted on one or more CH$_2$ groups with one or two $Ar^2$ substituents.

8. The compound according to claim 1, wherein $R^1$ and $R^2$ are taken together to form a bivalent radical -$R^1$-$R^2$- having formula (b-1), wherein (b-1) is substituted on one CH$_2$ group with one $Ar^2$ substituent.

9. The compound according to claim 1, wherein $R^1$ and $R^2$ are taken together to form a bivalent radical -$R^1$-$R^2$- having formula —(CH$_2$)$_3$—CH($Ar^2$)— or —(CH$_2$)$_2$—O—CH($Ar^2$)—.

10. The compound according to claim 1, wherein the compound is

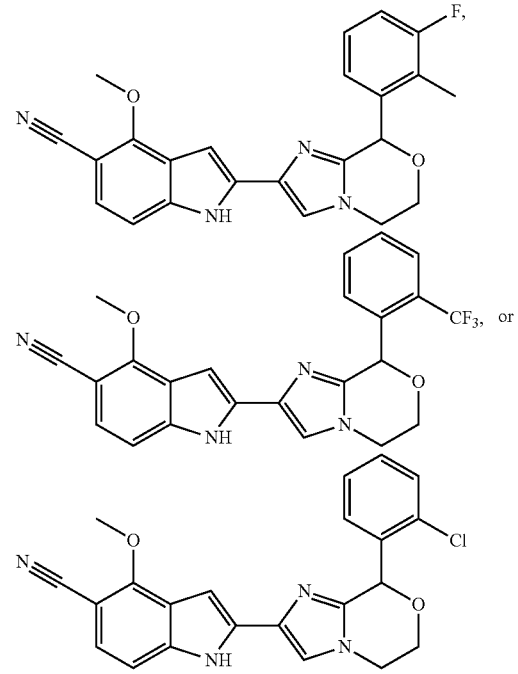

or, a tautomer, a pharmaceutically acceptable addition salt, or a solvate thereof.

11. The compound according to claim 1 wherein Y is CH.

12. A pharmaceutical composition comprising a pharmaceutically acceptable carrier and, as active ingredient, a compound according to claim 1.

13. A method for decreasing Aβ42 peptide in a subject comprising administering to the subject a composition according to claim 12.

14. A method for modulating γ-secretase activity in a subject comprising administering to the subject a composition according to claim 12.

* * * * *